United States Patent [19]
Croce et al.

[11] Patent Number: 5,633,135
[45] Date of Patent: May 27, 1997

[54] CHIMERIC NUCLEIC ACIDS AND PROTEINS RESULTING FROM ALL-1 REGION CHROMOSOME ABNORMALITIES

[75] Inventors: Carlo Croce, Philadelphia; Eli Canaani, Glenside, both of Pa.

[73] Assignee: Thomas Jefferson University, Philadelphia, Pa.

[21] Appl. No.: 320,559

[22] Filed: Oct. 11, 1994

Related U.S. Application Data

[63] Continuation of Ser. No. 62,443, filed as PCT/US92/10930, Dec. 9, 1992, abandoned, which is a continuation-in-part of Ser. No. 971,094, Oct. 30, 1992, abandoned, which is a continuation-in-part of Ser. No. 888,839, May 27, 1992, abandoned, which is a continuation-in-part of Ser. No. 805,093, Dec. 11, 1991, abandoned. WO]

[51] Int. Cl.$^6$ .............................. C07H 21/04; C12Q 1/68; C12P 19/34
[52] U.S. Cl. .......................... 435/6; 435/91.2; 536/24.31; 536/24.33; 935/8; 935/78
[58] Field of Search ................... 435/6, 91.2; 536/24.31, 536/24.33; 935/8, 78

[56] References Cited

PUBLICATIONS

Adams et al., "Sequence Identification of 2,375 Human Brain Genes", *Nature* 355: 632–634, 1992.

Arad et al., "Use of Reconstituted Sendai Virus Envelopes for Fusion-Mediated Microinjection of Double-Stranded RNA: Inhibition of Protein Synthesis in Interferon-Treated Cells", *Biochem. Biophy. Acta.* 859: 88–94, 1986.

Chen et al., "Breakpoint Clustering in t(4;11) (q21:q23) Acute Leukemia", *Blood* 78: 2498–2504, 1991.

Chu et al., "Mosaic Structure of Globular Domains in the Human Type VI Collagen α3 Chain: Similarity to Von Wilebrand Factor, Fibronectin, Actin, Salivary Proteins and Aprotinin Type Protease Inhibitors", *EMBO J.* 9: 385–393, 1990.

Cimino et al., "An Altered 11-Kilobase Transcript in Leukemic Cell Lines with the t(4;11) (q21;q23) Chromosome Translocation", *Cancer Research* 52: 3811–3813, 1992.

Capdevila and Garcia-Bellido, "Genes Involved in the Activation of the Bithorax Complex of Drosophila", *Roux's Arch. Dev. Biol.* 190: 339–350, 1981.

Croce, "Role of Chromosome Translocations in Human Neoplasia", *Cell* 49: 155–156, 1987.

Cohen et al., "Constitutive Expression and Role in Growth Regulation of Interleukin-1 and Multiple Cytokine Receptors in a Biphenotypic Leukemic Cell Line", *Blood* 78: 94–102, 1991.

Cotter et al., "Gene Mapping by Microdissection and Enzymatic Amplification: Heterogeneity in Leukaemia Associated Breakpoints on Chromosome II", *Genes, Chromosomes & Cancer* 3: 8–15, 1991.

(List continued on next page.)

*Primary Examiner*—Stephanie W. Zitomer
*Assistant Examiner*—Carla Myers
*Attorney, Agent, or Firm*—Woodcock Washburn Kurtz Mackiewicz & Norris

[57] ABSTRACT

Methods are provided for the diagnosis and treatment of human leukemias involving breakpoints on chromosome 11 in the ALL-1 locus. The ALL-1 breakpoint region, an approximately 8 kb region on chromosome 11, is also disclosed. The ALL-1 region is involved in translocations in acute lymphocytic, myelomonocytic, monocytic and myelogenous leukemias. Probes which identify chromosome aberrations involving the ALL-1 breakpoint region on chromosome 11 are also provided. cDNA sequences of the ALL-1 gene on chromosome 11, the AF-9 gene on chromosome 9 and the AF-4 gene, and corresponding amino acid sequences are also provided. Probes are provided for detecting chromosome abnormalities involving theses genes. Chimeric genes involved in translocations are disclosed. Monoclonal antibodies for diagnosis and treatment and antisense oligonucleotides for treatment of acute leukemias are also described.

8 Claims, 22 Drawing Sheets

PUBLICATIONS de Thè et al., "The PLM–RARα Fusion mRNA Generated by the t(15;17) Translocation in Acute Promyelocytic Leukemia Encodes a Functionally Altered RAR", *Cell* 66: 675–684, 1991.

Erikson et al., "Heterogeneity of Chromosome 22 Breakpoint in Philadelphia–Positive (Ph+) Acute Lymphocytic Leukemia", *Proc Natl. Acad. Sci. USA* 83: 1807–1811, 1986.

Yunis et al., "Gene Order, Amplification, and Rearrangement of Chromosome Band 11q23 in Hematologic Malignancies," *Genomics* 5: 84–90, 1989.

Gale and Canaani, "An 8–kilobase abl RNA Transcript in Chronic Myelogenous Leukemia", *Proc. Natl. Acad. Sci. USA* 81: 5648–5652, 1984.

Green et al., "Systematic Screening of Yeast Artificial–Chromosome Libraries by Use of the Polymerase Chain Reaction", *Proc. Natl. Acad. Sci. USA* 87:1213–1217, 1990.

Gu et al., "The t(4;11) Chromosome Translocation of Human Acute Leukemias Fuses the ALL–1 Gene, Related to Drosophila trithorax, to the AF–4 Gene", *Cell* 71: 701–708, 1992.

Gu et al., "The (4;11) (q21;q23) Chromosome Translocations in Acute Leukemias Involve the VDJ Recombinase", *Proc. Natl. Acad. Sci. USA* 89: 10464–10468 1992.

Heim and Mitelman, *Cancer Cytogenetics*, Alan R. Liss, New York, 1987.

Heisterkamp et al., "Structural Organization of the BCR Gene and its Role in the Ph' Translocation", *Nature* 315: 758–761, 1985.

Hoheisel et al., "Control of Partial Digestion Combining the Enzymes dam methylase and Mbol", *Nuc. Acid Res.* 17: 9571–9582, 1989.

Ingham, "Genetic Control of the Spatial Pattern of Selector Gene Expression in Drosophilia", *Cold Spring Harbor Symp. Quant. Biol.* 50: 201–208, 1985.

Kakizuka et al., "Chromosomal Translocation t(15;17) in Human Acute Promyelocytic Leukemia Fuses RARα with a Novel Putative Transcription Factor, PLM", *Cell* 66: 663–674, 1991.

Kamps et al., "A New Homeobox Gene Contributes the DNA Binding Domain of the t(1;19) Translocation Protein in Pre–B ALL", *Cell* 60 547–555, 1990.

Kitazawa et al., "Immunocytochemical Evaluation of AB1–Gene Products in Leukemic Cell Lines", *Med. Oncol Tumor Pharmacother* 7: 35–41, 1990. (Abstract).

Kurzrock et al., "Identification of Molecular Variants of $p210^{bcr-abl}$ in Chron Myelogenous Leukemia", *Blood* 70: 233–236, 1987.

Lange et al., "Growth Factor Requirements of Childhood Acute Leukemia: Establishment of GM–CSF–Dependent Cell Lines", *Blood* 70:192–199, 1987.

Lozzio and Lozzio, "Human Chronic Myelogenous Leukemia Cell–Line With Positive Philadelphia Chromosome", *Blood* 45: 321–334, 1975.

McGinnis and Krumlauf, "Homeobox Genes and Axial Patterning", *Cell* 68: 283–302, 1992.

Marcu et al., "Transcriptionally Active C–MYC Oncogene is Contained Within NIARD, a DNA Sequence Associated with Chromosome Translocations in B–cell Neoplasia", *Proc. Natl. Acad. Sci. USA* 80: 519–523, 1983.

Mazo et al., "The Trithorax Gene, a Trans–Acting Regulator of the Bithorax Complex in *Drosophila*, Encodes a Protein with Zinc–Binding Domains", *Proc. Natl. Acad. Sci. USA* 87: 2112–2116, 1990.

McKeon and Brock, "Interactions of the Polycomb Group of Genes with Homeotic Loci of Drosophila", *Roux's Arch. Dev. Biol.* 199: 387–396, 1991.

Mellentin et al., "The Gene for Enhancer Binding Proteins E12/E47 Lies at the t(1;19) Breakpoint in Acute Leukemias", *Science* 246: 379–382, 1989.

Garvey et al., *Methods in Immunology: A Laboratory Text for Instruction and Research, Third Ed.*, The Benjamin/Cummings Publishing Company: Reading, MA, Chapter 22:24–30, 1977.

Mozer and David, "Cloning and Molecular Characterization of the Trithorax Locus of *Drosophila Melanogaster*", *Proc. Natl. Acad. Sci. USA* 86: 3738–3742, 1989.

Nagasaka et al., "Four Cases of t(4;11) Acute Leukemia and Its Myelomonocytic Nature in Infants", *Blood* 61: 1174–1181, 1983.

Nourse et al., "Chromosomal Translocation t(1;19) Results in Synthesis of a Homeobox Fusion mRNA That Codes for a Potential Chimeric Transcription Factor", *Cell* 60: 535–545, 1990.

Watson et al., "The ets Sequence from the Transforming Gene of Avian Erythroblastosis Virus, E26, has Unique Domains on Human Chromosomes 11 and 21: Both Loci are Transcriptionally Active," *Proc. Natl. Acad. Sci. USA* 82:7294–7298, 1985.

Pui et al., "Clinical Characteristics and Treatment Outcome of Childhood Acute Lumphoblastic Leukemia With the t(4;11) (q21;q23): A Collaborative Study of 40 Case", *Blood* 77: 440–447, 1991.

Rabbitts, "Translocations, Master Genes, and Differences Between the Origins of Acute and Chronic Leukemias", *Cell* 67, 641–644, 1991.

Wei et al., "Physical Mapping of the Human Chromosome 11q23 Region Containing the Ataxia–Telangiectasia Locus," *Cancer Genet. Cytogenet.* 46:1–8, 1990.

Rowley et al., "Mapping Chromosome Band 11q23 in Human Acute Leukemia with Biotinylated Probes: Identification of 11q23 Translocation Breakpoints with a Yeast Artificial Chromosome", *Proc. Natl. Acad. Sci. USA* 87: 9358–9362, 1990.

Sacchi et al., "Hu–ets–1 and Hu–ets–2 Genes are Transposed in Acute Leukemias with (4;11) and (8;21) Translocations", *Science* 231: 379–382, 1986.

Saito et al., "Activation of the C–MYC Gene by Translocation: A Model for Translational Control", *Proc. Natl. Acad. Sci. USA* 80: 7476–7480, 1983.

Savage et al., "Mapping Studies and Expression of Genes Located on Human Chromosome 11, Band q23", *Cytogenet. Cell Genet.* 49: 289–292, 1988.

Shtivelman et al., "Fused Transcript of abl and bcr Genes in Chronic Myelogenous Leukaemia", *Nature* 315: 550–554, 1985.

Siminovitch et al., "Immunoglobulin Gene Rearrangements and Expression in Diffuse Histiocytic Lymphomas Reveal Cellular Lineage, Molecular Defects, and Sites of Chromosomal Translocation", *Blood* 67: 391–397, 1986.

Solomon et al., "Chromosome Aberrations and Cancer", *Science* 254: 1153–1160 1991.

Stong and Kersey, "In Vitro Culture of Leukemic Cells in t(4;11) Acute Leukemia" *Blood* 66: 439–443, 1985.

Tkachuk et al., "Involvement of a Homolog of Drosophila Trithorax by 11q23 Chromosomal Translocations in Acute Leukemias", *Cell* 71: 691–700, 1992.

Tsujimoto et al., "Molecular Cloning of the Chromosomal Breakpoint of B–Cell Lymphomas and Leukemias with the t(11;14) Chromosome Translocation", *Science* 224: 1403–1406, 1984.

Tsujimoto et al., "Cloning of the Chromosome Breakpoint of Neoplastic B Cells with the t(14;18) Chromosome Translocation", *Science* 226: 1097–1099, 1984.

van Den Elsen et al., "Exon/Intron Organization of the Genes Coding for the & Chains of the Human and Murine T–Cell Receptor/T3 Complex", *Proc. Natl. Acad. Sci. USA* 83: 2944–2948, 1986.

Watson et al., "Mammalian ets–1 and ets–2 Genes Encode Highly Conserved Proteins", *Proc. Natl. Acad. Sci. USA* 85; 7862–7866, 1988.

von Lindern et al., "The (6,9) Chtomosome Translocation, Associated with a Specific Subtype of Acute Nonlymphocytic Leukemia, Leads to Aberrant Transciption of a Target Gene on 9q34," *Mol. Cell. Biol.* 10:4016–4026, 1990.

von Lindern et al., "The Translocation (6;9), Associated with a Specific Subtype of Acute Myeloid Leukemia, Results in the Fusion of Two Genes, dek and can, and the Expression of a Chimeric, Leukemia–Specific dek–can mRNA," *Mol. Cell. Biol.* 12:1687–1697, 1992.

Ziemin–van der Poel et al., "Identification of a Gene, MLL, That Spans the Breakpointin 11q23 Translocations Associated with Human Leukemias", *Proc. Natl. Acad. Sci. USA* 88: 10735–10739, 1991.

Cimino et al., "Cloning of ALL–1, the Locus Involved in Leukemias with the t(4;11) (q21;q23), t(9;11) (p22;q23), and t(11;19) (q23–p13) Chromosome Translocations", *Cancer Research* 51, 6712–6714, 1991.

Bowden et al., "Studies on Locus Expansion, Library Representation, and Chromosome Walking Using an Efficient Method to Screen Cosmid Libraries" *Gene* 71: 391–400 (1988).

Djabali et al, "A Trithroax–like Gene is Interrupted by Chromosome 11q23 Translocations in Acute Leukemias," *Nature Genet* 2: 113–118 (1992) (Abstract).

Domer et al., "Acute, Mixed–Lineage Leukemia t(4;11) (q21;q23) generates an MLL–AF4 Fusion Product", *PNAS USA* 90: 7884–7888 (1993).

Morrissey et al., "A Serine/Proline–Rich Protein is Fushed to HRX in t(4;11) Acute Leukemias" *Blood* 81: 1124–1131 (1993).

Morse et al., "Acute Non–Lymphoblastic Leukemia in Childhood", *Cancer* 44: 164–170 (1979).

Nadkarni et al., "Antisense RNA Therapy for CML—An Hypothesis", *Med. Hypotheses* 35: 307–310, 1991.

Nakamura et al., "Genes on Chromosomes 4, 9, and 19 involved in 11q23 Abnormalities in Acute Leukemia Share Sequence Homology and/or Common Motifs" *PNAS USA* 90: 4631–4635 (1993).

Schichman et al., "All–1 Tandem Duplication in Acute Myeloid Leukemia with a Normal Karyotype Involves Homologous Recombination Between Alu Elements", *Cancer Res.* 54: 4277–4280 (1994).

Trent et al., "Report of the committee on Structural Chromosome Changes in Neoplasia", 10th International Workshop on Human Gene Mapping. *Cytogenet. Cell Genet.* 51: 533–562 (1989).

Yunis and Brunning, "Prognostic Significance of Chromosomal Abnormalities in Acute Leukemias and Myelodysplastic Syndromes." *Clinics in Haemotology* 15: 597–620 (1986) (Gale and Hoffbrand, Eds.).

```
GCGGCGGCGGGGAAGCAGCGGGGCTGGGGTTCCAGGGGGAGCGGCGGCCTCCTGCGTCGTCGCCTCGTCTTCG        90
 A  A  A  A  G  S  S  G  A  G  V  P  G  G  A  A  A  A  S  S  S  S  A  S  S  S     30
TCTTCGTCATCGTCTCAGCCTCTTCAGGGCCCGCTCCGGGTGGGCCCGGCGTTCGACGGGCGTCTCGGCCGCCATC       180
 S  S  S  S  S  A  S  S  G  P  A  L  L  R  V  G  P  G  F  D  A  A  L  Q  V  S  A  I  60
GGCACCAACCTGCGCCGGTTCCGGGCAGTCTTGGGGGAGAGCGGCGGGGGGAGCGGGGAGGATGAGCAATTCTTAGGTTTTGGC 270
 G  T  N  L  R  R  F  R  A  V  F  G  E  S  G  G  G  S  G  E  D  E  Q  F  L  G  F  G    90
TCAGATGAAGAAGTCAGAGTGCGAAGTCCCAAGTCTCCTCCTTCAGTTAAAACTAGTCCTCGAAAACCTCGTGGGAGACCTAGAAGTGGC 360
 S  D  E  E  V  R  V  R  S  P  T  R  S  P  S  V  K  T  S  P  R  K  P  R  G  R  P  R  S  G  120
TCTGACCGAAATTCAGCTATCCTCTCAGATCCATCTGTGTTTCCCCTAATAAATCAGAGACCAAATCTGGAGATAAGATCAAGAAG     450
 S  D  R  N  S  A  I  L  S  D  P  S  V  F  S  P  L  N  K  S  E  T  K  S  G  D  K  I  K  K  150
AAAGATTCTAAAAGTATAGAAAAGAAGAGAGAAGAAGATAGCCTGAAAAAATCAAAATAACACATGGAAGGACATTTCA             540
 K  D  S  K  S  I  E  K  K  R  G  R  P  P  T  F  P  G  V  K  I  K  I  T  H  G  K  D  I  S  180
GAGTTACCAAAGGGAAACAAGAAGATAGCCTGAAAGTCCTGTACCTTCAGCAAGCCACAAAGATTAAAAAA                      630
 E  L  P  K  G  N  K  E  D  S  L  K  K  I  K  R  T  P  S  A  T  F  Q  Q  A  T  K  I  K  K   210
TTAAGAGCAGGTAAACTCTCTCCTCAGTCTAAGTTTAAGACAGGAAGCTTCAATAGGAAGGAAAGTCCCCAGAAAGTCCGAAA          720
 L  R  A  G  K  L  S  P  L  K  S  K  F  K  T  G  K  L  Q  I  G  R  K  G  V  Q  I  V  R  R   240
AGAGGAAGGCCTCCATCAACAGAAAAGGATAAAGACCCTCACTTGTCAGACAGTTGTCAGAAGGATTAAGCCAGTTAGGATTATTCCT    810
 R  G  R  P  P  S  T  E  R  I  K  T  P  S  G  L  L  I  N  S  E  L  E  K  P  Q  K  V  R  K   270
GACAAGGAAGGAACACCTCCACTTACAAGAAGATCAACAACTCTTACAGAGGCAAAAAGGGGCTCAAAAGAAATTGAAAAAGAAGCAGCT  900
 D  K  E  G  T  P  P  L  T  K  E  D  K  T  V  V  R  Q  S  P  R  R  I  K  P  V  R  I  I  P  300
TCTTCAAAAAGGACAGATGCAACCATTGCTAAGCAACTCTTACAGAGACAATCAAAAATATTCGACAGTTGTCAGCTGTCTATCTCCTCCGGATCATT 990
 S  S  K  R  T  D  A  T  I  A  K  Q  L  L  Q  R  A  K  K  G  A  Q  K  K  I  E  K  E  A  A   330
CAGCTGCAGGAGAAGGTGAAGACACAGTGCAAAATATTCGACAGTTGTCAGCTGTCTATCTCCTCCGGATCATT                  1080
 Q  L  Q  G  R  K  V  K  T  Q  V  K  N  I  R  Q  F  I  M  P  V  V  S  A  I  S  S  R  I  I   360
AAGAACCCTCGGCCGGTTTATAGAGGATGAGGATTATGACCCTCCAATTAAAATGCCCGATTAGAGTCTTACACCGAATAGATTCAGT    1170
 K  N  P  R  P  V  Y  R  G  *  D  Y  D  P  P  I  K  I  A  R  L  E  S  T  P  N  S  R  F  S   390
GCCCCGTCCTGTGACTCTTCTGAAAAATCAAGTGCAGATTCAGAGGAGCGGATACCCTGAAGTTCATCCTCCA                    1260
 A  P  S  C  G  S  S  E  K  S  S  A  A  S  Q  H  S  S  Q  M  S  S  D  S  S  R  S  S  S  P   420
AGTGTTGATACCTCCACAGACTCTCAGGCTTCTGAGGAGATTCAGTTAGTGCCGGAAGTATTCAGTGTCGAGAAGTTTTGGATCTAGAACG 1350
 S  V  D  T  S  T  D  S  Q  A  S  E  E  I  Q  V  L  P  E  E  R  S  D  T  P  E  V  H  P  P   450
CTGCCCATTCCCAGTCCCCAGAAAATGAGAGTAATGATAGGAGAAGCAGAAGTATTCAGTGTCGAGAAGTTTTGGATCTAGAACG      1440
 L  P  I  S  Q  S  P  E  N  E  S  N  D  R  R  S  R  R  Y  S  V  S  E  R  S  F  G  S  R  T   480
ACGAAAAAATTATCAACTCTACAAAGTGCCCCCAGCAGGAGACCTCCTGCTCCAACATCCCTTAGCATCACCATTTTGCCTGCTCTTGCT 1530
 T  K  K  L  S  T  L  Q  S  A  P  Q  Q  E  T  S  S  P  P  P  L  L  T  P  P  P  L  L         510
CAGCCAGCCTCCAGTATCTCTGACCATCACACACCTTGGCTTATGCCTGGCTTATGCCTGACATCAACAATCCCTTAGCATCACCATTTTGCCTGCTCTTGCT 1620
 Q  P  A  S  S  I  S  D  H  T  P  W  L  M  P  P  T  I  P  L  A  S  P  F  L  P  A  S  T  A   540
```

FIG. 8A

```
CCTATGCAAGGAAGCGAAAATCTATTTGCGAGAACCGACATTTAGTGGACTTCTTTAAAGCATTCTAGTGTCAGAGCCACATACTTT    1710
 P   M   Q   G   K   R   K   S   I   L   R   E   P   T   F   R   W   T   S   L   K   H   S   R   S   E   P   Q   Y   F    570
TCCTCAGCAAAGTATGCCAAAGAAGTCTTATTCGCAAACCAATATTTCGACCCCTCCACTAACTCCCGAGGACGTTGGC               1800
 S   S   A   K   Y   A   K   E   G   L   I   R   K   P   I   F   D   N   F   R   P   P   L   T   P   E   D   V   G        600
TTTGCATCTGGTTTTCTGCATCTGGTACCCGCTGCTTCAGCCGCTGTTTTCGCCACTCCATTCTGGAACAAGTTTGATATGCACAAA      1890
 F   A   S   G   F   S   A   S   G   T   A   A   S   A   R   L   F   S   P   L   H   S   G   T   R   F   D   M   H   K    630
AGGAGCCCCTCTGTGGAACATCTTCTTCAGGAGTATCCAATAGAAAAGAAAAAGTGTTTAGTCCTATTCGATCTGAACCAAGATCTCCTTCT 1980
 R   S   P   L   L   R   A   P   R   F   T   P   S   E   A   H   S   R   I   F   E   S   V   T   L   P   S   N   R   T    660
TCTGCTGGAACATCTTCTTCAGGAGTATCCAATAGAAAAGAAAAAGTGTTTAGTCCTATTCGATCTGAACCAAGATCTCCTTCT         2070
 S   A   G   T   S   S   S   G   V   S   N   R   K   R   K   V   F   S   P   I   R   S   E   P   R   S   P   S           690
CACTCCATGAGGACAAGAAGTGGAAGGCTTAGTAGTTCTGAGCTCTCACCCCGTCTTCTGTCTTCTCGTTAAGCATT                 2160
 H   S   M   R   T   R   S   G   R   L   S   S   S   E   L   S   P   L   T   P   P   S   S   V   S   S   S   L   S   I    720
TCTGTTAGTCCTCTTGCCACTAGTGCCTTAAACCAACTTTTACTTTCATCAGTAGTCCTACTCCCTTGTTTACCCCAGGC              2250
 S   V   S   P   L   A   T   S   A   L   N   P   T   F   T   F   P   S   H   S   L   T   Q   S   G   E   S   A   E   K    750
AATCAGAGACCAAGGAAGCAGACTAGTGCTCCGGCAGAGCCATTTCATCAAGAGCTGTCCAAAGATCGAGATGCTGACAAGAGCGTGAAGGACAAGG 2340
 N   Q   R   P   R   K   Q   T   S   A   P   A   E   P   F   S   S   S   P   T   P   L   F   P   W   F   T   P   G        780
TCTCAGACTGAAAGAGGAGAGAAATAAAGACAAGGCGGGAGAGAGAAAAGGGAGTCAAGGAGTCAAGATGCTGACAAGAAG             2430
 S   Q   T   E   R   G   R   N   K   D   K   A   P   E   E   L   S   K   D   R   D   A   D   K   S   V   E   K   D   K    810
AGTAGAGAGAGACCGGGAGAGAGAAAAGGGAGTCAAGGAGTAAGCGGAGTCAAGATGTTGTGGTGAAGATGTTGCCACTTCATCTTCTGCCAAAAAGCAACAGGG 2520
 S   R   E   R   D   R   E   R   E   K   E   N   K   R   E   S   R   K   E   K   R   K   K   G   S   E   I   Q   S   S    840
TCTGCTTTGTATCCTGTGGGTAGGGTTTCCAAAGAGAAAGTTGTTGGTGAAGAGTGTTGCCACTTCATCTTCTGCCAAAAAGCAACAGGG     2610
 S   R   E   R   D   R   E   R   E   K   E   N   K   R   E   S   R   K   E   K   R   K   K   G   S   E   I   Q   S   S    870
CGGAAGAAGTCTTCATCACATGATTCTGGGACTCTTGTGACTTCTGTGATATTACTTCTGGGGATACAACAGCTGTCAAAACCAAAATACTTATA 2700
 S   A   L   Y   P   V   G   R   V   S   K   E   K   V   V   G   E   D   V   A   T   S   S   A   K   K   A   T   G        900
AAGAAAGGAGAGAAATCTGAAAAAACAACTTGGACCTCCGGCCCAACTGGACTCCTCCCTGGAGAAGAAAACCCTCTGCCTTTCC         2790
 R   K   K   S   S   H   D   S   G   T   D   I   T   S   V   T   L   G   D   T   T   A   V   K   T   K   I   L   I        930
ACTCCCTTCATCTAGACACTGTTAAACATTCCACTTCCTCCAGGCTCCATGTGGCTCAGCAGAACAAGCTTCCAATGACTGACAAGAGG     2880
 K   K   G   R   G   N   L   E   K   T   N   L   D   L   G   P   T   A   P   S   L   E   K   E   K   T   L   C   L   S    960
TPSSS TVK H STSSI G S M L A Q A D K L P M T D K R                                              2970
 T   P   S   S   S   T   V   K   H   S   T   S   S   I   G   S   M   L   A   Q   A   D   K   L   P   M   T   D   K   R    
GTTGCCAGCTCCTAAAAGGCCAAAGTCTCAGCTGCAAGATTGAGAGAGTCTTAAACAACCGACCAGCCAAAGCACAG                 
 V   A   S   L   L   K   K   A   K   A   Q   L   C   K   I   E   K   S   S   L   K   Q   T   D   Q   P   K   A   Q         990
GGTCAAGAAAGTGACTCATCAGAGACCTCTGTGCGAGGACCCTGATTAAACATGTCGAAGAGCAGCTGTTGCCCTTGGCCGAAAA         3060
 G   Q   E   S   D   S   S   E   T   S   V   R   G   P   R   I   K   H   V   C   R   R   A   A   V   A   L   G   R   K   1020
CGAGCTGTGTTCCTGATGACATGCCCACCCTGAGTCGCCTTACCATGGAAGAACGAGAAAAGATTTGTCTTCCATGGGAATGATGAC       3150
 R   A   V   F   P   D   D   M   P   T   L   S   A   L   P   W   E   E   R   E   K   I   L   S   S   M   G   N   D   D   1050
AAGTCATCAATTGCTGGCTCAGAAGATGCTGAACCTGTCACTAGAAACCAATTAAACCTGTCACTAGAAACAAGGCACCCCAG           3240
 K   S   S   I   A   G   S   E   D   A   E   P   L   A   P   P   I   K   P   V   T   R   N   K   A   P   Q              1080
```

FIG. 8B

```
GAACCTCCAGTAAAGAAGGACGTCGATCGAGCGGTCTGTGGGCAGTGCCTGAGGACTGTGGTGTTTGTACTAAT    3330
 E  P  P  V  K  K  G  R  R  S  R  R  C  G  Q  C  P  G  C  P  V  E  D  C  G  V  C  T  N    1110
TGCTTAGATAAGCCCAAGTTTGGTGTCGCAATATAAGAAGCAGTGCTGCAAGATGAGAAATGTCAGAATGATGCCTTCC   3420
 C  L  D  K  P  K  F  G  V  A  N  I  K  K  Q  C  C  K  M  R  K  C  Q  N  L  Q  W  M  P  S    1140
AAAGCCTACCTGCAGAAGCAAGCTAAAGCTGTGAAGAAGAGAAAAGAGCAGTGAAAGACAGCAAAGAGAGCAGT    3510
 K  A  Y  L  Q  K  Q  A  K  A  V  K  K  E  K  K  S  K  T  S  E  K  K  D  S  K  E  S  S    1170
GTTGTGAAGAACGTGTGTGACTCTAGTCAGAAGAGAAAGAGGATCCTGCCCAAAGAGAATCAGCAGTAGTGAGCCTCCT   3600
 V  V  K  N  V  C  D  S  S  Q  K  R  K  R  I  L  P  K  E  I  S  S  S  E  P  P    1200
CCACGAAAGCCCGTCGAGGAAAAGAGTCCCAGCCACTGGTCTCGGCCTGAATCCAACAGGCCACCACTCCAGTTCCAGG  3690
 P  R  K  P  V  E  E  K  S  P  S  H  W  S  R  P  E  S  N  R  P  P  L  Q  F  Q    1230
AAGTCAAGCAAGCAGGTCTCCCAGCCCTCCAGAATCCGCCTACACGGACCGCCAAGAAAAGAAGTTCCCAAACC        3780
 K  S  S  K  Q  V  S  Q  P  L  Q  N  P  P  T  R  T  A  K  K  E  V  P  K    1260
ACTCCAGTGAGCCCAAGAAAAGCAGCCTCCACCAGAATCAGTCCAGAGCAGAACAAAGAGTGGCTCCCCCAAGT        3870
 T  P  S  E  P  K  K  S  S  L  H  Q  N  Q  S  R  A  E  Q  R  V  A  P  R  P  S    1290
ATCCCTGTAAAACAAAACCAAAGAGAATCAGGAGAATGCAGGAGATCAGCCACTTTGAACATCCTCAGCACT          3960
 I  P  V  K  Q  N  Q  R  E  S  R  R  M  Q  E  I  S  H  F  E  H  P  Q  H    1320
CTCTCCAATGGCAATAGTTCTAAGCAAATAGTTGACTTGTTCTATAACACCCAGGGTGGTTTGCTTTCTCTGT        4050
 L  S  N  G  N  S  S  K  Q  I  V  D  L  F  Y  N  T  Q  G  G  L  L  S  L    1350
AATGTGTGGAGATGGGAGGCTTAGGAATCTGTTGCCAAGTCTGTGTATTGCAGAGAACGAGCCCTCTGGAGGA        4140
 N  V  W  E  M  G  G  L  G  I  L  T  S  V  P  I  T  P  R  V  C  F  L  C  A  S  S  G  H    1380
GTAGAGTTTGTGTATTGCCAAGTCTGTGTATTGCCAAATTCTGTCACGTTTGTGAAGGCAACATCAGGCTGGAG        4230
 V  E  F  V  Y  C  Q  V  C  C  E  P  F  H  K  F  C  L  E  E  N  E  R  P  L  E  D  Q  L    1410
AATTGGTGTGTTGTCGTTGCAAATTCTGTCACGTTTGTGAAGGCAACATCAGGCTGGAGTGTAATAAGTGCCGA       4320
 N  W  C  V  V  C  G  R  Q  H  Q  A  T  K  Q  L  L  E  C  N  K  C  R    1440
AACAGCTATCACCCTGAGTGCCTGGGACCAAACTACCCCACCAAAGAAGAAATCTGTACCAAGTGTGTTCGC        4410
 N  S  Y  H  P  E  C  L  G  P  N  Y  P  T  K  K  K  V  I  C  T  K  C  V  R    1470
TGTAAGAGCTGTGGATCTGGATCCACAACTCCAGGCAAAGGGTGGGATGCACAGTGGTCTCATGATTTCAGTCTC     4500
 C  K  S  C  G  S  T  T  P  G  K  G  W  D  A  Q  W  S  H  D  F  S  L  C  H  D  C  A  K  L    1500
TTTGCTAAAGGAAACTTCTGCCCTCTGTGACAAATGTTATGATGTATGAGAGTATGATGCAAGCAGGCAAGGTAT       4590
 F  A  K  G  N  F  C  P  L  C  D  K  C  Y  D  D  D  Y  E  S  K  M  M  Q  C  G  K  C  D    1530
CGCTGGGTCCATTCAAATGTGAGAATCTTTCAGTGACTACAGAAGATGTATGAGAATTCTAATCTTAATCTTGGCCTAC   4680
 R  W  V  H  S  K  C  E  N  L  S  G  T  E  D  E  M  Y  E  I  L  S  N  L  P  E  S  V  A  Y    1560
ACTTGTGTCAACTGTACTGAGCGGCACACCCTGCCAGCTGGCCAGCTGCACCGCTACCGCCAGGCTGCCAAGCCTCGACA  4770
 T  C  V  N  C  T  E  R  H  P  A  E  W  R  L  A  L  E  K  E  L  Q  I  S  L  K  Q  V  L  T    1590
GCTTTGTTGAATTCGGAATTCCTTCTGCTAGGTGCAAAGCCAGCCAAAAACAGGATGATCAGCAGCCTTTAGAGATCTAA  4860
 A  L  L  N  S  R  T  T  S  H  L  L  R  Y  R  Q  A  A  K  P  P  D  L  N  P  E  T  E  E  S    1620
ATACCTTCCCGCAGTCCCCAGAAGACCTGATCCACAGACCTCTTAGAGGATCAGCAGTCTGAAGACCAGCAGAGAAGT    4950
```

```
ALL-1   1369  RVVCFLCASSGHVEFVYCQVCCEEPFHKFCLEEN....ERPLED..........
              |.:||||:|.|   .:::|..||||::|:|:::   . :||
D.TRX   1266  RALCFLGSTGLDPLIFCACCCEPYHQYCVQDEYNLKHGSFEDTTLMGSL

..............QLENWCCRRCKFCHVCGRQHQATKQLLECNKCRN
                            ||.:  :.|..|.||   :  .:.|..
        LETTVNASTGPSSSLNQLTQRLNWLCPRCTVCYTCNMSSGSKVKCQKCQK

SYHPECLGPNYPTKPTKKKKVWICTKCVRCKSCGSTTPGKGWDAQWSHDF
        .||..||.  :  .:||.::|||:||||:.|.:|   ::   ::    FVGNL
        NYHSTCLGT..SKRLLGADRPLICVNCLKCKSCSTTKVSK......FVGNL

SLCHDCAKLFAKGNFCPLCDKCYDDDDYESKMMQCGKCDRWVHSKCENLS
        .:| :| || |||||:|::||:|::  |||:||.|.:.||||||.||
        PMCTGCFKLRKKGNFCPICQRCYDDNDFDLKMMECGDCGQWVHSKCEGLS

GTEDEMYEILSNLPESVAYTCVNCTERH  1569
        || |:::||.|||:.:.|  .|.  |:
        ...DEQYNLLSTLPESIEFICKKCARRN  1483
```

```
ALL-1   1810  DNRQCALCLCLTYGDDSANDAGRLLLYIGQNEWTHVNCALWSAEVFEDDDGSL
              |.|.:|.|.: :::.:||||:|:. |.|.|||:.|||||||:.||||
D.TRX   1733  DTRMCLFCRKSGEGLSGEEARLLYCGHDCWHTNCAMWSAEVFEEIDGSL

KNVHMAVIRGKQLRCEFCQKPGATVGCCLTSCTSNYHFMCSRAKNCVFLD
              .||| || ||. ::|.|.|..:|||||| :.||||:|. |.|.:|.||.
              QNVHSAVARGRMIKCTVCGNRGATVGCNVRSCGEHYHYPCARSIDCAFLT

DKKVYCQRH  1918
              ||.:||. |
              DKSMYCPAH  1841
```

```
ALL-1  3696  EPPLNPHGSARAEVHLRKSAFDMFNFLASKHRQPPEYNPNDEEEEVQLK
              |  . |:..:||.|. . .:|.:|||.::||:||..|        :..::.|:
D.TRX  3550  ELEENAYDCARCEPYSNRSEYDMFSWLASRHRKQPIQVFVQPSDNEL...

SARRATSMDLPMPMRFRHLKKTSKEAVGVYRSPIHGRGLFCKRNIDAGEM
              :||:  :|||:|:  ||.| |. |: |||.|.:|||||.::|:||||
             VPRRGTGSNLPMAMKYRTLKETYKDYVGVFRSHIHGRGLYCTKDIEAGEM

VIEYAGNVIRSIQTDKREKYYDSKGIGCYMFRIDDSEVVDATMHGNAARF
             |||||| :||| ||||||:||| :||||||||:||..||||||||||||
             VIEYAGELIRSTLTDKRERYYDSRGIGCYMFKIDDNLVVDATMRGNAARF

INHSCEPNCYSRVINIDGQKHIVIFAMRKIYRGEELTYDYKFPIEDASNK
             |||.|||||||| ::||.::|  |:||||||||||||||||||||:  :|
             INHCCEPNCYSKVVDILGHKHIIIFAVRRIVQGEELTYDYKFPFED..EK

LPCNCGAKKCRKFLN  3910
              :||.||.: .|:|||||
             IPCSCGSKRCRKYLN  3759
```

CLONE 16

```
GTTGCAATGCAGCAGAAGCCCACGGCTTATGTCCGGCCCATGGATGGTCAAGATCAGGCC
 V  A  M  Q  Q  K  P  T  A  Y  V  R  P  M  D  G  Q  D  Q  A

CCTAGTGAATCCCCTGAACTGAAACCACTGCCGGAGGACTATCGACAGCAGACCTTTGAA
 P  S  E  S  P  E  L  K  P  L  P  E  D  Y  R  Q  Q  T  F  E

AAAACAGACTTGAAAGTGCCTGCCAAAGCCAAGCTCACCAAACTGAAGATGCCTTCTCAG
 K  T  D  L  K  V  P  A  K  A  K  L  T  K  L  K  M  P  S  Q
```

AF-4 ──→ ┼ ←── ALL-1 exon 9

```
TCAGTTGAGTTTGTGTATTGCCAAGTCTGTTGTGAGCCCTTCCACAAGTTTTGTTTAGAG
 S  V  E  F  V  Y  C  Q  V  C  C  E  P  F  H  K  F  C  L  E

GAGAACGAGCGCCCTCTGGAGGACCAGCTGGAAAATTGGTGTTGTCGTCGTTGCAAATTC
 E  N  E  R  P  L  E  D  Q  L  E  N  W  C  C  R  R  C  K  F

TGTCACGTTTGTGGAAGGCAACATCAGGCTACAAAG
 C  H  V  C  G  R  Q  H  Q  A  T  K
```

FIG. 10B

CLONE 25

```
GAAAAACCACCTCCGGTCAATAAGCAGGAGAATGCAGGCACTTTGAACATCTTCAGCACT
 E  K  P  P  P  V  N  K  Q  E  N  A  G  T  L  N  I  F  S  T

CTCTCCAATGGCAATAGTTCTAAGCAAAAAATTCCAGCAGATGGAGTCCACAGGATCAGA
 L  S  N  G  N  S  S  K  Q  K  I  P  A  D  G  V  H  R  I  R
```

ALL-1 exon 7 ──→ ┼ ←── AF-4

```
GTGGACTTTAAGACCTACTCCAATGAAGTCCATTGTGTTGAAGAGATTCTGAAGGAAATG
 V  D  F  K  T  Y  S  N  E  V  H  C  V  E  E  I  L  K  E  M

ACCCATTCATGGCCGCCTCCTTTGACAGCAATACATACGCCTAGTACAGCTGAGCCATCC
 T  H  S  W  P  P  P  L  T  A  I  H  T  P  S  T  A  E  P  S

AAGTTTCCTTTCCCTACAAAGGACTCTCAGCATGTCAGTTCTGTAACCCAAAACCAAAAA
 K  F  P  F  P  T  K  D  S  Q  H  V  S  S  V  T  Q  N  Q  K

CAATATGATACATCTTCAAAAACTCACTCAAATTCTCAGCAAGGAACGTCATCCATGCTC
 Q  Y  D  T  S  S  K  T  H  S  N  S  Q  Q  G  T  S  S  M  L

GAAGACGACCTTCAGCTCAGTGACAGTGAGGACAGTGACAGT
 E  D  D  L  Q  L  S  D  S  E  D  S  D  S
```

FIG. 10C

CHIMERIC NUCLEIC ACIDS AND PROTEINS RESULTING FROM ALL-1 REGION CHROMOSOME ABNORMALITIES

CROSS REFERENCE TO RELATED PATENT APPLICATIONS

This application is a File Wrapper Continuation of U.S. Ser. No. 08/062,443, filed as PCT/US92/10930 Dec. 9, 1992 now abandoned, which is a continuation-in-part of Ser. No. 07/971,094 filed Oct. 30, 1992, now abandoned, which is a continuation-in-part of Ser. No. 07/888,839, filed May 27, 1992, now abandoned, which is a continuation-in-part of Ser. No. 07/805,093, filed Dec. 11, 1991, now abandoned, each of which is incorporated herein by reference.

ACKNOWLEDGEMENT OF GOVERNMENT SUPPORT

Research for this invention was supported in part by an OIG grant CA39860 from the National Cancer Institute. The United States Government may have certain rights in this invention.

FIELD OF THE INVENTION

The present invention relates to the field of methods for diagnosis and treatment of human leukemias wherein hematopoietic cells of patients have translocations in a small region of chromosome 11 designated as ALL-1. Diagnostics and therapeutics based on nucleic acid and amino acid sequences provided.

BACKGROUND OF THE INVENTION

Specific reciprocal chromosome translocations are very frequently found in human lymphomas and leukemias. These chromosomal abnormalities alter normal cellular genes leading to their deregulation. Chromosome translocations have been shown to play an important role in the pathogenesis of human leukemias and lymphomas by either activating cellular protooncogenes or by leading to the formation of chimeric genes capable of transforming hematopoietic cells. Erikson et al., *Proc. Natl. Acad. Sci. USA* 1983, 80,519–523; Tsujimoto et al., *Science* 1984, 226, 1097–1099; Tsujimoto et al., *Science* 1984, 224, 1403–1406; Shtivelman et al., *Nature* 1985, 315, 35–354; Mellentin et al., *Science* 1989, 246, 379–382.

Translocations can lead to gene fusion resulting in a chimeric oncoprotein whose transforming activity is derived from both genes. The prototype of such events is the t(9;22) of chronic myelogenous leukemia (CML) which leads to a BCR-ABL fusion mRNA and protein (Shtivelman, supra). Translocations t(1;19), t(15;17), and t(6;9) are other examples of gene fusions, involving in the first two cases transcription factors (Nourse et al., *Cell* 1990, 60, 535–545; Kamps et al., *Cell* 1990, 60, 547–555; Kakizuka et al., *Cell* 1991, 66, 663–674; de The et al., *Cell* 1991, 66, 675–684; von Lindern et al., *Mol. Cell. Biol.* 1990, 10, 4016–4026).

The alternative molecular consequence of translocations is deregulation of protooncogenes by their juxtapositioning to an enhancer or promoter which is active in the type of cell from which the tumor arises. The immunoglobulin (Ig) and T cell receptor (TCR) enhancers participate in at least 15 different translocations associated with Burkitt lymphoma, chronic lymphocytic leukemia, follicular lymphoma, mantle cell lymphoma, and acute T or B cell leukemia. (Croce, C. M., *Cell* 1987, 49, 155–156; Rabbitts, T. H., *Cell* 1991, 67, 641–644; Solomon et al., *Science* 1991, 254, 1153–1160).

Chromosomal region 11q23 has been shown to be involved in different chromosomal translocations in human acute leukemias of different hematopoietic lineages. 11q23 chromosome abnormalities have been reported in acute lymphoblastic leukemia and in acute nonlymphoblastic leukemia (ANLL), most commonly of the M4 and M5A subtypes. Heim and Mitelman, *Cancer Cytogenetics*, Alan R. Liss, New York 1987. Chromosome 11 band q23 is frequently rearranged in acute lymphocytic (ALL), in acute myelomonocytic (AMMOL), acute monocytic (AMOL) and acute myeloid (AML) leukemias, mostly in reciprocal exchanges with various translocation partners. The t(4;11) (q21;q23), t(11;19) (q23;p13), and t(1;11)(p32;q23) are found in 10%, 2% and <1% of ALL, respectively. Reciprocal translocation between 11q23 and chromosomal regions 9p22, 6q27, 1p21, 2p21, 10p11, 17q25 and 19p13 are found in 5–6% of AML. Heim and Mitelman, supra. In addition, interstitial deletions in 11q23 have been detected both in ALL and AML.

The same segment on chromosome 11 is apparently involved in the t(11;19)(q23;p13) and t(1;11)(p32;q23) translocations in ALL as well as in translocations with the chromosomal regions 9p21, 2p21 6q27, 17q25 and 19p13 associated with 5–6% of acute myelogenous leukemias (AML). Heim and Mitelman, *Cancer Cytogenetics*, Alan R. Liss, New York 1987. Reciprocal translocations between chromosome region 11q23 and chromosomal regions 9p22, 6q27, 1p21, 2p21, 10p11, 17p25 and 19p13 are found in 5–6% of ANLL.

In clinical terms, rearrangements of 11q23, in particular the t(4;11) chromosome translocation, have some distinct features. The patients are often quite young; t(4;11) accounts for the vast majority of cytogenetically abnormal ALLs in infants. In the majority of patients, the leukemic cells show both B-cell and myeloid marker (Stong et al. Blood 1986, 67, 391–397) and the disease is consequently considered "biphenotypic."

Among children, most patients with the t(4;11) abnormality are less than one year of age and have a poor prognosis. The leukemic cells have a CD10–/CD19+ early B cell precursor phenotype and most of them express a myeloid associated antigen (CD15); Pui et al., *Blood* 1991, 77,440–447. Myelomonocytic and biphenotypic leukemias carrying the t(4;11) aberration have also been reported; Nagasaka et al., *Blood* 983, 61, 1174–1181.

There remains an unmet need for identification of the breakpoint cluster region and the genes involved in chromosome 11 aberrations associated with acute leukemias in order to provide diagnostics and therapeutics for these diseases.

SUMMARY OF THE INVENTION

The cDNA sequence of the ALL-1 gene on chromosome 11 is provided. A partial sequence of the AF-4 gene is also provided in the context of the sequences of two reciprocal endproducts of a translocation. Amino acid sequences corresponding to the cDNA sequences of the entire ALL-1 gene and the partial sequence of the AF-4 gene, and sequences relating to chimeric genes formed by chromosome translocations with chromosome 4, 9 and 19, respectively, are provided. Probes are provided for detecting chromosome abnormalities involving the ALL-1 gene on chromosome 11, including probes for detecting chimeric genes generated by translocations. Monoclonal antibodies for diagnosis and treatment and antisense oligonucleotides for treatment of acute leukemias are also described.

DESCRIPTION OF THE DRAWINGS

Figure 8D:
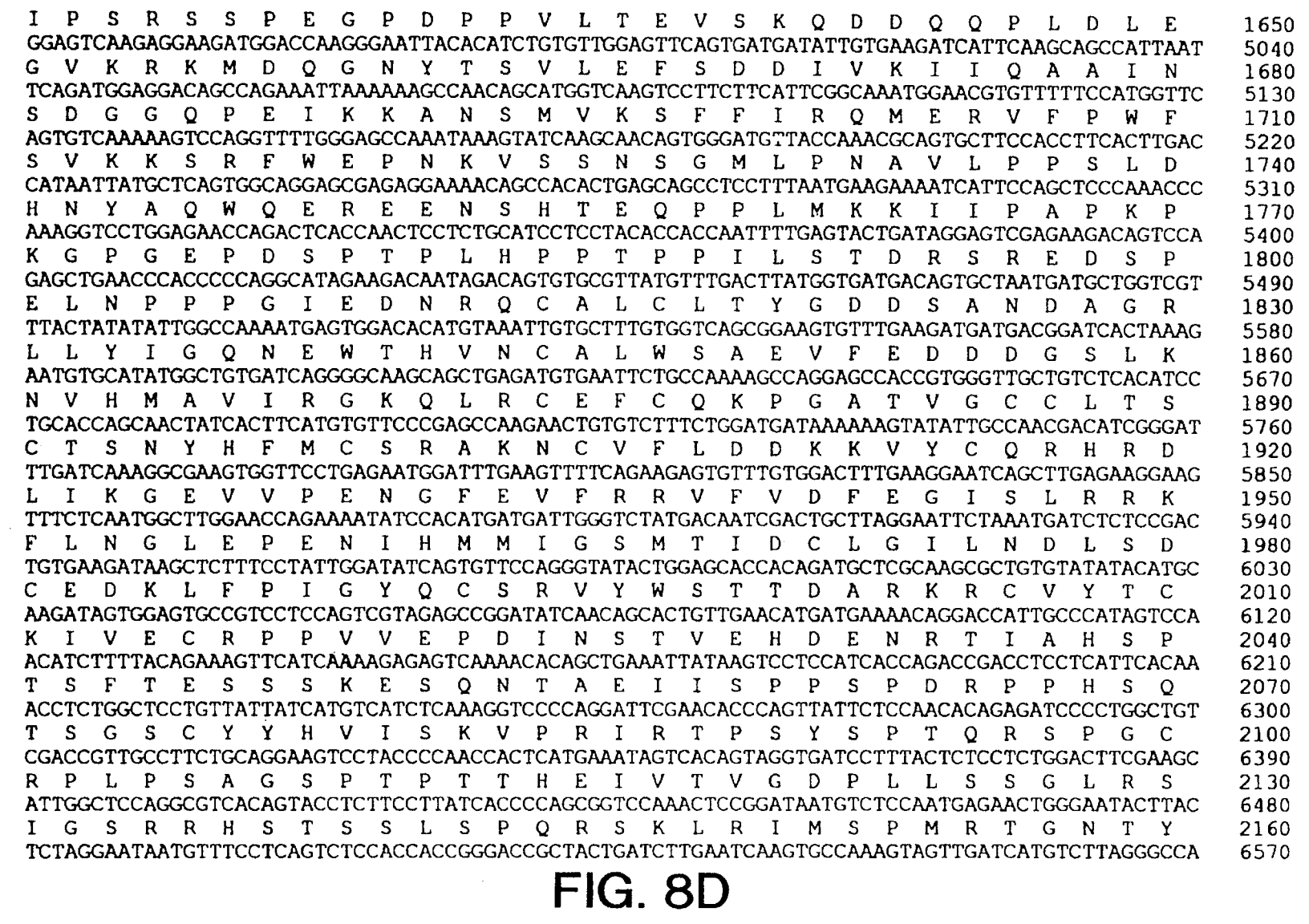
Figure 8E:
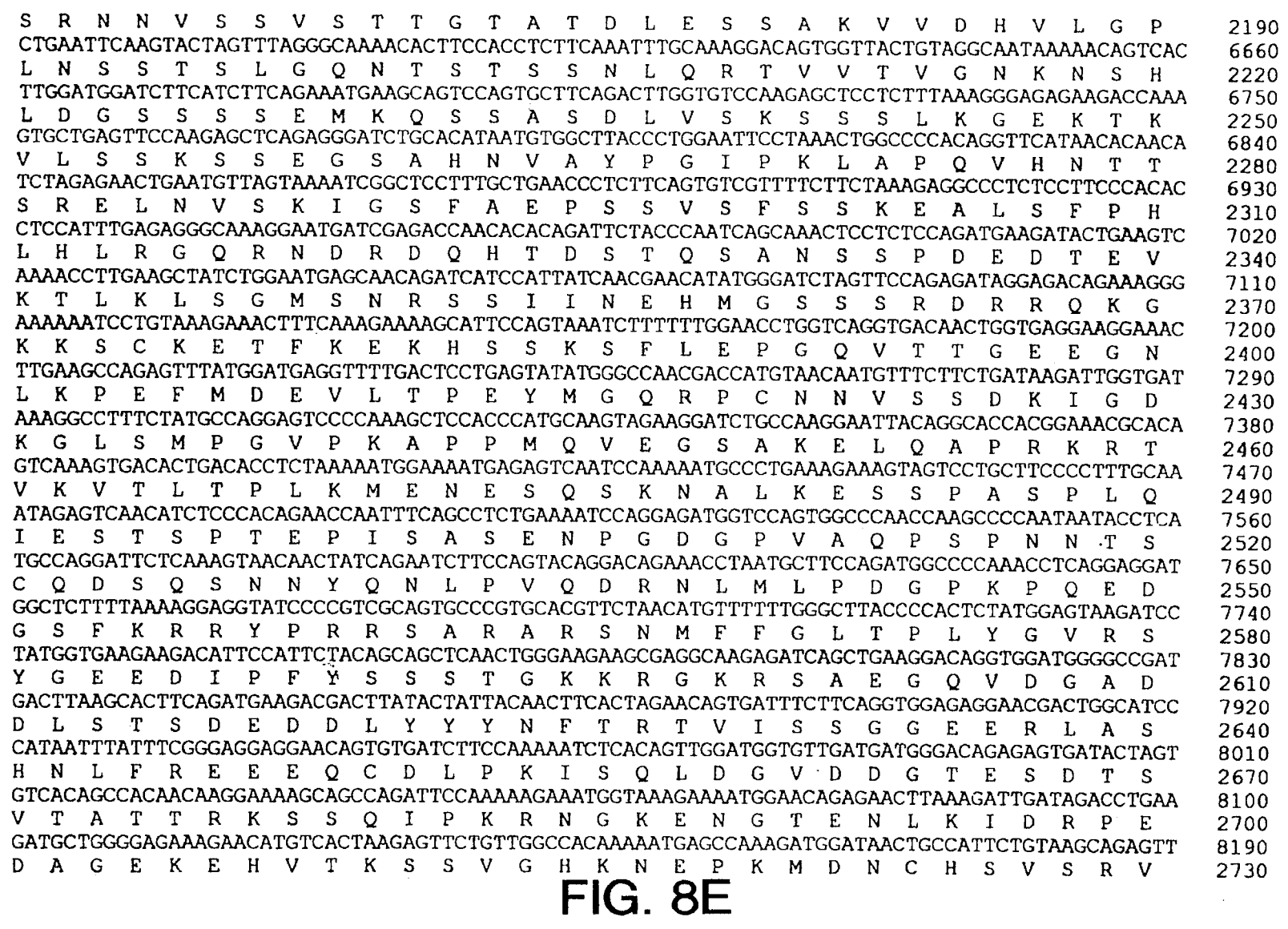
Figure 8F:
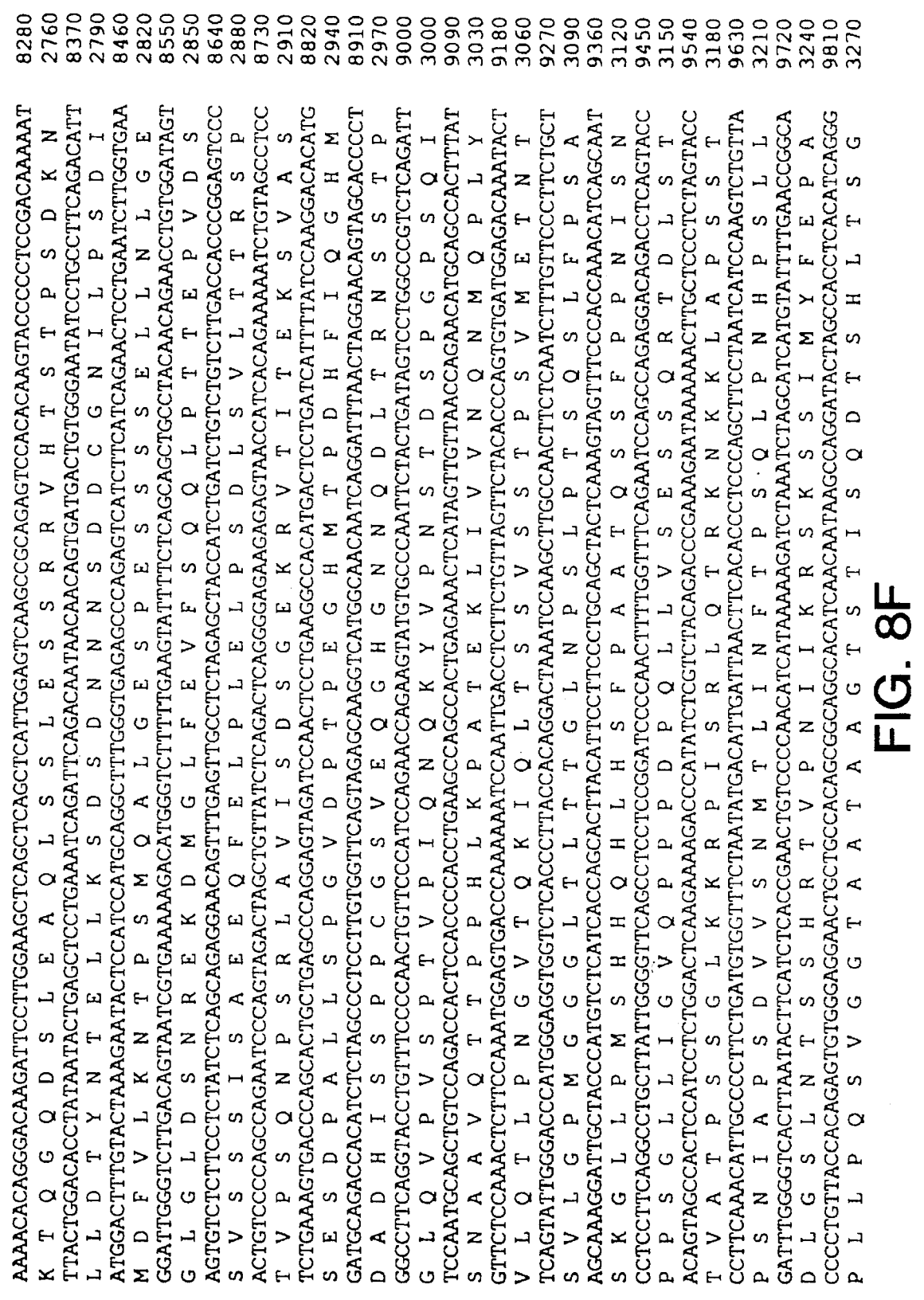
Figure 8G:
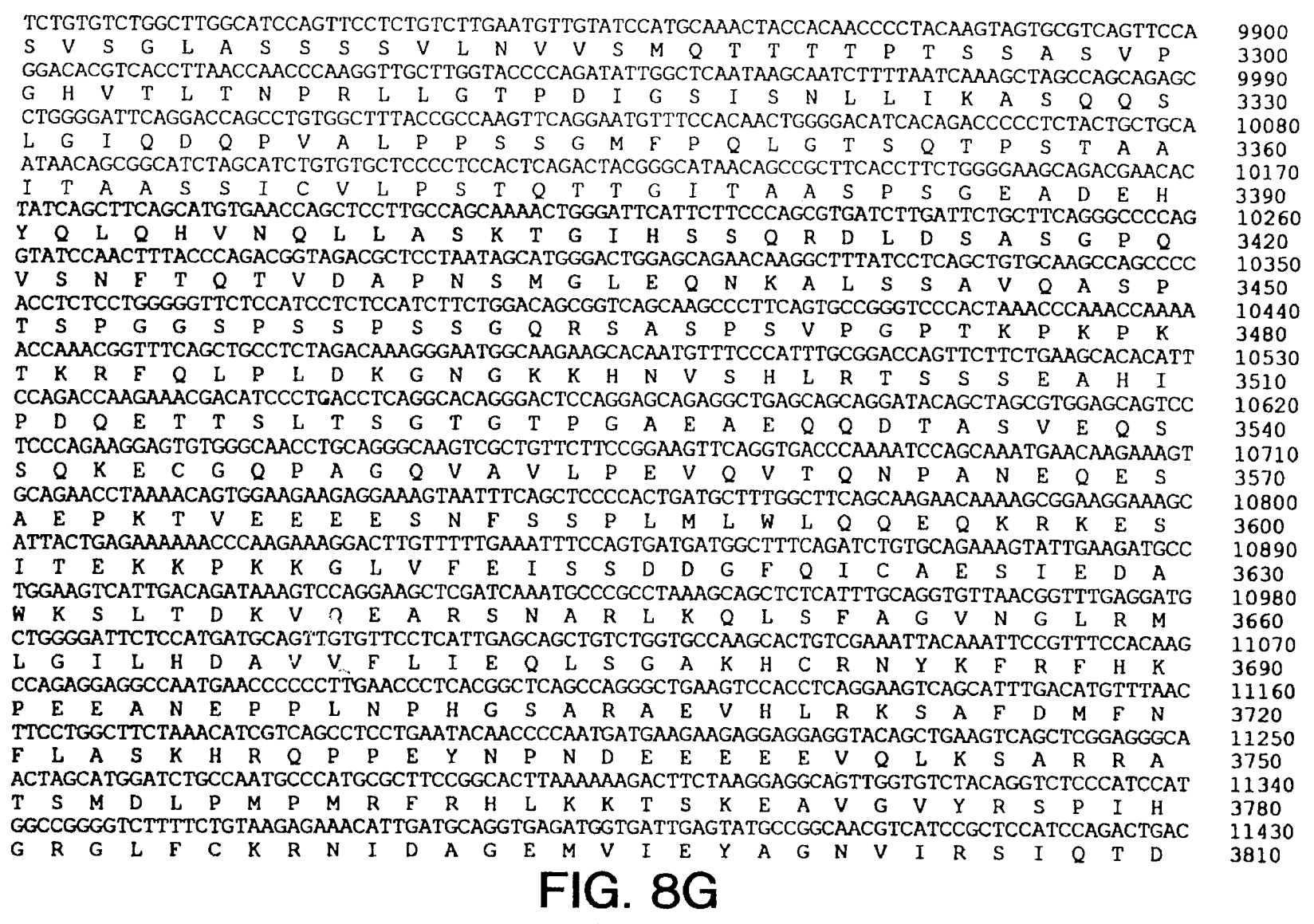
Figure 8H:
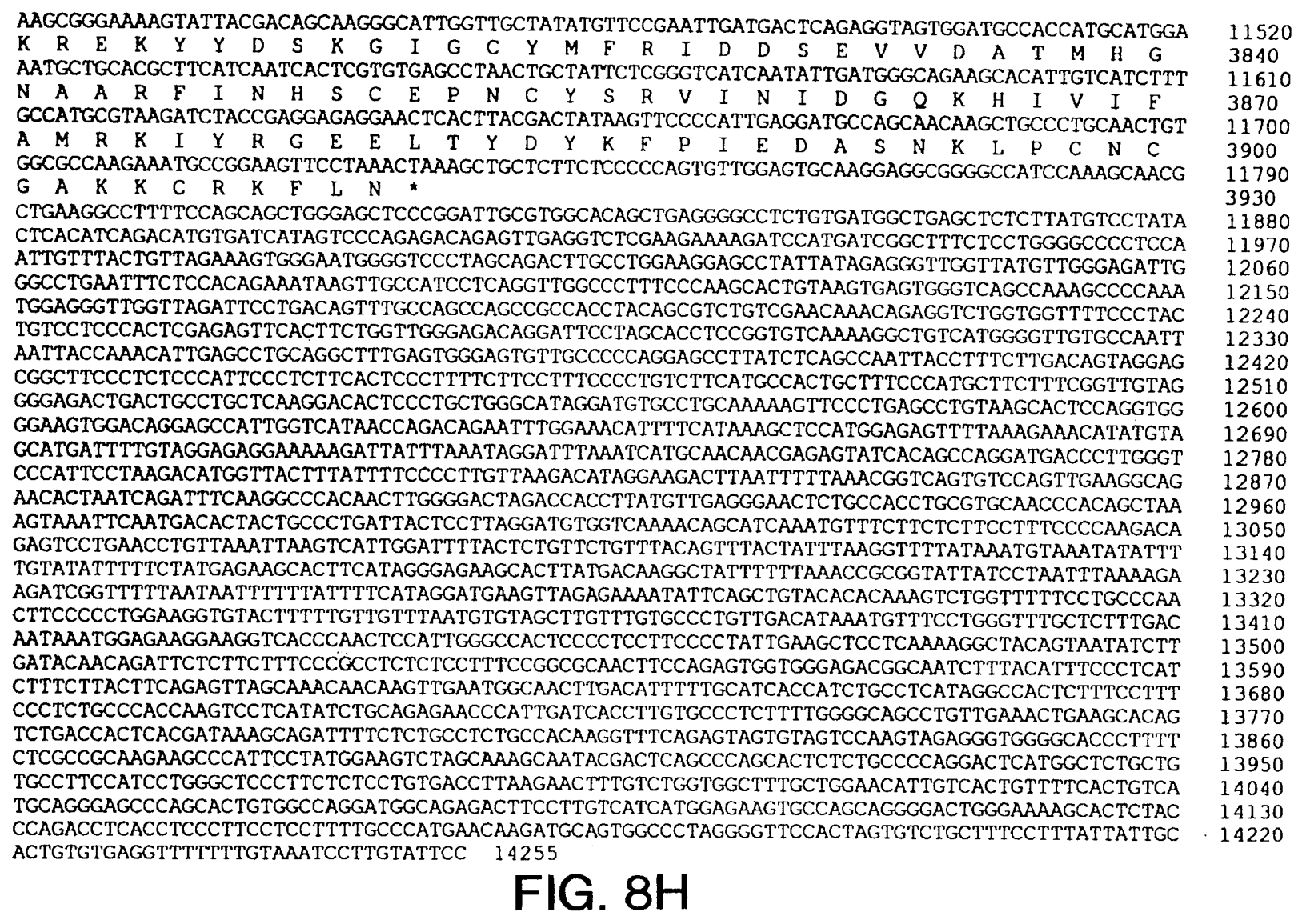

FIG. 8A–8H shows nucleotide sequence and predicted amino acid sequence of ALL-1 cDNA.

FIG. 9A–9D depicts homology between ALL-1 and Drosophila trithorax (D. Trx) proteins (top and center), and the structure of ALL-1 zinc finger-like domains (bottom). Bars indicate identical residues. One dot and two dots indicate first and second degree conservative differences, respectively.

FIG. 10A–10C shows exon-intron structure of ALL-1 breakpoint cluster region (A) and partial sequence of the two reciprocal ALL-1/AF-4 fused transcripts (B, C). In (A), exons containing the zinc finger-like domains (8–12) are represented by cross-hatched boxes. Among the five t(4;11) breakpoints shown (arrowheads in A), included are those of the MV4;11 (MV), RS4;11 (RS), and B1 (B1) cell lines. C.L. and I.V. represent leukemic cells with t(4;11) from two patients. B, R, G, X, H correspond to sites for the enzymes BamHI, EcoRI, BglII, XbaI, and HindIII, respectively. In sequences within (A), small and large letters represent introns and exons, respectively. Cytosine in position 4141 of ALL-1 sequence (FIG. 2) is replaced by thymidine in clone 25, resulting in alteration of Leucine into Phenylalanine (C).

DETAILED DESCRIPTION OF THE INVENTION

Figure 1:
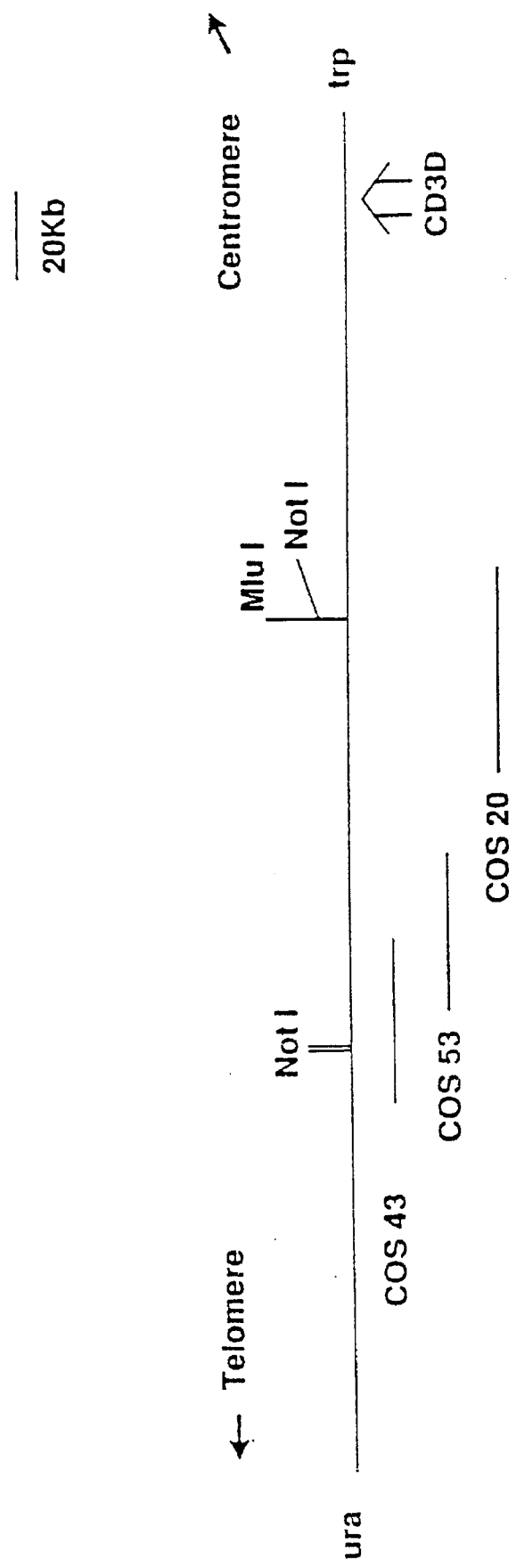
FIG. 1 is a drawing depicting a physical map of YAC B22B, which has been described in Rowley et al., *Proc. Natl. Acad. Sci. USA* 1990, 87, 9358–9362. ura and trp correspond to the termini of the vector. A 40 kb segment located towards the ura end and lacking NotI and MluI sites is not included in the map. Pulse field analysis indicates two or three SfiI sites located to the left of cosmid 43.

The ALL-1 gene located at human chromosome 11 band q23 is rearranged in acute leukemias with interstitial deletions or reciprocal translocations between this region and chromosomes 1, 2, 4, 6, 9, 10, 15, 17 or 19. The gene spans approximately 100 kb of DNA and contains at least 21 exons. It encodes a protein of approximately 4,000 amino acids containing three regions with homology to sequences within the Drosophila trithorax gene including cysteine-rich regions which can be folded into six zinc finger-like domains. The breakpoint cluster region within ALL-1 spans approximately 8 kb and encompasses several small exons (including exons 6–12), most of which begin in the same phase of the open reading frame.

The t(4;11) chromosome translocation results in two reciprocal fusion products coding for chimeric proteins derived from ALL-1 and from a gene on chromosome 4. This gene on chromosome 4 is termed "AF-4" while the chimeric gene resulting from the t(4;11) translocation is termed "ALL-1/AF-4." It is believed that the 11q23 abnormality of translocation with 4q21 gives rise to one or two specific oncogenic fusion proteins.

The t(9;11) chromosome translocation results in two reciprocal fusion products coding for chimeric proteins derived from ALL-1 and from a gene on chromosome 9. This gene on chromosome 9 is termed "AF-9" while the chimeric gene resulting from the t(9;11) translocation is termed "ALL-1/AF-9." It is believed that the 11q23 abnormality of translocation with 9p22 gives rise to one or two specific oncogenic fusion proteins.

The t(11;19) chromosome translocation results in two reciprocal fusion products coding for chimeric proteins derived from ALL-1 and from a gene on chromosome 19. This gene on chromosome 19 is termed "ENL" while the chimeric gene resulting from the t(11;19) translocation is termed "ALL-1/ENL."It is believed that the t(11;19) translocation gives rise to one or two specific oncogenic fusion proteins.

A DNA fragment which detects DNA rearrangements by Southern analysis in the majority of patients with t(4;11), t(9;11) and t(11;19) chromosomal aberrations has been cloned from chromosome 11. This locus is referred to as ALL-1 for acute lymphocytic leukemia, although the same locus is also involved in acute myelomonocytic, myelogenous and monocytic leukemias carrying translocations involving 11q23.

DNAs and RNAs were extracted from cell lines and primary tumors by conventional methods. Southern and Northern analysis were performed as described in Shtivelman et al., Nature 1985, 315, 550–554). To obtain unique (repeat free) probes, cosmids were digested with a variety of restriction enzymes, and analyzed by Southern blotting for fragments which do not react with radiolabeled total human DNA. End fragments of cosmids were identified by hybridizing cosmids' digests to radiolabeled oligonucleotides corresponding to the recognition sequences for T7 and T3 RNA polymerases. If the end fragments contained human repeats, they were isolated, digested with frequent cutters and analyzed as described above. The 0.7 kb DdeI probe was thus obtained from a terminal 3.5 kb EcoRV fragment of cosmid 53. A portion of the Washington University's human DNA-containing YAC library (Green et al., Proc. Natl. Acad. Sci. USA 1990, 87, 9358–9362) was screened for CD3 DNA sequences (van Den Elsen et al., Proc. Natl. Acad. Sci. USA 1986, 83, 2944–2948) by a polymerase chain reaction (PCR) -based screening protocol (Green et al., supra). The YAC clone obtained appeared to be identical to the one described by Rowley et al., Proc. Natl. Acad. Sci. USA 1990, 87, 9358–9362, and spanned the translocation breakpoint in a t(4;11) cell line as evidenced by hybridization analysis. By pulse field electrophoretic analysis, the size of the insert was estimated as 350 kb. A 310 kb version of the insert, generated by spontaneous deletion at the left (telomeric) side, predominated in the population of DNA molecules and was mapped (FIG. 1).

To obtain specific segments of the insert, the YAC was purified by pulse field electrophoresis and shotgun cloned into the Supercos (Stratagene) cosmid vector. For this purpose the insert was partially digested by a combined application of dam methylase and the restriction endonuclease MboI, Hoheisel et al., Nuc. Acid Res. 1989, 17, 9571–9582. Both enzymes act on the sequence GATC, but MboI is unable to cut the methylated form. More than a hundred cosmid clones, detected with a probe for human repetitive sequences, were obtained. The cosmids were mapped by screening for those with sites for NotI and MluI enzymes, and for those hybridizing to CD3, trp and ura probes. Some cosmids were established using unique (repeat free) probes obtained from termini of cosmids. The positions of 3 cosmids mapped to the center of the YAC are shown in FIG. 1. Unique probes from these cosmids as well as from cosmids mapped to other regions of the YAC were used to screen Southern blots of DNAs from tumors exhibiting translocations.

Figure 2:
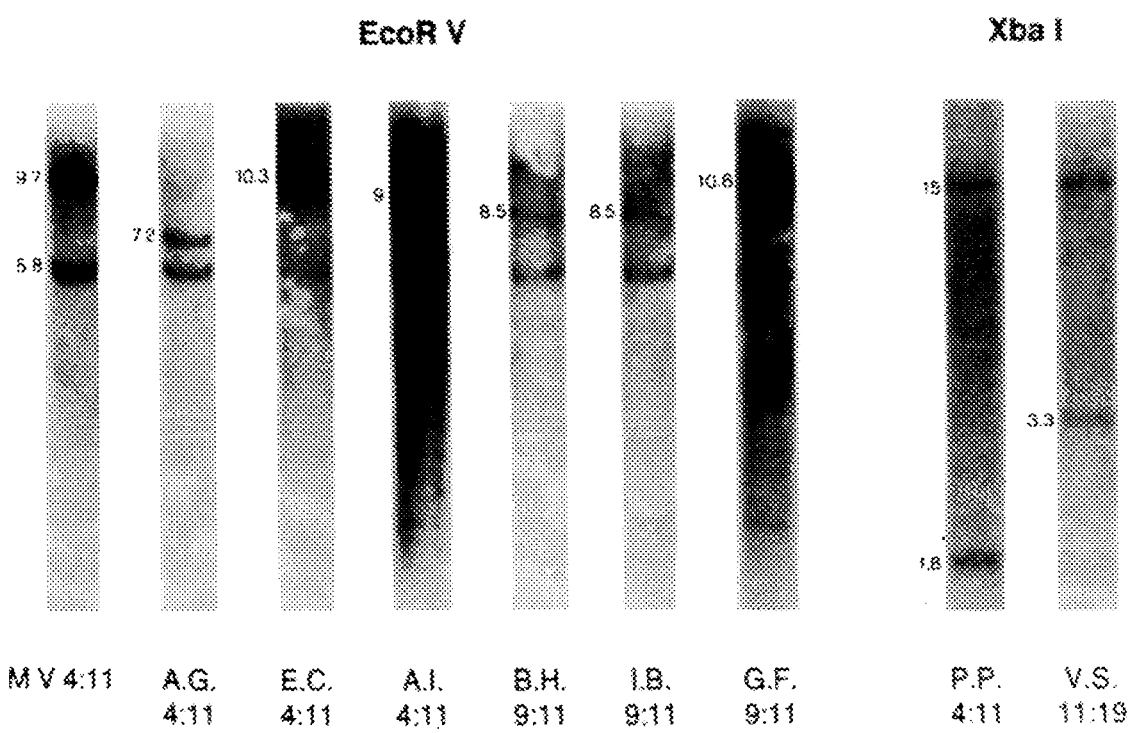
FIG. 2 is a photograph showing the results of Southern blot analysis of tumor DNAs. Blots were hybridized to the radiolabeled 0.7 kb DdeI fragment derived from the terminus of cosmid 53. Aliquots of 10 μg were analyzed.
Figure 3:
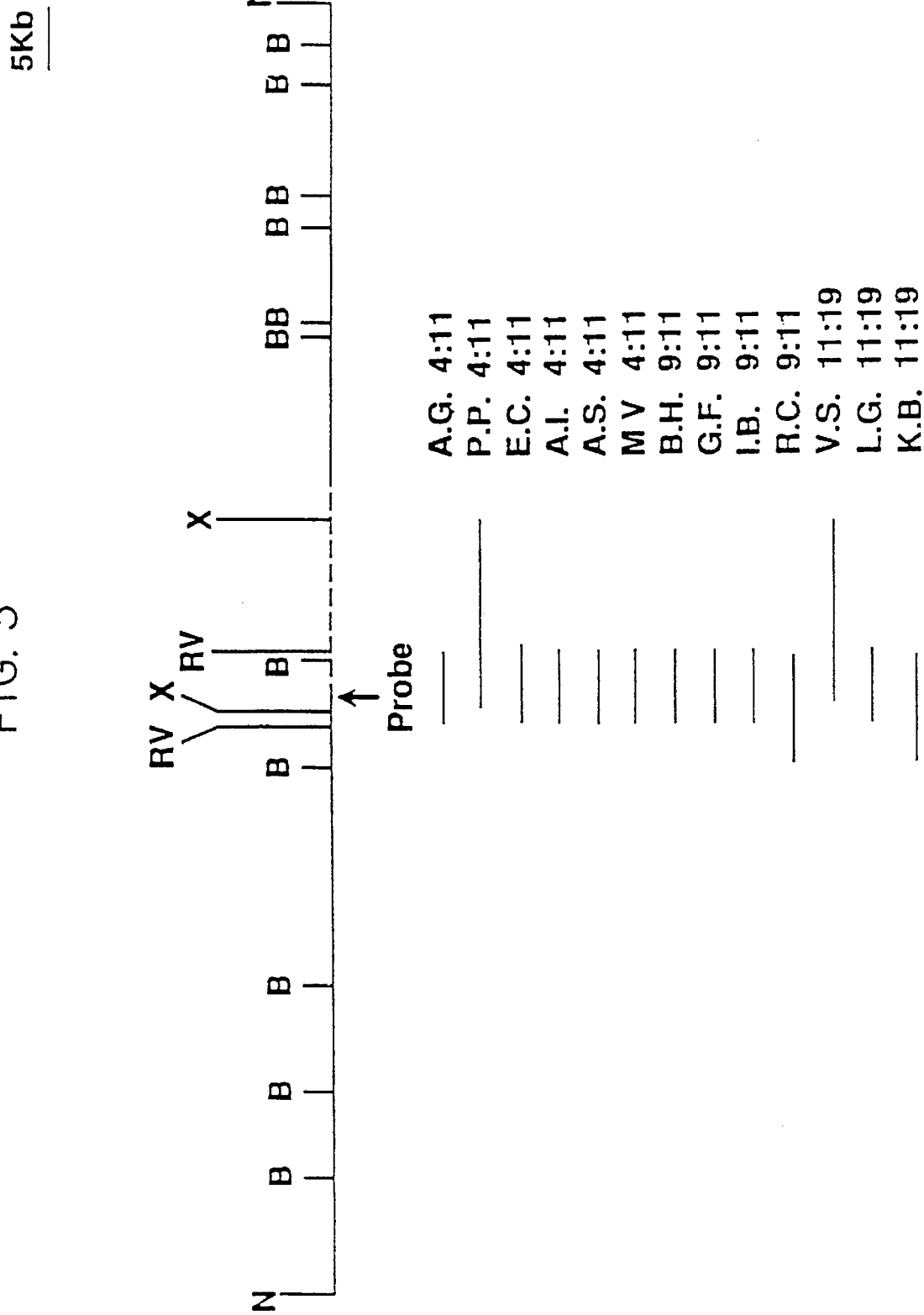
FIG. 3 is a drawing showing mapping of tumor breakpoints. The internal NotI fragment of YAC is shown in the same orientation as in FIG. 1. The dotted line represents a region not cloned in the cosmids. Restriction sites within this region are deduced from the size of the relevant germline fragments detected in genomic Southern blots using the indicated probe. Additional EcoRV and XbaI sites are not shown. Some of the samples were not analyzed with BamHI. Lines below the map correspond to the smallest genomic fragments found rearranged. N=NotI; B=BamHI; RV=EcoRV; X=XbaI. The breakpoint cluster region is believed to span approximately the region encompassed by the two nearest BamHI sites flanking the arrow; more specifically, the breakpoint cluster region is believed to span exons 6–12 illustrated in FIG. 10.

A 0.7 kb DdeI fragment derived from the terminus of cosmid 53 detected rearranged fragments in tumor DNAs digested with EcoRV, XbaI, or BamHI. Examples of these analyses are shown in FIG. 2. The leukemic cells from patients A.G., E.C., A.L., B.H., I.B., G.F., P.P., and V.S. contained novel EcoRV or XbaI fragments of various sizes. This probe detected rearrangements in 6/7, 4/5, and 3/4 patients with the t(4;11), t(9;11) and t(11;19) translocations, respectively. Upon determination of the smallest genomic fragment in which rearrangement could be identified, (FIG. 3) it became apparent that most or all breakpoints clustered within a small DNA region of approximately 8 kb. In three other patients two rearranged fragments (as well as a germline species) were detected, probably due to the presence of the breakpoint in these patients within the 0.7 kb DdeI segment corresponding to the probe. Finally, normal fibroblast DNAs from 7 additional individuals were used for comparison to show the germline fragments after digestions with EcoRV, XbaI or BamHI.

Figure 4:
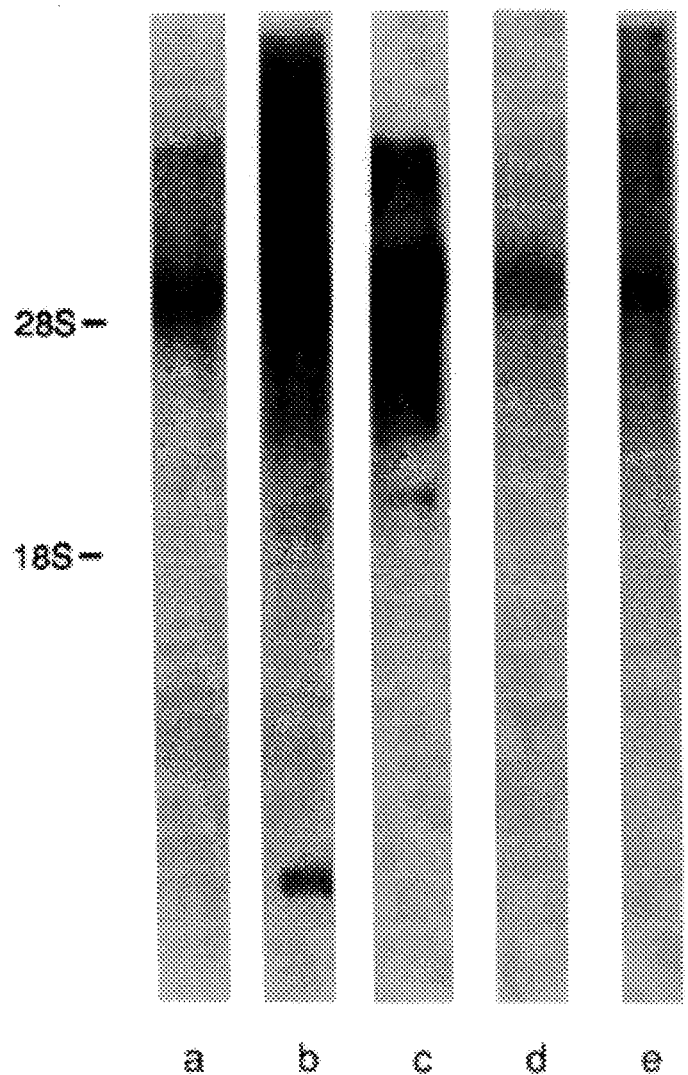
FIG. 4 is a photograph showing the results of Northern blot analysis of RNA from cell lines and a primary leukemia using pooled probes. 10–20 μg aliquots of total RNA were analyzed on a formaldehyde gel. Following hybridization, blots were washed in a solution containing 0.1% SSC and 0.1% SOS at 700. RNAs were obtained from: a) K562 cells; b) the glioblastoma T98G cell line; c) the SupB pre B ALL cell line; d) the MV4;11 cell line; and e) a patient with t(9;11).

As a first step toward identification of genes neighboring the breakpoint cluster region, pooled unique fragments from cosmid 20 were labeled, together with the terminal fragment of cosmid 53, and were used to probe RNAs from cell lines and patients with or without 11q23 translocations (FIG. 4). The pooled probe detected 5 kb and 10 kb RNA species in the K562, glioblastoma T986 and Sup B cell lines (lanes a, b, c). It also hybridized with a 5 kb RNA from patients with t(4;11), t(9;11), and t(11;19) (FIG. 4, lanes d, e,). In another patient with t(4;11) the probe detected the 10 kb RNA species alone.

It has been discovered that in leukemic cells of patients with the t(4;11), t(9;11) and t(11;19) translocations, the breakpoints on chromosome 11 cluster in a small region of approximately 8 kb. Other translocations in acute leukemias affecting 11q23 are believed to map to the same locus. This locus has been designated ALL-1 for acute lymphocytic leukemia, although the ALL-1 locus is also involved in translocations in acute myelomonocytic, monocytic and myelogenous leukemias. The tight clustering of breaks suggests that the gene involved is close to the breakpoints. The Northern analysis indicates that DNA sequences adjacent to the breakpoints are expressed. However, no new transcript was detected in the leukemic cells. Moreover, only one of the transcripts (usually the 5 kb species) found in cells without the translocation was detected in the patients.

Figure 5:
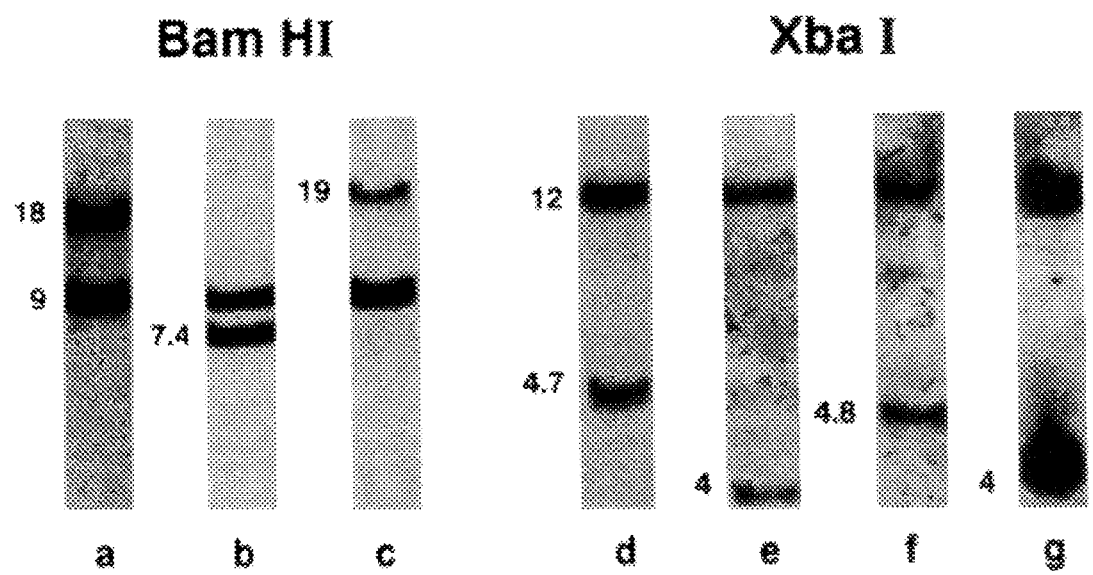
FIG. 5 is a photograph showing the results of Southern blot analysis of DNAs from primary tumors and cell lines with 11q23 abnormalities using a modified 0.5 kb DdeI probe. a) patient C. H. with t(6;11); b) the B1 cell line with t(4;11); c) the RS 4;11 cell line with t(4;11); d) patient J. B. with t(10;11); e) patient M. L. with t(1;11); f) patient S. O. with del(11)(q23); g) patient R. E. with del(11)(q23). Numbers indicate kilobases. The germline BamHI and XbaI fragments are of 9 and 12 kb, respectively.

The finding of tight clustering of the breakpoints on chromosome 11 in the three most common 11q23 abnormalities raised the possibility that the same region is rearranged in other chromosomal aberrations involving 11q23. To test this, tumor DNAs from the leukemic cells of patients with t(6;11) (q27;q23), t(1;11) (p34;q23), t(10;11) (p11–15;q23) and del (11)(q23) were digested with BamHI, XbaI, EcoRV and HindIII enzymes and subjected to Southern analysis using the modified 0.5 kb DdeI fragment as a probe. This probe was obtained from the 0.7 kb DdeI probe by digestion with AluI, which ultimately improved performance by removing a 0.24 kb internal fragment that had caused a higher background in Southern analyses. Following digestion with AluI, the internal fragment and the two end fragments were electrophoresed to isolate the two terminal fragments, which were then ligated to form a 0.5 kb fragment which was cloned into a plasmid vector. Results of Southern blotting are shown in FIG. 5. Rearranged fragments were found in the DNAs of patients with t(6;11), t(1;11) and t(10;11)(lanes a, d, e, respectively) and in two patients (lanes f, g) out of five with interstitial deletion in 11q23 (the 3 negative patients had del 11(q21;q23)). The patients with t(6;11) and t(10;11), as well as one of those with del(11)(q23) showing rearrangement had AML; the rest of the patients tested had ALL.

Figure 6:
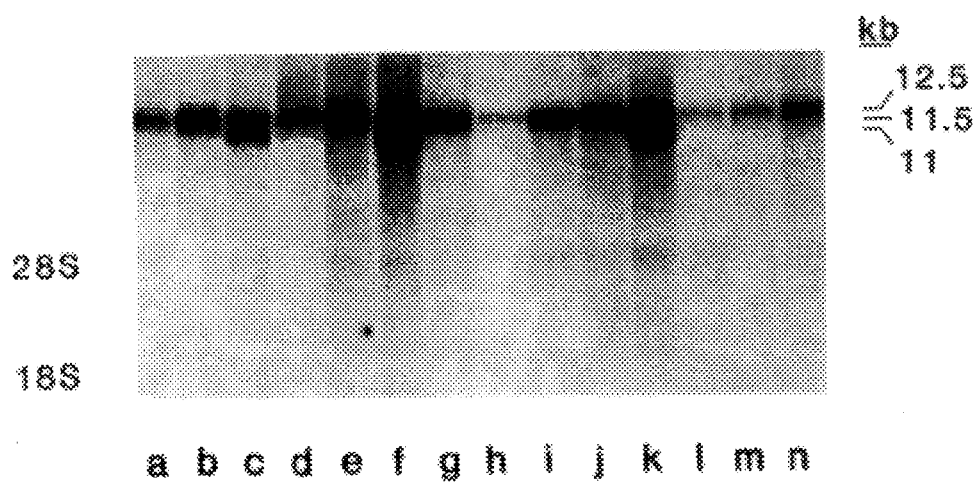
FIG. 6 is a photograph showing the results of Northern blot analysis of RNAs from cell lines using a 1.5 kb EcoRI probe generated from cosmid 20. Lanes included SK DHL (a); KCL22 (b); MV 4;11 (c); T98G (d); All-1 (e); B1 (f); K562 (g); Jurkat (h); GM607 (i); 697 (j); RS4;11 (k); GM1500 (l); LNCaPFGC (m); PC3 (n). 28S and 18S indicate migration of ribosomal RNA.

To further analyze transcription of the genomic DNA adjacent to the breakpoint cluster region, segments of cosmid 20 found fully or partially free of repetitive sequences were examined as probes to polyadenylated RNAs obtained from a variety of hematopoietic and non-hematopoietic cell lines. Three ALL cell lines, MV 4;11, RS 4;11 and B1 containing the t(4;11) chromosome translocation were included in the analysis. These three cell lines had rearrangements at the breakpoint cluster region, as shown in FIG. 5, lanes b and c. A 1.5 kb EcoRI DNA segment generated from cosmid 20 was used as a probe and identified a 12.5 kb RNA in all cell lines (FIG. 6). A minor species of 11.5 kb was detected in most of the samples without involvement of 11q23, but it was not possible to determine if this RNA was present in the cells with the t(4;11) translocation. A transcript of 11 kb was detected in the three cell lines with the t(4;11) chromosome translocation (FIG. 6; lanes c, f, k). The width of this band on the autoradiogram suggests that it corresponds to two comigrating RNA species. The 11 kb RNA was not detected in any of the cell lines lacking 11q23 aberrations (FIG. 6).

These results show that the same breakpoint cluster region is rearranged in at least seven different 11q23 abnormalities, including six types of translocations, as well as interstitial deletions. Three samples with 11(q21;q23) deletions, one sample with t(11;15)(q23;q22), and one sample with t(11;X) (q23;q26) did not show rearrangements within the locus. In addition, in 1 of 12, 1 of 9, and 2 of 9 patients with t(4;11), t(9;11), and t(11;19) chromosome translocations respectively, rearrangements were not detected using the DdeI probe. Finally, the breakpoint in the RC-K8 cell line containing the t(11;14)(q23;q32) is apparently telomeric to the locus discussed here. In all of these cases, other unidentified loci on chromosome 11 could be involved. Alternatively, the ALL-1 locus might also be affected in these patients, but this may occur at a different site.

Using a new probe, three polyadenylated transcripts were identified. Two of them, a 12.5 and an 11.5 kb species, are expressed as detected by Northern analysis in most or all cell lines, but the third, an 11 kb RNA, was detected solely in cell lines with the t(4;11) abnormality. RNA species of similar size have recently been reported by others. For example, Ziemin-van der Poel et al., Proc. Natl. Acad. Sci. USA 1991, 88, 10735–10739. However, while the instant probe, which is located centromeric to the breakpoints, detects all three RNAs; Ziemin-van der Poel et al. reported that their probe (#1), which is derived from the same general location, detects predominantly the 12.5 kb species. While the instant probe detects 11 kb transcript solely in leukemic cells with the t(4;11) chromosome translocation, the Ziemin-van der Poel et al. study identifies an 11 kb mRNA in the RS4;11 cell line, as well in small amounts in all cells tested. The results show, however, a clear qualitative alteration in expression of a region adjacent to the breakpoint cluster region on chromosome 11 in cells with the t(4;11) chromosome translocation.

Using either somatic cell hybrids (Savage et al., Cytogenet. Cell Genet. 1988, 49, 289–292; Wei et al., Cancer Genet. Cytogenet. 1990, 46, 1–8; Yunis et al., Genomics 1989, 5, 84–90), or the fluorescent in situ hybridization (FISH) technique (Rowley et al., Proc. Natl. Acad. Sci. USA 1990, 87, 9358–9362), it was possible to position the breakpoints on chromosome 11 to a region between the CD3 and PBGD genes. Rowley et al., supra, used a CD3-gamma probe to clone a 350 kb human DNA fragment from a yeast artificial chromosome (YAC) library. This YAC spanned the t(4;11), t(9;11), t(11;19), and t(6;11) breakpoints as indicated by FISH analysis. Using probes derived from both sides of the breakpoint cluster region, Rowley et al. identified a 12.5 kb RNA in cells with or without 11q23 abnormalities. Further, a probe located telomeric to the cluster region detected two additional transcripts of 11.5 and 11 kb in the RS 4;11 cell line, as well as in all hematopoietic and nonhematopoietic cells tested (Ziemin-van der Poel et al., Proc. Natl. Acad. Sci. USA 1991, 88, 10735–10739).

From a YAC clone similar to the one used by Rowley et al., a DNA segment was obtained which detected rearrangements in leukemic cells from patients with the t(1;11), t(4;11), t(6;11), t(9;11), t(10;11), t(11;19) or del (11q23) chromosome abnormalities on Southern blots (Cimino et al., Cancer Research 1991, 51, 6712–6714; Cimino et al., Cancer Research 1992, 52, 3811–3813). The breakpoints clustered within a small region of approximately 8 kb termed the ALL-1 locus. Translocation junction fragments were cloned from leukemic cells with t(4;11) and showed clustering of the breakpoints in an area of 7–8 kb on chromosome 4. Sequencing analysis indicated heptamer and nonamer-like sequences, associated with rearrangements of immunoglobulin and T cell receptor genes, near the breakpoints. These sequences suggested a direct involvement of the VDJ recombinase in the 11q23 translocations.

Transcription of the genomic DNA adjacent to the breakpoint cluster region was analyzed using segments of cloned DNAs as probes. Probes from both sides of the region identified a major transcript of 15–16 kb (previously estimated as 12.5 kb) (Cimino et al., Cancer Research 1991, 51, 6712–6714; Cimino et al., Cancer Research 1992, 52, 3811–3813) in cells with or without 11q23 abnormalities. The gene coding for these RNAs was termed ALL-1. Leukemic cells with the t(4;11) chromosome translocation contained, in addition to the normal species, shorter RNAs transcribed from the der (11) and der (4) chromosomes. These studies were extended to clone and sequence ALL-1 RNA, to further characterize the ALL-1 gene, and to identify chimeric transcripts produced in cells with the t(4;11) chromosome translocation.

Structure of the ALL-1 gene and cDNA

Utilizing a repeat-free genomic DNA segment located 10 kb centromeric to the breakpoint cluster region on chromosome 11 (Cimino et al., Cancer Research 1992, 52, 3811–3813), a human fibroblast cDNA library and a K562 cDNA library were screened (Chu et al., EMBO J. 1990, 9, 985–993; Shtivelman et al., Nature 1985, 315, 550–554).

Figure 7:
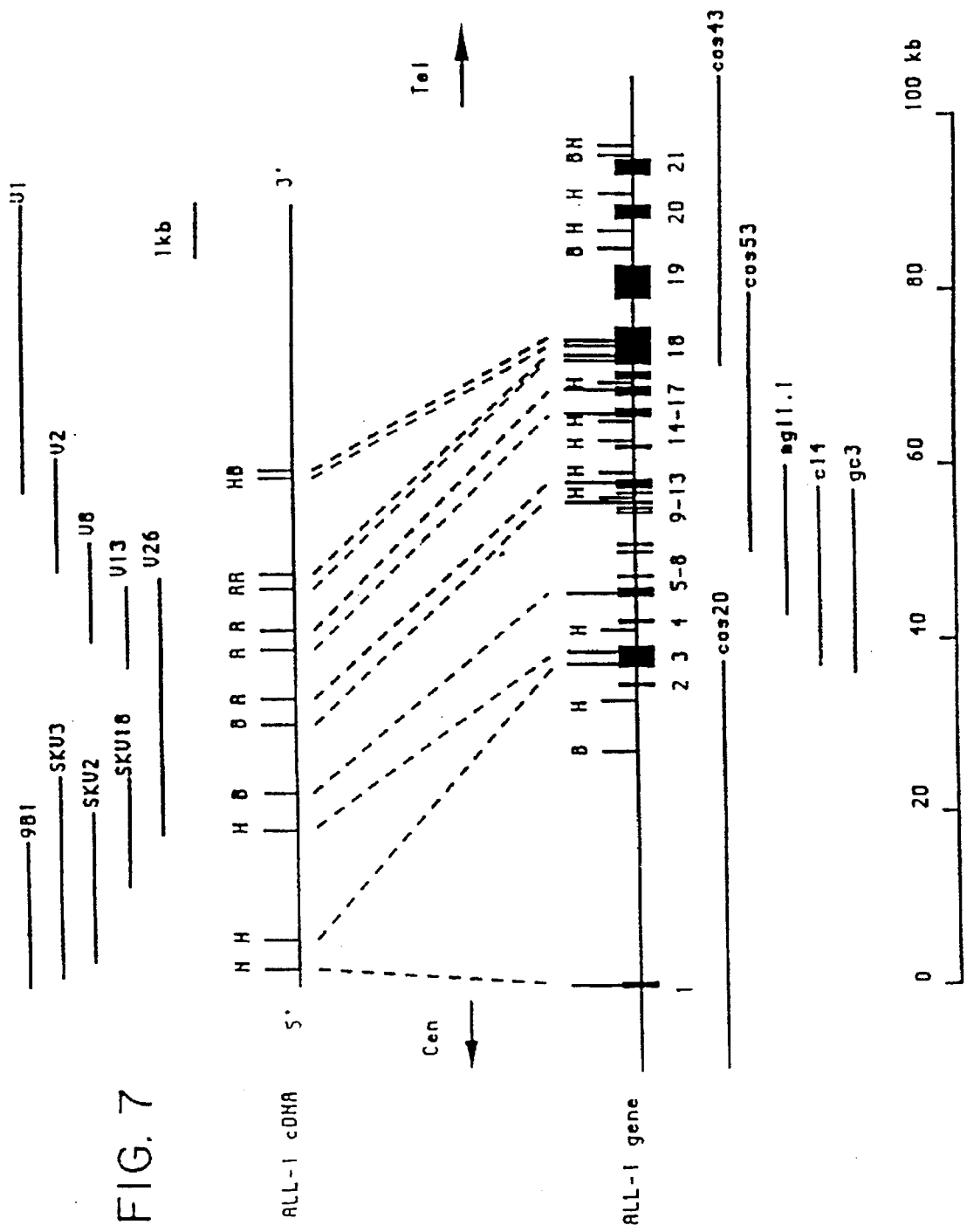
FIG. 7 shows physical maps of ALL-1 cDNA and gene. All NotI (N), HindIII (H), BamHI (B), and EcoRI (R) sites of the cDNA are shown; only some EcoRI sites are indicated within the gene and HindIII or BamHI sites within the 5' 25 kb of the first intron are not shown. Exons are depicted as rods or boxes extending above and below the line. Cen and Tel correspond to direction of the centromere and telomere, respectively. cDNA clones SKV2, SKV3, and SKV18 were obtained from K562 cDNA library. Clones V1–V26 were obtained from a normal fibroblast cDNA library. The 9B1 clone originated from a Burkitt lymphoma cDNA library.

Positive clones were used as probes for further screening. 5–10 µg aliquots of polyadenylated RNAs were electrophoresed on 1.1% agarose gels in formaldehyde, blotted onto nitrocellulose filters and analyzed by hybridization. (Gale, R. P. and Canaani, Proc. Natl. Acad. Sci. USA 1984, 81, 5648–5652). 20 µg aliquots of high molecular weight DNA were digested with BamHI and analyzed by the Southern technique. 3' and 5' ALL-1 probes were composed of phages V1 and SKV2 sequences, respectively (FIG. 7). Non ALL-1 probes were generated from clones 16 and 25 by PCR.

A series of overlapping clones spanning 14.7 kb (FIG. 7 top) was obtained. These cDNAs presumably originated from the major ALL-1 transcript. All cDNA sequences were found to hybridize to genomic DNA within the 95 kb internal Not I fragment of the YAC B22B (Cimino et al., *Cancer Research* 1991, 51, 6712–6714). This region was previously subcloned into cosmids 20, 43, and 53 and into phages gc3, c14, and mg 11.1 (FIG. 7). The cloning of cosmids 20, 43, and 53 from YAC B22B has been described (Cimino et al., *Cancer Research* 1991, 51, 6712–6714) and clones mg 11.1, c14, and gc3 were obtained from a genomic DNA library made in the EMBL-3 vector (Stratagene).

Restriction enzyme mapping of the cDNA and genomic clones and analysis of the hybridization pattern of cDNA fragments to genomic DNA indicated that the ALL-1 gene is composed of a minimum of 21 exons, some of them (6–12) very small (shorter than 150 bp). The first intron was found to be the largest, spanning approximately 35 kb of DNA.

The nucleotide sequence of ALL-1 cDNA was determined using an automatic sequencer (ABI). The sequence revealed a single long open reading frame predicting a protein of approximately 4,000 amino acids with molecular weight of approximately 400,000 Daltons (FIG. 8). To search for homologous nucleotide sequences and protein sequences the GenBank and SWISS data bases were screened by the FASTA program. Nucleotides 9353–9696 were found to be nearly identical to an anonymous sequence (EST00626) cloned from human fetal brain cDNA library (Adams et al., *Nature* 1992, 355, 632–634).

Figure 9D:
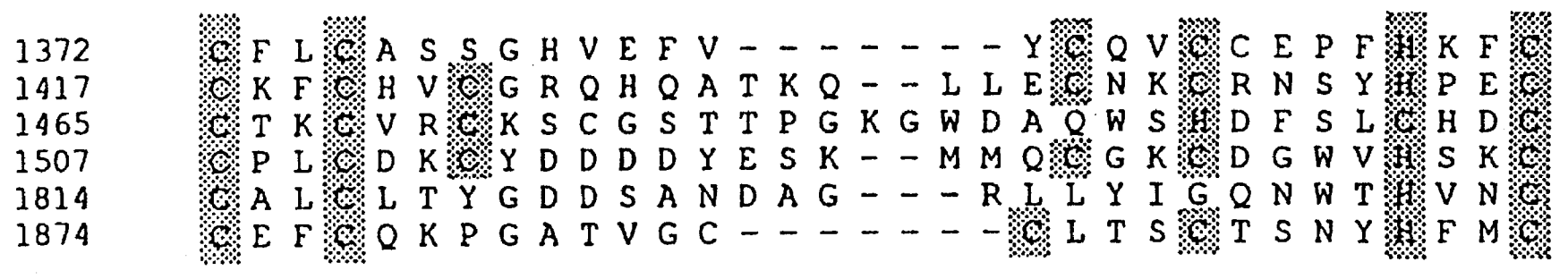

Three regions demonstrated homology to the trithorax gene of Drosophila (Mazo et al., *Proc. Natl. Acad. Sci.* USA 1990, 87, 2112–2116). Thus, predicted amino acids 1021–1221, 1462–1570, and 3348–3562 showed 64%, 66%, and 82% similarity, and 43%, 50%, and 61% identity, respectively, to the Drosophila gene (FIG. 9). The third region of homology constitutes the extreme C-terminus of the two proteins; both species end in an identical sequence. The first homology region is cysteine-rich and contains sequence motifs analogous to four zinc finger domains (3–6) within the trithorax gene (Mazo et al., supra). The second region of homology is also cysteine-rich and corresponds to zinc fingers 7 and 8 of the Drosophila gene. The human putative zinc finger structures are shown at the bottom of FIG. 9. The multiple conserved cysteines and histidines at the 3' end of the motifs allow two or three arrangements of the putative fingers. The structure of these cysteine-rich domains appears to be unique to the trithorax and ALL-1 genes.

Chimeric RNAs resulting from the t(4;11) chromosome translocations

Clustering of t(4;11) breakpoints has previously been found within a small segment of the ALL-1 locus (Cimino et al., *Cancer Research* 1991, 51, 6712–6714; Cimino et al., *Cancer Research* 1992, 52, 3811–3813). This region includes 7 coding exons (6–12) containing 74, 132, 114, 147, 96, 121, and 123 bp respectively. Exons 8–12 contain four zinc finger motifs. Exons 7–11 all begin in the first nucleotide of a codon. Precise mapping of five t(4;11) breakpoints localized them to introns between exons 6 and 7, 7 and 8, and 8 and 9 (FIG. 10A. These breaks in chromosome 11 result in removal of the N-terminal 996 amino acids from the ALL-1 protein, as well as in disjoining of the 5' noncoding region of the gene.

If the breaks on chromosome 4 occur within a gene positioned with its 5' terminus toward the centromere, t(4;11) translocations should result in fusion of the ALL-1 gene to the gene aforementioned and, consequently, in production of two reciprocal chimeric RNAs. To investigate this possibility, a cDNA library was constructed from RNA extracted from the RS4;11 leukemic cell line established from a patient with the t(4;11) chromosome translocation (Stong, R. G., and Kersey, J. H., *Blood* 1985, 66, 439–443). This RS4;11 cDNA library was constructed by treating polyadenylated RNA with 1 mM methyl mercury for 10 minutes at room temperature, followed by neutralization with 10 mM mercaptoethanol and alcohol precipitation. cDNA was prepared by using the Time Saver kit (Pharmacia) and was cloned into the lambda ZAP II vector (Stratagene).

The library ($2\times10^6$ clones) was screened with a probe composed of exons 3–13. Twenty positive clones were purified and mapped. Two clones varied from normal ALL-1 cDNA and were further analyzed by sequencing.

Figure 10A:
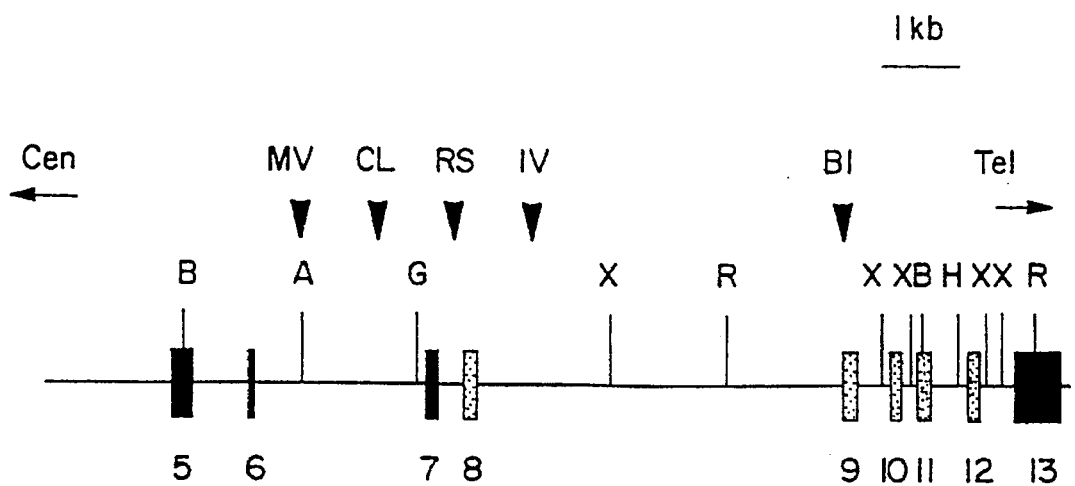

Clone 16 contained normal ALL-1 sequences 3' to the beginning of exon 9. 5' to this position, ALL-1 information was substituted with a new DNA fragment composed of an open reading frame (ORF) that joins in phase the rest of ALL-1 ORF (FIG. 10B). Clone 25 had a reciprocal configuration in which exon 7 of ALL-1 is linked to a new DNA segment containing an open reading frame. Here again, the two ORFs are joined in phase (FIG. 10C). Since, in the RS4;11 cell line, the breakpoint on chromosome 11 is within an intron located between ALL-1 exons 7 and 8 (FIG. 10A), it was expected that in the putative chimeric RNAs sequences of these exons will be directly linked to the new cDNA sequence. This is indeed the case in clone 25 but not in clone 16. In the latter, it was assumed that exon 8 was excluded from the fused transcript by a mechanism involving alternative splicing. Skipping this exon retains the fused ORFs in phase.

The identification of new sequences linked to ALL-1 cDNA in RS4;11 leukemic cells suggested that they originated from altered RNAs specific to cells with the t(4;11) chromosome translocation. Previously, two such transcripts were identified: a 14 kb RNA (previously estimated as 11.5 kb) containing 3' ALL-1 sequences and a 12.7 kb RNA (previously estimated as 11 kb) hybridizing to 5' ALL-1 probe. These RNAs were transcribed from chromosome derivatives 4 and 11, respectively.

A radiolabelled probe composed of non ALL-1 sequences of clone 16 was examined for hybridization to RNAs from cell lines with or without the t(4;11) chromosome translocation. As a control, the RNAs were first hybridized to 3' ALL-1 cDNA probe which detected the major normal transcript of 15–16 kb (previously estimated as 12.5 kb) in all cell lines and an altered 14 kb RNA (previously estimated as 11.5 kb) in the three cell lines with t(4;11) (FIG. 11A).

Figure 11:
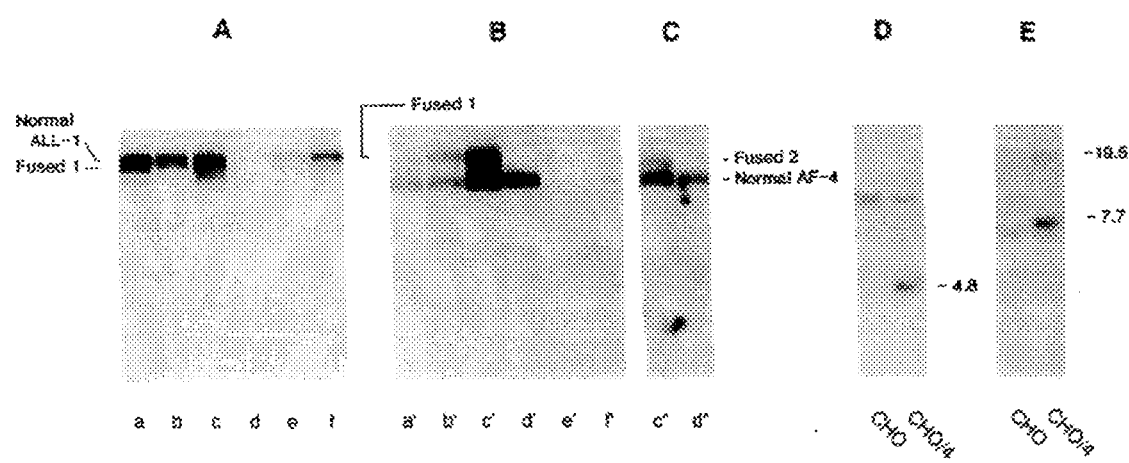
FIG. 11A–11E shows the non ALL-1 sequences within the fused RNAs unique to cells with t(4;11) chromosome translocations (A-C) originate from chromosome 4 (D, E). Cell lines with t(4;11) chromosome translocations included: RS4;11 (Stong, R. G., and Kersey, J. H., *Blood* 1985, 66, 439–443), MV4;11 (Lange et al., *Blood* 1987, 70, 192–198) and B1 (Cohen et al., *Blood* 1991, 78, 94–102). Northern blots with RNAs from cell lines with translocations t(4;11) -B-1 (a, a'), MV4;11 (b, b') and RS4;11 (c, c', c"), and RNAs from control cell lines without the translocation: ALL-1 (d, d', d"), K562 (e, e'), SKDHL (f, f'), were hybridized to 5'ALL-1 cDNA probe (A), to non ALL-1 sequences from cDNA clone 16 (B), and to non ALL-1 sequences from cDNA clone 25 (C). ALL-1 is a Philadelphia-chromosome positive cell line (B cell leukemia) lacking 11q23 aberrations (Erikson et al., *Proc Natl. Acad. Sci. USA* 1986, 83, 1807–1811). K562 originated from chronic myelogenous leukemia (Lozzio, C. B. and Lozzio, B. B., *Blood* 1975, 45, 321–324). SKDHL is a B cell lymphoma cell line (Saito et al., *Proc. Natl. Acad. Sci. USA* 1983, 80, 7476–7480). The second and third probes were also used in hybridization to Southern blots (D and E, respectively) with DNAs from Chinese hamster ovary (CHO cells and CHO cells containing chromosome 4 (CHO/4). "Fused 1" and "fused 2" correspond to the altered ALL-1 RNAs of 14 kb and 12.7 kb, respectively.

Clone 16 probe identified a 9.5 kb RNA in all cells examined and a 14 kb transcript in RS4;11, MV4;11 and B-1 cells (FIG. 11B). It was concluded that clone 16 originated from the 14 kb altered ALL-1 transcript and that the non-ALL-1 sequence within this RNA is expressed in human cells as a 9.5 kb transcript, which corresponds to the normal AF-4 transcript on a non-rearranged chromosome 4.

In an analogous experiment, a probe composed of non-ALL-1 sequences in clone 25 hybridized to the 12.7 kb altered RNA present in the RS4;11 cell line and to a 9.5 kb RNA species present in RS4;11 cells and in control cells (FIG. 11C). Thus, clone 25 originated from the second altered 12.7 kb ALL-1 RNA unique to cells with the t(4;11) chromosome translocation.

The chromosome from which the new sequences of clones 16 and 25 originated was then identified. High molecular weight DNAs from lines of Chinese hamster ovary (CHO) cells with or without human chromosome 4 were digested with BamHI enzyme and analyzed by Southern blotting for hybridization to the non ALL-1 sequence in clone 16 (FIG. 11D) and clone 25 (FIG. 11E). The cell lines showed an 11 kb or a 6.6 kb band representing CHO cell DNA cross-reacting with the probes. A fragment of 4.8 kb and fragments of 7.7 and 19.5 kb were detected in the somatic cell hybrid line containing human chromosome 4 (CHO/4) after hybridization with non ALL-1 sequences of clones 16 and 25, respectively (FIGS. 11D and E). The non-ALL-1 sequences in clone 25 hybridized to a specific segment within cloned chromosome 4 DNA spanning the RS4;11 breakpoint. Thus, clones 16 and 25 correspond to the two reciprocal fused transcripts of the ALL-1 gene and a gene on chromosome 4. The latter is denominated "AF-4" for ALL-1 fused gene from chromosome 4.

Cloning and sequence analysis of the ALL-1 gene indicates that it encodes an unusually large protein of 4,000 amino acids with a mass of approximately 400 kD. The striking feature of the protein is its homology to the Drosophila trithorax gene. The homology is reflected in three ways. First, the transcripts and proteins have a similar size; the Drosophila gene is transcribed into a 15 kb RNA encoding a protein of 3759 amino acids (Mozer, B. A., and David, I. B., *Proc. Natl. Acad. Sci.* USA 1989, 86, 3738–3742; Mazo et al., *Proc. Natl. Acad. Sci.* USA 1990, 87, 2112–2116).

Second, there is strong sequence homology in three regions, two of which contain zinc finger-like domains unique to the trithorax gene and presumably utilized in interaction with target DNA. The third region shows 82% similarity and 61% identity across 220 amino acids which end both proteins at their C-terminus.

Finally, there is colinearity of the homologous sequences in the two proteins. Although the sequence homology does not extend to other parts of the protein, the two genes very possibly evolved from a common ancestor and may carry out similar function(s). In this context, it has been previously noted that structural homology between Drosophila and mammalian genes such as the Antennapedia class homeobox genes, is frequently limited to the functional domains, e.g., the homeodomain (McGinnis, W., and Krumlauf, R., *Cell* 1992, 68,283–302).

The trithorax gene in Drosophila acts to maintain spatially-restricted expression patterns of the Antennapedia and Bithorax complexes during fruit fly development (Ingham, P. W., *Cold Spring Harbor Symp. Quant. Biol.* 1985, 50, 201–208). Trithorax activates transcription of multiple genes of the two complexes and, as such, counteracts the activity of Polycomb group genes which act as repressors of transcription for the same genes (McKeon, J. and Brock, H. W., *Roux's Arch. Dev. Biol.* 1991, 199, 387–396). Thus, mutations in the trithorax gene frequently result in homeotic transformations (Capdevila, M. P. and Garcia-Bellido, A., *Roux's Arch. Dev. Biol.* 1981, 190, 339–350). The discovery of zinc finger-like domains in the predicted amino acid sequence strongly suggested that the trithorax protein is a transcription factor which binds to DNA (Mazo et al., *Proc. Natl. Acad. Sci.* USA 1990, 87, 2112–2116). Indeed, antibodies to the protein react with specific regions of the chromatin in the salivary glands of Drosophila.

Based on what is known about the Drosophila gene, it is very likely that the ALL-1 gene is a transcription factor and that it is involved in regulation of genes controlling human development and/or differentiation. While expression of ALL-1 during embryonic development has not yet been investigated, the isolation of ALL-1 sequences from a human fetal cDNA library indicates transcription of the gene during fetal development. Previous studies (Cimino et al., *Cancer Research* 1992, 52, 3811–3813) demonstrated ALL-1 RNA in a variety of hematopoietic cell lines, as well as in tumors originating from precursors of epithelial and glial cells.

It was also found that the t(4; 11) chromosome translocation cleaves the ALL-1 gene within the coding region and results in fusion of the open reading frames of ALL-1 and a gene on chromosome 4 (termed AF-4) in phase. The breakpoints on chromosome 11 cluster in a region containing several small exons, 5 of them (exons 7–11) begin in the first letter of a codon. Splicing from the same exon on chromosome 4, adjacent to the breakpoint in RS4; 11, to each one of the five exons on chromosome 11 will retain the two open reading frames fused in phase. This situation is similar to the situation in the t(9;22) chromosome translocations where the breakpoints cluster near two BCR exons whose splicing to ABL exon 11 maintain the fused open reading frames in phase (Shtivelman et al., *Nature* 1985, 315, 550–554; Heisterkamp et al., *Nature* 1985, 315, 758–761). The clustering of breakpoints must also reflect the specific biological properties of the fused proteins and probably is also due to the presence of recombination signals in this region.

Two chimeric proteins from the 12.7 and 14 kb RNAs are predicted for cells with the t(4; 11) chromosome translocation. The lack of information about the normal AF-4 protein precludes at this time the determination if it is also a transcription factor that exchanges functional domains with ALL-1 to give a chimeric transcription factor. This occurs in the t(1;19) and t(15;17) chromosome translocations (Kamps et al., *Cell* 1990, 60, 547–555; Nourse et al., *Cell* 1990, 60,535–545; Kakizuka et al., *Cell* 1991, 66, 663–674; de The et al., *Cell* 1991, 66, 675–684).

Both the 12.7 and the 14 kb fused RNAs are found in the three cell lines with t(4;11), therefore it is not possible at this time to establish which of the two products is oncogenic. However, the presence of the three trithorax homologous domains within the 14 kb transcript makes it an attractive candidate. The substitution of the N-terminus 996 amino acids of ALL-1 with an AF-4 polypeptide could result in at least two scenarios, both based on the assumption that ALL-1 and ALL-1/AF-4 activate transcription of the same gene(s). First, the substitution could place ALL-1 DNA binding domain under the control of a new effector domain activated by either ubiquitous or tissue specific factors. This will result in transcription of the target genes in the wrong cells. Second, the fusion product may function as a dominant negative inhibitor of ALL-1 by forming inactive heterodimers or by occupying target DNA sites.

The present invention provides methods of diagnosis for human leukemia by providing a tissue sample from a person suspected of having acute lymphocytic, myelomonocytic, monocytic or myelogenous leukemia, and determining if there are breakpoints on chromosome 11 in the ALL-1 locus. The sequence of the ALL-1 cDNA can be used to generate probes to detect chromosome abnormalities in the ALL-1 breakpoint cluster region. These probes may be generated from both the sense and antisense strands of double-stranded DNA. The term "ALL-1 probe" refers to both genomic and cDNA probes derived from the ALL-1 gene.

It is believed that genomic probes capable of detecting chromosomal translocations involving the ALL-1 breakpoint cluster region span sequences from 10 kb centromeric to 10 kb telomeric to the breakpoint cluster region, which has been shown to span at least exons 6–9, and may span exons 6–12 of the ALL-1 gene. It is believed that cDNA probes capable of detecting chromosomal translocations involving the ALL-1 breakpoint cluster region span sequences ranging from 2 kb centromeric to 2 kb telomeric to the breakpoint cluster region. Thus, preferred embodiments of the present invention for detecting chromosomal abnormalities involving ALL-1 provide genomic and cDNA probes spanning the chromosome 11 regions described above. cDNA probes are more preferred, and probes comprising the exons included in the breakpoint cluster region are most preferred.

Part or all of the ALL-1 cDNA sequence may be used to create a probe capable of detecting aberrant transcripts resulting from chromosome 11 translocations. The EcoRI probe, for example, was derived from a genomic clone but its location lies within an exon. Thus, preferred embodiments of the present invention for detecting aberrant transcripts provide cDNA probes spanning the ALL-1 gene.

The ALL-1/AF-4 sequences provided in SEQ ID NO: 23 and SEQ ID NO:24 can be used to create probes to detect t(4;11) chromosome abnormalities and aberrant transcripts corresponding to t(4;11) translocations.

Using the probes of the present invention, several methods are available for detecting chromosome abnormalities in the ALL-1 gene on chromosome 11. Such methods include, for example, Polymerase Chain Reaction (PCR) technology, restriction fragment length analysis, and oligonucleotide hybridization using, for example, Southern and Northern blotting and in situ hybridization.

PCR technology is practiced routinely by those having ordinary skill in the art and its uses in diagnostics are well known and accepted. Methods for practicing PCR technology are disclosed in PCR Protocols: *A Guide to Methods and Applications*, Innis, M. A. et al., Eds., Academic Press, San Diego, Calif. 1990, and RT-PCR, Clontech Laboratories (1991), which are incorporated herein by reference. Applications of PCR technology are disclosed in *Polymerase Chain Reaction*, Erlich, H. A. et al., Eds., Cold Spring Harbor Press, Cold Spring Harbor, N.Y. 1989, which is incorporated herein by reference.

PCR technology allows for the rapid generation of multiple copies of DNA sequences by providing 5' and 3' primers that hybridize to sequences present in a DNA molecule, and further providing free nucleotides and an enzyme which fills in the complementary bases to the DNA sequence between the primers with the free nucleotides to produce a complementary strand of DNA. The enzyme will fill in the complementary sequences between probes only if both the 5' primer and 3' primer hybridize to DNA sequences on the same strand of DNA.

To detect rearrangements involving chromosomes 11 and 4, one of the two probes can be generated from the ALL-1 cDNA and one probe from the AF-4 gene. RNA is isolated from hematopoietic cells of a person suspected of having acute lymphoblastic or nonlymphoblastic leukemia, and cDNA is generated from the mRNA. If the cDNA of the chimeric ALL-1/AF-4 gene is present, both primers will hybridize to the cDNA and the intervening sequence will be amplified. The PCR technology therefore provides a straightforward and reliable method of detecting the chimeric gene.

The preferred primers for PCR are selected, one from a portion of SEQ ID NO: 1, corresponding to the ALL-1 cDNA, and one from a portion of either SEQ ID NO: 19 or SEQ ID NO: 22, corresponding to AF-4 gene sequences. Preferably, the sequences chosen from SEQ ID NO: 1 comprise at least a portion of SEQ ID NO: 20, which corresponds to exon 9, or SEQ ID NO: 21, which corresponds to exon 7.

According to the invention, diagnostic kits can be assembled which are useful to practice oligonucleotide hybridization methods of distinguishing chromosome 11 abnormalities from non-rearranged chromosomes 11. Such diagnostic kits comprise a labelled oligonucleotide which hybridizes, for example, to the chimeric transcript that results from t(4;11) translocations but which does not hybridize to nucleic acid transcripts not associated with aberrations. Accordingly, diagnostic kits of the present invention comprise, for example, a labelled probe that includes ALL-1 and AF-4 sequences which make up the chimeric transcript associated with t(4;11) translocations. Such probes comprise oligonucleotides having at least a portion of the sequence of the ALL-1/AF-4 gene of SEQ ID NO: 23 or SEQ ID NO: 24.

It is preferred that labelled probes of the oligonucleotide diagnostic kits according to the present invention are labelled with a radionucleotide. The oligonucleotide hybridization-based diagnostic kits according to the invention preferably comprise DNA samples that represent positive and negative controls. A positive control DNA sample is one that comprises a nucleic acid molecule which has a nucleotide sequence that is fully complementary to the probes of the kit such that the probes will hybridize to the molecule under assay conditions. A negative control DNA sample is one that comprises at least one nucleic acid molecule, the nucleotide sequence of which is partially complementary to the sequences of the probe of the kit. Under assay conditions, the probe will not hybridize to the negative control DNA sample.

Antisense oligonucleotides which hybridize to at least a portion of an aberrant transcript resulting from chromosome 11 abnormalities involving the ALL-1 gene are also contemplated by the present invention. The oligonucleotide may match the target region exactly or may contain several mismatches. Thus, molecules which bind competitively to RNA coded by the chimeric ALL-1/AF-4 gene, for example, are envisioned for therapeutics. Preferred embodiments include antisense oligonucleotides capable of binding to at least a portion of SEQ ID NO: 23 and SEQ ID NO: 24.

Preferred embodiments of the present invention include antisense oligonucleotides capable of binding to a region of the ALL-1/AF-4 mRNA corresponding to the ALL-1 sequences which encode a peptide having homology with the Drosophila trithorax protein and antisense oligonucleotides capable of binding to a region of the mRNA encoding a zinc finger-like domain in the ALL-1 protein.

While any length oligonucleotide may be utilized, sequences shorter than 15 bases may be less specific in hybridizing to the target and may be more easily destroyed by enzymatic degradation. Hence, oligonucleotides having at least 15 nucleotides are preferred. Sequences longer than 21 nucleotides may be somewhat less effective in interfering with ALL-1 expression because of decreased uptake by the target cell. Therefore, oligonucleotides of 15–21 nucleotides are most preferred.

The term "oligonucleotide" as used herein includes both ribonucleotides and deoxyribonucleotides, and includes molecules which may be long enough to be termed "polynucleotides." Oligodeoxyribonucleotides are preferred since oligoribonucleotides are more susceptible to enzymatic attack by ribonucleotides than deoxyribonucleotides. It will also be understood that the bases, sugars or internucleotide linkages may be chemically modified by methods known in the art. Modifications may be made, for example, to improve stability and/or lipid solubility. For instance, it is known that enhanced lipid solubility and/or resistance to nuclease digestion results by substituting a methyl group or sulfur atom for a phosphate oxygen in the internucleotide phosphodiester linkage. The phosphorothioates, in particular, are stable to nuclease cleavage and soluble in lipid. Modified oligonucleotides are termed "derivatives."

The oligonucleotides of the present invention may be synthesized by any of the known chemical oligonucleotide synthesis methods. See for example, Gait, M. J., ed. (1984), *Oligonucleotide Synthesis* (IRL, Oxford). Since the entire sequence of the ALL-1 gene has been provided along with partial sequences of the AF-4 gene, antisense oligonucleotides hybridizable with any portion of these sequences may be prepared by the synthetic methods known by those skilled in the art.

It is generally preferred to apply the therapeutic agent in accordance with this invention internally such as intravenously, transdermally or intramuscularly. Other forms of administration such as topically or interlesionally may also be useful. Inclusion in suppositories is presently believed to be likely to be highly useful. Use of pharmacologically acceptable carriers is also preferred for some embodiments.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like. In addition to administration with conventional carriers, the antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.* 1986, 859, 88–94.

For in vivo use, the antisense oligonucleotides may be administered in an amount effective to result in extracellular concentrations approximating in vitro concentrations described below. The actual dosage administered may take into account the size and weight of the patient, whether the nature of the treatment is prophylactic or therapeutic in nature, the age, weight, health and sex of the patient, the route of administration, and other factors. The daily dosage may range from about 0.1 to 1,000 mg oligonucleotide per day, preferably from about 10 to about 1,000 mg per day. Greater or lesser amounts of oligonucleotide may be administered, as required.

It is also possible to administer the antisense oligonucleotides ex vivo by isolating white blood cells from peripheral blood, treating them with the antisense oligonucleotides, then returning the cells to the donor's blood. Ex vivo techniques have been used in the treatment of cancer patients with interleukin-2 activated lymphocytes.

For ex vivo application, for example, in bone marrow purging, the antisense oligonucleotides may be administered in amounts effective to kill leukemic cells while maintaining the viability of normal hematologic cells. Such amounts may vary depending on the nature and extent of the leukemia, the particular oligonucleotide utilized, the relative sensitivity of the leukemia to the oligonucleotide, and other factors. Concentrations from about 10 to 100 µg/ml per $10^5$ cells may be employed, preferably from about 40 to about 60 µg/ml per $10^5$ cells. Supplemental dosing of the same or lesser amounts of oligonucleotide are advantageous to optimize the treatment. Thus, for purging bone marrow containing $2 \times 10^7$ per ml of marrow volume, dosages from about 2 to about 20 mg antisense per ml of marrow may be effectively utilized, preferably from about 8 to 12 mg/ml. Greater or lesser amounts of oligonucleotide may be employed.

The present invention is also directed to monoclonal antibodies capable of binding to the chimeric ALL-1/AF-4 protein, including monoclonal antibodies capable of binding to a region of the protein having homology with the Drosophila trithorax protein and monoclonal antibodies capable of binding to a zinc finger-like domain. Such monoclonal antibodies are useful as diagnostic and therapeutic agents for leukemias characterized by t(4;11) translocations. Thus, the present invention encompasses immunoassays for detecting at least a portion of the ALL-1/AF-4 protein. In addition, the instant invention contemplates diagnostic kits comprising a monoclonal antibody to at least a portion of ALL-1/AF-4 in combination with conventional diagnostic kit components.

The present invention is also directed to pharmaceutical compositions comprising monoclonal antibodies and a suitable pharmaceutical carrier, which are well known in the pharmaceutical art, and are described, for example, in Remington's *Pharmaceutical Sciences*, Gennaro, A. R., ed., Mack Publishing Co., Easton, Pa. 1985. The useful dosage will vary depending upon the age, weight, and particular patient treated.

Polyclonal antibodies to the instant polypeptides are also within the ambit of the invention. Such polyclonal antibodies may be produced using standard techniques, for example, by immunizing a rabbit or a rat with a protein or peptide of the invention, removing serum from the rabbit, and harvesting the resultant polyclonal antibodies from the serum. If desired, the polyclonal antibodies may be used as an IgG fraction or may be further purified in varying degrees. Procedures for preparing, harvesting and purifying polyclonal antibodies are well known in the art, and are described, for example, in *Methods in Immunology: A Laboratory Text* for *Instruction and Research*, Garvey et al., Ed., W. A. Benjamin, Reading Mass., 1977, 3rd ed., chapter 22, 24–30.

Experiments reported in Example 1 provide further data for designing methods of diagnosing and treating acute lymphoblastic or nonlymphoblastic leukemia, particularly those involving a chimeric gene in t(4;11) translocations. The information provided in example 1 includes complete cDNA sequences encoding AF-4. These sequences may be used design probes of at least 15 nucleotides which are capable of identifying chromosome abnormalities within the ALL-1 gene of chromosome 11. Examples of such probes comprise an oligonucleotide sequence or derivatives thereof comprising at least a portion of SEQ ID NO:25 or SEQ ID NO:27. The procedures for using such probes are described above.

Experiments reported in Example 2 provide further data for designing methods of diagnosing and treating acute lymphoblastic or nonlymphoblastic leukemia, particularly those involving a chimeric gene in t(9;11) translocations. The information provided in example 2 may be used design probes of at least 15 nucleotides which is capable of identifying chromosome abnormalities within the ALL-1 gene of chromosome 11. Examples of such probes may comprise at least a portion of SEQ ID NO:32, SEQ ID NO:33 or SEQ ID NO:34. Further, probes capable of identifying chromosome abnormalities within the AF-9 gene of chromosome 9 may be designed. Examples of such probes comprise an oligonucleotide sequence or derivatives thereof comprising at least a portion of SEQ ID NO:29, SEQ ID NO:32, SEQ ID NO:33 or SEQ ID NO:34. The procedures for using such probes are described above.

A method of diagnosing acute lymphoblastic or nonlymphoblastic leukemia involving a chimeric gene in t(9;11) translocations may be performed by first providing a tissue sample containing hematopoietic cells from a person suspected of having acute lymphoblastic or nonlymphoblastic leukemia; then isolating RNA from the sample followed by generating cDNA from said RNA and amplifying a chimeric gene sequence in said cDNA which is generated by said translocation using a set of PCR primers if said chimeric gene is present such that detecting the presence of amplified DNA indicates the tissue sample is derived from an individual suffering from lymphoblastic or nonlymphoblastic leukemia involving a chimeric gene in t(9;11) translocations. The method, which is generally described in detail above, may be performed using sets of primers which can be used to amplify a chimeric gene generated by the translocation. Examples of such primers can be designed, for example, using the sequence information in SEQ ID NO:32, SEQ ID NO:33 or SEQ ID NO:34. Examples of primers include SEQ ID NO:39 and SEQ ID NO:40; SEQ ID NO:41 and SEQ ID NO:42; and SEQ ID NO:43 and SEQ ID NO:44.

Monoclonal antibody capable of binding to at least a portion of the chimeric ALL-1/AF-9 protein may be produced by standard techniques. Examples of such a monoclonal antibodies, which can bind specifically to at least a portion of the amino acid sequences encoded by SEQ ID NO:9, SEQ ID NO:11 or SEQ ID NO:13, may be produced using peptides which comprise at least a portion of SEQ ID NO:9, SEQ ID NO:11 or SEQ ID NO:13.

In one method of diagnosing acute lymphoblastic or nonlymphoblastic leukemia, tissue sample containing hematopoietic cells from a person suspected of having acute lymphocytic or nonlymphoblastic leukemia is examined to detect the ALL-1/AF-9 chimeric protein or a portion of the chimeric ALL-1/AF-9 protein. In one embodiment of such a method, a monoclonal antibody capable of binding to at least a portion of the chimeric ALL-1/AF-9 protein is used.

The present invention provides antisense oligonucleotides capable of binding to at least a portion of the chimeric ALL-1/AF-9 mRNA. Such antisense oligonucleotides include those capable of binding to at least a portion of SEQ ID NO:32, SEQ ID NO:33 or SEQ ID NO:34.

Method of treating acute lymphoblastic or nonlymphoblastic leukemia are provide which comprise administering an antisense oligonucleotide capable of binding to at least a portion of the chimeric ALL-1/AF-9 mRNA or, alternatively, administering a monoclonal antibody capable of binding to at least a portion of the chimeric ALL-1/AF-9 protein. The formulation and administration of therapeutics are outlined above.

EXAMPLE 1

Experiments were performed to determine the CDNA sequence of AF-4 and study ALL-1/AF-4 chimeric genes.

Results

Cloning and Sequencing AF-4-cDNA.

cDNA clones containing the two reciprocal ALL-1/AF-4 RNA junctions were cloned from RNA of the RS4 11 cell line carrying the t(4:11) chromosome translocation. AF-4 specific probes obtained from these clones were used to screen cDNA libraries prepared from RNAs of the K562 and KC122 hematopoietic cell lines. Positive clones were sequenced and utilized to prepare end probes for further screening. Overlapping clones spanning most or all of the 9.5 kb AF-4 transcript were obtained. Analysis of the longest cDNA composite indicated an open reading frame initiated with a consensus ATG and coding for a protein or 1210 amino acids (SEQ ID NO:25 and SEQ ID NO:27; and SEQ ID NO:26 and SEQ ID NO:28, respectively).

cDNA clone k 12, SEQ ID NO:25, diverged from cDNA clone kcl 6, SEQ ID NO:27, at nucleotide 435 of the latter. 5' of this position the two sequences completely varied. The open reading frames of clones kcl 6 and k 12 started 5 and 12 codons, respectively 5' of the divergence point. This suggests an alternative first exon for AF-4. A third cDNA clone, k 1.1, represents another RNA variant probably resulting from alternative splicing; an in frame termination codon is present in this clone immediately 3' to the divergence point. Thus, AF-4 encodes 2 or more proteins varying at their termini. AF-4 contains an unusually long 3' untranslated region of 5 3 kb . This region includes multiple AATAAA sequences located 20 nucleotides 5' of the poly A, as well as in several upstream positions; it also contains several stretches of T.

Using the Swiss, Prosite and Profilescan data bases, the complete AF-4 protein sequence was searched for homology to other proteins and for the presence of motifs. The sequence AKKRK at positions 811–815 matched the consensus nuclear targeting sequence—(RKTA) KK (RQNTSG) K-(Gomez-Marquez and Segada, 1988). AF-4 was relatively rich in serine (16%) and proline (11%) compared to the average frequency of these amino acids (7.1% and 4.6%, respectively).

Inspection of AF-4 sequence at the fusion point to ALL-1 RNA in the RS4:11 cell line indicates that three nucleotides (1959–1961) of AF-4 RNA are missing from cDNA clone 25 corresponding to ALL-1/AF-4 fused RNA; these nucleotides might have been excluded through an error in the splicing process where an Ag at positions 1960–1961 was mistaken to the 3' end of an intron.

We have previously shown that in leukemic cells with t(4:11) abnormalities the breakpoints cluster in a region of approximately 8 kb on chromosome 4. This region corresponds to a single intron flanked by an exon located within a 1 kb BamHI-EcoRI fragment, and an exon positioned >20 kb away towards the telomere.

EXAMPLE 2

Cloning of AF-9/ALL-1 Genomic Junctions

The nonavailability of cell lines with the t(9:11) abnormality made it impossible to obtain intact mRNA in amounts sufficient for preparation of a cDNA library and cloning from it fused ALL-1/AF-9 cDNA. To circumvent this problem, we first cloned (clone C19) to genomic junction fragment from the leukemic cells of patient C() with acute myeloid leukemia (AML) and t(9:11). We also cloned (clone F2) the genomic junction fragment from tumor cells of patient FI with acute lymphocytic leukemia (ALL) and t(9:11). The cloned genomic fragments were derived from the der 9 chromosomes of the patients. Mapping and hybridization analysis of the non-ALL-1 segments within the two phage clones indicated no homology between them.

A 1 kb HindIII fragment from non-ALL-1 region in clone F2 was used to clone the corresponding normal DNA. A 0.4 kb HindIII fragment from clone 3 and 0.4 kb HindIII-AvaII probe from clone C19 hybridized to human DNA within Chinese hamster cell hybrids containing human chromosome 9. This established that in both patients' DNAs the ALL-1 gene is linked to chromosome 9 sequences. Subsequent work showed that both sequences are included in a single gene which we term AF-9, for ALL-1 fused gene from chromosome 9.

The same repeat-free fragments were used as probes for detecting rearrangements in DNAs from leukemic cells with t(9:11) chromosome translocations. Samples from three patients with ALL and from five patients with AML were studied. The 0.4 kb HindIII fragment detected rearrangement in DNA of the ALL patient CU. The HindIII-AvaII probe showed rearrangements in patients TA, SU and AG, all with AML. This indicated that at least two regions in the AF-9 gene are involved in recurrent t(9:11) aberrations. Presently, it is not known whether one region is preferentially rearranged in AML and the second in ALL; it is also not clear whether the AF-9 gene is involved in all t(9:11) abnormalities.

Characterization of Normal and Chimeric cDNAs of AF-9

We examined repeat-free fragments from AF-9 DNA for hybridization to cDNA libraries. The 1 kb HindIII fragment reacted with several overlapping cDNAs spanning 3.4 kb. These cDNAs reacted in northern analysis with a major 5 kb transcript expressed in several hematopoietic cell lines.

Nucleotide sequence analysis of AF-9 cDNA revealed an open reading frame beginning in a consensus initiation codon (SEQ ID NO:29) and coding for a protein of 568 amino acids (SEQ ID NO:30). The protein encloses a nuclear targeting sequence AKKQK at positions 297–301. AF-9 protein is serine rich (20%) and includes a remarkable uninterrupted stretch of 42 serines at positions 149–190; it also contains proline at a frequency of 7% which is above the average frequency of 4.1%.

A homology search showed, unexpectedly, that the predicted protein shared high similarity with the ENL protein SEQ ID NO:31. The latter is located on chromosome 19 and is fused to the ALL-1/HRX gene in t(11:19) chromosome translocations. The two proteins show 56% identity and 68% similarly. The homology is highest within the 140 amino acids at the N terminus where the proteins are 82% identical, and 92% similar, and within the 67 amino acids at the C terminus where the corresponding values are 82% and 91%.

To demonstrate chimeric ALL-1/AF-9 RNAs, we designed primers supposed to flank the RNA junction points in the two genes and used them in RT-PCR reactions with RNA from patient FI. Two reciprocal cDNA products were amplified SEQ ID NO:32 and SEQ ID NO:34 (encoding protein products SEQ ID NO:33 and SEQ ID NO:35 respectively). Close examination of sequences at the RNA junctions showed a stretch of 11 nucleotides of AF-9 (ATTCTTGAAGT; SEQ ID NO:38) at both RNA junctions. In an attempt to understand this, we sequenced the genomic junction in clone F2 and determined exon-intron boundaries of AF-9 exons in this region. This analysis suggested that the two derivative chromosomes of patient FI were formed by staggered breaks in the DNAs of chromosomes 9 and 11 resulting in a small overlapping AF-9 genomic DNA segment and consequently in the overlapping of 11 nucleotides of AF-9 at the RNA junction points. The der 9 chromosome resulted from a break within exon 7 of ALL-1 and a break within an exon of AF-9 (11 nucleotides 3' of the intron-exon boundary). The hybrid exon spans the fusion point in cDNA clone EN (ALL-1 exon 8 was skipped during splicing). The der 11 chromosome was due to a break in the other ALL-1 DNA strands within the intron flanked by exons 6 and 7, and to a breakage of the second AF-9 DNA strand within an intron located 5' of the AF-9 exon mentioned above. The der 11 is transcribed into an RNA corresponding to cDNA clone E2.

A BamHI-StuI cDNA probe detected some normal genomic fragments, which were also detected by the 0.4 kb HindIII-AvaII probe-derived from the genomic junction cloned from DNA of patient CO. This enabled designing primers predicted to flank the RNA fusion point of patient CO and use them in a RT-PCR reaction to amplify AF-9/ALL-1 RNA SEQ ID NO:36 (encoding protein SEQ ID NO:37). In this patient the AF-9 protein is linked at position 375 to the ALL-1 moiety, while in patient FI the junction point is at amino acids 444 or 477 of AF-9. In the three junctions examined the reading frames of the two genes are joined in phase.

Discussion

Perhaps the most unusual feature of 11q23 abnormalities is the multitude of chromosome partners participating in translocations with the ALL-1 locus. Using a probe containing sequences of ALL-1 exons 5 and 11, which flank the breakpoint cluster region, we have been able to detect rearrangements in 10 types of 11q23 chromosome translocations. This promiscuity in partners for rearrangement and fusion could suggest that the only critical event in all these different translocations is the separation of a DNA binding domain (either the zinc fingers or the AT hooks in the ALL-1 gene) from a positive or negative regulatory element, and that the proteins encoded by the partner genes solely provide initiation or termination codons.

Our sequence analysis of AF-4 and AF-9 proteins and a comparison to the sequence of the ENL protein is not consistent with such interpretation. The finding that AF-9 and ENL share extensive sequence homology indicates that the two proteins have similar biological function and that presumably they contribute an identical activity to the chimeric proteins. Possibly, other genes participating in 11q23 aberrations have also sequence homology with AF-9 and ENL. Moreover, these two proteins share with AF-4 several common motifs: 1) a nuclear targeting sequence (NTS) (suggesting that the three proteins are nuclear), 2) serine-rich domains, the most prominent being an uninterrupted stretch of 42 serines in AF-9, 3) stretches rich in proline or in basic amino acids reaching frequency of ~30% in some regions. While serine-rich regions have not yet been implicated in function of transcription factors, domains with abundant prolines were shown to act as transcription activators, and domains rich in positively charged amino acids were found to bind DNA. These common structural motifs suggest that AF-4, AF-9, and ENL are involved in transcription regulation, possibly representing a new class of transcription factors. Proteins coded by the other genes involved in 11q23 chromosome translocations might belong to this class.

Inspection of the position of the elements discussed above in relation to the fusion point(s) with the ALL-1 protein shows that the NTS of AF-4 is linked to the N-terminus of ALL-1 containing the AT hooks, while AF-4 domains rich in serine, proline, or basic amino acids are fused to both reciprocal products of ALL-1 cleavage. In patient FI with t(9:11), the NTS and most of AF-9 domains rich in specific amino acids are linked to the C-terminus of ALL-1 which contains the zinc tingers. In leukemic cells with t(11:19) all landmarks observed in the ENL protein will be linked to the N-termininus of ALL-1; this may suggest that N-ALL-1/ENL-C is the oncogenic product of the t(11:19) abnormality. The opposite distribution of the common elements in AF-9 fusion products in patients such as FI raises the possibility that in these cases N-AF-9/ALL-1-C is the oncogenic species. Determination of which one (or both) of the fusion products of 11q23 translocations induce malignancy should be resolved by biological assays in cells in culture and in transgenic mice. Transcription assays utilizing elements of AF-4, AF-9 and ENL should help in understanding the normal function of these elements, as well as their role in the fused proteins.

Experimental procedures

DNA and Sequencing Analysis Aliquots (20 micrograms) of high molecular weight DNAs were digested with excess of restriction enzymes and analyzed by the Southern technique using the Probe Tech™2 system (ONCOR). Sequencing was done with an automatic sequencer (ABI).

Genomic and cDNA libraries High molecular weight DNAs from patients with t(9:11) chromosome translocation were partially digested with Mbol enzyme and cloned into the EMBL-3 phage vector (Promega). To reduce the frequency of rearrangements during propagation in bacteria, the libraries were plated into the host bacteria CES200 (Wyman et al., 1986). The libraries were screened with an ALL-1 specific probe (Cimino et al., 1992) and positive clones were mapped with restriction enzymes. To construct a cDNA library from RNA of the KC122 cell line, cytoplasmic RNA was extracted by standard techniques (Berger & Chirgwin, 1989) and polyadenylated RNA purified on an oligo dT column. cDNA was prepared using the Timesaver kit of Pharmacia and cloned into the lambda ZAPII vector (Stratagene).

Construction of cDNA libraries from K562 or fibroblasts RNA was described (Shtivelman et al., 1985; Chu et al., 1990). AF-4 cDNA clones k1.1, k1.2, k11 and k12 originated from the K562 library and the clones kcl 6, kcl 10, and kcl 12 were cloned from the KC122 library. AF-9 cDNA clones v4 and v7 were obtained from the fibroblasts library, and k 16 was cloned from the K562 library.

RT PCR Two micrograms of RNA from a patient FI were reverse transcribed in a reaction utilizing the AF-9 oligonucleotide TCCTCAGGATGTTCCAGATGT (SEQ ID NO:39) or the ALL-1 oligonucleotide GGCTCACAACAGACTTGGCAA (SEQ ID NO:40) as primers. The cDNAs were amplified with Taq 1 polymerase (Boeringer) using the same primers together with the ALL-1 primer ACCTACTACAGGACCGCCAAG (SEQ ID NO:41), and the AF-9 primer CAGATGAAGTGGAGGATAACG (SEQ ID NO:42), respectively. The reaction products were purified by gel electrophoresis and cloned into the SK plasmid vector (Stratagene). Recombinants with AF-9/ALL-1 or ALL-1/AF-9 DNA were identified by colony hybridization and were subsequently sequenced. The AF-9/ALL-1 RNA function of patient C() was obtained in a similar way using the ALL-1 primer CAGCGAACACACTTGGTACAG (SEQ ID N0:43) for synthesis of cDNA and the same primer together with the AF-9 primer CAACGTTACCGCCATTTGAT (SEQ ID NO:44) for PCR amplification.

We claim:

1. A method of identifying a t(9;11) translocation in a patient comprising:

providing a tissue sample containing hematopoietic cells from said patient;

isolating RNA from said sample;

generating cDNA from said RNA;

amplifying a nucleotide sequence of a chimeric gene in said cDNA using a set of PCR primers selected from the group consisting of SEQ ID NO:39 and SEQ ID NO:41; SEQ ID NO:40 and SEQ ID NO:42; are SEQ ID NO:43 and SEQ ID NO:44, if said chimeric gene is present and wherein said chimeric gene results from said translocation; and detecting the presence of amplified DNA as indicative of the presence of a t(9;11) translocation.

2. The method of claim 1, wherein said PCR primers are SEQ ID NO:39 and SEQ ID NO:41.

3. The method of claim 1, wherein said PCR primers are SEQ ID NO:40 and SEQ ID NO:42.

4. The method of claim 1, wherein said PCR primers are SEQ ID NO: 43 and SEQ ID NO: 44.

5. A method of screening samples from a patient for a t(9;11) translocation comprising:

providing a tissue sample containing hematopoietic cells from said patient;

isolating RNA from said sample;

generating cDNA from said RNA;

amplifying a nucleotide sequence of a chimeric gene in said cDNA using a set of PCR primers selected from the group consisting of SEQ ID NO:39 and SEQ ID NO:41; SEQ ID NO:40 and SEQ ID NO:42; are SEQ ID NO:43 and SEQ ID NO:44, if said chimeric gene is present and wherein said chimeric gene results from said translocation; and detecting the presence of amplified DNA as indicative of the presence of a t(9;11) translocation.

6. The method of claim 5 wherein said PCR primers are SEQ ID NO:39 and SEQ ID NO:41.

7. The method of claim 5 wherein said PCR primers are SEQ ID NO:40 and SEQ ID NO:42.

8. The method of claim 5 wherein said PCR primers are SEQ ID NO:43 and SEQ ID NO:44.

* * * * *

SEQUENCE LISTING ( 1 ) GENERAL INFORMATION:

( i i i ) NUMBER OF SEQUENCES: 44

( 2 ) INFORMATION FOR SEQ ID NO: 1:

( i ) SEQUENCE CHARACTERISTICS:
        ( A ) LENGTH: 14255
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 1:

```
GCG  GCG  GCG  GCG  GCG  GGA  AGC  AGC  GGG  GCT  GGG  GTT  CCA  GGG  GGA   45
Ala  Ala  Ala  Ala  Ala  Gly  Ser  Ser  Gly  Ala  Gly  Val  Pro  Gly  Gly
 5                        10                       15

GCG  GCC  GCC  GCC  TCA  GCA  GCC  TCC  TCG  TCG  TCC  GCC  TCG  TCT  TCG   90
Ala  Ala  Ala  Ala  Ser  Ala  Ala  Ser  Ser  Ser  Ser  Ala  Ser  Ser  Ser
                     20                       25                       30

TCT  TCG  TCA  TCG  TCC  TCA  GCC  TCT  TCA  GGG  CCG  GCC  CTG  CTC  CGG   135
Ser  Ser  Ser  Ser  Ser  Ser  Ala  Ser  Ser  Gly  Pro  Ala  Leu  Leu  Arg
                     35                       40                       45

GTG  GGC  CCG  GGC  TTC  GAC  GCG  GCG  CTG  CAG  GTC  TCG  GCC  GCC  ATC   180
Val  Gly  Pro  Gly  Phe  Asp  Ala  Ala  Leu  Gln  Val  Ser  Ala  Ala  Ile
                     50                       55                       60

GGC  ACC  AAC  CTG  CGC  CGG  TTC  CGG  GCC  GTG  TTT  GGG  GAG  AGC  GGC   225
Gly  Thr  Asn  Leu  Arg  Arg  Phe  Arg  Ala  Val  Phe  Gly  Glu  Ser  Gly
                     65                       70                       75

GGG  GGA  GGC  GGC  AGC  GGA  GAG  GAT  GAG  CAA  TTC  TTA  GGT  TTT  GGC   270
Gly  Gly  Gly  Gly  Ser  Gly  Glu  Asp  Glu  Gln  Phe  Leu  Gly  Phe  Gly
                     80                       85                       90

TCA  GAT  GAA  GAA  GTC  AGA  GTG  CGA  AGT  CCC  ACA  AGG  TCT  CCT  TCA   315
```

```
Ser  Asp  Glu  Glu  Val  Arg  Val  Arg  Ser  Pro  Thr  Arg  Ser  Pro  Ser
                    95                       100                      105

GTT  AAA  ACT  AGT  CCT  CGA  AAA  CCT  CGT  GGG  AGA  CCT  AGA  AGT  GGC   360
Val  Lys  Thr  Ser  Pro  Arg  Lys  Pro  Arg  Gly  Arg  Pro  Arg  Ser  Gly
                    110                      115                      120

TCT  GAC  CGA  AAT  TCA  GCT  ATC  CTC  TCA  GAT  CCA  TCT  GTG  TTT  TCC   405
Ser  Asp  Arg  Asn  Ser  Ala  Ile  Leu  Ser  Asp  Pro  Ser  Val  Phe  Ser
                    125                      130                      135

CCT  CTA  AAT  AAA  TCA  GAG  ACC  AAA  TCT  GGA  GAT  AAG  ATC  AAG  AAG   450
Pro  Leu  Asn  Lys  Ser  Glu  Thr  Lys  Ser  Gly  Asp  Lys  Ile  Lys  Lys
                    140                      145                      150

AAA  GAT  TCT  AAA  AGT  ATA  GAA  AAG  AAG  AGA  GGA  AGA  CCT  CCC  ACC   495
Lys  Asp  Ser  Lys  Ser  Ile  Glu  Lys  Lys  Arg  Gly  Arg  Pro  Pro  Thr
                    155                      160                      165

TTC  CCT  GGA  GTA  AAA  ATC  AAA  ATA  ACA  CAT  GGA  AAG  GAC  ATT  TCA   540
Phe  Pro  Gly  Val  Lys  Ile  Lys  Ile  Thr  His  Gly  Lys  Asp  Ile  Ser
                    170                      175                      180

GAG  TTA  CCA  AAG  GGA  AAC  AAA  GAA  GAT  AGC  CTG  AAA  AAA  ATT  AAA   585
Glu  Leu  Pro  Lys  Gly  Asn  Lys  Glu  Asp  Ser  Leu  Lys  Lys  Ile  Lys
                    185                      190                      195

AGG  ACA  CCT  TCT  GCT  ACG  TTT  CAG  CAA  GCC  ACA  AAG  ATT  AAA  AAA   630
Arg  Thr  Pro  Ser  Ala  Thr  Phe  Gln  Gln  Ala  Thr  Lys  Ile  Lys  Lys
                    200                      205                      210

TTA  AGA  GCA  GGT  AAA  CTC  TCT  CCT  CTC  AAG  TCT  AAG  TTT  AAG  ACA   675
Leu  Arg  Ala  Gly  Lys  Leu  Ser  Pro  Leu  Lys  Ser  Lys  Phe  Lys  Thr
                    215                      220                      225

GGG  AAG  CTT  CAA  ATA  GGA  AGG  AAG  GGG  GTA  CAA  ATT  GTA  CGA  CGG   720
Gly  Lys  Leu  Gln  Ile  Gly  Arg  Lys  Gly  Val  Gln  Ile  Val  Arg  Arg
                    230                      235                      240

AGA  GGA  AGG  CCT  CCA  TCA  ACA  GAA  AGG  ATA  AAG  ACC  CCT  TCG  GGT   765
Arg  Gly  Arg  Pro  Pro  Ser  Thr  Glu  Arg  Ile  Lys  Thr  Pro  Ser  Gly
                    245                      250                      255

CTC  CTC  ATT  AAT  TCT  GAA  CTG  GAA  AAG  CCC  CAG  AAA  GTC  CGG  AAA   810
Leu  Leu  Ile  Asn  Ser  Glu  Leu  Glu  Lys  Pro  Gln  Lys  Val  Arg  Lys
                    260                      265                      270

GAC  AAG  GAA  GGA  ACA  CCT  CCA  CTT  ACA  AAA  GAA  GAT  AAG  ACA  GTT   855
Asp  Lys  Glu  Gly  Thr  Pro  Pro  Leu  Thr  Lys  Glu  Asp  Lys  Thr  Val
                    275                      280                      285

GTC  AGA  CAA  AGC  CCT  CGA  AGG  ATT  AAG  CCA  GTT  AGG  ATT  ATT  CCT   900
Val  Arg  Gln  Ser  Pro  Arg  Arg  Ile  Lys  Pro  Val  Arg  Ile  Ile  Pro
                    290                      295                      300

TCT  TCA  AAA  AGG  ACA  GAT  GCA  ACC  ATT  GCT  AAG  CAA  CTC  TTA  CAG   945
Ser  Ser  Lys  Arg  Thr  Asp  Ala  Thr  Ile  Ala  Lys  Gln  Leu  Leu  Gln
                    305                      310                      315

AGG  GCA  AAA  AAG  GGG  GCT  CAA  AAG  AAA  ATT  GAA  AAA  GAA  GCA  GCT   990
Arg  Ala  Lys  Lys  Gly  Ala  Gln  Lys  Lys  Ile  Glu  Lys  Glu  Ala  Ala
                    320                      325                      330

CAG  CTG  CAG  GGA  AGA  AAG  GTG  AAG  ACA  CAG  GTC  AAA  AAT  ATT  CGA  1035
Gln  Leu  Gln  Gly  Arg  Lys  Val  Lys  Thr  Gln  Val  Lys  Asn  Ile  Arg
                    335                      340                      345

CAG  TTC  ATC  ATG  CCT  GTT  GTC  AGT  GCT  ATC  TCC  TCG  CGG  ATC  ATT  1080
Gln  Phe  Ile  Met  Pro  Val  Val  Ser  Ala  Ile  Ser  Ser  Arg  Ile  Ile
                    350                      355                      360

AAG  ACC  CCT  CGG  CGG  TTT  ATA  GAG  GAT  GAG  GAT  TAT  GAC  CCT  CCA  1125
Lys  Thr  Pro  Arg  Arg  Phe  Ile  Glu  Asp  Glu  Asp  Tyr  Asp  Pro  Pro
                    365                      370                      375

ATT  AAA  ATT  GCC  CGA  TTA  GAG  TCT  ACA  CCG  AAT  AGT  AGA  TTC  AGT  1170
Ile  Lys  Ile  Ala  Arg  Leu  Glu  Ser  Thr  Pro  Asn  Ser  Arg  Phe  Ser
                    380                      385                      390

GCC  CCG  TCC  TGT  GGA  TCT  TCT  GAA  AAA  TCA  AGT  GCA  GCT  TCT  CAG  1215
```

|  |  |  |  |  |  |  |  |  |  |  |  |  |  |  |
|---|---|---|---|---|---|---|---|---|---|---|---|---|---|---|
| Ala | Pro | Ser | Cys | Gly | Ser | Ser | Glu | Lys | Ser | Ser | Ala | Ala | Ser | Gln |
|  |  |  |  | 395 |  |  |  | 400 |  |  |  |  |  | 405 |

```
CAC TCC TCT CAA ATG TCT TCA GAC TCC TCT CGA TCT AGT AGC CCC    1260
His Ser Ser Gln Met Ser Ser Asp Ser Ser Arg Ser Ser Ser Pro
            410             415                         420

AGT GTT GAT ACC TCC ACA GAC TCT CAG GCT TCT GAG GAG ATT CAG    1305
Ser Val Asp Thr Ser Thr Asp Ser Gln Ala Ser Glu Glu Ile Gln
            425             430                         435

GTA CTT CCT GAG GAG CGG AGC GAT ACC CCT GAA GTT CAT CCT CCA    1350
Val Leu Pro Glu Glu Arg Ser Asp Thr Pro Glu Val His Pro Pro
            440             445                         450

CTG CCC ATT TCC CAG TCC CCA GAA AAT GAG AGT AAT GAT AGG AGA    1395
Leu Pro Ile Ser Gln Ser Pro Glu Asn Glu Ser Asn Asp Arg Arg
            455             460                         465

AGC AGA AGG TAT TCA GTG TCG GAG AGA AGT TTT GGA TCT AGA ACG    1440
Ser Arg Arg Tyr Ser Val Ser Glu Arg Ser Phe Gly Ser Arg Thr
            470             475                         480

ACG AAA AAA TTA TCA ACT CTA CAA AGT GCC CCC CAG CAG GAG ACC    1485
Thr Lys Lys Leu Ser Thr Leu Gln Ser Ala Pro Gln Gln Glu Thr
            485             490                         495

TCC TCG TCT CCA CCT CCA CCT CTG CTG ACT CCA CCG CCA CCA CTG    1530
Ser Ser Ser Pro Pro Pro Pro Leu Leu Thr Pro Pro Pro Pro Leu
            500             505                         510

CAG CCA GCC TCC AGT ATC TCT GAC CAC ACA CCT TGG CTT ATG CCT    1575
Gln Pro Ala Ser Ser Ile Ser Asp His Thr Pro Trp Leu Met Pro
            515             520                         525

CCA ACA ATC CCC TTA GCA TCA CCA TTT TTG CCT GCT TCC ACT GCT    1620
Pro Thr Ile Pro Leu Ala Ser Pro Phe Leu Pro Ala Ser Thr Ala
            530             535                         540

CCT ATG CAA GGG AAG CGA AAA TCT ATT TTG CGA GAA CCG ACA TTT    1665
Pro Met Gln Gly Lys Arg Lys Ser Ile Leu Arg Glu Pro Thr Phe
            545             550                         555

AGG TGG ACT TCT TTA AAG CAT TCT AGG TCA GAG CCA CAA TAC TTT    1710
Arg Trp Thr Ser Leu Lys His Ser Arg Ser Glu Pro Gln Tyr Phe
            560             565                         570

TCC TCA GCA AAG TAT GCC AAA GAA GGT CTT ATT CGC AAA CCA ATA    1755
Ser Ser Ala Lys Tyr Ala Lys Glu Gly Leu Ile Arg Lys Pro Ile
            575             580                         585

TTT GAT AAT TTC CGA CCC CCT CCA CTA ACT CCC GAG GAC GTT GGC    1800
Phe Asp Asn Phe Arg Pro Pro Pro Leu Thr Pro Glu Asp Val Gly
            590             595                         600

TTT GCA TCT GGT TTT TCT GCA TCT GGT ACC GCT GCT TCA GCC CGA    1845
Phe Ala Ser Gly Phe Ser Ala Ser Gly Thr Ala Ala Ser Ala Arg
            605             610                         615

TTG TTT TCG CCA CTC CAT TCT GGA ACA AGG TTT GAT ATG CAC AAA    1890
Leu Phe Ser Pro Leu His Ser Gly Thr Arg Phe Asp Met His Lys
            620             625                         630

AGG AGC CCT CTT CTG AGA GCT CCA AGA TTT ACT CCA AGT GAG GCT    1935
Arg Ser Pro Leu Leu Arg Ala Pro Arg Phe Thr Pro Ser Glu Ala
            635             640                         645

CAC TCT AGA ATA TTT GAG TCT GTA ACC TTG CCT AGT AAT CGA ACT    1980
His Ser Arg Ile Phe Glu Ser Val Thr Leu Pro Ser Asn Arg Thr
            650             655                         660

TCT GCT GGA ACA TCT TCT TCA GGA GTA TCC AAT AGA AAA AGG AAA    2025
Ser Ala Gly Thr Ser Ser Ser Gly Val Ser Asn Arg Lys Arg Lys
            665             670                         675

AGA AAA GTG TTT AGT CCT ATT CGA TCT GAA CCA AGA TCT CCT TCT    2070
Arg Lys Val Phe Ser Pro Ile Arg Ser Glu Pro Arg Ser Pro Ser
            680             685                         690

CAC TCC ATG AGG ACA AGA AGT GGA AGG CTT AGT AGT TCT GAG CTC    2115
```

```
            His Ser Met Arg Thr Arg Ser Gly Arg Leu Ser Ser Ser Glu Leu
                        695             700                 705

TCA CCT CTC ACC CCC CCG TCT TCT GTC TCT TCC TCG TTA AGC ATT           2160
Ser Pro Leu Thr Pro Pro Ser Ser Val Ser Ser Ser Leu Ser Ile
            710             715                 720

TCT GTT AGT CCT CTT GCC ACT AGT GCC TTA AAC CCA ACT TTT ACT           2205
Ser Val Ser Pro Leu Ala Thr Ser Ala Leu Asn Pro Thr Phe Thr
            725             730                 735

TTT CCT TCT CAT TCC CTG ACT CAG TCT GGG GAA TCT GCA GAG AAA           2250
Phe Pro Ser His Ser Leu Thr Gln Ser Gly Glu Ser Ala Glu Lys
            740             745                 750

AAT CAG AGA CCA AGG AAG CAG ACT AGT GCT CCG GCA GAG CCA TTT           2295
Asn Gln Arg Pro Arg Lys Gln Thr Ser Ala Pro Ala Glu Pro Phe
            755             760                 765

TCA TCA AGT AGT CCT ACT CCT CTC TTC CCT TGG TTT ACC CCA GGC           2340
Ser Ser Ser Ser Pro Thr Pro Leu Phe Pro Trp Phe Thr Pro Gly
            770             775                 780

TCT CAG ACT GAA AGA GGG AGA AAT AAA GAC AAG GCC CCC GAG GAG           2385
Ser Gln Thr Glu Arg Gly Arg Asn Lys Asp Lys Ala Pro Glu Glu
            785             790                 795

CTG TCC AAA GAT CGA GAT GCT GAC AAG AGC GTG GAG AAG GAC AAG           2430
Leu Ser Lys Asp Arg Asp Ala Asp Lys Ser Val Glu Lys Asp Lys
            800             805                 810

AGT AGA GAG AGA GAC CGG GAG AGA GAA AAG GAG AAT AAG CGG GAG           2475
Ser Arg Glu Arg Asp Arg Glu Arg Glu Lys Glu Asn Lys Arg Glu
            815             820                 825

TCA AGG AAA GAG AAA AGG AAA AAG GGA TCA GAA ATT CAG AGT AGT           2520
Ser Arg Lys Glu Lys Arg Lys Lys Gly Ser Glu Ile Gln Ser Ser
            830             835                 840

TCT GCT TTG TAT CCT GTG GGT AGG GTT TCC AAA GAG AAG GTT GTT           2565
Ser Ala Leu Tyr Pro Val Gly Arg Val Ser Lys Glu Lys Val Val
            845             850                 855

GGT GAA GAT GTT GCC ACT TCA TCT TCT GCC AAA AAA GCA ACA GGG           2610
Gly Glu Asp Val Ala Thr Ser Ser Ser Ala Lys Lys Ala Thr Gly
            860             865                 870

CGG AAG AAG TCT TCA TCA CAT GAT TCT GGG ACT GAT ATT ACT TCT           2655
Arg Lys Lys Ser Ser Ser His Asp Ser Gly Thr Asp Ile Thr Ser
            875             880                 885

GTG ACT CTT GGG GAT ACA ACA GCT GTC AAA ACC AAA ATA CTT ATA           2700
Val Thr Leu Gly Asp Thr Thr Ala Val Lys Thr Lys Ile Leu Ile
            890             895                 900

AAG AAA GGG AGA GGA AAT CTG GAA AAA ACC AAC TTG GAC CTC GGC           2745
Lys Lys Gly Arg Gly Asn Leu Glu Lys Thr Asn Leu Asp Leu Gly
            905             910                 915

CCA ACT GCC CCA TCC CTG GAG AAG GAG AAA ACC CTC TGC CTT TCC           2790
Pro Thr Ala Pro Ser Leu Glu Lys Glu Lys Thr Leu Cys Leu Ser
            920             925                 930

ACT CCT TCA TCT AGC ACT GTT AAA CAT TCC ACT TCC TCC ATA GGC           2835
Thr Pro Ser Ser Ser Thr Val Lys His Ser Thr Ser Ser Ile Gly
            935             940                 945

TCC ATG TTG GCT CAG GCA GAC AAG CTT CCA ATG ACT GAC AAG AGG           2880
Ser Met Leu Ala Gln Ala Asp Lys Leu Pro Met Thr Asp Lys Arg
            950             955                 960

GTT GCC AGC CTC CTA AAA AAG GCC AAA GCT CAG CTC TGC AAG ATT           2925
Val Ala Ser Leu Leu Lys Lys Ala Lys Ala Gln Leu Cys Lys Ile
            965             970                 975

GAG AAG AGT AAG AGT CTT AAA CAA ACC GAC CAG CCC AAA GCA CAG           2970
Glu Lys Ser Lys Ser Leu Lys Gln Thr Asp Gln Pro Lys Ala Gln
            980             985                 990

GGT CAA GAA AGT GAC TCA TCA GAG ACC TCT GTG CGA GGA CCC CGG           3015
```

```
              Gly  Gln  Glu  Ser  Asp  Ser  Ser  Glu  Thr  Ser  Val  Arg  Gly  Pro  Arg
                             995                      1000                     1005

ATT  AAA  CAT  GTC  TGC  AGA  AGA  GCA  GCT  GTT  GCC  CTT  GGC  CGA  AAA      3060
Ile  Lys  His  Val  Cys  Arg  Arg  Ala  Ala  Val  Ala  Leu  Gly  Arg  Lys
               1010                     1015                     1020

CGA  GCT  GTG  TTT  CCT  GAT  GAC  ATG  CCC  ACC  CTG  AGT  GCC  TTA  CCA      3105
Arg  Ala  Val  Phe  Pro  Asp  Asp  Met  Pro  Thr  Leu  Ser  Ala  Leu  Pro
               1025                     1030                     1035

TGG  GAA  GAA  CGA  GAA  AAG  ATT  TTG  TCT  TCC  ATG  GGG  AAT  GAT  GAC      3150
Trp  Glu  Glu  Arg  Glu  Lys  Ile  Leu  Ser  Ser  Met  Gly  Asn  Asp  Asp
               1040                     1045                     1050

AAG  TCA  TCA  ATT  GCT  GGC  TCA  GAA  GAT  GCT  GAA  CCT  CTT  GCT  CCA      3195
Lys  Ser  Ser  Ile  Ala  Gly  Ser  Glu  Asp  Ala  Glu  Pro  Leu  Ala  Pro
               1055                     1060                     1065

CCC  ATC  AAA  CCA  ATT  AAA  CCT  GTC  ACT  AGA  AAC  AAG  GCA  CCC  CAG      3240
Pro  Ile  Lys  Pro  Ile  Lys  Pro  Val  Thr  Arg  Asn  Lys  Ala  Pro  Gln
               1070                     1075                     1080

GAA  CCT  CCA  GTA  AAG  AAA  GGA  CGT  CGA  TCG  AGG  CGG  TGT  GGG  CAG      3285
Glu  Pro  Pro  Val  Lys  Lys  Gly  Arg  Arg  Ser  Arg  Arg  Cys  Gly  Gln
               1085                     1090                     1095

TGT  CCC  GGC  TGC  CAG  GTG  CCT  GAG  GAC  TGT  GGT  GTT  TGT  ACT  AAT      3330
Cys  Pro  Gly  Cys  Gln  Val  Pro  Glu  Asp  Cys  Gly  Val  Cys  Thr  Asn
               1100                     1105                     1110

TGC  TTA  GAT  AAG  CCC  AAG  TTT  GGT  GGT  CGC  AAT  ATA  AAG  AAG  CAG      3375
Cys  Leu  Asp  Lys  Pro  Lys  Phe  Gly  Gly  Arg  Asn  Ile  Lys  Lys  Gln
               1115                     1120                     1125

TGC  TGC  AAG  ATG  AGA  AAA  TGT  CAG  AAT  CTA  CAA  TGG  ATG  CCT  TCC      3420
Cys  Cys  Lys  Met  Arg  Lys  Cys  Gln  Asn  Leu  Gln  Trp  Met  Pro  Ser
               1130                     1135                     1140

AAA  GCC  TAC  CTG  CAG  AAG  CAA  GCT  AAA  GCT  GTG  AAA  AAG  AAA  GAG      3465
Lys  Ala  Tyr  Leu  Gln  Lys  Gln  Ala  Lys  Ala  Val  Lys  Lys  Lys  Glu
               1145                     1150                     1155

AAA  AAG  TCT  AAG  ACC  AGT  GAA  AAG  AAA  GAC  AGC  AAA  GAG  AGC  AGT      3510
Lys  Lys  Ser  Lys  Thr  Ser  Glu  Lys  Lys  Asp  Ser  Lys  Glu  Ser  Ser
               1160                     1165                     1170

GTT  GTG  AAG  AAC  GTG  GTG  GAC  TCT  AGT  CAG  AAA  CCT  ACC  CCA  TCA      3555
Val  Val  Lys  Asn  Val  Val  Asp  Ser  Ser  Gln  Lys  Pro  Thr  Pro  Ser
               1175                     1180                     1185

GCA  AGA  GAG  GAT  CCT  GCC  CCA  AAG  AAA  AGC  AGT  AGT  GAG  CCT  CCT      3600
Ala  Arg  Glu  Asp  Pro  Ala  Pro  Lys  Lys  Ser  Ser  Ser  Glu  Pro  Pro
               1190                     1195                     1200

CCA  CGA  AAG  CCC  GTC  GAG  GAA  AAG  AGT  GAA  GAA  GGG  AAT  GTC  TCG      3645
Pro  Arg  Lys  Pro  Val  Glu  Glu  Lys  Ser  Glu  Glu  Gly  Asn  Val  Ser
               1205                     1210                     1215

GCC  CCT  GGG  CCT  GAA  TCC  AAA  CAG  GCC  ACC  ACT  CCA  GCT  TCC  AGG      3690
Ala  Pro  Gly  Pro  Glu  Ser  Lys  Gln  Ala  Thr  Thr  Pro  Ala  Ser  Arg
               1220                     1225                     1230

AAG  TCA  AGC  AAG  CAG  GTC  TCC  CAG  CCA  GCA  CTG  GTC  ATC  CCG  CCT      3735
Lys  Ser  Ser  Lys  Gln  Val  Ser  Gln  Pro  Ala  Leu  Val  Ile  Pro  Pro
               1235                     1240                     1245

CAG  CCA  CCT  ACT  ACA  GGA  CCG  CCA  AGA  AAA  GAA  GTT  CCC  AAA  ACC      3780
Gln  Pro  Pro  Thr  Thr  Gly  Pro  Pro  Arg  Lys  Glu  Val  Pro  Lys  Thr
               1250                     1255                     1260

ACT  CCT  AGT  GAG  CCC  AAG  AAA  AAG  CAG  CCT  CCA  CCA  CCA  GAA  TCA      3825
Thr  Pro  Ser  Glu  Pro  Lys  Lys  Lys  Gln  Pro  Pro  Pro  Pro  Glu  Ser
               1265                     1270                     1275

GGT  CCA  GAG  CAG  AGC  AAA  CAG  AAA  AAA  GTG  GCT  CCC  CGC  CCA  AGT      3870
Gly  Pro  Glu  Gln  Ser  Lys  Gln  Lys  Lys  Val  Ala  Pro  Arg  Pro  Ser
               1280                     1285                     1290

ATC  CCT  GTA  AAA  CAA  AAA  CCA  AAA  GAA  AAG  GAA  AAA  CCA  CCT  CCG      3915
```

```
Ile Pro Val Lys Gln Lys Pro Lys Glu Lys Glu Lys Pro Pro Pro
        1295                1300               1305

GTC AAT AAG CAG GAG AAT GCA GGC ACT TTG AAC ATC CTC AGC ACT   3960
Val Asn Lys Gln Glu Asn Ala Gly Thr Leu Asn Ile Leu Ser Thr
        1310                1315               1320

CTC TCC AAT GGC AAT AGT TCT AAG CAA AAA ATT CCA GCA GAT GGA   4005
Leu Ser Asn Gly Asn Ser Ser Lys Gln Lys Ile Pro Ala Asp Gly
        1325                1330               1335

GTC CAC AGG ATC AGA GTG GAC TTT AAG GAG GAT TGT GAA GCA GAA   4050
Val His Arg Ile Arg Val Asp Phe Lys Glu Asp Cys Glu Ala Glu
        1340                1345               1350

AAT GTG TGG GAG ATG GGA GGC TTA GGA ATC TTG ACT TCT GTT CCT   4095
Asn Val Trp Glu Met Gly Gly Leu Gly Ile Leu Thr Ser Val Pro
        1355                1360               1365

ATA ACA CCC AGG GTG GTT TGC TTT CTC TGT GCC AGT AGT GGG CAT   4140
Ile Thr Pro Arg Val Val Cys Phe Leu Cys Ala Ser Ser Gly His
        1370                1375               1380

GTA GAG TTT GTG TAT TGC CAA GTC TGT TGT GAG CCC TTC CAC AAG   4185
Val Glu Phe Val Tyr Cys Gln Val Cys Cys Glu Pro Phe His Lys
        1385                1390               1395

TTT TGT TTA GAG GAG AAC GAG CGC CCT CTG GAG GAC CAG CTG GAA   4230
Phe Cys Leu Glu Glu Asn Glu Arg Pro Leu Glu Asp Gln Leu Glu
        1400                1405               1410

AAT TGG TGT TGT CGT CGT TGC AAA TTC TGT CAC GTT TGT GGA AGG   4275
Asn Trp Cys Cys Arg Arg Cys Lys Phe Cys His Val Cys Gly Arg
        1415                1420               1425

CAA CAT CAG GCT ACA AAG CAG CTG CTG GAG TGT AAT AAG TGC CGA   4320
Gln His Gln Ala Thr Lys Gln Leu Leu Glu Cys Asn Lys Cys Arg
        1430                1435               1440

AAC AGC TAT CAC CCT GAG TGC CTG GGA CCA AAC TAC CCC ACC AAA   4365
Asn Ser Tyr His Pro Glu Cys Leu Gly Pro Asn Tyr Pro Thr Lys
        1445                1450               1455

CCC ACA AAG AAG AAG AAA GTC TGG ATC TGT ACC AAG TGT GTT CGC   4410
Pro Thr Lys Lys Lys Lys Val Trp Ile Cys Thr Lys Cys Val Arg
        1460                1465               1470

TGT AAG AGC TGT GGA TCC ACA ACT CCA GGC AAA GGG TGG GAT GCA   4455
Cys Lys Ser Cys Gly Ser Thr Thr Pro Gly Lys Gly Trp Asp Ala
        1475                1480               1485

CAG TGG TCT CAT GAT TTC TCA CTG TGT CAT GAT TGC GCC AAG CTC   4500
Gln Trp Ser His Asp Phe Ser Leu Cys His Asp Cys Ala Lys Leu
        1490                1495               1500

TTT GCT AAA GGA AAC TTC TGC CCT CTC TGT GAC AAA TGT TAT GAT   4545
Phe Ala Lys Gly Asn Phe Cys Pro Leu Cys Asp Lys Cys Tyr Asp
        1505                1510               1515

GAT GAT GAC TAT GAG AGT AAG ATG ATG CAA TGT GGA AAG TGT GAT   4590
Asp Asp Asp Tyr Glu Ser Lys Met Met Gln Cys Gly Lys Cys Asp
        1520                1525               1530

CGC TGG GTC CAT TCC AAA TGT GAG AAT CTT TCA GGT ACA GAA GAT   4635
Arg Trp Val His Ser Lys Cys Glu Asn Leu Ser Gly Thr Glu Asp
        1535                1540               1545

GAG ATG TAT GAG ATT CTA TCT AAT CTG CCA GAA AGT GTG GCC TAC   4680
Glu Met Tyr Glu Ile Leu Ser Asn Leu Pro Glu Ser Val Ala Tyr
        1550                1555               1560

ACT TGT GTG AAC TGT ACT GAG CGG CAC CCT GCA GAG TGG CGA CTG   4725
Thr Cys Val Asn Cys Thr Glu Arg His Pro Ala Glu Trp Arg Leu
        1565                1570               1575

GCC CTT GAA AAA GAG CTG CAG ATT TCT CTG AAG CAA GTT CTG ACA   4770
Ala Leu Glu Lys Glu Leu Gln Ile Ser Leu Lys Gln Val Leu Thr
        1580                1585               1590

GCT TTG TTG AAT TCT CGG ACT ACC AGC CAT TTG CTA CGC TAC CGG   4815
```

-continued

```
Ala Leu Leu Asn Ser Arg Thr Thr Ser His Leu Leu Arg Tyr Arg
            1595                1600            1605

CAG GCT GCC AAG CCT CCA GAC TTA AAT CCC GAG ACA GAG GAG AGT    4860
Gln Ala Ala Lys Pro Pro Asp Leu Asn Pro Glu Thr Glu Glu Ser
            1610                1615            1620

ATA CCT TCC CGC AGC TCC CCC GAA GGA CCT GAT CCA CCA GTT CTT    4905
Ile Pro Ser Arg Ser Ser Pro Glu Gly Pro Asp Pro Pro Val Leu
            1625                1630            1635

ACT GAG GTC AGC AAA CAG GAT GAT CAG CAG CCT TTA GAT CTA GAA    4950
Thr Glu Val Ser Lys Gln Asp Asp Gln Gln Pro Leu Asp Leu Glu
            1640                1645            1650

GGA GTC AAG AGG AAG ATG GAC CAA GGG AAT TAC ACA TCT GTG TTG    4995
Gly Val Lys Arg Lys Met Asp Gln Gly Asn Tyr Thr Ser Val Leu
            1655                1660            1665

GAG TTC AGT GAT GAT ATT GTG AAG ATC ATT CAA GCA GCC ATT AAT    5040
Glu Phe Ser Asp Asp Ile Val Lys Ile Ile Gln Ala Ala Ile Asn
            1670                1675            1680

TCA GAT GGA GGA CAG CCA GAA ATT AAA AAA GCC AAC AGC ATG GTC    5085
Ser Asp Gly Gly Gln Pro Glu Ile Lys Lys Ala Asn Ser Met Val
            1685                1690            1695

AAG TCC TTC TTC ATT CGG CAA ATG GAA CGT GTT TTT CCA TGG TTC    5130
Lys Ser Phe Phe Ile Arg Gln Met Glu Arg Val Phe Pro Trp Phe
            1700                1705            1710

AGT GTC AAA AAG TCC AGG TTT TGG GAG CCA AAT AAA GTA TCA AGC    5175
Ser Val Lys Lys Ser Arg Phe Trp Glu Pro Asn Lys Val Ser Ser
            1715                1720            1725

AAC AGT GGG ATG TTA CCA AAC GCA GTG CTT CCA CCT TCA CTT GAC    5220
Asn Ser Gly Met Leu Pro Asn Ala Val Leu Pro Pro Ser Leu Asp
            1730                1735            1740

CAT AAT TAT GCT CAG TGG CAG GAG CGA GAG GAA AAC AGC CAC ACT    5265
His Asn Tyr Ala Gln Trp Gln Glu Arg Glu Glu Asn Ser His Thr
            1745                1750            1755

GAG CAG CCT CCT TTA ATG AAG AAA ATC ATT CCA GCT CCC AAA CCC    5310
Glu Gln Pro Pro Leu Met Lys Lys Ile Ile Pro Ala Pro Lys Pro
            1760                1765            1770

AAA GGT CCT GGA GAA CCA GAC TCA CCA ACT CCT CTG CAT CCT CCT    5355
Lys Gly Pro Gly Glu Pro Asp Ser Pro Thr Pro Leu His Pro Pro
            1775                1780            1785

ACA CCA CCA ATT TTG AGT ACT GAT AGG AGT CGA GAA GAC AGT CCA    5400
Thr Pro Pro Ile Leu Ser Thr Asp Arg Ser Arg Glu Asp Ser Pro
            1790                1795            1800

GAG CTG AAC CCA CCC CCA GGC ATA GAA GAC AAT AGA CAG TGT GCG    5445
Glu Leu Asn Pro Pro Pro Gly Ile Glu Asp Asn Arg Gln Cys Ala
            1805                1810            1815

TTA TGT TTG ACT TAT GGT GAT GAC AGT GCT AAT GAT GCT GGT CGT    5490
Leu Cys Leu Thr Tyr Gly Asp Asp Ser Ala Asn Asp Ala Gly Arg
            1820                1825            1830

TTA CTA TAT ATT GGC CAA AAT GAG TGG ACA CAT GTA AAT TGT GCT    5535
Leu Leu Tyr Ile Gly Gln Asn Glu Trp Thr His Val Asn Cys Ala
            1835                1840            184

TTG TGG TCA GCG GAA GTG TTT GAA GAT GAT GAC GGA TCA CTA AAG    5580
Leu Trp Ser Ala Glu Val Phe Glu Asp Asp Asp Gly Ser Leu Lys
            1850                1855            1860

AAT GTG CAT ATG GCT GTG ATC AGG GGC AAG CAG CTG AGA TGT GAA    5625
Asn Val His Met Ala Val Ile Arg Gly Lys Gln Leu Arg Cys Glu
            1865                1870            1875

TTC TGC CAA AAG CCA GGA GCC ACC GTG GGT TGC TGT CTC ACA TCC    5670
Phe Cys Gln Lys Pro Gly Ala Thr Val Gly Cys Cys Leu Thr Ser
            1880                1885            1890

TGC ACC AGC AAC TAT CAC TTC ATG TGT TCC CGA GCC AAG AAC TGT    5715
```

```
Cys Thr Ser Asn Tyr His Phe Met Cys Ser Arg Ala Lys Asn Cys
            1895                1900                1905

GTC TTT CTG GAT GAT AAA AAA GTA TAT TGC CAA CGA CAT CGG GAT      5760
Val Phe Leu Asp Asp Lys Lys Val Tyr Cys Gln Arg His Arg Asp
            1910                1915                1920

TTG ATC AAA GGC GAA GTG GTT CCT GAG AAT GGA TTT GAA GTT TTC      5805
Leu Ile Lys Gly Glu Val Val Pro Glu Asn Gly Phe Glu Val Phe
            1925                1930                1935

AGA AGA GTG TTT GTG GAC TTT GAA GGA ATC AGC TTG AGA AGG AAG      5850
Arg Arg Val Phe Val Asp Phe Glu Gly Ile Ser Leu Arg Arg Lys
            1940                1945                1950

TTT CTC AAT GGC TTG GAA CCA GAA AAT ATC CAC ATG ATG ATT GGG      5895
Phe Leu Asn Gly Leu Glu Pro Glu Asn Ile His Met Met Ile Gly
            1955                1960                1965

TCT ATG ACA ATC GAC TGC TTA GGA ATT CTA AAT GAT CTC TCC GAC      5940
Ser Met Thr Ile Asp Cys Leu Gly Ile Leu Asn Asp Leu Ser Asp
            1970                1975                1980

TGT GAA GAT AAG CTC TTT CCT ATT GGA TAT CAG TGT TCC AGG GTA      5985
Cys Glu Asp Lys Leu Phe Pro Ile Gly Tyr Gln Cys Ser Arg Val
            1985                1990                1995

TAC TGG AGC ACC ACA GAT GCT CGC AAG CGC TGT GTA TAT ACA TGC      6030
Tyr Trp Ser Thr Thr Asp Ala Arg Lys Arg Cys Val Tyr Thr Cys
            2000                2005                2010

AAG ATA GTG GAG TGC CGT CCT CCA GTC GTA GAG CCG GAT ATC AAC      6075
Lys Ile Val Glu Cys Arg Pro Pro Val Val Glu Pro Asp Ile Asn
            2015                2020                2025

AGC ACT GTT GAA CAT GAT GAA AAC AGG ACC ATT GCC CAT AGT CCA      6120
Ser Thr Val Glu His Asp Glu Asn Arg Thr Ile Ala His Ser Pro
            2030                2035                2040

ACA TCT TTT ACA GAA AGT TCA TCA AAA GAG AGT CAA AAC ACA GCT      6165
Thr Ser Phe Thr Glu Ser Ser Ser Lys Glu Ser Gln Asn Thr Ala
            2045                2050                2055

GAA ATT ATA AGT CCT CCA TCA CCA GAC CGA CCT CCT CAT TCA CAA      6210
Glu Ile Ile Ser Pro Pro Ser Pro Asp Arg Pro Pro His Ser Gln
            2060                2065                2070

ACC TCT GGC TCC TGT TAT TAT CAT GTC ATC TCA AAG GTC CCC AGG      6255
Thr Ser Gly Ser Cys Tyr Tyr His Val Ile Ser Lys Val Pro Arg
            2075                2080                2085

ATT CGA ACA CCC AGT TAT TCT CCA ACA CAG AGA TCC CCT GGC TGT      6300
Ile Arg Thr Pro Ser Tyr Ser Pro Thr Gln Arg Ser Pro Gly Cys
            2090                2095                2100

CGA CCG TTG CCT TCT GCA GGA AGT CCT ACC CCA ACC ACT CAT GAA      6345
Arg Pro Leu Pro Ser Ala Gly Ser Pro Thr Pro Thr Thr His Glu
            2105                2110                2115

ATA GTC ACA GTA GGT GAT CCT TTA CTC TCC TCT GGA CTT CGA AGC      6390
Ile Val Thr Val Gly Asp Pro Leu Leu Ser Ser Gly Leu Arg Ser
            2120                2125                2130

ATT GGC TCC AGG CGT CAC AGT ACC TCT TCC TTA TCA CCC CAG CGG      6435
Ile Gly Ser Arg Arg His Ser Thr Ser Ser Leu Ser Pro Gln Arg
            2135                2140                2145

TCC AAA CTC CGG ATA ATG TCT CCA ATG AGA ACT GGG AAT ACT TAC      6480
Ser Lys Leu Arg Ile Met Ser Pro Met Arg Thr Gly Asn Thr Tyr
            2150                2155                2160

TCT AGG AAT AAT GTT TCC TCA GTC TCC ACC ACC GGG ACC GCT ACT      6525
Ser Arg Asn Asn Val Ser Ser Val Ser Thr Thr Gly Thr Ala Thr
            2165                2170                2175

GAT CTT GAA TCA AGT GCC AAA GTA GTT GAT CAT GTC TTA GGG CCA      6570
Asp Leu Glu Ser Ser Ala Lys Val Val Asp His Val Leu Gly Pro
            2180                2185                2190

CTG AAT TCA AGT ACT AGT TTA GGG CAA AAC ACT TCC ACC TCT TCA      6615
```

-continued

```
Leu Asn Ser Ser Thr Ser Leu Gly Gln Asn Thr Ser Thr Ser Ser
            2195                2200                2205

AAT TTG CAA AGG ACA GTG GTT ACT GTA GGC AAT AAA AAC AGT CAC   6660
Asn Leu Gln Arg Thr Val Val Thr Val Gly Asn Lys Asn Ser His
            2210                2215                2220

TTG GAT GGA TCT TCA TCT TCA GAA ATG AAG CAG TCC AGT GCT TCA   6705
Leu Asp Gly Ser Ser Ser Ser Glu Met Lys Gln Ser Ser Ala Ser
            2225                2230                2235

GAC TTG GTG TCC AAG AGC TCC TCT TTA AAG GGA GAG AAG ACC AAA   6750
Asp Leu Val Ser Lys Ser Ser Ser Leu Lys Gly Glu Lys Thr Lys
            2240                2245                2250

GTG CTG AGT TCC AAG AGC TCA GAG GGA TCT GCA CAT AAT GTG GCT   6795
Val Leu Ser Ser Lys Ser Ser Glu Gly Ser Ala His Asn Val Ala
            2255                2260                2265

TAC CCT GGA ATT CCT AAA CTG GCC CCA CAG GTT CAT AAC ACA ACA   6840
Tyr Pro Gly Ile Pro Lys Leu Ala Pro Gln Val His Asn Thr Thr
            2270                2275                2280

TCT AGA GAA CTG AAT GTT AGT AAA ATC GGC TCC TTT GCT GAA CCC   6885
Ser Arg Glu Leu Asn Val Ser Lys Ile Gly Ser Phe Ala Glu Pro
            2285                2290                2295

TCT TCA GTG TCG TTT TCT TCT AAA GAG GCC CTC TCC TTC CCA CAC   6930
Ser Ser Val Ser Phe Ser Ser Lys Glu Ala Leu Ser Phe Pro His
            2300                2305                2310

CTC CAT TTG AGA GGG CAA AGG AAT GAT CGA GAC CAA CAC ACA GAT   6975
Leu His Leu Arg Gly Gln Arg Asn Asp Arg Asp Gln His Thr Asp
            2315                2320                2325

TCT ACC CAA TCA GCA AAC TCC TCT CCA GAT GAA GAT ACT GAA GTC   7020
Ser Thr Gln Ser Ala Asn Ser Ser Pro Asp Glu Asp Thr Glu Val
            2330                2335                2340

AAA ACC TTG AAG CTA TCT GGA ATG AGC AAC AGA TCA TCC ATT ATC   7065
Lys Thr Leu Lys Leu Ser Gly Met Ser Asn Arg Ser Ser Ile Ile
            2345                2350                2355

AAC GAA CAT ATG GGA TCT AGT TCC AGA GAT AGG AGA CAG AAA GGG   7110
Asn Glu His Met Gly Ser Ser Ser Arg Asp Arg Arg Gln Lys Gly
            2360                2365                2370

AAA AAA TCC TGT AAA GAA ACT TTC AAA GAA AAG CAT TCC AGT AAA   7155
Lys Lys Ser Cys Lys Glu Thr Phe Lys Glu Lys His Ser Ser Lys
            2375                2380                2385

TCT TTT TTG GAA CCT GGT CAG GTG ACA ACT GGT GAG GAA GGA AAC   7200
Ser Phe Leu Glu Pro Gly Gln Val Thr Thr Gly Glu Glu Gly Asn
            2390                2395                2400

TTG AAG CCA GAG TTT ATG GAT GAG GTT TTG ACT CCT GAG TAT ATG   7245
Leu Lys Pro Glu Phe Met Asp Glu Val Leu Thr Pro Glu Tyr Met
            2405                2410                2415

GGC CAA CGA CCA TGT AAC AAT GTT TCT TCT GAT AAG ATT GGT GAT   7290
Gly Gln Arg Pro Cys Asn Asn Val Ser Ser Asp Lys Ile Gly Asp
            2420                2425                2430

AAA GGC CTT TCT ATG CCA GGA GTC CCC AAA GCT CCA CCC ATG CAA   7335
Lys Gly Leu Ser Met Pro Gly Val Pro Lys Ala Pro Pro Met Gln
            2435                2440                2445

GTA GAA GGA TCT GCC AAG GAA TTA CAG GCA CCA CGG AAA CGC ACA   7380
Val Glu Gly Ser Ala Lys Glu Leu Gln Ala Pro Arg Lys Arg Thr
            2450                2455                2460

GTC AAA GTG ACA CTG ACA CCT CTA AAA ATG GAA AAT GAG AGT CAA   7425
Val Lys Val Thr Leu Thr Pro Leu Lys Met Glu Asn Glu Ser Gln
            2465                2470                2475

TCC AAA AAT GCC CTG AAA GAA AGT AGT CCT GCT TCC CCT TTG CAA   7470
Ser Lys Asn Ala Leu Lys Glu Ser Ser Pro Ala Ser Pro Leu Gln
            2480                2485                2490

ATA GAG TCA ACA TCT CCC ACA GAA CCA ATT TCA GCC TCT GAA AAT   7515
```

```
Ile Glu Ser Thr Ser Pro Thr Glu Pro Ile Ser Ala Ser Glu Asn
            2495                2500                 2505

CCA GGA GAT GGT CCA GTG GCC CAA CCA AGC CCC AAT AAT ACC TCA   7560
Pro Gly Asp Gly Pro Val Ala Gln Pro Ser Pro Asn Asn Thr Ser
            2510                2515                 2520

TGC CAG GAT TCT CAA AGT AAC AAC TAT CAG AAT CTT CCA GTA CAG   7605
Cys Gln Asp Ser Gln Ser Asn Asn Tyr Gln Asn Leu Pro Val Gln
            2525                2530                 2535

GAC AGA AAC CTA ATG CTT CCA GAT GGC CCC AAA CCT CAG GAG GAT   7650
Asp Arg Asn Leu Met Leu Pro Asp Gly Pro Lys Pro Gln Glu Asp
            2540                2545                 2550

GGC TCT TTT AAA AGG AGG TAT CCC CGT CGC AGT GCC CGT GCA CGT   7695
Gly Ser Phe Lys Arg Arg Tyr Pro Arg Arg Ser Ala Arg Ala Arg
            2555                2560                 2565

TCT AAC ATG TTT TTT GGG CTT ACC CCA CTC TAT GGA GTA AGA TCC   7740
Ser Asn Met Phe Phe Gly Leu Thr Pro Leu Tyr Gly Val Arg Ser
            2570                2575                 2580

TAT GGT GAA GAA GAC ATT CCA TTC TAC AGC AGC TCA ACT GGG AAG   7785
Tyr Gly Glu Glu Asp Ile Pro Phe Tyr Ser Ser Ser Thr Gly Lys
            2585                2590                 2595

AAG CGA GGC AAG AGA TCA GCT GAA GGA CAG GTG GAT GGG GCC GAT   7830
Lys Arg Gly Lys Arg Ser Ala Glu Gly Gln Val Asp Gly Ala Asp
            2600                2605                 2610

GAC TTA AGC ACT TCA GAT GAA GAC GAC TTA TAC TAT TAC AAC TTC   7875
Asp Leu Ser Thr Ser Asp Glu Asp Asp Leu Tyr Tyr Tyr Asn Phe
            2615                2620                 2625

ACT AGA ACA GTG ATT TCT TCA GGT GGA GAG GAA CGA CTG GCA TCC   7920
Thr Arg Thr Val Ile Ser Ser Gly Gly Glu Glu Arg Leu Ala Ser
            2630                2635                 2640

CAT AAT TTA TTT CGG GAG GAG GAA CAG TGT GAT CTT CCA AAA ATC   7965
His Asn Leu Phe Arg Glu Glu Glu Gln Cys Asp Leu Pro Lys Ile
            2645                2650                 2655

TCA CAG TTG GAT GGT GTT GAT GAT GGG ACA GAG AGT GAT ACT AGT   8010
Ser Gln Leu Asp Gly Val Asp Asp Gly Thr Glu Ser Asp Thr Ser
            2660                2665                 2670

GTC ACA GCC ACA ACA AGG AAA AGC AGC CAG ATT CCA AAA AGA AAT   8055
Val Thr Ala Thr Thr Arg Lys Ser Ser Gln Ile Pro Lys Arg Asn
            2675                2680                 2685

GGT AAA GAA AAT GGA ACA GAG AAC TTA AAG ATT GAT AGA CCT GAA   8100
Gly Lys Glu Asn Gly Thr Glu Asn Leu Lys Ile Asp Arg Pro Glu
            2690                2695                 2700

GAT GCT GGG GAG AAA GAA CAT GTC ACT AAG AGT TCT GTT GGC CAC   8145
Asp Ala Gly Glu Lys Glu His Val Thr Lys Ser Ser Val Gly His
            2705                2710                 2715

AAA AAT GAG CCA AAG ATG GAT AAC TGC CAT TCT GTA AGC AGA GTT   8190
Lys Asn Glu Pro Lys Met Asp Asn Cys His Ser Val Ser Arg Val
            2720                2725                 2730

AAA ACA CAG GGA CAA GAT TCC TTG GAA GCT CAG CTC AGC TCA TTG   8235
Lys Thr Gln Gly Gln Asp Ser Leu Glu Ala Gln Leu Ser Ser Leu
            2735                2740                 2745

GAG TCA AGC CGC AGA GTC CAC ACA AGT ACC CCC TCC GAC AAA AAT   8280
Glu Ser Ser Arg Arg Val His Thr Ser Thr Pro Ser Asp Lys Asn
            2750                2755                 2760

TTA CTG GAC ACC TAT AAT ACT GAG CTC CTG AAA TCA GAT TCA GAC   8325
Leu Leu Asp Thr Tyr Asn Thr Glu Leu Leu Lys Ser Asp Ser Asp
            2765                2770                 2775

AAT AAC AAC AGT GAT GAC TGT GGG AAT ATC CTG CCT TCA GAC ATT   8370
Asn Asn Asn Ser Asp Asp Cys Gly Asn Ile Leu Pro Ser Asp Ile
            2780                2785                 2790

ATG GAC TTT GTA CTA AAG AAT ACT CCA TCC ATG CAG GCT TTG GGT   8415
```

```
                Met  Asp  Phe  Val  Leu  Lys  Asn  Thr  Pro  Ser  Met  Gln  Ala  Leu  Gly
                                         2795                2800                     2805

GAG  AGC  CCA  GAG  TCA  TCT  TCA  TCA  GAA  CTC  CTG  AAT  CTT  GGT  GAA       8460
Glu  Ser  Pro  Glu  Ser  Ser  Ser  Ser  Glu  Leu  Leu  Asn  Leu  Gly  Glu
               2810                     2815                          2820

GGA  TTG  GGT  CTT  GAC  AGT  AAT  CGT  GAA  AAA  GAC  ATG  GGT  CTT  TTT       8505
Gly  Leu  Gly  Leu  Asp  Ser  Asn  Arg  Glu  Lys  Asp  Met  Gly  Leu  Phe
                    2825                     2830                     2835

GAA  GTA  TTT  TCT  CAG  CAG  CTG  CCT  ACA  ACA  GAA  CCT  GTG  GAT  AGT       8550
Glu  Val  Phe  Ser  Gln  Gln  Leu  Pro  Thr  Thr  Glu  Pro  Val  Asp  Ser
                    2840                     2845                     2850

AGT  GTC  TCT  TCC  TCT  ATC  TCA  GCA  GAG  GAA  CAG  TTT  GAG  TTG  CCT       8595
Ser  Val  Ser  Ser  Ser  Ile  Ser  Ala  Glu  Glu  Gln  Phe  Glu  Leu  Pro
                    2855                     2860                     2865

CTA  GAG  CTA  CCA  TCT  GAT  CTG  TCT  GTC  TTG  ACC  ACC  CGG  AGT  CCC       8640
Leu  Glu  Leu  Pro  Ser  Asp  Leu  Ser  Val  Leu  Thr  Thr  Arg  Ser  Pro
                    2870                     2875                     2880

ACT  GTC  CCC  AGC  CAG  AAT  CCC  AGT  AGA  CTA  GCT  GTT  ATC  TCA  GAC       8685
Thr  Val  Pro  Ser  Gln  Asn  Pro  Ser  Arg  Leu  Ala  Val  Ile  Ser  Asp
                    2885                     2990                     2895

TCA  GGG  GAG  AAG  AGA  GTA  ACC  ATC  ACA  GAA  AAA  TCT  GTA  GCC  TCC       8730
Ser  Gly  Glu  Lys  Arg  Val  Thr  Ile  Thr  Glu  Lys  Ser  Val  Ala  Ser
               2900                     2905                          2910

TCT  GAA  AGT  GAC  CCA  GCA  CTG  CTG  AGC  CCA  GGA  GTA  GAT  CCA  ACT       8775
Ser  Glu  Ser  Asp  Pro  Ala  Leu  Leu  Ser  Pro  Gly  Val  Asp  Pro  Thr
                    2915                     2920                     2925

CCT  GAA  GGC  CAC  ATG  ACT  CCT  GAT  CAT  TTT  ATC  CAA  GGA  CAC  ATG       8820
Pro  Glu  Gly  His  Met  Thr  Pro  Asp  His  Phe  Ile  Gln  Gly  His  Met
                    2930                     2935                     2940

GAT  GCA  GAC  CAC  ATC  TCT  AGC  CCT  CCT  TGT  GGT  TCA  GTA  GAG  CAA       8865
Asp  Ala  Asp  His  Ile  Ser  Ser  Pro  Pro  Cys  Gly  Ser  Val  Glu  Gln
                    2945                     2950                     2955

GGT  CAT  GGC  AAC  AAT  CAG  GAT  TTA  ACT  AGG  AAC  AGT  AGC  ACC  CCT       8910
Gly  His  Gly  Asn  Asn  Gln  Asp  Leu  Thr  Arg  Asn  Ser  Ser  Thr  Pro
                    2960                     2965                     2970

GGC  CTT  CAG  GTA  CCT  GTT  TCC  CCA  ACT  GTT  CCC  ATC  CAG  AAC  CAG       8955
Gly  Leu  Gln  Val  Pro  Val  Ser  Pro  Thr  Val  Pro  Ile  Gln  Asn  Gln
                    2975                     2980                     2985

AAG  TAT  GTG  CCC  AAT  TCT  ACT  GAT  AGT  CCT  GGC  CCG  TCT  CAG  ATT       9000
Lys  Tyr  Val  Pro  Asn  Ser  Thr  Asp  Ser  Pro  Gly  Pro  Ser  Gln  Ile
                    2990                     2995                     3000

TCC  AAT  GCA  GCT  GTC  CAG  ACC  ACT  CCA  CCC  CAC  CTG  AAG  CCA  GCC       9045
Ser  Asn  Ala  Ala  Val  Gln  Thr  Thr  Pro  Pro  His  Leu  Lys  Pro  Ala
                    3005                     3010                     3015

ACT  GAG  AAA  CTC  ATA  GTT  GTT  AAC  CAG  AAC  ATG  CAG  CCA  CTT  TAT       9090
Thr  Glu  Lys  Leu  Ile  Val  Val  Asn  Gln  Asn  Met  Gln  Pro  Leu  Tyr
                    3020                     3025                     3030

GTT  CTC  CAA  ACT  CTT  CCA  AAT  GGA  GTG  ACC  CAA  AAA  ATC  CAA  TTG       9135
Val  Leu  Gln  Thr  Leu  Pro  Asn  Gly  Val  Thr  Gln  Lys  Ile  Gln  Leu
                    3035                     3040                     3045

ACC  TCT  TCT  GTT  AGT  TCT  ACA  CCC  AGT  GTG  ATG  GAG  ACA  AAT  ACT       9180
Thr  Ser  Ser  Val  Ser  Ser  Thr  Pro  Ser  Val  Met  Glu  Thr  Asn  Thr
                    3050                     3055                     3060

TCA  GTA  TTG  GGA  CCC  ATG  GGA  GGT  GGT  CTC  ACC  CTT  ACC  ACA  GGA       9225
Ser  Val  Leu  Gly  Pro  Met  Gly  Gly  Gly  Leu  Thr  Leu  Thr  Thr  Gly
                    3065                     3070                     3075

CTA  AAT  CCA  AGC  TTG  CCA  ACT  TCT  CAA  TCT  TTG  TTC  CCT  TCT  GCT       9270
Leu  Asn  Pro  Ser  Leu  Pro  Thr  Ser  Gln  Ser  Leu  Phe  Pro  Ser  Ala
                    3080                     3085                     3090

AGC  AAA  GGA  TTG  CTA  CCC  ATG  TCT  CAT  CAC  CAG  CAC  TTA  CAT  TCC       9315
```

```
        Ser Lys Gly Leu Leu Pro Met Ser His His Gln His Leu His Ser
                    3095                3100                3105

TTC CCT GCA GCT ACT CAA AGT AGT TTC CCA CCA AAC ATC AGC AAT  9360
Phe Pro Ala Ala Thr Gln Ser Ser Phe Pro Pro Asn Ile Ser Asn
            3110                3115                3120

CCT CCT TCA GGC CTG CTT ATT GGG GTT CAG CCT CCT CCG GAT CCC  9405
Pro Pro Ser Gly Leu Leu Ile Gly Val Gln Pro Pro Pro Asp Pro
            3125                3130                3135

CAA CTT TTG GTT TCA GAA TCC AGC CAG AGG ACA GAC CTC AGT ACC  9450
Gln Leu Leu Val Ser Glu Ser Ser Gln Arg Thr Asp Leu Ser Thr
            3140                3145                3150

ACA GTA GCC ACT CCA TCC TCT GGA CTC AAG AAA AGA CCC ATA TCT  9495
Thr Val Ala Thr Pro Ser Ser Gly Leu Lys Lys Arg Pro Ile Ser
            3155                3160                3165

CGT CTA CAG ACC CGA AAG AAT AAA AAA CTT GCT CCC TCT AGT ACC  9540
Arg Leu Gln Thr Arg Lys Asn Lys Lys Leu Ala Pro Ser Ser Thr
            3170                3175                3180

CCT TCA AAC ATT GCC CCT TCT GAT GTG GTT TCT AAT ATG ACA TTG  9585
Pro Ser Asn Ile Ala Pro Ser Asp Val Val Ser Asn Met Thr Leu
            3185                3190                3195

ATT AAC TTC ACA CCC TCC CAG CTT CCT AAT CAT CCA AGT CTG TTA  9630
Ile Asn Phe Thr Pro Ser Gln Leu Pro Asn His Pro Ser Leu Leu
            3200                3205                3210

GAT TTG GGG TCA CTT AAT ACT TCA TCT CAC CGA ACT GTC CCC AAC  9675
Asp Leu Gly Ser Leu Asn Thr Ser Ser His Arg Thr Val Pro Asn
            3215                3220                3225

ATC ATA AAA AGA TCT AAA TCT AGC ATC ATG TAT TTT GAA CCG GCA  9720
Ile Ile Lys Arg Ser Lys Ser Ser Ile Met Tyr Phe Glu Pro Ala
            3230                3235                3240

CCC CTG TTA CCA CAG AGT GTG GGA GGA ACT GCT GCC ACA GCG GCA  9765
Pro Leu Leu Pro Gln Ser Val Gly Gly Thr Ala Ala Thr Ala Ala
            3245                3250                3255

GGC ACA TCA ACA ATA AGC CAG GAT ACT AGC CAC CTC ACA TCA GGG  9810
Gly Thr Ser Thr Ile Ser Gln Asp Thr Ser His Leu Thr Ser Gly
            3260                3265                3270

TCT GTG TCT GGC TTG GCA TCC AGT TCC TCT GTC TTG AAT GTT GTA  9855
Ser Val Ser Gly Leu Ala Ser Ser Ser Val Leu Asn Val Val
            3275                3280                3285

TCC ATG CAA ACT ACC ACA ACC CCT ACA AGT AGT GCG TCA GTT CCA  9900
Ser Met Gln Thr Thr Thr Thr Pro Thr Ser Ser Ala Ser Val Pro
            3290                3295                3300

GGA CAC GTC ACC TTA ACC AAC CCA AGG TTG CTT GGT ACC CCA GAT  9945
Gly His Val Thr Leu Thr Asn Pro Arg Leu Leu Gly Thr Pro Asp
            3305                3310                3315

ATT GGC TCA ATA AGC AAT CTT TTA ATC AAA GCT AGC CAG CAG AGC  9990
Ile Gly Ser Ile Ser Asn Leu Leu Ile Lys Ala Ser Gln Gln Ser
            3320                3325                3330

CTG GGG ATT CAG GAC CAG CCT GTG GCT TTA CCG CCA AGT TCA GGA 10035
Leu Gly Ile Gln Asp Gln Pro Val Ala Leu Pro Pro Ser Ser Gly
            3335                3340                3345

ATG TTT CCA CAA CTG GGG ACA TCA CAG ACC CCC TCT ACT GCT GCA 10080
Met Phe Pro Gln Leu Gly Thr Ser Gln Thr Pro Ser Thr Ala Ala
            3350                3355                3360

ATA ACA GCG GCA TCT AGC ATC TGT GTG CTC CCC TCC ACT CAG ACT 10125
Ile Thr Ala Ala Ser Ser Ile Cys Val Leu Pro Ser Thr Gln Thr
            3365                3370                3375

ACG GGC ATA ACA GCC GCT TCA CCT TCT GGG AAA GCA GAC GAA CAC 10170
Thr Gly Ile Thr Ala Ala Ser Pro Ser Gly Glu Ala Asp Glu His
            3380                3385                3390

TAT CAG CTT CAG CAT GTG AAC CAG CTC CTT GCC AGC AAA ACT GGG 10215
```

```
              Tyr Gln Leu Gln His Val Asn Gln Leu Leu Ala Ser Lys Thr Gly
                      3395            3400                3405

ATT CAT TCT TCC CAG CGT GAT CTT GAT TCT GCT TCA GGG CCC CAG       10260
Ile His Ser Ser Gln Arg Asp Leu Asp Ser Ala Ser Gly Pro Gln
            3410                3415                3420

GTA TCC AAC TTT ACC CAG ACG GTA GAC GCT CCT AAT AGC ATG GGA       10305
Val Ser Asn Phe Thr Gln Thr Val Asp Ala Pro Asn Ser Met Gly
            3425                3430                3435

CTG GAG CAG AAC AAG GCT TTA TCC TCA GCT GTG CAA GCC AGC CCC       10350
Leu Glu Gln Asn Lys Ala Leu Ser Ser Ala Val Gln Ala Ser Pro
            3440                3445                3450

ACC TCT CCT GGG GGT TCT CCA TCC TCT CCA TCT TCT GGA CAG CGG       10395
Thr Ser Pro Gly Gly Ser Pro Ser Ser Pro Ser Ser Gly Gln Arg
            3455                3460                3465

TCA GCA AGC CCT TCA GTG CCG GGT CCC ACT AAA CCC AAA CCA AAA       10440
Ser Ala Ser Pro Ser Val Pro Gly Pro Thr Lys Pro Lys Pro Lys
            3470                3475                3480

ACC AAA CGG TTT CAG CTG CCT CTA GAC AAA GGG AAT GGC AAG AAG       10485
Thr Lys Arg Phe Gln Leu Pro Leu Asp Lys Gly Asn Gly Lys Lys
            3485                3490                3495

CAC AAT GTT TCC CAT TTG CGG ACC AGT TCT TCT GAA GCA CAC ATT       10530
His Asn Val Ser His Leu Arg Thr Ser Ser Ser Glu Ala His Ile
            3500                3505                3510

CCA GAC CAA GAA ACG ACA TCC CTG ACC TCA GGC ACA GGG ACT CCA       10575
Pro Asp Gln Glu Thr Thr Ser Leu Thr Ser Gly Thr Gly Thr Pro
            3515                3520                3525

GGA GCA GAG GCT GAG CAG CAG GAT ACA GCT AGC GTG GAG CAG TCC       10620
Gly Ala Glu Ala Glu Gln Gln Asp Thr Ala Ser Val Glu Gln Ser
            3530                3535                3540

TCC CAG AAG GAG TGT GGG CAA CCT GCA GGG CAA GTC GCT GTT CTT       10665
Ser Gln Lys Glu Cys Gly Gln Pro Ala Gly Gln Val Ala Val Leu
            3545                3550                3555

CCG GAA GTT CAG GTG ACC CAA AAT CCA GCA AAT GAA CAA GAA AGT       10710
Pro Glu Val Gln Val Thr Gln Asn Pro Ala Asn Glu Gln Glu Ser
            3560                3565                3570

GCA GAA CCT AAA ACA GTG GAA GAA GAG GAA AGT AAT TTC AGC TCC       10755
Ala Glu Pro Lys Thr Val Glu Glu Glu Glu Ser Asn Phe Ser Ser
            3575                3580                3585

CCA CTG ATG CTT TGG CTT CAG CAA GAA CAA AAG CGG AAG GAA AGC       10800
Pro Leu Met Leu Trp Leu Gln Gln Glu Gln Lys Arg Lys Glu Ser
            3590                3595                3600

ATT ACT GAG AAA AAA CCC AAG AAA GGA CTT GTT TTT GAA ATT TCC       10845
Ile Thr Glu Lys Lys Pro Lys Lys Gly Leu Val Phe Glu Ile Ser
            3605                3610                3615

AGT GAT GAT GGC TTT CAG ATC TGT GCA GAA AGT ATT GAA GAT GCC       10890
Ser Asp Asp Gly Phe Gln Ile Cys Ala Glu Ser Ile Glu Asp Ala
            3620                3625                3530

TGG AAG TCA TTG ACA GAT AAA GTC CAG GAA GCT CGA TCA AAT GCC       10935
Trp Lys Ser Leu Thr Asp Lys Val Gln Glu Ala Arg Ser Asn Ala
            3535                3540                3545

CGC CTA AAG CAG CTC TCA TTT GCA GGT GTT AAC GGT TTG AGG ATG       10980
Arg Leu Lys Gln Leu Ser Phe Ala Gly Val Asn Gly Leu Arg Met
            3550                3555                3560

CTG GGG ATT CTC CAT GAT GCA GTT GTG TTC CTC ATT GAG CAG CTG       11025
Leu Gly Ile Leu His Asp Ala Val Val Phe Leu Ile Glu Gln Leu
            3565                3570                3575

TCT GGT GCC AAG CAC TGT CGA AAT TAC AAA TTC CGT TTC CAC AAG       11070
Ser Gly Ala Lys His Cys Arg Asn Tyr Lys Phe Arg Phe His Lys
            3580                3585                3590

CCA GAG GAG GCC AAT GAA CCC CCC TTG AAC CCT CAC GGC TCA GCC       11115
```

| | | | | | | | | | | | | | | |
|---|---|---|---|---|---|---|---|---|---|---|---|---|---|---|
|Pro|Glu|Glu|Ala|Asn|Glu|Pro|Pro|Leu|Asn|Pro|His|Gly|Ser|Ala|
| | | |3595| | | |3600| | | |3605| | | |

```
AGG GCT GAA GTC CAC CTC AGG AAG TCA GCA TTT GAC ATG TTT AAC   11160
Arg Ala Glu Val His Leu Arg Lys Ser Ala Phe Asp Met Phe Asn
             3610            3615                3620

TTC CTG GCT TCT AAA CAT CGT CAG CCT CCT GAA TAC AAC CCC AAT   11205
Phe Leu Ala Ser Lys His Arg Gln Pro Pro Glu Tyr Asn Pro Asn
             3625            3630                3635

GAT GAA GAA GAG GAG GAG GTA CAG CTG AAG TCA GCT CGG AGG GCA   11250
Asp Glu Glu Glu Glu Glu Val Gln Leu Lys Ser Ala Arg Arg Ala
             3640            3645                3650

ACT AGC ATG GAT CTG CCA ATG CCC ATG CGC TTC CGG CAC TTA AAA   11295
Thr Ser Met Asp Leu Pro Met Pro Met Arg Phe Arg His Leu Lys
             3655            3660                3665

AAG ACT TCT AAG GAG GCA GTT GGT GTC TAC AGG TCT CCC ATC CAT   11340
Lys Thr Ser Lys Glu Ala Val Gly Val Tyr Arg Ser Pro Ile His
             3670            3675                3680

GGC CGG GGT CTT TTC TGT AAG AGA AAC ATT GAT GCA GGT GAG ATG   11385
Gly Arg Gly Leu Phe Cys Lys Arg Asn Ile Asp Ala Gly Glu Met
             3685            3690                3695

GTG ATT GAG TAT GCC GGC AAC GTC ATC CGC TCC ATC CAG ACT GAC   11430
Val Ile Glu Tyr Ala Gly Asn Val Ile Arg Ser Ile Gln Thr Asp
             3700            3705                3710

AAG CGG GAA AAG TAT TAC GAC AGC AAG GGC ATT GGT TGC TAT ATG   11475
Lys Arg Glu Lys Tyr Tyr Asp Ser Lys Gly Ile Gly Cys Tyr Met
             3715            3720                3725

TTC CGA ATT GAT GAC TCA GAG GTA GTG GAT GCC ACC ATG CAT GGA   11520
Phe Arg Ile Asp Asp Ser Glu Val Val Asp Ala Thr Met His Gly
             3730            3735                3740

AAT GCT GCA CGC TTC ATC AAT CAC TCG TGT GAG CCT AAC TGC TAT   11565
Asn Ala Ala Arg Phe Ile Asn His Ser Cys Glu Pro Asn Cys Tyr
             3745            3750                3755

TCT CGG GTC ATC AAT ATT GAT GGG CAG AAG CAC ATT GTC ATC TTT   11610
Ser Arg Val Ile Asn Ile Asp Gly Gln Lys His Ile Val Ile Phe
             3760            3765                3770

GCC ATG CGT AAG ATC TAC CGA GGA GAG GAA CTC ACT TAC GAC TAT   11655
Ala Met Arg Lys Ile Tyr Arg Gly Glu Glu Leu Thr Tyr Asp Tyr
             3775            3780                3785

AAG TTC CCC ATT GAG GAT GCC AGC AAC AAG CTG CCC TGC AAC TGT   11700
Lys Phe Pro Ile Glu Asp Ala Ser Asn Lys Leu Pro Cys Asn Cys
             3790            3795                3800

GGC GCC AAG AAA TGC CGG AAG TTC CTA AAC TAA AGC TGC TCT TCT   11745
Gly Ala Lys Lys Cys Arg Lys Phe Leu Asn
3805                 3810

CCCCCAGTGT TGGAGTGCAA GGAGGCGGGG CCATCCAAAG CAACG           11790

CTGAAGGCCT TTTCCAGCAG CTGGGAGCTC CCGGATTGCG TGGCACAGCT       11840

GAGGGGCCTC TGTGATGGCT GAGCTCTCTT ATGTCCTATA CTCACATCAG       11890

ACATGTGATC ATAGTCCCAG AGACAGAGTT GAGGTCTCGA AGAAAAGATC       11940

CATGATCGGC TTTCTCCTGG GGCCCCTCCA ATTGTTTACT GTTAGAAAGT       11990

GGGAATGGGG TCCCTAGCAG ACTTGCCTGG AAGGAGCCTA TTATAGAGGG       12040

TTGGTTATGT TGGGAGATTG GGCCTGAATT TCTCCACAGA AATAAGTTGC       12090

CATCCTCAGG TTGGCCCTTT CCCAAGCACT GTAAGTGAGT GGGTCAGCCA       12140

AAGCCCCAAA TGGAGGGTTG GTTAGATTCC TGACAGTTTG CCAGCCAGCC       12190

GCCACCTACA GCGTCTGTCG AACAAACAGA GGTCTGGTGG TTTTCCCTAC       12240

TGTCCTCCCA CTCGAGAGTT CACTTCTGGT TGGGAGACAG GATTCCTAGC       12290
```

```
ACCTCCGGTG TCAAAAGGCT GTCATGGGGT TGTGCCAATT AATTACCAAA    12340
CATTGAGCCT GCAGGCTTTG AGTGGGAGTG TTGCCCCCAG GAGCCTTATC    12390
TCAGCCAATT ACCTTTCTTG ACAGTAGGAG CGGCTTCCCT CTCCCATTCC    12440
CTCTTCACTC CCTTTTCTTC CTTTCCCCTG TCTTCATGCC ACTGCTTTCC    12490
CATGCTTCTT TCGGTTGTAG GGGAGACTGA CTGCCTGCTC AAGGACACTC    12540
CCTGCTGGGC ATAGGATGTG CCTGCAAAAA GTTCCTGAG CCTGTAAGCA     12590
CTCCAGGTGG GGAAGTGGAC AGGAGCCATT GGTCATAACC AGACAGAATT    12640
TGGAAACATT TTCATAAAGC TCCATGGAGA GTTTAAAGA AACATATGTA     12690
GCATGATTTT GTAGGAGAGG AAAAAGATTA TTTAAATAGG ATTTAAATCA    12740
TGCAACAACG AGAGTATCAC AGCCAGGATG ACCCTTGGGT CCCATTCCTA    12790
AGACATGGTT ACTTTATTTT CCCCTTGTTA AGACATAGGA AGACTTAATT    12840
TTTAAACGGT CAGTGTCCAG TTGAAGGCAG AACACTAATC AGATTTCAAG    12890
GCCCACAACT TGGGGACTAG ACCACCTTAT GTTGAGGGAA CTCTGCCACC    12940
TGCGTGCAAC CCACAGCTAA AGTAAATTCA ATGACACTAC TGCCCTGATT    12990
ACTCCTTAGG ATGTGGTCAA AACAGCATCA AATGTTTCTT CTCTTCCTTT    13040
CCCCAAGACA GAGTCCTGAA CCTGTTAAAT TAAGTCATTG GATTTACTC     13090
TGTTCTGTTT ACAGTTACT ATTTAAGGTT TTATAAATGT AAATATATTT     13140
TGTATATTTT TCTATGAGAA GCACTTCATA GGGAGAAGCA CTTATGACAA    13190
GGCTATTTTT TAAACCGCGG TATTATCCTA ATTAAAAGA AGATCGGTTT     13240
TTAATAATTT TTTATTTTCA TAGGATGAAG TTAGAGAAAA TATTCAGCTG    13290
TACACACAAA GTCTGGTTTT TCCTGCCCAA CTTCCCCCTG GAAGGTGTAC    13340
TTTTGTTGT TTAATGTGTA GCTTGTTTGT GCCCTGTTGA CATAAATGTT     13390
TCCTGGGTTT GCTCTTTGAC AATAAATGGA GAAGGAAGGT CACCCAACTC    13440
CATTGGGCCA CTCCCCTCCT TCCCTATTG AAGCTCCTCA AAAGGCTACA     13490
GTAATATCTT GATACAACAG ATTCTCTTCT TTCCCGCCTC TCTCCTTTCC    13540
GGCGCAACTT CCAGAGTGGT GGGAGACGGC AATCTTTACA TTTCCCTCAT    13590
CTTTCTTACT TCAGAGTTAG CAAACAACAA GTTGAATGGC AACTTGACAT    13640
TTTTGCATCA CCATCTGCCT CATAGGCCAC TCTTTCCTTT CCCTCTGCCC    13690
ACCAAGTCCT CATATCTGCA GAGAACCCAT TGATCACCTT GTGCCCTCTT    13740
TTGGGGCAGC CTGTTGAAAC TGAAGCACAG TCTGACCACT CACGATAAAG    13790
CAGATTTTCT CTGCCTCTGC CACAAGGTTT CAGAGTAGTG TAGTCCAAGT    13840
AGAGGGTGGG GCACCCTTTT CTCGCCGCAA GAAGCCCATT CCTATGGAAG    13890
TCTAGCAAAG CAATACGACT CAGCCCAGCA CTCTCTGCCC CAGGACTCAT    13940
GGCTCTGCTG TGCCTTCCAT CCTGGGCTCC CTTCTCTCCT GTGACCTTAA    13990
GAACTTTGTC TGGTGGCTTT GCTGGAACAT TGTCACTGTT TTCACTGTCA    14040
TGCAGGGAGC CCAGCACTGT GGCCAGGATG GCAGAGACTT CCTTGTCATC    14090
ATGGAGAAGT GCCAGCAGGG GACTGGGAAA AGCACTCTAC CCAGACCTCA    14140
CCTCCCTTCC TCCTTTTGCC CATGAACAAG ATGCAGTGGC CCTAGGGGTT    14190
CCACTAGTGT CTGCTTTCCT TTATTATTGC ACTGTGTGAG GTTTTTTTGT    14240
AAATCCTTGT ATTCC                                         14255
```

( 2 ) INFORMATION FOR SEQ ID NO: 2:

( i ) SEQUENCE CHARACTERISTICS:
        ( A ) LENGTH: 218
        ( B ) TYPE: amino acid
        ( D ) TOPOLOGY: linear ( x i ) SEQUENCE DESCRIPTION: SEQ ID NO: 2:

```
Arg Ala Leu Cys Phe Leu Cys Gly Ser Thr Gly Leu Asp Pro Leu
              5                  10                  15
Ile Phe Cys Ala Cys Cys Glu Pro Tyr His Gln Tyr Cys Val
             20                  25                  30
Gln Asp Glu Tyr Asn Leu Lys His Gly Ser Phe Glu Asp Thr Thr
             35                  40                  45
Leu Met Gly Ser Leu Leu Glu Thr Thr Val Asn Ala Ser Thr Gly
             50                  55                  60
Pro Ser Ser Ser Leu Asn Gln Leu Thr Gln Arg Leu Asn Trp Leu
             65                  70                  75
Cys Pro Arg Cys Thr Val Cys Tyr Thr Cys Asn Met Ser Ser Gly
             80                  85                  90
Ser Lys Val Lys Cys Gln Lys Cys Gln Lys Asn Tyr His Ser Thr
             95                 100                 105
Cys Leu Gly Thr Ser Lys Arg Leu Leu Gly Ala Asp Arg Pro Leu
            110                 115                 120
Ile Cys Val Asn Cys Leu Lys Cys Lys Ser Cys Ser Thr Thr Lys
            125                 130                 135
Val Ser Lys Phe Val Gly Asn Leu Pro Met Cys Thr Gly Cys Phe
            140                 145                 150
Lys Leu Arg Lys Lys Gly Asn Phe Cys Pro Ile Cys Gln Arg Cys
            155                 160                 165
Tyr Asp Asp Asn Asp Phe Asp Leu Lys Met Met Glu Cys Gly Asp
            170                 175                 180
Cys Gly Gln Trp Val His Ser Lys Cys Glu Gly Leu Ser Asp Glu
            185                 190                 195
Gln Tyr Asn Leu Leu Ser Thr Leu Pro Glu Ser Ile Glu Phe Ile
            200                 205                 210
Cys Lys Lys Cys Ala Arg Arg Asn
            215
```

( 2 ) INFORMATION FOR SEQ ID NO: 3:

( i ) SEQUENCE CHARACTERISTICS:
        ( A ) LENGTH: 109
        ( B ) TYPE: amino acid
        ( D ) TOPOLOGY: linear ( x i ) SEQUENCE DESCRIPTION: SEQ ID NO: 3:

```
Asp Thr Arg Met Cys Leu Phe Cys Arg Lys Ser Gly Glu Gly Leu
              5                  10                  15
Ser Gly Glu Glu Ala Arg Leu Leu Tyr Cys Gly His Asp Cys Trp
             20                  25                  30
Val His Thr Asn Cys Ala Met Trp Ser Ala Glu Val Phe Glu Glu
             35                  40                  45
Ile Asp Gly Ser Leu Gln Asn Val His Ser Ala Val Ala Arg Gly
             50                  55                  60
Arg Met Ile Lys Cys Thr Val Cys Gly Asn Arg Gly Ala Thr Val
             65                  70                  75
```

```
Gly Cys Asn Val Arg Ser Cys Gly Glu His Tyr His Tyr Pro Cys
             80                  85                  90

Ala Arg Ser Ile Asp Cys Ala Phe Leu Thr Asp Lys Ser Met Tyr
             95                 100                 105

Cys Pro Ala His
         109
```

( 2 ) INFORMATION FOR SEQ ID NO: 4:

( i ) SEQUENCE CHARACTERISTICS:
        ( A ) LENGTH: 210
        ( B ) TYPE: amino acid
        ( D ) TOPOLOGY: linear ( x i ) SEQUENCE DESCRIPTION: SEQ ID NO: 4:

```
Glu Leu Glu Glu Asn Ala Tyr Asp Cys Ala Arg Cys Glu Pro Tyr
              5                 10                  15

Ser Asn Arg Ser Glu Tyr Asp Met Phe Ser Trp Leu Ala Ser Arg
             20                 25                  30

His Arg Lys Gln Pro Ile Gln Val Phe Val Gln Pro Ser Asp Asn
             35                 40                  45

Glu Leu Val Pro Arg Arg Gly Thr Gly Ser Asn Leu Pro Met Ala
             50                 55                  60

Met Lys Tyr Arg Thr Leu Lys Glu Thr Tyr Lys Asp Tyr Val Gly
             65                 70                  75

Val Phe Arg Ser His Ile His Gly Arg Gly Leu Tyr Cys Thr Lys
             80                 85                  90

Asp Ile Glu Ala Gly Glu Met Val Ile Glu Tyr Ala Gly Glu Leu
             95                100                 105

Ile Arg Ser Thr Leu Thr Asp Lys Arg Glu Arg Tyr Tyr Asp Ser
            110                115                 120

Arg Gly Ile Gly Cys Tyr Met Phe Lys Ile Asp Asp Asn Leu Val
            125                130                 135

Val Asp Ala Thr Met Arg Gly Asn Ala Ala Arg Phe Ile Asn His
            140                145                 150

Cys Cys Glu Pro Asn Cys Tyr Ser Lys Val Val Asp Ile Leu Gly
            155                160                 165

His Lys His Ile Ile Ile Phe Ala Val Arg Arg Ile Val Gln Gly
            170                175                 180

Glu Glu Leu Thr Tyr Asp Tyr Lys Phe Pro Phe Glu Asp Glu Lys
            185                190                 195

Ile Pro Cys Ser Cys Gly Ser Lys Arg Cys Arg Lys Tyr Leu Asn
            200                205                 210
```

( 2 ) INFORMATION FOR SEQ ID NO: 5:

( i ) SEQUENCE CHARACTERISTICS:
        ( A ) LENGTH: 17
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 5:

```
          TGAATTTTTT AGGTCCA                17
```

( 2 ) INFORMATION FOR SEQ ID NO: 6:

( i ) SEQUENCE CHARACTERISTICS:

( A ) LENGTH: 16
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 6:
GAAAAGGTGA GGAGAG    16

( 2 ) INFORMATION FOR SEQ ID NO: 7:

( i ) SEQUENCE CHARACTERISTICS:
( A ) LENGTH: 18
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 7:
TTGGCTCCTT CGGAAAAA    18

( 2 ) INFORMATION FOR SEQ ID NO: 8:

( i ) SEQUENCE CHARACTERISTICS:
( A ) LENGTH: 16
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 8:
TTTAAGGTAA AGGTGT    16

( 2 ) INFORMATION FOR SEQ ID NO: 9:

( i ) SEQUENCE CHARACTERISTICS:
( A ) LENGTH: 18
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 9:
CTCTCTCCAC AGGAGGAT    18

( 2 ) INFORMATION FOR SEQ ID NO: 10:

( i ) SEQUENCE CHARACTERISTICS:
( A ) LENGTH: 16
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 10:
ATAGAGGTAA GGCATC    16

( 2 ) INFORMATION FOR SEQ ID NO: 11:

( i ) SEQUENCE CHARACTERISTICS:
( A ) LENGTH: 18
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 11:
TTCTTACTAT AGTTTGTG    18

( 2 ) INFORMATION FOR SEQ ID NO: 12:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( i v ) ANTI-SENSE: No ( x i ) SEQUENCE DESCRIPTION: SEQ ID NO: 12:
          ACAAAGGTAC AAAACT          16

( 2 ) INFORMATION FOR SEQ ID NO: 13:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i v ) ANTI-SENSE: No ( x i ) SEQUENCE DESCRIPTION: SEQ ID NO: 13:
          ATTTTCTTAC AGCAGCTG        18

( 2 ) INFORMATION FOR SEQ ID NO: 14:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( i v ) ANTI-SENSE: No ( x i ) SEQUENCE DESCRIPTION: SEQ ID NO: 14:
          GTCTGGGTGA GTTATA          16

( 2 ) INFORMATION FOR SEQ ID NO: 15:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i v ) ANTI-SENSE: No ( x i ) SEQUENCE DESCRIPTION: SEQ ID NO: 15:
          CTTCTTTTCT AGATCTGT        18

( 2 ) INFORMATION FOR SEQ ID NO: 16:

( i ) SEQUENCE CHARACTERISTICS:
    ( A ) LENGTH: 14
    ( B ) TYPE: nucleic acid
    ( C ) STRANDEDNESS: single
    ( D ) TOPOLOGY: linear ( i v ) ANTI-SENSE: No ( x i ) SEQUENCE DESCRIPTION: SEQ ID NO: 16:
          AAAGGTACCC AAAA            14

( 2 ) INFORMATION FOR SEQ ID NO: 17:

( i ) SEQUENCE CHARACTERISTICS:
    ( A ) LENGTH: 17
    ( B ) TYPE: nucleic acid
    ( C ) STRANDEDNESS: single
    ( D ) TOPOLOGY: linear ( i v ) ANTI-SENSE: No ( x i ) SEQUENCE DESCRIPTION: SEQ ID NO: 17:

CTTTGCTTTC AGGAAAC 17

( 2 ) INFORMATION FOR SEQ ID NO: 18:

( i ) SEQUENCE CHARACTERISTICS:
( A ) LENGTH: 14
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 18:

GAAGGTTGGA GTCT 14

( 2 ) INFORMATION FOR SEQ ID NO: 19:

( i ) SEQUENCE CHARACTERISTICS:
( A ) LENGTH: 189
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 19:

| GTT | GCA | ATG | CAG | CAG | AAG | CCC | ACG | GCT | TAT | GTC | CGG | CCC | ATG | GAT | 45 |
| Val | Ala | Met | Gln | Gln | Lys | Pro | Thr | Ala | Tyr | Val | Arg | Pro | Met | Asp | |
| 5 | | | | | 10 | | | | | 15 | | | | | |

| GGT | CAA | GAT | CAG | GCC | CCT | AGT | GAA | TCC | CCT | GAA | CTG | AAA | CCA | CTG | 90 |
| Gly | Gln | Asp | Gln | Ala | Pro | Ser | Glu | Ser | Pro | Glu | Leu | Lys | Pro | Leu | |
| | | | | 20 | | | | | 25 | | | | | 30 | |

| CCG | GAG | GAC | TAT | CGA | CAG | CAG | ACC | TTT | GAA | AAA | ACA | GAC | TTG | AAA | 135 |
| Pro | Glu | Asp | Tyr | Arg | Gln | Gln | Thr | Phe | Glu | Lys | Thr | Asp | Leu | Lys | |
| | | | | 35 | | | | | 40 | | | | | 45 | |

| GTG | CCT | GCC | AAA | GCC | AAG | CTC | ACC | AAA | CTG | AAG | ATG | CCT | TCT | CAG | 180 |
| Val | Pro | Ala | Lys | Ala | Lys | Leu | Thr | Lys | Leu | Lys | Met | Pro | Ser | Gln | |
| | | | | 50 | | | | | 55 | | | | | 60 | |

| TCA | GTT | GAG | | | | | | | | | | | | | 189 |
| Ser | Val | Glu | | | | | | | | | | | | | |
| | | 63 | | | | | | | | | | | | | |

( 2 ) INFORMATION FOR SEQ ID NO: 20:

( i ) SEQUENCE CHARACTERISTICS:
( A ) LENGTH: 147
( B ) TYPE: nucleic acid
( C ) STRANDEDNESS: single
( D ) TOPOLOGY: linear ( i v ) ANTI-SENSE: No ( x i ) SEQUENCE DESCRIPTION: SEQ ID NO: 20:

| TTT | GTG | TAT | TGC | CAA | GTC | TGT | TGT | GAG | CCC | TTC | CAC | AAG | TTT | TGT | 45 |
| Phe | Val | Tyr | Cys | Gln | Val | Cys | Cys | Glu | Pro | Phe | His | Lys | Phe | Cys | |
| | | | | 5 | | | | | 10 | | | | | 15 | |

| TTA | GAG | GAG | AAC | GAG | CGC | CCT | CTG | GAG | GAC | CAG | CTG | GAA | AAT | TGG | 90 |
| Leu | Glu | Glu | Asn | Glu | Arg | Pro | Leu | Glu | Asp | Gln | Leu | Glu | Asn | Trp | |
| | | | | 20 | | | | | 25 | | | | | 30 | |

| TGT | TGT | CGT | CGT | TGC | AAA | TTC | TGT | CAC | GTT | TGT | GGA | AGG | CAA | CAT | 135 |
| Cys | Cys | Arg | Arg | Cys | Lys | Phe | Cys | His | Val | Cys | Gly | Arg | Gln | His | |
| | | | | 35 | | | | | 40 | | | | | 45 | |

| CAG | GCT | ACA | AAG | | | | | | | | | | | | 147 |
| Gln | Ala | Thr | Lys | | | | | | | | | | | | |
| | | | 49 | | | | | | | | | | | | |

( 2 ) INFORMATION FOR SEQ ID NO: 21:

( i ) SEQUENCE CHARACTERISTICS:
        ( A ) LENGTH: 132
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 21:

```
GAA  AAA  CCA  CCT  CCG  GTC  AAT  AAG  CAG  GAG  AAT  GCA  GGC  ACT  TTG   45
Glu  Lys  Pro  Pro  Pro  Val  Asn  Lys  Gln  Glu  Asn  Ala  Gly  Thr  Leu
                    5                        10                       15

AAC  ATC  TTC  AGC  ACT  CTC  TCC  AAT  GGC  AAT  AGT  TCT  AAG  CAA  AAA   90
Asn  Ile  Phe  Ser  Thr  Leu  Ser  Asn  Gly  Asn  Ser  Ser  Lys  Gln  Lys
                    20                       25                       30

ATT  CCA  GCA  GAT  GGA  GTC  CAC  AGG  ATC  AGA  GTG  GAC  TTT  AAG       132
Ile  Pro  Ala  Asp  Gly  Val  His  Arg  Ile  Arg  Val  Asp  Phe  Lys
                    35                       40
```

( 2 ) INFORMATION FOR SEQ ID NO: 22:

( i ) SEQUENCE CHARACTERISTICS:
        ( A ) LENGTH: 270
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 22:

```
ACC  TAC  TCC  AAT  GAA  GTC  CAT  TGT  GTT  GAA  GAG  ATT  CTG  AAG  GAA   45
Thr  Tyr  Ser  Asn  Glu  Val  His  Cys  Val  Glu  Glu  Ile  Leu  Lys  Glu
                    5                        10                       15

ATG  ACC  CAT  TCA  TGG  CCG  CCT  CCT  TTG  ACA  GCA  ATA  CAT  ACG  CCT   90
Met  Thr  His  Ser  Trp  Pro  Pro  Pro  Leu  Thr  Ala  Ile  His  Thr  Pro
                    20                       25                       30

AGT  ACA  GCT  GAG  CCA  TCC  AAG  TTT  CCT  TTC  CCT  ACA  AAG  GAC  TCT  135
Ser  Thr  Ala  Glu  Pro  Ser  Lys  Phe  Pro  Phe  Pro  Thr  Lys  Asp  Ser
                    35                       40                       45

CAG  CAT  GTC  AGT  TCT  GTA  ACC  CAA  AAC  CAA  AAA  CAA  TAT  GAT  ACA  180
Gln  His  Val  Ser  Ser  Val  Thr  Gln  Asn  Gln  Lys  Gln  Tyr  Asp  Thr
                    50                       55                       60

TCT  TCA  AAA  ACT  CAC  TCA  AAT  TCT  CAG  CAA  GGA  ACG  TCA  TCC  ATG  225
Ser  Ser  Lys  Thr  His  Ser  Asn  Ser  Gln  Gln  Gly  Thr  Ser  Ser  Met
                    65                       70                       75

CTC  GAA  GAC  GAC  CTT  CAG  CTC  AGT  GAC  AGT  GAG  GAC  AGT  GAC  AGT  270
Leu  Glu  Asp  Asp  Leu  Gln  Leu  Ser  Asp  Ser  Glu  Asp  Ser  Asp  Ser
                    80                       85                       90
```

( 2 ) INFORMATION FOR SEQ ID NO: 23:

( i ) SEQUENCE CHARACTERISTICS:
        ( A ) LENGTH: 336
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 23:

```
GTT  GCA  ATG  CAG  CAG  AAG  CCC  ACG  GCT  TAT  GTC  CGG  CCC  ATG  GAT   45
Val  Ala  Met  Gln  Gln  Lys  Pro  Thr  Ala  Tyr  Val  Arg  Pro  Met  Asp
                    5                        10                       15

GGT  CAA  GAT  CAG  GCC  CCT  AGT  GAA  TCC  CCT  GAA  CTG  AAA  CCA  CTG   90
```

```
Gly Gln Asp Gln Ala Pro Ser Glu Ser Pro Glu Leu Lys Pro Leu
             20                  25                  30

CCG GAG GAC TAT CGA CAG CAG ACC TTT GAA AAA ACA GAC TTG AAA    135
Pro Glu Asp Tyr Arg Gln Gln Thr Phe Glu Lys Thr Asp Leu Lys
             35                  40                  45

GTG CCT GCC AAA GCC AAG CTC ACC AAA CTG AAG ATG CCT TCT CAG    180
Val Pro Ala Lys Ala Lys Leu Thr Lys Leu Lys Met Pro Ser Gln
             50                  55                  60

TCA GTT GAG TTT GTG TAT TGC CAA GTC TGT TGT GAG CCC TTC CAC    225
Ser Val Glu Phe Val Tyr Cys Gln Val Cys Cys Glu Pro Phe His
             65                  70                  75

AAG TTT TGT TTA GAG GAG AAC GAG CGC CCT CTG GAG GAC CAG CTG    270
Lys Phe Cys Leu Glu Glu Asn Glu Arg Pro Leu Glu Asp Gln Leu
             80                  85                  90

GAA AAT TGG TGT TGT CGT CGT TGC AAA TTC TGT CAC GTT TGT GGA    315
Glu Asn Trp Cys Cys Arg Arg Cys Lys Phe Cys His Val Cys Gly
             95                 100                 105

AGG CAA CAT CAG GCT ACA AAG                                    336
Arg Gln His Gln Ala Thr Lys
            110
```

( 2 ) INFORMATION FOR SEQ ID NO: 24:

( i ) SEQUENCE CHARACTERISTICS:
        ( A ) LENGTH: 402
        ( B ) TYPE: nucleic acid
        ( C ) STRANDEDNESS: single
        ( D ) TOPOLOGY: linear ( i v ) ANTI-SENSE: No ( x i ) SEQUENCE DESCRIPTION: SEQ ID NO: 24:

```
GAA AAA CCA CCT CCG GTC AAT AAG CAG GAG AAT GCA GGC ACT TTG    45
Glu Lys Pro Pro Pro Val Asn Lys Gln Glu Asn Ala Gly Thr Leu
              5                  10                  15

AAC ATC TTC AGC ACT CTC TCC AAT GGC AAT AGT TCT AAG CAA AAA    90
Asn Ile Phe Ser Thr Leu Ser Asn Gly Asn Ser Ser Lys Gln Lys
             20                  25                  30

ATT CCA GCA GAT GGA GTC CAC AGG ATC AGA GTG GAC TTT AAG ACC    135
Ile Pro Ala Asp Gly Val His Arg Ile Arg Val Asp Phe Lys Thr
             35                  40                  45

TAC TCC AAT GAA GTC CAT TGT GTT GAA GAG ATT CTG AAG GAA ATG    180
Tyr Ser Asn Glu Val His Cys Val Glu Glu Ile Leu Lys Glu Met
             50                  55                  60

ACC CAT TCA TGG CCG CCT CCT TTG ACA GCA ATA CAT ACG CCT AGT    225
Thr His Ser Trp Pro Pro Pro Leu Thr Ala Ile His Thr Pro Ser
             65                  70                  75

ACA GCT GAG CCA TCC AAG TTT CCT TTC CCT ACA AAG GAC TCT CAG    270
Thr Ala Glu Pro Ser Lys Phe Pro Phe Pro Thr Lys Asp Ser Gln
             80                  85                  90

CAT GTC AGT TCT GTA ACC CAA AAC CAA AAA CAA TAT GAT ACA TCT    315
His Val Ser Ser Val Thr Gln Asn Gln Lys Gln Tyr Asp Thr Ser
             95                 100                 105

TCA AAA ACT CAC TCA AAT TCT CAG CAA GGA ACG TCA TCC ATG CTC    360
Ser Lys Thr His Ser Asn Ser Gln Gln Gly Thr Ser Ser Met Leu
            110                 115                 120

GAA GAC GAC CTT CAG CTC AGT GAC AGT GAG GAC AGT GAC AGT        402
Glu Asp Asp Leu Gln Leu Ser Asp Ser Glu Asp Ser Asp Ser
            125                 130
```

( 2 ) INFORMATION FOR SEQ ID NO:25:

( i ) SEQUENCE CHARACTERISTICS:
   ( A ) LENGTH: 9391 base pairs
   ( B ) TYPE: nucleic acid
   ( C ) STRANDEDNESS: double
   ( D ) TOPOLOGY: linear ( i i ) MOLECULE TYPE: DNA (genomic)

( i x ) FEATURE:
   ( A ) NAME/KEY: CDS
   ( B ) LOCATION: 421..4053

( x i ) SEQUENCE DESCRIPTION: SEQ ID NO:25:

```
GGCAATTTCT TTTCCTTTCT AACTGTGGCC CGCGTTGTGC TGTTGCTGGG CAGGCGTTGG      60

GCGCCGGCGG TCTTCGAGCG TGGGGGCCCG CTGGCTTTCC CTTCTCAGAA ACTGCGCCGG     120

GGGCGCTCGC TTGCCCCGGA TTCGGACGCG GCGCTCCCCG GGCTCGTCTG AAGTGCAGAT     180

CGCCGCAGAG GCCCCAGTGC CCGGATGTCC ATCAGGATTA GCGCGAGCCA ATACGGGCCG     240

AGCCCGGGGC TGCGCCGAGG ACGCCGGGG  CTCGAGAGCA GGTAGTCCCG TAACATCGGG     300

GCGCCGCGCC GGGACGCGTC CCCGCCCGGC TCCGCCAAAT GGTGAGCGCG GCGCTGGCAG     360

CAGGGCCCGC GGGGTGAAGG CGCTCATGGA CGGAAGACCC CTGGCTCTAT AAGCTGAATT     420
```

| | | | | | | | | | | | | | | | |
|---|---|---|---|---|---|---|---|---|---|---|---|---|---|---|---|
| ATG | GCA | GCC | CAG | TCA | AGT | TTG | TAC | AAT | GAC | GAC | AGA | AAC | CTG | CTT | CGA | 468 |
| Met | Ala | Ala | Gln | Ser | Ser | Leu | Tyr | Asn | Asp | Asp | Arg | Asn | Leu | Leu | Arg | |
| 1 | | | | 5 | | | | | 10 | | | | | 15 | | |

| | | | | | | | | | | | | | | | |
|---|---|---|---|---|---|---|---|---|---|---|---|---|---|---|---|
| ATT | AGA | GAG | AAG | GAA | AGA | CGC | AAC | CAG | GAA | GCC | CAC | CAA | GAG | AAA | GAG | 516 |
| Ile | Arg | Glu | Lys | Glu | Arg | Arg | Asn | Gln | Glu | Ala | His | Gln | Glu | Lys | Glu | |
| | | | 20 | | | | | 25 | | | | | 30 | | | |

| | | | | | | | | | | | | | | | |
|---|---|---|---|---|---|---|---|---|---|---|---|---|---|---|---|
| GCA | TTT | CCT | GAA | AAG | ATT | CCC | CTT | TTT | GGA | GAG | CCC | TAC | AAG | ACA | GCA | 564 |
| Ala | Phe | Pro | Glu | Lys | Ile | Pro | Leu | Phe | Gly | Glu | Pro | Tyr | Lys | Thr | Ala | |
| | | 35 | | | | | 40 | | | | | 45 | | | | |

| | | | | | | | | | | | | | | | |
|---|---|---|---|---|---|---|---|---|---|---|---|---|---|---|---|
| AAA | GGT | GAT | GAG | CTG | TCT | AGT | CGA | ATA | CAG | AAC | ATG | TTG | GGA | AAC | TAC | 612 |
| Lys | Gly | Asp | Glu | Leu | Ser | Ser | Arg | Ile | Gln | Asn | Met | Leu | Gly | Asn | Tyr | |
| | 50 | | | | | 55 | | | | | 60 | | | | | |

| | | | | | | | | | | | | | | | |
|---|---|---|---|---|---|---|---|---|---|---|---|---|---|---|---|
| GAA | GAA | GTG | AAG | GAG | TTC | CTT | AGT | ACT | AAG | TCT | CAC | ACT | CAT | CGC | CTG | 660 |
| Glu | Glu | Val | Lys | Glu | Phe | Leu | Ser | Thr | Lys | Ser | His | Thr | His | Arg | Leu | |
| 65 | | | | | 70 | | | | | 75 | | | | | 80 | |

| | | | | | | | | | | | | | | | |
|---|---|---|---|---|---|---|---|---|---|---|---|---|---|---|---|
| GAT | GCT | TCT | GAA | AAT | AGG | TTG | GGA | AAG | CCG | AAA | TAT | CCT | TTA | ATT | CCT | 708 |
| Asp | Ala | Ser | Glu | Asn | Arg | Leu | Gly | Lys | Pro | Lys | Tyr | Pro | Leu | Ile | Pro | |
| | | | | 85 | | | | | 90 | | | | | 95 | | |

| | | | | | | | | | | | | | | | |
|---|---|---|---|---|---|---|---|---|---|---|---|---|---|---|---|
| GAC | AAA | GGG | AGC | AGC | ATT | CCA | TCC | AGC | TCC | TTC | CAC | ACT | AGT | GTC | CAC | 756 |
| Asp | Lys | Gly | Ser | Ser | Ile | Pro | Ser | Ser | Ser | Phe | His | Thr | Ser | Val | His | |
| | | | 100 | | | | | 105 | | | | | 110 | | | |

| | | | | | | | | | | | | | | | |
|---|---|---|---|---|---|---|---|---|---|---|---|---|---|---|---|
| CAC | CAG | TCC | ATT | CAC | ACT | CCT | GCG | TCT | GGA | CCA | CTT | TCT | GTT | GGC | AAC | 804 |
| His | Gln | Ser | Ile | His | Thr | Pro | Ala | Ser | Gly | Pro | Leu | Ser | Val | Gly | Asn | |
| | | 115 | | | | | 120 | | | | | 125 | | | | |

| | | | | | | | | | | | | | | | |
|---|---|---|---|---|---|---|---|---|---|---|---|---|---|---|---|
| ATT | AGC | CAC | AAT | CCA | AAG | ATG | GCG | CAG | CCA | AGA | ACT | GAA | CCA | ATG | CCA | 852 |
| Ile | Ser | His | Asn | Pro | Lys | Met | Ala | Gln | Pro | Arg | Thr | Glu | Pro | Met | Pro | |
| | 130 | | | | | 135 | | | | | 140 | | | | | |

| | | | | | | | | | | | | | | | |
|---|---|---|---|---|---|---|---|---|---|---|---|---|---|---|---|
| AGT | CTC | CAT | GCC | AAA | AGC | TGC | GGC | CCA | CCG | GAC | AGC | CAG | CAC | CTG | ACC | 900 |
| Ser | Leu | His | Ala | Lys | Ser | Cys | Gly | Pro | Pro | Asp | Ser | Gln | His | Leu | Thr | |
| 145 | | | | | 150 | | | | | 155 | | | | | 160 | |

| | | | | | | | | | | | | | | | |
|---|---|---|---|---|---|---|---|---|---|---|---|---|---|---|---|
| CAG | GAT | CGC | CTT | GGT | CAG | GAG | GGG | TTC | GGC | TCT | AGT | CAT | CAC | AAG | AAA | 948 |
| Gln | Asp | Arg | Leu | Gly | Gln | Glu | Gly | Phe | Gly | Ser | Ser | His | His | Lys | Lys | |
| | | | | 165 | | | | | 170 | | | | | 175 | | |

| | | | | | | | | | | | | | | | |
|---|---|---|---|---|---|---|---|---|---|---|---|---|---|---|---|
| GGT | GAC | CGA | AGA | GCT | GAC | GGA | GAC | CAC | TGT | GCT | TCG | GTG | ACA | GAT | TCG | 996 |
| Gly | Asp | Arg | Arg | Ala | Asp | Gly | Asp | His | Cys | Ala | Ser | Val | Thr | Asp | Ser | |
| | | | 180 | | | | | 185 | | | | | 190 | | | |

| | | | | | | | | | | | | | | | |
|---|---|---|---|---|---|---|---|---|---|---|---|---|---|---|---|
| GCT | CCA | GAG | AGG | GAG | CTT | TCT | CCC | TTA | ATC | TCT | TTG | CCT | TCC | CCA | GTT | 1044 |
| Ala | Pro | Glu | Arg | Glu | Leu | Ser | Pro | Leu | Ile | Ser | Leu | Pro | Ser | Pro | Val | |
| | | 195 | | | | | 200 | | | | | 205 | | | | |

| | | | | | | | | | | | | | | | |
|---|---|---|---|---|---|---|---|---|---|---|---|---|---|---|---|
| CCC | CCT | TTG | TCA | CCT | ATA | CAT | TCC | AAC | CAG | CAA | ACT | CTT | CCC | CGG | ACG | 1092 |
| Pro 210 | Pro | Leu | Ser | Pro | Ile 215 | His | Ser | Asn | Gln | Gln 220 | Thr | Leu | Pro | Arg | Thr | |
| CAA | GGA | AGC | AGC | AAG | GTT | CAT | GGC | AGC | AGC | AAT | AAC | AGT | AAA | GGC | TAT | 1140 |
| Gln 225 | Gly | Ser | Ser | Lys | Val 230 | His | Gly | Ser | Ser | Asn 235 | Asn | Ser | Lys | Gly | Tyr 240 | |
| TGC | CCA | GCC | AAA | TCT | CCC | AAG | GAC | CTA | GCA | GTG | AAA | GTC | CAT | GAT | AAA | 1188 |
| Cys | Pro | Ala | Lys | Ser 245 | Pro | Lys | Asp | Leu | Ala 250 | Val | Lys | Val | His | Asp 255 | Lys | |
| GAG | ACC | CCT | CAA | GAC | AGT | TTG | GTG | GCC | CCT | GCC | CAG | CCG | CCT | TCT | CAG | 1236 |
| Glu | Thr | Pro | Gln | Asp 260 | Ser | Leu | Val | Ala | Pro 265 | Ala | Gln | Pro | Pro 270 | Ser | Gln | |
| ACA | TTT | CCA | CCT | CCC | TCC | CTC | CCC | TCA | AAA | AGT | GTT | GCA | ATG | CAG | CAG | 1284 |
| Thr | Phe | Pro 275 | Pro | Pro | Ser | Leu | Pro 280 | Ser | Lys | Ser | Val | Ala 285 | Met | Gln | Gln | |
| AAG | CCC | ACG | GCT | TAT | GTC | CGG | CCC | ATG | GAT | GGT | CAA | GAT | CAG | GCC | CCT | 1332 |
| Lys | Pro | Thr 290 | Ala | Tyr | Val | Arg | Pro 295 | Met | Asp | Gly | Gln 300 | Asp | Gln | Ala | Pro | |
| AGT | GAA | TCC | CCT | GAA | CTG | AAA | CCA | CTG | CCG | GAG | GAC | TAT | CGA | CAG | CAG | 1380 |
| Ser 305 | Glu | Ser | Pro | Glu | Leu 310 | Lys | Pro | Leu | Pro | Glu 315 | Asp | Tyr | Arg | Gln | Gln 320 | |
| ACC | TTT | GAA | AAA | ACA | GAC | TTG | AAA | GTG | CCT | GCC | AAA | GCC | AAG | CTC | ACC | 1428 |
| Thr | Phe | Glu | Lys | Thr 325 | Asp | Leu | Lys | Val | Pro 330 | Ala | Lys | Ala | Lys | Leu 335 | Thr | |
| AAA | CTG | AAG | ATG | CCT | TCT | CAG | TCA | GTT | GAG | CAG | ACC | TAC | TCC | AAT | GAA | 1476 |
| Lys | Leu | Lys | Met 340 | Pro | Ser | Gln | Ser | Val 345 | Glu | Gln | Thr | Tyr | Ser 350 | Asn | Glu | |
| GTC | CAT | TGT | GTT | GAA | GAG | ATT | CTG | AAG | GAA | ATG | ACC | CAT | TCA | TGG | CCG | 1524 |
| Val | His | Cys 355 | Val | Glu | Glu | Ile | Leu 360 | Lys | Glu | Met | Thr | His 365 | Ser | Trp | Pro | |
| CCT | CCT | TTG | ACA | GCA | ATA | CAT | ACG | CCT | AGT | ACA | GCT | GAG | CCA | TCC | AAG | 1572 |
| Pro | Pro 370 | Leu | Thr | Ala | Ile | His 375 | Thr | Pro | Ser | Thr | Ala 380 | Glu | Pro | Ser | Lys | |
| TTT | CCT | TTC | CCT | ACA | AAG | GAC | TCT | CAG | CAT | GTC | AGT | TCT | GTA | ACC | CAA | 1620 |
| Phe 385 | Pro | Phe | Pro | Thr | Lys 390 | Asp | Ser | Gln | His | Val 395 | Ser | Ser | Val | Thr | Gln 400 | |
| AAC | CAA | AAA | CAA | TAT | GAT | ACA | TCT | TCA | AAA | ACT | CAC | TCA | AAT | TCT | CAG | 1668 |
| Asn | Gln | Lys | Gln | Tyr 405 | Asp | Thr | Ser | Ser | Lys 410 | Thr | His | Ser | Asn | Ser 415 | Gln | |
| CAA | GGA | ACG | TCA | TCC | ATG | CTC | GAA | GAC | GAC | CTT | CAG | CTC | AGT | GAC | AGT | 1716 |
| Gln | Gly | Thr | Ser 420 | Ser | Met | Leu | Glu | Asp 425 | Asp | Leu | Gln | Leu | Ser 430 | Asp | Ser | |
| GAG | GAC | AGT | GAC | AGT | GAA | CAA | ACC | CCA | GAG | AAG | CCT | CCC | TCC | TCA | TCT | 1764 |
| Glu | Asp | Ser 435 | Asp | Ser | Glu | Gln | Thr 440 | Pro | Glu | Lys | Pro | Pro 445 | Ser | Ser | Ser | |
| GCA | CCT | CCA | AGT | GCT | CCA | CAG | TCC | CTT | CCA | GAA | CCA | GTG | GCA | TCA | GCA | 1812 |
| Ala | Pro 450 | Pro | Ser | Ala | Pro | Gln 455 | Ser | Leu | Pro | Glu | Pro 460 | Val | Ala | Ser | Ala | |
| CAT | TCC | AGC | AGT | GCA | GAG | TCA | GAA | AGC | ACC | AGT | GAC | TCA | GAC | AGT | TCC | 1860 |
| His 465 | Ser | Ser | Ser | Ala | Glu 470 | Ser | Glu | Ser | Thr | Ser 475 | Asp | Ser | Asp | Ser | Ser 480 | |
| TCA | GAC | TCA | GAG | AGC | GAG | AGC | AGT | TCA | AGT | GAC | AGC | GAA | GAA | AAT | GAG | 1908 |
| Ser | Asp | Ser | Glu | Ser 485 | Glu | Ser | Ser | Ser | Ser 490 | Asp | Ser | Glu | Glu | Asn 495 | Glu | |
| CCC | CTA | GAA | ACC | CCA | GCT | CCG | GAG | CCT | GAG | CCT | CCA | ACA | ACA | AAC | AAA | 1956 |
| Pro | Leu | Glu | Thr 500 | Pro | Ala | Pro | Glu | Pro 505 | Glu | Pro | Pro | Thr | Thr 510 | Asn | Lys | |
| TGG | CAG | CTG | GAC | AAC | TGG | CTG | ACC | AAA | GTC | AGC | CAG | CCA | GCT | GCG | CCA | 2004 |
| Trp | Gln | Leu | Asp | Asn 515 | Trp | Leu | Thr | Lys | Val 520 | Ser | Gln | Pro | Ala | Ala 525 | Pro | |

| | | | | | | | | | | | | | | | | |
|---|---|---|---|---|---|---|---|---|---|---|---|---|---|---|---|---|
| CCA | GAG | GGC | CCC | AGG | AGC | ACA | GAG | CCC | CCA | CGG | CGG | CAC | CCA | GAG | AGT | 2052 |
| Pro | Glu | Gly | Pro | Arg | Ser | Thr | Glu | Pro | Pro | Arg | Arg | His | Pro | Glu | Ser | |
| | 530 | | | | | 535 | | | | | 540 | | | | | |
| AAG | GGC | AGC | AGC | GAC | AGT | GCC | ACG | AGT | CAG | GAG | CAT | TCT | GAA | TCC | AAA | 2100 |
| Lys | Gly | Ser | Ser | Asp | Ser | Ala | Thr | Ser | Gln | Glu | His | Ser | Glu | Ser | Lys | |
| 545 | | | | | 550 | | | | | 555 | | | | | 560 | |
| GAT | CCT | CCC | CCT | AAA | AGC | TCC | AGC | AAA | GCC | CCC | CGG | GCC | CCA | CCC | GAA | 2148 |
| Asp | Pro | Pro | Pro | Lys | Ser | Ser | Ser | Lys | Ala | Pro | Arg | Ala | Pro | Pro | Glu | |
| | | | | 565 | | | | | 570 | | | | | 575 | | |
| GCC | CCC | CAC | CCC | GGA | AAG | AGG | AGC | TGT | CAG | AAG | TCT | CCG | GCA | CAG | CAG | 2196 |
| Ala | Pro | His | Pro | Gly | Lys | Arg | Ser | Cys | Gln | Lys | Ser | Pro | Ala | Gln | Gln | |
| | | | 580 | | | | | 585 | | | | | 590 | | | |
| GAG | CCC | CCA | CAA | AGG | CAA | ACC | GTT | GGA | ACC | AAA | CAA | CCC | AAA | AAA | CCT | 2244 |
| Glu | Pro | Pro | Gln | Arg | Gln | Thr | Val | Gly | Thr | Lys | Gln | Pro | Lys | Lys | Pro | |
| | | 595 | | | | | 600 | | | | | 605 | | | | |
| GTC | AAG | GCC | TCT | GCC | CGG | GCA | GGT | TCA | CGG | ACC | AGC | CTG | CAG | GGG | GAA | 2292 |
| Val | Lys | Ala | Ser | Ala | Arg | Ala | Gly | Ser | Arg | Thr | Ser | Leu | Gln | Gly | Glu | |
| | 610 | | | | | 615 | | | | | 620 | | | | | |
| AGG | GAG | CCA | GGG | CTT | CTT | CCC | TAT | GGC | TCC | CGA | GAC | CAG | ACT | TCC | AAA | 2340 |
| Arg | Glu | Pro | Gly | Leu | Leu | Pro | Tyr | Gly | Ser | Arg | Asp | Gln | Thr | Ser | Lys | |
| 625 | | | | | 630 | | | | | 635 | | | | | 640 | |
| GAC | AAG | CCC | AAG | GTG | AAG | ACG | AAA | GGA | CGG | CCC | CGG | GCC | GCA | GCA | AGC | 2388 |
| Asp | Lys | Pro | Lys | Val | Lys | Thr | Lys | Gly | Arg | Pro | Arg | Ala | Ala | Ala | Ser | |
| | | | | 645 | | | | | 650 | | | | | 655 | | |
| AAC | GAA | CCC | AAG | CCA | GCA | GTG | CCC | CCC | TCC | AGT | GAG | AAG | AAG | AAG | CAC | 2436 |
| Asn | Glu | Pro | Lys | Pro | Ala | Val | Pro | Pro | Ser | Ser | Glu | Lys | Lys | Lys | His | |
| | | | 660 | | | | | 665 | | | | | 670 | | | |
| AAG | AGC | TCC | CTC | CCT | GCC | CCC | TCT | AAG | GCT | CTC | TCA | GGC | CCA | GAA | CCC | 2484 |
| Lys | Ser | Ser | Leu | Pro | Ala | Pro | Ser | Lys | Ala | Leu | Ser | Gly | Pro | Glu | Pro | |
| | | 675 | | | | | 680 | | | | | 685 | | | | |
| GCG | AAG | GAC | AAT | GTG | GAG | GAC | AGG | ACC | CCT | GAG | CAC | TTT | GCT | CTT | GTT | 2532 |
| Ala | Lys | Asp | Asn | Val | Glu | Asp | Arg | Thr | Pro | Glu | His | Phe | Ala | Leu | Val | |
| | 690 | | | | | 695 | | | | | 700 | | | | | |
| CCC | CTG | ACT | GAG | AGC | CAG | GGC | CCA | CCC | CAC | AGT | GGC | AGC | GGC | AGC | AGG | 2580 |
| Pro | Leu | Thr | Glu | Ser | Gln | Gly | Pro | Pro | His | Ser | Gly | Ser | Gly | Ser | Arg | |
| 705 | | | | | 710 | | | | | 715 | | | | | 720 | |
| ACT | AGT | GGC | TGC | CGC | CAA | GCC | GTG | GTG | GTC | CAG | GAG | GAC | AGC | CGC | AAA | 2628 |
| Thr | Ser | Gly | Cys | Arg | Gln | Ala | Val | Val | Val | Gln | Glu | Asp | Ser | Arg | Lys | |
| | | | | 725 | | | | | 730 | | | | | 735 | | |
| GAC | AGA | CTC | CCA | TTG | CCT | TTG | AGA | GAC | ACC | AAG | CTG | CTC | TCA | CCG | CTC | 2676 |
| Asp | Arg | Leu | Pro | Leu | Pro | Leu | Arg | Asp | Thr | Lys | Leu | Leu | Ser | Pro | Leu | |
| | | | 740 | | | | | 745 | | | | | 750 | | | |
| AGG | GAC | ACT | CCT | CCC | CCA | CAA | AGC | TTG | ATG | GTG | AAG | ATC | ACC | CTA | GAC | 2724 |
| Arg | Asp | Thr | Pro | Pro | Pro | Gln | Ser | Leu | Met | Val | Lys | Ile | Thr | Leu | Asp | |
| | | 755 | | | | | 760 | | | | | 765 | | | | |
| CTG | CTC | TCT | CGG | ATA | CCC | CAG | CCT | CCC | GGG | AAG | GGG | AGC | CGC | CAG | AGG | 2772 |
| Leu | Leu | Ser | Arg | Ile | Pro | Gln | Pro | Pro | Gly | Lys | Gly | Ser | Arg | Gln | Arg | |
| | 770 | | | | | 775 | | | | | 780 | | | | | |
| AAA | GCA | GAA | GAT | AAA | CAG | CCG | CCC | GCA | GGG | AAG | AAG | CAC | AGC | TCT | GAG | 2820 |
| Lys | Ala | Glu | Asp | Lys | Gln | Pro | Pro | Ala | Gly | Lys | Lys | His | Ser | Ser | Glu | |
| 785 | | | | | 790 | | | | | 795 | | | | | 800 | |
| AAG | AGG | AGC | TCA | GAC | AGC | TCA | AGC | AAG | TTG | GCC | AAA | AAG | AGA | AAG | GGT | 2868 |
| Lys | Arg | Ser | Ser | Asp | Ser | Ser | Ser | Lys | Leu | Ala | Lys | Lys | Arg | Lys | Gly | |
| | | | | 805 | | | | | 810 | | | | | 815 | | |
| GAA | GCA | GAA | AGA | GAC | TGT | GAT | AAC | AAG | AAA | ATC | AGA | CTG | GAG | AAG | GAA | 2916 |
| Glu | Ala | Glu | Arg | Asp | Cys | Asp | Asn | Lys | Lys | Ile | Arg | Leu | Glu | Lys | Glu | |
| | | | 820 | | | | | 825 | | | | | 830 | | | |
| ATC | AAA | TCA | CAG | TCA | TCT | TCA | TCT | TCA | TCC | TCC | CAC | AAA | GAA | TCT | TCT | 2964 |
| Ile | Lys | Ser | Gln | Ser | Ser | Ser | Ser | Ser | Ser | Ser | His | Lys | Glu | Ser | Ser | |
| | | 835 | | | | | 840 | | | | | 845 | | | | |

| | | | | | | | | | | | | | | | |
|---|---|---|---|---|---|---|---|---|---|---|---|---|---|---|---|
| AAA | ACA | AAG | CCC | TCC | AGG | CCC | TCC | TCA | CAG | TCC | TCA | AAG | AAG | GAA | ATG | 3012
| Lys | Thr | Lys | Pro | Ser | Arg | Pro | Ser | Ser | Gln | Ser | Ser | Lys | Lys | Glu | Met |
| 850 | | | | | 855 | | | | | 860 | | | | | |
| CTC | CCC | CCG | CCA | CCC | GTG | TCC | TCG | TCC | TCC | CAG | AAG | CCA | GCC | AAG | CCT | 3060
| Leu | Pro | Pro | Pro | Pro | Val | Ser | Ser | Ser | Ser | Gln | Lys | Pro | Ala | Lys | Pro |
| 865 | | | | | 870 | | | | | 875 | | | | | 880 |
| GCA | CTT | AAG | AGG | TCA | AGG | CGG | GAA | GCA | GAC | ACC | TGT | GGC | CAG | GAC | CCT | 3108
| Ala | Leu | Lys | Arg | Ser | Arg | Arg | Glu | Ala | Asp | Thr | Cys | Gly | Gln | Asp | Pro |
| | | | | 885 | | | | 890 | | | | | 895 | | |
| CCC | AAA | AGT | GCC | AGC | AGT | ACC | AAG | AGC | AAC | CAC | AAA | GAC | TCT | TCC | ATT | 3156
| Pro | Lys | Ser | Ala | Ser | Ser | Thr | Lys | Ser | Asn | His | Lys | Asp | Ser | Ser | Ile |
| 900 | | | | | | | 905 | | | | | | 910 | | |
| CCC | AAG | CAG | AGA | AGA | GTA | GAG | GGG | AAG | GGC | TCC | AGA | AGC | TCC | TCG | GAG | 3204
| Pro | Lys | Gln | Arg | Arg | Val | Glu | Gly | Lys | Gly | Ser | Arg | Ser | Ser | Ser | Glu |
| | 915 | | | | | 920 | | | | | 925 | | | | |
| CAC | AAG | GGT | TCT | TCC | GGA | GAT | ACT | GCA | AAT | CCT | TTT | CCA | GTG | CCT | TCT | 3252
| His | Lys | Gly | Ser | Ser | Gly | Asp | Thr | Ala | Asn | Pro | Phe | Pro | Val | Pro | Ser |
| | 930 | | | | | 935 | | | | 940 | | | | | |
| TTG | CCA | AAT | GGT | AAC | TCT | AAA | CCA | GGG | AAG | CCT | CAA | GTG | AAG | TTT | GAC | 3300
| Leu | Pro | Asn | Gly | Asn | Ser | Lys | Pro | Gly | Lys | Pro | Gln | Val | Lys | Phe | Asp |
| 945 | | | | | 950 | | | | | 955 | | | | | 960 |
| AAA | CAA | CAA | GCA | GAC | CTT | CAC | ATG | AGG | GAG | GCA | AAA | AAG | ATG | AAG | CAG | 3348
| Lys | Gln | Gln | Ala | Asp | Leu | His | Met | Arg | Glu | Ala | Lys | Lys | Met | Lys | Gln |
| | | | | 965 | | | | 970 | | | | | 975 | | |
| AAA | GCA | GAG | TTA | ATG | ACG | GAC | AGG | GTT | GGA | AAG | GCT | TTT | AAG | TAC | CTG | 3396
| Lys | Ala | Glu | Leu | Met | Thr | Asp | Arg | Val | Gly | Lys | Ala | Phe | Lys | Tyr | Leu |
| | | | 980 | | | | | 985 | | | | | 990 | | |
| GAA | GCC | GTC | TTG | TCC | TTC | ATT | GAG | TGC | GGA | ATT | GCC | ACA | GAG | TCT | GAA | 3444
| Glu | Ala | Val | Leu | Ser | Phe | Ile | Glu | Cys | Gly | Ile | Ala | Thr | Glu | Ser | Glu |
| | | 995 | | | | | 1000 | | | | | 1005 | | | |
| AGC | CAG | TCA | TCC | AAG | TCA | GCT | TAC | TCT | GTC | TAC | TCA | GAA | ACT | GTA | GAT | 3492
| Ser | Gln | Ser | Ser | Lys | Ser | Ala | Tyr | Ser | Val | Tyr | Ser | Glu | Thr | Val | Asp |
| | 1010 | | | | | 1015 | | | | | 1020 | | | | |
| CTC | ATT | AAA | TTC | ATA | ATG | TCA | TTA | AAA | TCC | TTC | TCA | GAT | GCC | ACA | GCG | 3540
| Leu | Ile | Lys | Phe | Ile | Met | Ser | Leu | Lys | Ser | Phe | Ser | Asp | Ala | Thr | Ala |
| 1025 | | | | | 1030 | | | | | 1035 | | | | | 1040 |
| CCA | ACA | CAA | GAG | AAA | ATA | TTT | GCT | GTT | TTA | TGC | ATG | CGT | TGC | CAG | TCC | 3588
| Pro | Thr | Gln | Glu | Lys | Ile | Phe | Ala | Val | Leu | Cys | Met | Arg | Cys | Gln | Ser |
| | | | | 1045 | | | | | 1050 | | | | | 1055 | |
| ATT | TTG | AAC | ATG | GCG | ATG | TTT | CGT | TGT | AAA | AAA | GAC | ATA | GCA | ATA | AAG | 3636
| Ile | Leu | Asn | Met | Ala | Met | Phe | Arg | Cys | Lys | Lys | Asp | Ile | Ala | Ile | Lys |
| | | | | 1060 | | | | | 1065 | | | | | 1070 | |
| TAT | TCT | CGT | ACT | CTT | AAT | AAA | CAC | TTC | GAG | AGT | TCT | TCC | AAA | GTC | GCC | 3684
| Tyr | Ser | Arg | Thr | Leu | Asn | Lys | His | Phe | Glu | Ser | Ser | Ser | Lys | Val | Ala |
| | | 1075 | | | | | 1080 | | | | | 1085 | | | |
| CAG | GCA | CCT | TCT | CCA | TGC | ATT | GCA | AGC | ACA | GGC | ACA | CCA | TCC | CCT | CTT | 3732
| Gln | Ala | Pro | Ser | Pro | Cys | Ile | Ala | Ser | Thr | Gly | Thr | Pro | Ser | Pro | Leu |
| | 1090 | | | | | 1095 | | | | | 1100 | | | | |
| TCC | CCA | ATG | CCT | TCT | CCT | GCC | AGC | TCC | GTA | GGG | TCC | CAG | TCA | AGT | GCT | 3780
| Ser | Pro | Met | Pro | Ser | Pro | Ala | Ser | Ser | Val | Gly | Ser | Gln | Ser | Ser | Ala |
| 1105 | | | | | 1110 | | | | | 1115 | | | | | 1120 |
| GGC | AGT | GTG | GGG | AGC | AGT | GGG | GTG | GCT | GCC | ACT | ATC | AGC | ACC | CCA | GTC | 3828
| Gly | Ser | Val | Gly | Ser | Ser | Gly | Val | Ala | Ala | Thr | Ile | Ser | Thr | Pro | Val |
| | | | | 1125 | | | | | 1130 | | | | | 1135 | |
| ACC | ATC | CAG | AAT | ATG | ACA | TCT | TCC | TAT | GTC | ACC | ATC | ACA | TCC | CAT | GTT | 3876
| Thr | Ile | Gln | Asn | Met | Thr | Ser | Ser | Tyr | Val | Thr | Ile | Thr | Ser | His | Val |
| | | | | 1140 | | | | | 1145 | | | | | 1150 | |
| CTT | ACC | GCC | TTT | GAC | CTT | TGG | GAA | CAG | GCC | GAG | GCC | CTC | ACG | AGG | AAG | 3924
| Leu | Thr | Ala | Phe | Asp | Leu | Trp | Glu | Gln | Ala | Glu | Ala | Leu | Thr | Arg | Lys |
| | | | | 1155 | | | | | 1160 | | | | | 1165 | |

-continued

| | | |
|---|---|---|
| AAT AAA GAA TTC TTT GCT CGG CTC AGC ACA AAT GTG TGC ACC TTG GCC<br>Asn Lys Glu Phe Phe Ala Arg Leu Ser Thr Asn Val Cys Thr Leu Ala<br>　　1170　　　　　　　　1175　　　　　　　　1180 | | 3972 |
| CTC AAC AGC AGT TTG GTG GAC CTG GTG CAC TAT ACA CGA CAG GGT TTT<br>Leu Asn Ser Ser Leu Val Asp Leu Val His Tyr Thr Arg Gln Gly Phe<br>1185　　　　　　　　1190　　　　　　　　1195　　　　　　　　1200 | | 4020 |
| CAG CAG CTA CAA GAA TTA ACC AAA ACA CCT TAATGGAGCC CCAGGTTGAT<br>Gln Gln Leu Gln Glu Leu Thr Lys Thr Pro<br>　　　　　　　　1205　　　　　　　　1210 | | 4070 |
| TCAATGCCTT | GGGAACTATT TTTGCACATT GGAAGCCTCA AAAACAGTCC AGACGTTTGT | 4130 |
| TTCATCAGGA | CACCAAACTC TAAAAAGAA GCACCACGAG ATGGCCAGGA CATTTGTCCA | 4190 |
| CTTAAACTCT | CAACAACAGT GTGATCATTG GTTGGACACT GTGGTTATGC AGAAGCAGAG | 4250 |
| ATGAGGAGGC | TGGCCCCAGA GATGATCTTG CCCTTCCTAA CTAAAGGACA GAAGTGCAAT | 4310 |
| TTAGCTTAAA | TGGGTGTATG AATGGTCTAG AAACATTTCT ATTTTTTTT TAAACCAGCA | 4370 |
| GGATACAAGT | TGCAAATGAA ATGAGGAGAA ACAGTTTCAA CTCTGAAAGT GAATTTCACG | 4430 |
| TCATCTCAGT | AGCCACGCTA GTCCATTCCC AGAAGGAAAT TTTTTTTTT AACAATGACT | 4490 |
| TTTGGTAAAG | GGTTTTGTGG ATGATTTTT TTCTTTGAG TTTGGGAGA AATATTTGTT | 4550 |
| TAATAACTTC | TAATGGCCAT CTGTAAACCA TAAGTAATGA AGGACTCCAC TGTGCCCCAC | 4610 |
| TTTCTGCCAA | TGAACAGTGG CTTGATAATA CCAAGTATTG TTGTAATTTA TAAAATTGAA | 4670 |
| GGCAACCCCC | GCTCCTGCCG CCCCCAATCT CCCCATTGCC TAGAGCGCTG CACATTGACC | 4730 |
| CCAGCTCTGA | CTTCTCATTA CTGTGCTGAA AGTCAGCCCA CGTCGGAGCG GTGAGGAGGA | 4790 |
| GCCACAGCAC | ATGGGGTGCC ACCTCGAGGT CTGCACAGGA GGACTTGGCG CTGCCATTTC | 4850 |
| CTACCCCTGC | CATTTCCCAC CCCTGCTTCA GCGAAGGGA CTCTCTAACA GGGCAGTCAC | 4910 |
| TGTTGACTCT | ATTCTGAATT CCTCCCTTG GGGAAGAAGG GAACCAACAT TTATACCTGA | 4970 |
| CCAGATGGCT | AAAGTGCTTT TAAAGTTTTG TTAAGTAGA GCTGGAATTT GAGGTGCTGA | 5030 |
| TCTGTGGTCT | ACAGTTATGT GGTAACTCAT GTTGTCCAGC CAACTCAGAG TTTCGTCAGT | 5090 |
| GAACAAGAAA | CATGAAATCT GCTTCTTAGA GAGGCTATAT TTTTCTGCTA CAAATATTTT | 5150 |
| ATATTTATAG | CAAAACTAGA CTTTCAGAGT CCTTGATTGT CTAGGGGAAG TTAACTCCCT | 5210 |
| GAGAGGATGT | AGAGATTTGG GGTGGTTGAT TAGACTTTTG AAAAACTCAT CACCACATGC | 5270 |
| CTTCACTCCA | GAGTGTTCTC AGCTAGATTT GATTGGTTG AGGAGGAACT GTGGCCCTCC | 5330 |
| GTAAGTTATT | GCCATAGTGT ATGCATTAAA CCAAGTCCAT TTGAATGAC CTAAAATGAA | 5390 |
| GTAACACAAT | CAGAAATCCC ATGTGCCCAT AAGCACAGAT TTTTCTTTTT CATTGAAACT | 5450 |
| TTAAAGGTTA | TTATTGGAAA CATTACTTTG AGTGCAGTGT TTTAAAAGC CAATTCTTTT | 5510 |
| TTATCCCTTT | TAGAAGTAGA ATTTGCACAC TTACTACAAT TGAGGAGTGT CATCTCTATA | 5570 |
| ACTTTTTCTC | CGCCTTTGTC CCATTCTGCC CCTGGACATG TTTCCTACCA AGCATGTTTC | 5630 |
| ACATTTTCCT | ATTAGTGGAG GAGGGAGAAC CATATTTATT TATAATGAAG ACATCTAAGA | 5690 |
| TCCCTATGAT | GAATGCAGGA ACTCTCTTGG TAGTTTGTAA ATACACAAAG GGATGTGTCG | 5750 |
| AGGGATGGGA | GCGATGCTTA TCTCTCACAG TGTGAGTGGT CTGTGTGAGG CTGTTCCTTC | 5810 |
| AGTTCTTCTC | CAGACTGTTC TTTGGTTGTC ACTTAAGTCA GAGGTCTGGT CCCTCATGTT | 5870 |
| TAGGTGAAAG | CCAGAGAATG ACAGCTGTAG TCATATCTGA GCATAAGACC TTGATGTGTG | 5930 |
| ATTCCTGATG | ACCGGTTTCA TTTATTCATG TAATAAAGCA AAGGCCCTGG TCCTTTTTAA | 5990 |
| ACTACTAGTT | TTAAAAACCT GTGTTAAATG AACAGTAATT GCCTGGTAGG TTTGGTGTGT | 6050 |
| GTGTAGCATT | GTGTGTCCAT CTGTTATATG TAAAGGACAA GGCACCAGAA TCAGGCTTTA | 6110 |

| | | | | | |
|---|---|---|---|---|---|
| TTTCGATATT | GAAGATGTTA | TTTAACATCT | TTCTTTTTC | CTTACTCCCT | TAGCCATCCC | 6170 |
| CTCCCCTTTT | GTCCTATCAT | TCCCTAGAAC | AAGCCACCTG | TCAATTGTGA | AGGGTTGTGT | 6230 |
| TCTTTATGGC | AGGTTCTATG | CAGATTGTGC | CAGAGCATGT | GCGTGTTCTG | TTGGCAAGCC | 6290 |
| ACAGTGCTCC | CTTGACTGAA | GACATTTCCA | GGTAGATTTC | TCAGCCAGCT | CTAAAACAGA | 6350 |
| TTGCTTTTTC | AGTGGCCTTA | CTCTTTGTGG | GTTTTTTTT | TTCTCTGAAC | TTGATATAAA | 6410 |
| GATTTTATTT | GTCCCTTGAA | AAAGTAACAA | ATGTGCATAG | ATCAATTTGT | ACTACTTTGG | 6470 |
| TCATTGGATA | TTTCTGATCC | TTATTGCATT | GTACCTAAAG | GAGAGTAACT | AATGGTAACC | 6530 |
| TTTTAATAG | AGTATGTGAA | AGGTAGTGGC | TGATGAATCC | TTAACGTTCA | TAGGGTCTTT | 6590 |
| TTGCTGTTAC | GGTTGTATAT | AGAGGTCTGA | AGGATTTTA | AAATGATTTG | CACTTTTTCA | 6650 |
| CTGCATGCTT | ACAATTCCCA | AAGGCAAAAT | CTGTACTGAG | GTAGATCATT | TGAAAGGGCT | 6710 |
| AGATTATAAA | ATTAAGCCTT | AGAGTATGGA | AAGTTCTTAT | AACAATAATA | GTACACACTT | 6770 |
| CAGAGTAAGA | CAAATGCAAA | GCATCTTAAG | GAGTGAAAAT | AGAGTCTAAA | TCTTGCCTTT | 6830 |
| GGCACTACAA | GGTGTGTGTG | TGTGTGTGTG | TTGTGTGTCT | TTAGTAGGAA | ATGGAAGAAC | 6890 |
| ACTGTTTTAT | TTTTAAAGT | GTTTAATGTT | TCTGTCCTTT | CTGTGAATTA | TTGAATTTAA | 6950 |
| GAGCCCTGCT | AAATAATGAA | AAAACACTTT | ACTAAAATTT | ATCAAATTAT | ACTGGGTTCG | 7010 |
| GATTGTGAAA | ACATTGGCCA | CCTAGTAGCA | GTGGTGAGGA | GTGGGAGGGC | CCAGCAAGCA | 7070 |
| TTTATCAGAA | ATAGAATCAC | AATAGGAGGA | GAATTTGGCT | GTCTGATATT | ATGATTTGAT | 7130 |
| TACAATACTG | AATGGGAAAA | GTATCTAATA | TTTTGTAACA | AAAAGACCTT | CATATTATCT | 7190 |
| GTTTTGACCA | AAATATGTAG | CTATTTCCCT | TACACAGATT | GGACCGCACT | TATCTCCCTT | 7250 |
| GTCCTGTATC | CTTTAATTTC | AGGTCTCAGG | ATGTTTAGAA | AGCTAAAACC | CCCTACCCCT | 7310 |
| TTCTGGCTGA | AAACTTGCCT | TATTGGTAT | CTTACACATT | AATGTTACTA | GCATCAGGAG | 7370 |
| CTTACTGTTT | TATTATGATT | CATCTTCAGT | AATTTTTAGA | AGCAAGAAGA | AAGCCATTGT | 7430 |
| GTCCTCTACA | AATTAACAAA | ACTTATCTCT | GATATACAAA | GGGATATAAA | TATATACACT | 7490 |
| TAAATAGAGA | AAAAGAGGTT | GATTGAATTG | TGCCTTTGAG | TGAACCCAGT | TTTTAAATAC | 7550 |
| CGCTGTGTTT | GTTTCGCCAT | GGCTTCAGGG | ATGCTACATG | GCTCTTGCAC | CTTTTACTCC | 7610 |
| TCTGCTTTAT | GAAGTTTGAG | TTGTATTGT | GCATCTTAAA | GTAGGTTGAG | GCTTGAGGCT | 7670 |
| GGGCTTTCGG | GTTTTTTTGT | TTTTGTTTT | GTTTGTTTT | GTTTGTTTT | CTTGTACTTA | 7730 |
| AACCTGCTTG | CTTCCTACCA | CAGATTCTTT | ATTTCCCAA | ACACTACAAA | AAAACTTTTA | 7790 |
| AAACTTTGCC | ATTTCATCTG | TTTACACTCT | TTGCCACTGA | TTAGCAGTAT | TTAAATCTTG | 7850 |
| CAAGAATATT | TTGTGCTTTC | TTTAGAAACA | CAAGAGTAGA | GATTTTCTC | ACTGAAAAGT | 7910 |
| GAGAGTTACG | CATTGCAGCC | ATGAAGGGAT | GCTAGGATCA | ATTATGGCAG | TACCTTTTTT | 7970 |
| CCCCTCCTGT | TCTTGAGCCA | GTTGTCTCTT | TTGTGTTGGG | TCCCACTTAG | GATTAACGGA | 8030 |
| TGTAAGGTAT | TTTCCTGTGC | CTTTATTTTG | TGTCATTCTA | TTGGAAGGAG | GTGTAACGGC | 8090 |
| AGAATAGCAT | CGTGTTGGGG | GTTTTCCTTC | AAACACTGCA | AGTGATATTG | CCACCATGTG | 8150 |
| AACCTCAAAT | ATGCAATCCA | GTTGTGTTGG | TTTCTCGGTG | ACTTGGAGTG | TTCATCTCTT | 8210 |
| CATGAATTGT | GAGCACTGAC | CATGTTCTTC | AGTTCTTAAT | TATGGTGAGT | TGACAAATAC | 8270 |
| CAACTACTGC | TTTTCTTTAG | GTGGCTATAA | ATTTCTTACT | GTCAGGAGGA | AATGACATTA | 8330 |
| TATTCTGTTC | CACTGAACGT | CAGAGATCAG | CAGGCACTGT | ACTGGGTAGA | GAAGTGCCTA | 8390 |
| TACTTCTCTA | CCTAAGAGGG | CAGGAGGGAA | ACCCTACAGC | TCCTTGTGAG | CCTATATATT | 8450 |
| AGTATATCGG | CCTGGAGAGG | ACAAGGGAAT | AAGACCACTC | ATAGTGAGGC | TGGCCAAGCT | 8510 |

-continued

```
GCACTGGTCG GACCAGGCAG TGGCTGACCT AAGGAAGGCA ACTTGCTTTG CTTAAAAGTA    8570
GATTTTTTAA GCAATGCTTA ACACAGGCAG CATTCACCTT TGTTCAGGCC ATCGACATGT    8630
ATTGTTAAAA TTACTGCATA TCCCCCTCAG ATATCAAGTA TACACTGTTC ATGTTGGGGT    8690
TGTGTGTGTG TATGTGTGTA TGTACGCACG CATGTGTCCC AAATCTTGTT TTAATTTTTT    8750
TTTTCTGAAT GTGATCATGT TTGGATAAT  ACCTGAGCAG GGTTGCCTTT TTTTTATTTA    8810
TTACCATTAT ATATTATATT ATATTATATA TTTTTGCTT  TCTTATAACT TGGAGGAAA     8870
GTCAAATCTT GGTATTATTA AAATTGTTTT AAAAAGGAGT AAATTTTCCA GTTGATAAAT    8930
GAAAATCACT GGCCTATGTT TAATAAGTTT TTCTTTAATT ACTGTGGAAT AACGTGCCAG    8990
CTATCATCAA CACAATGATT TTGTACATAG GGTAGGGAAG CAGTGATGCT CTCAATGGGA    9050
AGATGTGCAA CACAAATTAA GGGGAACTCC ATGTATTTTA CCTACTTCAG CAATGGAACT    9110
GCAACTTGGG GCTTTGTGAA TAAAATTTAG CTGCCTTGTA TAGTCGTTTG AAAGAATATG    9170
TGATCTGTGA GAGAATTATA GTTTTTTTT  AGAAGAAAAA TCTGCAAAAG ATCTTCCAA     9230
AGACAATGTG CCACAGATCT TTGTTCTCT  GTAATGAGGA TTAATTGCTG TTTAAACAAA    9290
AATGTAATTG TTCATCTTTA AATTCTTTCC TTTTCATAAG AGGATCAAGC TGTAAAAAAA    9350
CAAAAAAATT AATAAAAATT TCGAGAAATC AAAAAAAAA  A                        9391
```

( 2 ) INFORMATION FOR SEQ ID NO:26:

( i ) SEQUENCE CHARACTERISTICS:
        ( A ) LENGTH: 1210 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Ala Ala Gln Ser Ser Leu Tyr Asn Asp Asp Arg Asn Leu Leu Arg
 1               5                  10                  15

Ile Arg Glu Lys Glu Arg Arg Asn Gln Glu Ala His Gln Lys Glu
            20                  25                  30

Ala Phe Pro Glu Lys Ile Pro Leu Phe Gly Glu Pro Tyr Lys Thr Ala
        35                  40                  45

Lys Gly Asp Glu Leu Ser Ser Arg Ile Gln Asn Met Leu Gly Asn Tyr
 50                  55                  60

Glu Glu Val Lys Glu Phe Leu Ser Thr Lys Ser His Thr His Arg Leu
 65                  70                  75                  80

Asp Ala Ser Glu Asn Arg Leu Gly Lys Pro Lys Tyr Pro Leu Ile Pro
                85                  90                  95

Asp Lys Gly Ser Ser Ile Pro Ser Ser Ser Phe His Thr Ser Val His
            100                 105                 110

His Gln Ser Ile His Thr Pro Ala Ser Gly Pro Leu Ser Val Gly Asn
        115                 120                 125

Ile Ser His Asn Pro Lys Met Ala Gln Pro Arg Thr Glu Pro Met Pro
130                 135                 140

Ser Leu His Ala Lys Ser Cys Gly Pro Pro Asp Ser Gln His Leu Thr
145                 150                 155                 160

Gln Asp Arg Leu Gly Gln Glu Gly Phe Gly Ser Ser His His Lys Lys
                165                 170                 175

Gly Asp Arg Arg Ala Asp Gly Asp His Cys Ala Ser Val Thr Asp Ser
            180                 185                 190

Ala Pro Glu Arg Glu Leu Ser Pro Leu Ile Ser Leu Pro Ser Pro Val
        195                 200                 205
```

```
Pro  Pro  Leu  Ser  Pro  Ile  His  Ser  Asn  Gln  Gln  Thr  Leu  Pro  Arg  Thr
     210                 215                 220

Gln  Gly  Ser  Ser  Lys  Val  His  Gly  Ser  Ser  Asn  Asn  Ser  Lys  Gly  Tyr
225                      230                 235                      240

Cys  Pro  Ala  Lys  Ser  Pro  Lys  Asp  Leu  Ala  Val  Lys  Val  His  Asp  Lys
               245                      250                      255

Glu  Thr  Pro  Gln  Asp  Ser  Leu  Val  Ala  Pro  Ala  Gln  Pro  Pro  Ser  Gln
               260                 265                      270

Thr  Phe  Pro  Pro  Pro  Ser  Leu  Pro  Ser  Lys  Ser  Val  Ala  Met  Gln  Gln
          275                 280                      285

Lys  Pro  Thr  Ala  Tyr  Val  Arg  Pro  Met  Asp  Gly  Gln  Asp  Gln  Ala  Pro
290                      295                 300

Ser  Glu  Ser  Pro  Glu  Leu  Lys  Pro  Leu  Pro  Glu  Asp  Tyr  Arg  Gln  Gln
305                      310                 315                           320

Thr  Phe  Glu  Lys  Thr  Asp  Leu  Lys  Val  Pro  Ala  Lys  Ala  Lys  Leu  Thr
               325                 330                           335

Lys  Leu  Lys  Met  Pro  Ser  Gln  Ser  Val  Glu  Gln  Thr  Tyr  Ser  Asn  Glu
               340                 345                      350

Val  His  Cys  Val  Glu  Glu  Ile  Leu  Lys  Glu  Met  Thr  His  Ser  Trp  Pro
          355                 360                      365

Pro  Pro  Leu  Thr  Ala  Ile  His  Thr  Pro  Ser  Thr  Ala  Glu  Pro  Ser  Lys
     370                 375                      380

Phe  Pro  Phe  Pro  Thr  Lys  Asp  Ser  Gln  His  Val  Ser  Ser  Val  Thr  Gln
385                      390                 395                           400

Asn  Gln  Lys  Gln  Tyr  Asp  Thr  Ser  Ser  Lys  Thr  His  Ser  Asn  Ser  Gln
               405                      410                      415

Gln  Gly  Thr  Ser  Ser  Met  Leu  Glu  Asp  Asp  Leu  Gln  Leu  Ser  Asp  Ser
               420                 425                      430

Glu  Asp  Ser  Asp  Ser  Glu  Gln  Thr  Pro  Glu  Lys  Pro  Pro  Ser  Ser  Ser
          435                 440                      445

Ala  Pro  Pro  Ser  Ala  Pro  Gln  Ser  Leu  Pro  Glu  Pro  Val  Ala  Ser  Ala
450                      455                      460

His  Ser  Ser  Ser  Ala  Glu  Ser  Glu  Ser  Thr  Ser  Asp  Ser  Asp  Ser  Ser
465                      470                      475                      480

Ser  Asp  Ser  Glu  Ser  Glu  Ser  Ser  Ser  Asp  Ser  Glu  Glu  Asn  Glu
               485                      490                 495

Pro  Leu  Glu  Thr  Pro  Ala  Pro  Glu  Pro  Glu  Pro  Pro  Thr  Thr  Asn  Lys
               500                 505                      510

Trp  Gln  Leu  Asp  Asn  Trp  Leu  Thr  Lys  Val  Ser  Gln  Pro  Ala  Ala  Pro
          515                 520                      525

Pro  Glu  Gly  Pro  Arg  Ser  Thr  Glu  Pro  Pro  Arg  Arg  His  Pro  Glu  Ser
530                      535                      540

Lys  Gly  Ser  Ser  Asp  Ser  Ala  Thr  Ser  Gln  Glu  His  Ser  Glu  Ser  Lys
545                      550                      555                      560

Asp  Pro  Pro  Pro  Lys  Ser  Ser  Lys  Ala  Pro  Arg  Ala  Pro  Pro  Glu
               565                      570                 575

Ala  Pro  His  Pro  Gly  Lys  Arg  Ser  Cys  Gln  Lys  Ser  Pro  Ala  Gln  Gln
          580                      585                      590

Glu  Pro  Pro  Gln  Arg  Gln  Thr  Val  Gly  Thr  Lys  Gln  Pro  Lys  Lys  Pro
          595                 600                      605

Val  Lys  Ala  Ser  Ala  Arg  Ala  Gly  Ser  Arg  Thr  Ser  Leu  Gln  Gly  Glu
          610                 615                      620

Arg  Glu  Pro  Gly  Leu  Leu  Pro  Tyr  Gly  Ser  Arg  Asp  Gln  Thr  Ser  Lys
```

-continued

| 625 | | | | | 630 | | | | | 635 | | | | | 640 |
|---|---|---|---|---|---|---|---|---|---|---|---|---|---|---|---|
| Asp | Lys | Pro | Lys | Val | Lys | Thr | Lys | Gly | Arg | Pro | Arg | Ala | Ala | Ala | Ser |
| | | | | 645 | | | | | 650 | | | | | 655 | |
| Asn | Glu | Pro | Lys | Pro | Ala | Val | Pro | Pro | Ser | Ser | Glu | Lys | Lys | Lys | His |
| | | | | 660 | | | | | 665 | | | | | 670 | |
| Lys | Ser | Ser | Leu | Pro | Ala | Pro | Ser | Lys | Ala | Leu | Ser | Gly | Pro | Glu | Pro |
| | | | | 675 | | | | | 680 | | | | | 685 | |
| Ala | Lys | Asp | Asn | Val | Glu | Asp | Arg | Thr | Pro | Glu | His | Phe | Ala | Leu | Val |
| | | | | 690 | | | | | 695 | | | | | 700 | |
| Pro | Leu | Thr | Glu | Ser | Gln | Gly | Pro | Pro | His | Ser | Gly | Ser | Gly | Ser | Arg |
| 705 | | | | | 710 | | | | | 715 | | | | | 720 |
| Thr | Ser | Gly | Cys | Arg | Gln | Ala | Val | Val | Gln | Glu | Asp | Ser | Arg | Lys | |
| | | | | 725 | | | | | 730 | | | | | 735 | |
| Asp | Arg | Leu | Pro | Leu | Pro | Leu | Arg | Asp | Thr | Lys | Leu | Leu | Ser | Pro | Leu |
| | | | | 740 | | | | | 745 | | | | | 750 | |
| Arg | Asp | Thr | Pro | Pro | Pro | Gln | Ser | Leu | Met | Val | Lys | Ile | Thr | Leu | Asp |
| | | | | 755 | | | | | 760 | | | | | 765 | |
| Leu | Leu | Ser | Arg | Ile | Pro | Gln | Pro | Pro | Gly | Lys | Gly | Ser | Arg | Gln | Arg |
| | | | | 770 | | | | | 775 | | | | | 780 | |
| Lys | Ala | Glu | Asp | Lys | Gln | Pro | Pro | Ala | Gly | Lys | Lys | His | Ser | Ser | Glu |
| 785 | | | | | 790 | | | | | 795 | | | | | 800 |
| Lys | Arg | Ser | Ser | Asp | Ser | Ser | Ser | Lys | Leu | Ala | Lys | Lys | Arg | Lys | Gly |
| | | | | 805 | | | | | 810 | | | | | 815 | |
| Glu | Ala | Glu | Arg | Asp | Cys | Asp | Asn | Lys | Lys | Ile | Arg | Leu | Glu | Lys | Glu |
| | | | | 820 | | | | | 825 | | | | | 830 | |
| Ile | Lys | Ser | Gln | Ser | Ser | Ser | Ser | Ser | Ser | His | Lys | Glu | Ser | Ser | |
| | | | | 835 | | | | | 840 | | | | | 845 | |
| Lys | Thr | Lys | Pro | Ser | Arg | Pro | Ser | Ser | Gln | Ser | Ser | Lys | Lys | Glu | Met |
| | | | | 850 | | | | | 855 | | | | | 860 | |
| Leu | Pro | Pro | Pro | Pro | Val | Ser | Ser | Ser | Gln | Lys | Pro | Ala | Lys | Pro | |
| 865 | | | | | 870 | | | | | 875 | | | | | 880 |
| Ala | Leu | Lys | Arg | Ser | Arg | Arg | Glu | Ala | Asp | Thr | Cys | Gly | Gln | Asp | Pro |
| | | | | 885 | | | | | 890 | | | | | 895 | |
| Pro | Lys | Ser | Ala | Ser | Ser | Thr | Lys | Ser | Asn | His | Lys | Asp | Ser | Ser | Ile |
| | | | | 900 | | | | | 905 | | | | | 910 | |
| Pro | Lys | Gln | Arg | Arg | Val | Glu | Gly | Lys | Gly | Ser | Arg | Ser | Ser | Ser | Glu |
| | | | | 915 | | | | | 920 | | | | | 925 | |
| His | Lys | Gly | Ser | Ser | Gly | Asp | Thr | Ala | Asn | Pro | Phe | Pro | Val | Pro | Ser |
| | | | | 930 | | | | | 935 | | | | | 940 | |
| Leu | Pro | Asn | Gly | Asn | Ser | Lys | Pro | Gly | Lys | Pro | Gln | Val | Lys | Phe | Asp |
| 945 | | | | | 950 | | | | | 955 | | | | | 960 |
| Lys | Gln | Gln | Ala | Asp | Leu | His | Met | Arg | Glu | Ala | Lys | Lys | Met | Lys | Gln |
| | | | | 965 | | | | | 970 | | | | | 975 | |
| Lys | Ala | Glu | Leu | Met | Thr | Asp | Arg | Val | Gly | Lys | Ala | Phe | Lys | Tyr | Leu |
| | | | | 980 | | | | | 985 | | | | | 990 | |
| Glu | Ala | Val | Leu | Ser | Phe | Ile | Glu | Cys | Gly | Ile | Ala | Thr | Glu | Ser | Glu |
| | | | | 995 | | | | | 1000 | | | | | 1005 | |
| Ser | Gln | Ser | Ser | Lys | Ser | Ala | Tyr | Ser | Val | Tyr | Ser | Glu | Thr | Val | Asp |
| | | | | 1010 | | | | | 1015 | | | | | 1020 | |
| Leu | Ile | Lys | Phe | Ile | Met | Ser | Leu | Lys | Ser | Phe | Ser | Asp | Ala | Thr | Ala |
| | | | | 1025 | | | | | 1030 | | | | | 1035 | 1040 |
| Pro | Thr | Gln | Glu | Lys | Ile | Phe | Ala | Val | Leu | Cys | Met | Arg | Cys | Gln | Ser |
| | | | | 1045 | | | | | 1050 | | | | | 1055 | |

| Ile | Leu | Asn | Met | Ala | Met | Phe | Arg | Cys | Lys | Lys | Asp | Ile | Ala | Ile | Lys |
|---|---|---|---|---|---|---|---|---|---|---|---|---|---|---|---|
| | | | 1060 | | | | 1065 | | | | | 1070 | | | |

| Tyr | Ser | Arg | Thr | Leu | Asn | Lys | His | Phe | Glu | Ser | Ser | Ser | Lys | Val | Ala |
|---|---|---|---|---|---|---|---|---|---|---|---|---|---|---|---|
| | | 1075 | | | | | 1080 | | | | | 1085 | | | |

| Gln | Ala | Pro | Ser | Pro | Cys | Ile | Ala | Ser | Thr | Gly | Thr | Pro | Ser | Pro | Leu |
|---|---|---|---|---|---|---|---|---|---|---|---|---|---|---|---|
| | 1090 | | | | | 1095 | | | | | 1100 | | | | |

| Ser | Pro | Met | Pro | Ser | Pro | Ala | Ser | Ser | Val | Gly | Ser | Gln | Ser | Ser | Ala |
|---|---|---|---|---|---|---|---|---|---|---|---|---|---|---|---|
| 1105 | | | | 1110 | | | | | 1115 | | | | | 1120 | |

| Gly | Ser | Val | Gly | Ser | Ser | Gly | Val | Ala | Ala | Thr | Ile | Ser | Thr | Pro | Val |
|---|---|---|---|---|---|---|---|---|---|---|---|---|---|---|---|
| | | | | 1125 | | | | | 1130 | | | | | 1135 | |

| Thr | Ile | Gln | Asn | Met | Thr | Ser | Ser | Tyr | Val | Thr | Ile | Thr | Ser | His | Val |
|---|---|---|---|---|---|---|---|---|---|---|---|---|---|---|---|
| | | | | 1140 | | | | | 1145 | | | | | 1150 | |

| Leu | Thr | Ala | Phe | Asp | Leu | Trp | Glu | Gln | Ala | Glu | Ala | Leu | Thr | Arg | Lys |
|---|---|---|---|---|---|---|---|---|---|---|---|---|---|---|---|
| | | | 1155 | | | | | 1160 | | | | | 1165 | | |

| Asn | Lys | Glu | Phe | Phe | Ala | Arg | Leu | Ser | Thr | Asn | Val | Cys | Thr | Leu | Ala |
|---|---|---|---|---|---|---|---|---|---|---|---|---|---|---|---|
| | 1170 | | | | | 1175 | | | | | 1180 | | | | |

| Leu | Asn | Ser | Ser | Leu | Val | Asp | Leu | Val | His | Tyr | Thr | Arg | Gln | Gly | Phe |
|---|---|---|---|---|---|---|---|---|---|---|---|---|---|---|---|
| 1185 | | | | | 1190 | | | | | 1195 | | | | | 1200 |

| Gln | Gln | Leu | Gln | Glu | Leu | Thr | Lys | Thr | Pro |
|---|---|---|---|---|---|---|---|---|---|
| | | | | 1205 | | | | 1210 | |

( 2 ) INFORMATION FOR SEQ ID NO:27:

( i ) SEQUENCE CHARACTERISTICS:
        ( A ) LENGTH: 9370 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 469..4032

( x i ) SEQUENCE DESCRIPTION: SEQ ID NO:27:

```
GGCAATTTCT  TTTCCTTTCT  AACTGTGGCC  CGCGTTGTGC  TGTTGCTGGG  CAGGCGTTGG        60

GCGCCGGCGG  TCTTCGAGCG  TGGGGCCCCG  CTGGCTTTCC  CTTCTCAGAA  ACTGCGCCGG       120

GGGCGCTCGC  TTGCCCCGGA  TTCGGACGCG  GCGCTCCCCG  GCTCGTCTG   AAGTGCAGAT       180

CGCCGCAGAG  GCCCCAGTGC  CCGGATGTCC  ATCAGGATTA  GCGCGAGCCA  ATACGGGCCG       240

AGCCCGGGGC  TGCGCCGAGG  ACGCCCGGGG  AGTCTGAGAG  GCGTGGAGAA  TTTTGCTTGT       300

GCAAGATTAT  TTCAGAGCAA  GGTCGTGCGG  TGTGTGTAGA  AGATGAACAG  ACTAGCCACT       360

TTGCATTGAC  TGGAAACAAT  GGCATTTACA  GAAAGAGTCA  ACAGCAGTGG  CAACAGTTTG       420

TACAATGACG  ACAGAAACCT  GCTTCGAATT  AGAGAGAAGG  AAAGACGC    AAC CAG GAA      477
                                                          Asn Gln Glu
                                                            1
```

| GCC | CAC | CAA | GAG | AAA | GAG | GCA | TTT | CCT | GAA | AAG | ATT | CCC | CTT | TTT | GGA | 525 |
|---|---|---|---|---|---|---|---|---|---|---|---|---|---|---|---|---|
| Ala | His | Gln | Glu | Lys | Glu | Ala | Phe | Pro | Glu | Lys | Ile | Pro | Leu | Phe | Gly | |
| | 5 | | | | 10 | | | | | 15 | | | | | | |

| GAG | CCC | TAC | AAG | ACA | GCA | AAA | GGT | GAT | GAG | CTG | TCT | AGT | CGA | ATA | CAG | 573 |
|---|---|---|---|---|---|---|---|---|---|---|---|---|---|---|---|---|
| Glu | Pro | Tyr | Lys | Thr | Ala | Lys | Gly | Asp | Glu | Leu | Ser | Ser | Arg | Ile | Gln | |
| 20 | | | | 25 | | | | | 30 | | | | | | 35 | |

| AAC | ATG | TTG | GGA | AAC | TAC | GAA | GAA | GTG | AAG | GAG | TTC | CTT | AGT | ACT | AAG | 621 |
|---|---|---|---|---|---|---|---|---|---|---|---|---|---|---|---|---|
| Asn | Met | Leu | Gly | Asn | Tyr | Glu | Glu | Val | Lys | Glu | Phe | Leu | Ser | Thr | Lys | |
| | | | 40 | | | | | 45 | | | | | 50 | | | |

| TCT | CAC | ACT | CAT | CGC | CTG | GAT | GCT | TCT | GAA | AAT | AGG | TTG | GGA | AAG | CCG | 669 |
|---|---|---|---|---|---|---|---|---|---|---|---|---|---|---|---|---|
| Ser | His | Thr | His | Arg | Leu | Asp | Ala | Ser | Glu | Asn | Arg | Leu | Gly | Lys | Pro | |

-continued

|  |  |  | 55 |  |  |  |  | 60 |  |  |  |  | 65 |  |  |  |
|---|---|---|---|---|---|---|---|---|---|---|---|---|---|---|---|---|
| AAA | TAT | CCT | TTA | ATT | CCT | GAC | AAA | GGG | AGC | AGC | ATT | CCA | TCC | AGC | TCC | 717 |
| Lys | Tyr | Pro | Leu | Ile | Pro | Asp | Lys | Gly | Ser | Ser | Ile | Pro | Ser | Ser | Ser |  |
|  |  | 70 |  |  |  |  | 75 |  |  |  |  | 80 |  |  |  |  |
| TTC | CAC | ACT | AGT | GTC | CAC | CAC | CAG | TCC | ATT | CAC | ACT | CCT | GCG | TCT | GGA | 765 |
| Phe | His | Thr | Ser | Val | His | His | Gln | Ser | Ile | His | Thr | Pro | Ala | Ser | Gly |  |
|  | 85 |  |  |  |  | 90 |  |  |  |  | 95 |  |  |  |  |  |
| CCA | CTT | TCT | GTT | GGC | AAC | ATT | AGC | CAC | AAT | CCA | AAG | ATG | GCG | CAG | CCA | 813 |
| Pro | Leu | Ser | Val | Gly | Asn | Ile | Ser | His | Asn | Pro | Lys | Met | Ala | Gln | Pro |  |
| 100 |  |  |  |  | 105 |  |  |  |  | 110 |  |  |  |  | 115 |  |
| AGA | ACT | GAA | CCA | ATG | CCA | AGT | CTC | CAT | GCC | AAA | AGC | TGC | GGC | CCA | CCG | 861 |
| Arg | Thr | Glu | Pro | Met | Pro | Ser | Leu | His | Ala | Lys | Ser | Cys | Gly | Pro | Pro |  |
|  |  |  | 120 |  |  |  |  | 125 |  |  |  |  | 130 |  |  |  |
| GAC | AGC | CAG | CAC | CTG | ACC | CAG | GAT | CGC | CTT | GGT | CAG | GAG | GGG | TTC | GGC | 909 |
| Asp | Ser | Gln | His | Leu | Thr | Gln | Asp | Arg | Leu | Gly | Gln | Glu | Gly | Phe | Gly |  |
|  |  |  | 135 |  |  |  |  | 140 |  |  |  |  | 145 |  |  |  |
| TCT | AGT | CAT | CAC | AAG | AAA | GGT | GAC | CGA | AGA | GCT | GAC | GGA | GAC | CAC | TGT | 957 |
| Ser | Ser | His | His | Lys | Lys | Gly | Asp | Arg | Arg | Ala | Asp | Gly | Asp | His | Cys |  |
|  |  | 150 |  |  |  |  | 155 |  |  |  |  | 160 |  |  |  |  |
| GCT | TCG | GTG | ACA | GAT | TCG | GCT | CCA | GAG | AGG | GAG | CTT | TCT | CCC | TTA | ATC | 1005 |
| Ala | Ser | Val | Thr | Asp | Ser | Ala | Pro | Glu | Arg | Glu | Leu | Ser | Pro | Leu | Ile |  |
|  | 165 |  |  |  |  | 170 |  |  |  |  | 175 |  |  |  |  |  |
| TCT | TTG | CCT | TCC | CCA | GTT | CCC | CCT | TTG | TCA | CCT | ATA | CAT | TCC | AAC | CAG | 1053 |
| Ser | Leu | Pro | Ser | Pro | Val | Pro | Pro | Leu | Ser | Pro | Ile | His | Ser | Asn | Gln |  |
| 180 |  |  |  |  | 185 |  |  |  |  | 190 |  |  |  |  | 195 |  |
| CAA | ACT | CTT | CCC | CGG | ACG | CAA | GGA | AGC | AGC | AAG | GTT | CAT | GGC | AGC | AGC | 1101 |
| Gln | Thr | Leu | Pro | Arg | Thr | Gln | Gly | Ser | Ser | Lys | Val | His | Gly | Ser | Ser |  |
|  |  |  |  | 200 |  |  |  |  | 205 |  |  |  |  | 210 |  |  |
| AAT | AAC | AGT | AAA | GGC | TAT | TGC | CCA | GCC | AAA | TCT | CCC | AAG | GAC | CTA | GCA | 1149 |
| Asn | Asn | Ser | Lys | Gly | Tyr | Cys | Pro | Ala | Lys | Ser | Pro | Lys | Asp | Leu | Ala |  |
|  |  |  | 215 |  |  |  |  | 220 |  |  |  |  | 225 |  |  |  |
| GTG | AAA | GTC | CAT | GAT | AAA | GAG | ACC | CCT | CAA | GAC | AGT | TTG | GTG | GCC | CCT | 1197 |
| Val | Lys | Val | His | Asp | Lys | Glu | Thr | Pro | Gln | Asp | Ser | Leu | Val | Ala | Pro |  |
|  |  | 230 |  |  |  |  | 235 |  |  |  |  | 240 |  |  |  |  |
| GCC | CAG | CCG | CCT | TCT | CAG | ACA | TTT | CCA | CCT | CCC | TCC | CTC | CCC | TCA | AAA | 1245 |
| Ala | Gln | Pro | Pro | Ser | Gln | Thr | Phe | Pro | Pro | Pro | Ser | Leu | Pro | Ser | Lys |  |
|  | 245 |  |  |  |  | 250 |  |  |  |  | 255 |  |  |  |  |  |
| AGT | GTT | GCA | ATG | CAG | CAG | AAG | CCC | ACG | GCT | TAT | GTC | CGG | CCC | ATG | GAT | 1293 |
| Ser | Val | Ala | Met | Gln | Gln | Lys | Pro | Thr | Ala | Tyr | Val | Arg | Pro | Met | Asp |  |
| 260 |  |  |  |  | 265 |  |  |  |  | 270 |  |  |  |  | 275 |  |
| GGT | CAA | GAT | CAG | GCC | CCT | AGT | GAA | TCC | CCT | GAA | CTG | AAA | CCA | CTG | CCG | 1341 |
| Gly | Gln | Asp | Gln | Ala | Pro | Ser | Glu | Ser | Pro | Glu | Leu | Lys | Pro | Leu | Pro |  |
|  |  |  |  | 280 |  |  |  |  | 285 |  |  |  |  | 290 |  |  |
| GAG | GAC | TAT | CGA | CAG | CAG | ACC | TTT | GAA | AAA | ACA | GAC | TTG | AAA | GTG | CCT | 1389 |
| Glu | Asp | Tyr | Arg | Gln | Gln | Thr | Phe | Glu | Lys | Thr | Asp | Leu | Lys | Val | Pro |  |
|  |  |  | 295 |  |  |  |  | 300 |  |  |  |  | 305 |  |  |  |
| GCC | AAA | GCC | AAG | CTC | ACC | AAA | CTG | AAG | ATG | CCT | TCT | CAG | TCA | GTT | GAG | 1437 |
| Ala | Lys | Ala | Lys | Leu | Thr | Lys | Leu | Lys | Met | Pro | Ser | Gln | Ser | Val | Glu |  |
|  |  | 310 |  |  |  |  | 315 |  |  |  |  | 320 |  |  |  |  |
| CAG | ACC | TAC | TCC | AAT | GAA | GTC | CAT | TGT | GTT | GAA | GAG | ATT | CTG | AAG | GAA | 1485 |
| Gln | Thr | Tyr | Ser | Asn | Glu | Val | His | Cys | Val | Glu | Glu | Ile | Leu | Lys | Glu |  |
|  | 325 |  |  |  |  | 330 |  |  |  |  | 335 |  |  |  |  |  |
| ATG | ACC | CAT | TCA | TGG | CCG | CCT | CCT | TTG | ACA | GCA | ATA | CAT | ACG | CCT | AGT | 1533 |
| Met | Thr | His | Ser | Trp | Pro | Pro | Pro | Leu | Thr | Ala | Ile | His | Thr | Pro | Ser |  |
| 340 |  |  |  |  | 345 |  |  |  |  | 350 |  |  |  |  | 355 |  |
| ACA | GCT | GAG | CCA | TCC | AAG | TTT | CCT | TTC | CCT | ACA | AAG | GAC | TCT | CAG | CAT | 1581 |
| Thr | Ala | Glu | Pro | Ser | Lys | Phe | Pro | Phe | Pro | Thr | Lys | Asp | Ser | Gln | His |  |
|  |  |  |  | 360 |  |  |  |  | 365 |  |  |  |  | 370 |  |  |
| GTC | AGT | TCT | GTA | ACC | CAA | AAC | CAA | AAA | CAA | TAT | GAT | ACA | TCT | TCA | AAA | 1629 |
| Val | Ser | Ser | Val | Thr | Gln | Asn | Gln | Lys | Gln | Tyr | Asp | Thr | Ser | Ser | Lys |  |

|  |  |  |  |  |  |  |  |  |  |  |  |  |  |  |  |
|---|---|---|---|---|---|---|---|---|---|---|---|---|---|---|---|
|  |  |  | 375 |  |  |  |  | 380 |  |  |  |  | 385 |  |  |
| ACT | CAC | TCA | AAT | TCT | CAG | CAA | GGA | ACG | TCA | TCC | ATG | CTC | GAA | GAC | GAC | 1677 |
| Thr | His | Ser | Asn | Ser | Gln | Gln | Gly | Thr | Ser | Ser | Met | Leu | Glu | Asp | Asp |  |
|  |  | 390 |  |  |  |  | 395 |  |  |  |  | 400 |  |  |  |
| CTT | CAG | CTC | AGT | GAC | AGT | GAG | GAC | AGT | GAC | AGT | GAA | CAA | ACC | CCA | GAG | 1725 |
| Leu | Gln | Leu | Ser | Asp | Ser | Glu | Asp | Ser | Asp | Ser | Glu | Gln | Thr | Pro | Glu |  |
|  | 405 |  |  |  |  | 410 |  |  |  |  | 415 |  |  |  |  |
| AAG | CCT | CCC | TCC | TCA | TCT | GCA | CCT | CCA | AGT | GCT | CCA | CAG | TCC | CTT | CCA | 1773 |
| Lys | Pro | Pro | Ser | Ser | Ser | Ala | Pro | Pro | Ser | Ala | Pro | Gln | Ser | Leu | Pro |  |
| 420 |  |  |  |  | 425 |  |  |  |  | 430 |  |  |  |  | 435 |
| GAA | CCA | GTG | GCA | TCA | GCA | CAT | TCC | AGC | AGT | GCA | GAG | TCA | GAA | AGC | ACC | 1821 |
| Glu | Pro | Val | Ala | Ser | Ala | His | Ser | Ser | Ser | Ala | Glu | Ser | Glu | Ser | Thr |  |
|  |  |  |  | 440 |  |  |  |  | 445 |  |  |  |  | 450 |  |
| AGT | GAC | TCA | GAC | AGT | TCC | TCA | GAC | TCA | GAG | AGC | GAG | AGC | AGT | TCA | AGT | 1869 |
| Ser | Asp | Ser | Asp | Ser | Ser | Ser | Asp | Ser | Glu | Ser | Glu | Ser | Ser | Ser | Ser |  |
|  |  |  | 455 |  |  |  |  | 460 |  |  |  |  | 465 |  |  |
| GAC | AGC | GAA | GAA | AAT | GAG | CCC | CTA | GAA | ACC | CCA | GCT | CCG | GAG | CCT | GAG | 1917 |
| Asp | Ser | Glu | Glu | Asn | Glu | Pro | Leu | Glu | Thr | Pro | Ala | Pro | Glu | Pro | Glu |  |
|  |  | 470 |  |  |  |  | 475 |  |  |  |  | 480 |  |  |  |
| CCT | CCA | ACA | ACA | AAC | AAA | TGG | CAG | CTG | GAC | AAC | TGG | CTG | ACC | AAA | GTC | 1965 |
| Pro | Pro | Thr | Thr | Asn | Lys | Trp | Gln | Leu | Asp | Asn | Trp | Leu | Thr | Lys | Val |  |
|  | 485 |  |  |  |  | 490 |  |  |  |  | 495 |  |  |  |  |
| AGC | CAG | CCA | GCT | GCG | CCA | CCA | GAG | GGC | CCC | AGG | AGC | ACA | GAG | CCC | CCA | 2013 |
| Ser | Gln | Pro | Ala | Ala | Pro | Pro | Glu | Gly | Pro | Arg | Ser | Thr | Glu | Pro | Pro |  |
| 500 |  |  |  |  | 505 |  |  |  |  | 510 |  |  |  |  | 515 |
| CGG | CGG | CAC | CCA | GAG | AGT | AAG | GGC | AGC | AGC | GAC | AGT | GCC | ACG | AGT | CAG | 2061 |
| Arg | Arg | His | Pro | Glu | Ser | Lys | Gly | Ser | Ser | Asp | Ser | Ala | Thr | Ser | Gln |  |
|  |  |  |  | 520 |  |  |  |  | 525 |  |  |  |  | 530 |  |
| GAG | CAT | TCT | GAA | TCC | AAA | GAT | CCT | CCC | CCT | AAA | AGC | TCC | AGC | AAA | GCC | 2109 |
| Glu | His | Ser | Glu | Ser | Lys | Asp | Pro | Pro | Pro | Lys | Ser | Ser | Ser | Lys | Ala |  |
|  |  |  | 535 |  |  |  |  | 540 |  |  |  |  | 545 |  |  |
| CCC | CGG | GCC | CCA | CCC | GAA | GCC | CCC | CAC | CCC | GGA | AAG | AGG | AGC | TGT | CAG | 2157 |
| Pro | Arg | Ala | Pro | Pro | Glu | Ala | Pro | His | Pro | Gly | Lys | Arg | Ser | Cys | Gln |  |
|  |  | 550 |  |  |  |  | 555 |  |  |  |  | 560 |  |  |  |
| AAG | TCT | CCG | GCA | CAG | CAG | GAG | CCC | CCA | CAA | AGG | CAA | ACC | GTT | GGA | ACC | 2205 |
| Lys | Ser | Pro | Ala | Gln | Gln | Glu | Pro | Pro | Gln | Arg | Gln | Thr | Val | Gly | Thr |  |
|  | 565 |  |  |  |  | 570 |  |  |  |  | 575 |  |  |  |  |
| AAA | CAA | CCC | AAA | AAA | CCT | GTC | AAG | GCC | TCT | GCC | CGG | GCA | GGT | TCA | CGG | 2253 |
| Lys | Gln | Pro | Lys | Lys | Pro | Val | Lys | Ala | Ser | Ala | Arg | Ala | Gly | Ser | Arg |  |
| 580 |  |  |  |  | 585 |  |  |  |  | 590 |  |  |  |  | 595 |
| ACC | AGC | CTG | CAG | GGG | GAA | AGG | GAG | CCA | GGG | CTT | CTT | CCC | TAT | GGC | TCC | 2301 |
| Thr | Ser | Leu | Gln | Gly | Glu | Arg | Glu | Pro | Gly | Leu | Leu | Pro | Tyr | Gly | Ser |  |
|  |  |  |  | 600 |  |  |  |  | 605 |  |  |  |  | 610 |  |
| CGA | GAC | CAG | ACT | TCC | AAA | GAC | AAG | CCC | AAG | GTG | AAG | ACG | AAA | GGA | CGG | 2349 |
| Arg | Asp | Gln | Thr | Ser | Lys | Asp | Lys | Pro | Lys | Val | Lys | Thr | Lys | Gly | Arg |  |
|  |  |  | 615 |  |  |  |  | 620 |  |  |  |  | 625 |  |  |
| CCC | CGG | GCC | GCA | GCA | AGC | AAC | GAA | CCC | AAG | CCA | GCA | GTG | CCC | CCC | TCC | 2397 |
| Pro | Arg | Ala | Ala | Ala | Ser | Asn | Glu | Pro | Lys | Pro | Ala | Val | Pro | Pro | Ser |  |
|  |  | 630 |  |  |  |  | 635 |  |  |  |  | 640 |  |  |  |
| AGT | GAG | AAG | AAG | AAG | CAC | AAG | AGC | TCC | CTC | CCT | GCC | CCC | TCT | AAG | GCT | 2445 |
| Ser | Glu | Lys | Lys | Lys | His | Lys | Ser | Ser | Leu | Pro | Ala | Pro | Ser | Lys | Ala |  |
|  | 645 |  |  |  |  | 650 |  |  |  |  | 655 |  |  |  |  |
| CTC | TCA | GGC | CCA | GAA | CCC | GCG | AAG | GAC | AAT | GTG | GAG | GAC | AGG | ACC | CCT | 2493 |
| Leu | Ser | Gly | Pro | Glu | Pro | Ala | Lys | Asp | Asn | Val | Glu | Asp | Arg | Thr | Pro |  |
| 660 |  |  |  |  | 665 |  |  |  |  | 670 |  |  |  |  | 675 |
| GAG | CAC | TTT | GCT | CTT | GTT | CCC | CTG | ACT | GAG | AGC | CAG | GGC | CCA | CCC | CAC | 2541 |
| Glu | His | Phe | Ala | Leu | Val | Pro | Leu | Thr | Glu | Ser | Gln | Gly | Pro | Pro | His |  |
|  |  |  |  | 680 |  |  |  |  | 685 |  |  |  |  | 690 |  |
| AGT | GGC | AGC | GGC | AGC | AGG | ACT | AGT | GGC | TGC | CGC | CAA | GCC | GTG | GTG | GTC | 2589 |
| Ser | Gly | Ser | Gly | Ser | Arg | Thr | Ser | Gly | Cys | Arg | Gln | Ala | Val | Val | Val |  |

-continued

|     |     |     | 695 |     |     |     | 700 |     |     |     | 705 |     |     |     |      |
|-----|-----|-----|-----|-----|-----|-----|-----|-----|-----|-----|-----|-----|-----|-----|------|
| CAG | GAG | GAC | AGC | CGC | AAA | GAC | AGA | CTC | CCA | TTG | CCT | TTG | AGA | GAC | ACC  | 2637
| Gln | Glu | Asp | Ser | Arg | Lys | Asp | Arg | Leu | Pro | Leu | Pro | Leu | Arg | Asp | Thr  |
|     |     | 710 |     |     |     |     | 715 |     |     |     |     | 720 |     |     |      |
| AAG | CTG | CTC | TCA | CCG | CTC | AGG | GAC | ACT | CCT | CCC | CCA | CAA | AGC | TTG | ATG  | 2685
| Lys | Leu | Leu | Ser | Pro | Leu | Arg | Asp | Thr | Pro | Pro | Pro | Gln | Ser | Leu | Met  |
|     |     | 725 |     |     |     |     | 730 |     |     |     |     | 735 |     |     |      |
| GTG | AAG | ATC | ACC | CTA | GAC | CTG | CTC | TCT | CGG | ATA | CCC | CAG | CCT | CCC | GGG  | 2733
| Val | Lys | Ile | Thr | Leu | Asp | Leu | Leu | Ser | Arg | Ile | Pro | Gln | Pro | Pro | Gly  |
| 740 |     |     |     |     | 745 |     |     |     |     | 750 |     |     |     |     | 755  |
| AAG | GGG | AGC | CGC | CAG | AGG | AAA | GCA | GAA | GAT | AAA | CAG | CCG | CCC | GCA | GGG  | 2781
| Lys | Gly | Ser | Arg | Gln | Arg | Lys | Ala | Glu | Asp | Lys | Gln | Pro | Pro | Ala | Gly  |
|     |     |     |     | 760 |     |     |     |     | 765 |     |     |     |     | 770 |      |
| AAG | AAG | CAC | AGC | TCT | GAG | AAG | AGG | AGC | TCA | GAC | AGC | TCA | AGC | AAG | TTG  | 2829
| Lys | Lys | His | Ser | Ser | Glu | Lys | Arg | Ser | Ser | Asp | Ser | Ser | Ser | Lys | Leu  |
|     |     |     | 775 |     |     |     |     | 780 |     |     |     |     | 785 |     |      |
| GCC | AAA | AAG | AGA | AAG | GGT | GAA | GCA | GAA | AGA | GAC | TGT | GAT | AAC | AAG | AAA  | 2877
| Ala | Lys | Lys | Arg | Lys | Gly | Glu | Ala | Glu | Arg | Asp | Cys | Asp | Asn | Lys | Lys  |
|     |     | 790 |     |     |     |     | 795 |     |     |     |     | 800 |     |     |      |
| ATC | AGA | CTG | GAG | AAG | GAA | ATC | AAA | TCA | CAG | TCA | TCT | TCA | TCT | TCA | TCC  | 2925
| Ile | Arg | Leu | Glu | Lys | Glu | Ile | Lys | Ser | Gln | Ser | Ser | Ser | Ser | Ser | Ser  |
|     | 805 |     |     |     |     | 810 |     |     |     |     | 815 |     |     |     |      |
| TCC | CAC | AAA | GAA | TCT | TCT | AAA | ACA | AAG | CCC | TCC | AGG | CCC | TCC | TCA | CAG  | 2973
| Ser | His | Lys | Glu | Ser | Ser | Lys | Thr | Lys | Pro | Ser | Arg | Pro | Ser | Ser | Gln  |
| 820 |     |     |     |     | 825 |     |     |     |     | 830 |     |     |     |     | 835  |
| TCC | TCA | AAG | AAG | GAA | ATG | CTC | CCC | CCG | CCA | CCC | GTG | TCC | TCG | TCC | TCC  | 3021
| Ser | Ser | Lys | Lys | Glu | Met | Leu | Pro | Pro | Pro | Pro | Val | Ser | Ser | Ser | Ser  |
|     |     |     |     | 840 |     |     |     |     | 845 |     |     |     |     | 850 |      |
| CAG | AAG | CCA | GCC | AAG | CCT | GCA | CTT | AAG | AGG | TCA | AGG | CGG | GAA | GCA | GAC  | 3069
| Gln | Lys | Pro | Ala | Lys | Pro | Ala | Leu | Lys | Arg | Ser | Arg | Arg | Glu | Ala | Asp  |
|     |     |     | 855 |     |     |     |     | 860 |     |     |     |     | 865 |     |      |
| ACC | TGT | GGC | CAG | GAC | CCT | CCC | AAA | AGT | GCC | AGC | AGT | ACC | AAG | AGC | AAC  | 3117
| Thr | Cys | Gly | Gln | Asp | Pro | Pro | Lys | Ser | Ala | Ser | Ser | Thr | Lys | Ser | Asn  |
|     |     | 870 |     |     |     |     | 875 |     |     |     |     | 880 |     |     |      |
| CAC | AAA | GAC | TCT | TCC | ATT | CCC | AAG | CAG | AGA | AGA | GTA | GAG | GGG | AAG | GGC  | 3165
| His | Lys | Asp | Ser | Ser | Ile | Pro | Lys | Gln | Arg | Arg | Val | Glu | Gly | Lys | Gly  |
|     | 885 |     |     |     |     | 890 |     |     |     |     | 895 |     |     |     |      |
| TCC | AGA | AGC | TCC | TCG | GAG | CAC | AAG | GGT | TCT | TCC | GGA | GAT | ACT | GCA | AAT  | 3213
| Ser | Arg | Ser | Ser | Ser | Glu | His | Lys | Gly | Ser | Ser | Gly | Asp | Thr | Ala | Asn  |
| 900 |     |     |     |     | 905 |     |     |     |     | 910 |     |     |     |     | 915  |
| CCT | TTT | CCA | GTG | CCT | TCT | TTG | CCA | AAT | GGT | AAC | TCT | AAA | CCA | GGG | AAG  | 3261
| Pro | Phe | Pro | Val | Pro | Ser | Leu | Pro | Asn | Gly | Asn | Ser | Lys | Pro | Gly | Lys  |
|     |     |     |     | 920 |     |     |     |     | 925 |     |     |     |     | 930 |      |
| CCT | CAA | GTG | AAG | TTT | GAC | AAA | CAA | CAA | GCA | GAC | CTT | CAC | ATG | AGG | GAG  | 3309
| Pro | Gln | Val | Lys | Phe | Asp | Lys | Gln | Gln | Ala | Asp | Leu | His | Met | Arg | Glu  |
|     |     |     | 935 |     |     |     |     | 940 |     |     |     |     | 945 |     |      |
| GCA | AAA | AAG | ATG | AAG | CAG | AAA | GCA | GAG | TTA | ATG | ACG | GAC | AGG | GTT | GGA  | 3357
| Ala | Lys | Lys | Met | Lys | Gln | Lys | Ala | Glu | Leu | Met | Thr | Asp | Arg | Val | Gly  |
|     |     | 950 |     |     |     |     | 955 |     |     |     |     | 960 |     |     |      |
| AAG | GCT | TTT | AAG | TAC | CTG | GAA | GCC | GTC | TTG | TCC | TTC | ATT | GAG | TGC | GGA  | 3405
| Lys | Ala | Phe | Lys | Tyr | Leu | Glu | Ala | Val | Leu | Ser | Phe | Ile | Glu | Cys | Gly  |
|     | 965 |     |     |     |     | 970 |     |     |     |     | 975 |     |     |     |      |
| ATT | GCC | ACA | GAG | TCT | GAA | AGC | CAG | TCA | TCC | AAG | TCA | GCT | TAC | TCT | GTC  | 3453
| Ile | Ala | Thr | Glu | Ser | Glu | Ser | Gln | Ser | Ser | Lys | Ser | Ala | Tyr | Ser | Val  |
| 980 |     |     |     |     | 985 |     |     |     |     | 990 |     |     |     |     | 995  |
| TAC | TCA | GAA | ACT | GTA | GAT | CTC | ATT | AAA | TTC | ATA | ATG | TCA | TTA | AAA | TCC  | 3501
| Tyr | Ser | Glu | Thr | Val | Asp | Leu | Ile | Lys | Phe | Ile | Met | Ser | Leu | Lys | Ser  |
|     |     |     |     | 1000|     |     |     |     | 1005|     |     |     |     | 1010|      |
| TTC | TCA | GAT | GCC | ACA | GCG | CCA | ACA | CAA | GAG | AAA | ATA | TTT | GCT | GTT | TTA  | 3549
| Phe | Ser | Asp | Ala | Thr | Ala | Pro | Thr | Gln | Glu | Lys | Ile | Phe | Ala | Val | Leu  |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     |     |     | 1015 |     |     |     |     | 1020 |     |     |     |     | 1025 |     |     |
| TGC | ATG | CGT | TGC | CAG | TCC | ATT | TTG | AAC | ATG | GCG | ATG | TTT | CGT | TGT | AAA |  3597 |
| Cys | Met | Arg | Cys | Gln | Ser | Ile | Leu | Asn | Met | Ala | Met | Phe | Arg | Cys | Lys |  |
|     |     | 1030 |     |     |     |     | 1035 |     |     |     |     | 1040 |     |     |     |  |
| AAA | GAC | ATA | GCA | ATA | AAG | TAT | TCT | CGT | ACT | CTT | AAT | AAA | CAC | TTC | GAG |  3645 |
| Lys | Asp | Ile | Ala | Ile | Lys | Tyr | Ser | Arg | Thr | Leu | Asn | Lys | His | Phe | Glu |  |
|     | 1045 |     |     |     |     | 1050 |     |     |     |     | 1055 |     |     |     |     |  |
| AGT | TCT | TCC | AAA | GTC | GCC | CAG | GCA | CCT | TCT | CCA | TGC | ATT | GCA | AGC | ACA |  3693 |
| Ser | Ser | Ser | Lys | Val | Ala | Gln | Ala | Pro | Ser | Pro | Cys | Ile | Ala | Ser | Thr |  |
| 1060 |     |     |     |     | 1065 |     |     |     |     | 1070 |     |     |     |     | 1075 |  |
| GGC | ACA | CCA | TCC | CCT | CTT | TCC | CCA | ATG | CCT | TCT | CCT | GCC | AGC | TCC | GTA |  3741 |
| Gly | Thr | Pro | Ser | Pro | Leu | Ser | Pro | Met | Pro | Ser | Pro | Ala | Ser | Ser | Val |  |
|     |     |     |     | 1080 |     |     |     |     | 1085 |     |     |     |     | 1090 |     |  |
| GGG | TCC | CAG | TCA | AGT | GCT | GGC | AGT | GTG | GGG | AGC | AGT | GGG | GTG | GCT | GCC |  3789 |
| Gly | Ser | Gln | Ser | Ser | Ala | Gly | Ser | Val | Gly | Ser | Ser | Gly | Val | Ala | Ala |  |
|     |     |     | 1095 |     |     |     |     | 1100 |     |     |     |     | 1105 |     |     |  |
| ACT | ATC | AGC | ACC | CCA | GTC | ACC | ATC | CAG | AAT | ATG | ACA | TCT | TCC | TAT | GTC |  3837 |
| Thr | Ile | Ser | Thr | Pro | Val | Thr | Ile | Gln | Asn | Met | Thr | Ser | Ser | Tyr | Val |  |
|     |     | 1110 |     |     |     |     | 1115 |     |     |     |     | 1120 |     |     |     |  |
| ACC | ATC | ACA | TCC | CAT | GTT | CTT | ACC | GCC | TTT | GAC | CTT | TGG | GAA | CAG | GCC |  3885 |
| Thr | Ile | Thr | Ser | His | Val | Leu | Thr | Ala | Phe | Asp | Leu | Trp | Glu | Gln | Ala |  |
|     | 1125 |     |     |     |     | 1130 |     |     |     |     | 1135 |     |     |     |     |  |
| GAG | GCC | CTC | ACG | AGG | AAG | AAT | AAA | GAA | TTC | TTT | GCT | CGG | CTC | AGC | ACA |  3933 |
| Glu | Ala | Leu | Thr | Arg | Lys | Asn | Lys | Glu | Phe | Phe | Ala | Arg | Leu | Ser | Thr |  |
| 1140 |     |     |     |     | 1145 |     |     |     |     | 1150 |     |     |     |     | 1155 |  |
| AAT | GTG | TGC | ACC | TTG | GCC | CTC | AAC | AGC | AGT | TTG | GTG | GAC | CTG | GTG | CAC |  3981 |
| Asn | Val | Cys | Thr | Leu | Ala | Leu | Asn | Ser | Ser | Leu | Val | Asp | Leu | Val | His |  |
|     |     |     |     | 1160 |     |     |     |     | 1165 |     |     |     |     | 1170 |     |  |
| TAT | ACA | CGA | CAG | GGT | TTT | CAG | CAG | CTA | CAA | GAA | TTA | ACC | AAA | ACA | CCT |  4029 |
| Tyr | Thr | Arg | Gln | Gly | Phe | Gln | Gln | Leu | Gln | Glu | Leu | Thr | Lys | Thr | Pro |  |
|     |     |     | 1175 |     |     |     |     | 1180 |     |     |     |     | 1185 |     |     |  |

| | | | | |
|---|---|---|---|---|
| TAATGGAGCC | CCAGGTTGAT | TCAATGCCTT | GGGAACTATT | TTTGCACATT | GGAAGCCTCA | 4089 |
| AAAACAGTCC | AGACGTTTGT | TTCATCAGGA | CACCAAACTC | TAAAAAGAA | GCACCACGAG | 4149 |
| ATGGCCAGGA | CATTTGTCCA | CTTAAACTCT | CAACAACAGT | GTGATCATTG | GTTGGACACT | 4209 |
| GTGGTTATGC | AGAAGCAGAG | ATGAGGAGGC | TGGCCCCAGA | GATGATCTTG | CCCTTCCTAA | 4269 |
| CTAAAGGACA | GAAGTGCAAT | TTAGCTTAAA | TGGGTGTATG | AATGGTCTAG | AAACATTTCT | 4329 |
| ATTTTTTTT | TAAACCAGCA | GGATACAAGT | TGCAAATGAA | ATGAGGAGAA | ACAGTTTCAA | 4389 |
| CTCTGAAAGT | GAATTTCACG | TCATCTCAGT | AGCCACGCTA | GTCCATTCCC | AGAAGGAAAT | 4449 |
| TTTTTTTTT | AACAATGACT | TTTGGTAAAG | GGTTTTGTGG | ATGATTTTT | TTCTTTTGAG | 4509 |
| TTTTGGGAGA | AATATTTGTT | TAATAACTTC | TAATGGCCAT | CTGTAAACCA | TAAGTAATGA | 4569 |
| AGGACTCCAC | TGTGCCCCAC | TTTCTGCCAA | TGAACAGTGG | CTTGATAATA | CCAAGTATTG | 4629 |
| TTGTAATTTA | TAAAATTGAA | GGCAACCCCC | GCTCCTGCCG | CCCCAATCT | CCCCATTGCC | 4689 |
| TAGAGCGCTG | CACATTGACC | CCAGCTCTGA | CTTCTCATTA | CTGTGCTGAA | AGTCAGCCCA | 4749 |
| CGTCGGAGCG | GTGAGGAGGA | GCCACAGCAC | ATGGGGTGCC | ACCTCGAGGT | CTGCACAGGA | 4809 |
| GGACTTGGCG | CTGCCATTTC | CTACCCCTGC | CATTTCCCAC | CCCTGCTTCA | GCGAAAGGGA | 4869 |
| CTCTCTAACA | GGGCAGTCAC | TGTTGACTCT | ATTCTGAATT | TCCTCCCTTG | GGGAAGAAGG | 4929 |
| GAACCAACAT | TTATACCTGA | CCAGATGGCT | AAAGTGCTTT | TAAAGTTTTG | TTTAAGTAGA | 4989 |
| GCTGGAATTT | GAGGTGCTGA | TCTGTGGTCT | ACAGTTATGT | GGTAACTCAT | GTTGTCCAGC | 5049 |
| CAACTCAGAG | TTTCGTCAGT | GAACAAGAAA | CATGAAATCT | GCTTCTTAGA | GAGGCTATAT | 5109 |
| TTTTCTGCTA | CAAATATTTT | ATATTTATAG | CAAAACTAGA | CTTTCAGAGT | CCTTGATTGT | 5169 |

```
CTAGGGGAAG TTAACTCCCT GAGAGGATGT AGAGATTTGG GGTGGTTGAT TAGACTTTTG    5229
AAAAACTCAT CACCACATGC CTTCACTCCA GAGTGTTCTC AGCTAGATTT GATTTGGTTG    5289
AGGAGGAACT GTGGCCCTCC GTAAGTTATT GCCATAGTGT ATGCATTAAA CCAAGTCCAT    5349
TTTGAATGAC CTAAAATGAA GTAACACAAT CAGAAATCCC ATGTGCCCAT AAGCACAGAT    5409
TTTTCTTTTT CATTGAAACT TTAAAGGTTA TTATTGGAAA CATTACTTTG AGTGCAGTGT    5469
TTTTAAAAGC CAATTCTTTT TTATCCCTTT TAGAAGTAGA ATTTGCACAC TTACTACAAT    5529
TGAGGAGTGT CATCTCTATA ACTTTTTCTC CGCCTTTGTC CCATTCTGCC CCTGGACATG    5589
TTTCCTACCA AGCATGTTTC ACATTTTCCT ATTAGTGGAG GAGGGAGAAC CATATTTATT    5649
TATAATGAAG ACATCTAAGA TCCCTATGAT GAATGCAGGA ACTCTCTTGG TAGTTTGTAA    5709
ATACACAAAG GGATGTGTCG AGGGATGGGA GCGATGCTTA TCTCTCACAG TGTGAGTGGT    5769
CTGTGTGAGG CTGTTCCTTC AGTTCTTCTC CAGACTGTTC TTTGGTTGTC ACTTAAGTCA    5829
GAGGTCTGGT CCCTCATGTT TAGGTGAAAG CCAGAGAATG ACAGCTGTAG TCATATCTGA    5889
GCATAAGACC TTGATGTGTG ATTCCTGATG ACCGGTTTCA TTTATTCATG TAATAAAGCA    5949
AAGGCCCTGG TCCTTTTTAA ACTACTAGTT TTAAAAACCT GTGTTAAATG AACAGTAATT    6009
GCCTGGTAGG TTTGGTGTGT GTGTAGCATT GTGTGTCCAT CTGTTATATG TAAAGGACAA    6069
GGCACCAGAA TCAGGCTTTA TTTCGATATT GAAGATGTTA TTTAACATCT TTCTTTTTTC    6129
CTTACTCCCT TAGCCATCCC CTCCCCTTTT GTCCTATCAT TCCCTAGAAC AAGCCACCTG    6189
TCAATTGTGA AGGGTTGTGT TCTTTATGGC AGGTTCTATG CAGATTGTGC CAGAGCATGT    6249
GCGTGTTCTG TTGGCAAGCC ACAGTGCTCC CTTGACTGAA GACATTTCCA GGTAGATTTC    6309
TCAGCCAGCT CTAAAACAGA TTGCTTTTTC AGTGGCCTTA CTCTTTGTGG GTTTTTTTT    6369
TTCTCTGAAC TTGATATAAA GATTTTATTT GTCCCTTGAA AAAGTAACAA ATGTGCATAG    6429
ATCAATTTGT ACTACTTTGG TCATTGGATA TTTCTGATCC TTATTGCATT GTACCTAAAG    6489
GAGAGTAACT AATGGTAACC TTTTAATAG AGTATGTGAA AGGTAGTGGC TGATGAATCC    6549
TTAACGTTCA TAGGGTCTTT TTGCTGTTAC GGTTGTATAT AGAGGTCTGA AGGATTTTA    6609
AAATGATTTG CACTTTTTCA CTGCATGCTT ACAATTCCCA AAGGCAAAAT CTGTACTGAG    6669
GTAGATCATT TGAAAGGGCT AGATTATAAA ATTAAGCCTT AGAGTATGGA AAGTTCTTAT    6729
AACAATAATA GTACACACTT CAGAGTAAGA CAAATGCAAA GCATCTTAAG GAGTGAAAAT    6789
AGAGTCTAAA TCTTGCCTTT GGCACTACAA GGTGTGTGTG TGTGTGTGTG TTGTGTGTCT    6849
TTAGTAGGAA ATGGAAGAAC ACTGTTTTAT TTTTTAAAGT GTTAATGTT TCTGTCCTTT    6909
CTGTGAATTA TTGAATTTAA GAGCCCTGCT AAATAATGAA AAAACACTTT ACTAAAATTT    6969
ATCAAATTAT ACTGGGTTCG GATTGTGAAA ACATTGGCCA CCTAGTAGCA GTGGTGAGGA    7029
GTGGGAGGGC CCAGCAAGCA TTTATCAGAA ATAGAATCAC AATAGGAGGA GAATTTGGCT    7089
GTCTGATATT ATGATTTGAT TACAATACTG AATGGGAAAA GTATCTAATA TTTTGTAACA    7149
AAAAGACCTT CATATTATCT GTTTGACCA AAATATGTAG CTATTTCCCT TACACAGATT    7209
GGACCGCACT TATCTCCCTT GTCCTGTATC CTTAATTTC AGGTCTCAGG ATGTTAGAA    7269
AGCTAAAACC CCCTACCCCT TTCTGGCTGA AAACTTGCCT TATTTGGTAT CTTACACATT    7329
AATGTTACTA GCATCAGGAG CTTACTGTTT TATTATGATT CATCTTCAGT AATTTTTAGA    7389
AGCAAGAAGA AAGCCATTGT GTCCTCTACA AATTAACAAA ACTTATCTCT GATATACAAA    7449
GGGATATAAA TATATACACT TAAATAGAGA AAAAGAGGTT GATTGAATTG TGCCTTTGAG    7509
TGAACCCAGT TTTTAAATAC CGCTGTGTTT GTTTCGCCAT GGCTTCAGGG ATGCTACATG    7569
```

```
GCTCTTGCAC  CTTTTACTCC  TCTGCTTTAT  GAAGTTTGAG  TTGTATTTGT  GCATCTTAAA    7629
GTAGGTTGAG  GCTTGAGGCT  GGGCTTTCGG  GTTTTTTGT   TTTTGTTTT   GTTTGTTTT     7689
GTTTTGTTTT  CTTGTACTTA  AACCTGCTTG  CTTCCTACCA  CAGATTCTTT  ATTTTCCCAA    7749
ACACTACAAA  AAAACTTTTA  AAACTTTGCC  ATTTCATCTG  TTTACACTCT  TTGCCACTGA    7809
TTAGCAGTAT  TTAAATCTTG  CAAGAATATT  TTGTGCTTTC  TTTAGAAACA  CAAGAGTAGA    7869
GATTTTTCTC  ACTGAAAAGT  GAGAGTTACG  CATTGCAGCC  ATGAAGGGAT  GCTAGGATCA    7929
ATTATGGCAG  TACCTTTTTT  CCCCTCCTGT  TCTTGAGCCA  GTTGTCTCTT  TTGTGTTGGG    7989
TCCCACTTAG  GATTAACGGA  TGTAAGGTAT  TTTCCTGTGC  CTTTATTTTG  TGTCATTCTA    8049
TTGGAAGGAG  GTGTAACGGC  AGAATAGCAT  CGTGTTGGGG  GTTTTCCTTC  AAACACTGCA    8109
AGTGATATTG  CCACCATGTG  AACCTCAAAT  ATGCAATCCA  GTTGTGTTGG  TTTCTCGGTG    8169
ACTTGGAGTG  TTCATCTCTT  CATGAATTGT  GAGCACTGAC  CATGTTCTTC  AGTTCTTAAT    8229
TATGGTGAGT  TGACAAATAC  CAACTACTGC  TTTTCTTTAG  GTGGCTATAA  ATTTCTTACT    8289
GTCAGGAGGA  AATGACATTA  TATTCTGTTC  CACTGAACGT  CAGAGATCAG  CAGGCACTGT    8349
ACTGGGTAGA  GAAGTGCCTA  TACTTCTCTA  CCTAAGAGGG  CAGGAGGGAA  ACCCTACAGC    8409
TCCTTGTGAG  CCTATATATT  AGTATATCGG  CCTGGAGAGG  ACAAGGGAAT  AAGACCACTC    8469
ATAGTGAGGC  TGGCCAAGCT  GCACTGGTCG  GACCAGGCAG  TGGCTGACCT  AAGGAAGGCA    8529
ACTTGCTTTG  CTTAAAAGTA  GATTTTTTAA  GCAATGCTTA  ACACAGGCAG  CATTCACCTT    8589
TGTTCAGGCC  ATCGACATGT  ATTGTTAAAA  TTACTGCATA  TCCCCCTCAG  ATATCAAGTA    8649
TACACTGTTC  ATGTTGGGGT  TGTGTGTGTG  TATGTGTGTA  TGTACGCACG  CATGTGTCCC    8709
AAATCTTGTT  TTAATTTTTT  TTTCTGAAT   GTGATCATGT  TTTGGATAAT  ACCTGAGCAG    8769
GGTTGCCTTT  TTTTTATTTA  TTACCATTAT  ATATTATATT  ATATTATATA  TTTTTTGCTT    8829
TCTTATAACT  TTGGAGGAAA  GTCAAATCTT  GGTATTATTA  AAATTGTTTT  AAAAAGGAGT    8889
AAATTTTCCA  GTTGATAAAT  GAAAATCACT  GGCCTATGTT  TAATAAGTTT  TTCTTTAATT    8949
ACTGTGGAAT  AACGTGCCAG  CTATCATCAA  CACAATGATT  TTGTACATAG  GGTAGGGAAG    9009
CAGTGATGCT  CTCAATGGGA  AGATGTGCAA  CACAAATTAA  GGGGAACTCC  ATGTATTTA     9069
CCTACTTCAG  CAATGGAACT  GCAACTTGGG  GCTTTGTGAA  TAAAATTTAG  CTGCCTTGTA    9129
TAGTCGTTTG  AAAGAATATG  TGATCTGTGA  GAGAATTATA  GTTTTTTTT   AGAAGAAAAA    9189
TCTGCAAAAG  ATCTTTCCAA  AGACAATGTG  CCACAGATCT  TTTGTTCTCT  GTAATGAGGA    9249
TTAATTGCTG  TTTAAACAAA  AATGTAATTG  TTCATCTTTA  AATTCTTCC   TTTTCATAAG    9309
AGGATCAAGC  TGTAAAAAAA  CAAAAAAATT  AATAAAAATT  TCGAGAAATC  AAAAAAAAA     9369
A                                                                        9370
```

(2) INFORMATION FOR SEQ ID NO:28:

(i) SEQUENCE CHARACTERISTICS:
(A) LENGTH: 1187 amino acids
(B) TYPE: amino acid
(D) TOPOLOGY: linear (ii) MOLECULE TYPE: protein (xi) SEQUENCE DESCRIPTION: SEQ ID NO:28:

```
Asn  Gln  Glu  Ala  His  Gln  Glu  Lys  Glu  Ala  Phe  Pro  Glu  Lys  Ile  Pro
 1                       5                      10                      15

Leu  Phe  Gly  Glu  Pro  Tyr  Lys  Thr  Ala  Lys  Gly  Asp  Glu  Leu  Ser  Ser
              20                      25                      30
```

```
Arg  Ile  Gln  Asn  Met  Leu  Gly  Asn  Tyr  Glu  Glu  Val  Lys  Glu  Phe  Leu
          35                       40                      45

Ser  Thr  Lys  Ser  His  Thr  His  Arg  Leu  Asp  Ala  Ser  Glu  Asn  Arg  Leu
          50                       55                      60

Gly  Lys  Pro  Lys  Tyr  Pro  Leu  Ile  Pro  Asp  Lys  Gly  Ser  Ser  Ile  Pro
65                       70                      75                            80

Ser  Ser  Ser  Phe  His  Thr  Ser  Val  His  His  Gln  Ser  Ile  His  Thr  Pro
                    85                       90                      95

Ala  Ser  Gly  Pro  Leu  Ser  Val  Gly  Asn  Ile  Ser  His  Asn  Pro  Lys  Met
                    100                      105                     110

Ala  Gln  Pro  Arg  Thr  Glu  Pro  Met  Pro  Ser  Leu  His  Ala  Lys  Ser  Cys
               115                      120                     125

Gly  Pro  Pro  Asp  Ser  Gln  His  Leu  Thr  Gln  Asp  Arg  Leu  Gly  Gln  Glu
          130                      135                     140

Gly  Phe  Gly  Ser  Ser  His  His  Lys  Lys  Gly  Asp  Arg  Arg  Ala  Asp  Gly
145                           150                     155                     160

Asp  His  Cys  Ala  Ser  Val  Thr  Asp  Ser  Ala  Pro  Glu  Arg  Glu  Leu  Ser
                    165                      170                     175

Pro  Leu  Ile  Ser  Leu  Pro  Ser  Pro  Val  Pro  Pro  Leu  Ser  Pro  Ile  His
               180                      185                     190

Ser  Asn  Gln  Gln  Thr  Leu  Pro  Arg  Thr  Gln  Gly  Ser  Ser  Lys  Val  His
          195                      200                     205

Gly  Ser  Ser  Asn  Asn  Ser  Lys  Gly  Tyr  Cys  Pro  Ala  Lys  Ser  Pro  Lys
     210                      215                     220

Asp  Leu  Ala  Val  Lys  Val  His  Asp  Lys  Glu  Thr  Pro  Gln  Asp  Ser  Leu
225                      230                      235                          240

Val  Ala  Pro  Ala  Gln  Pro  Pro  Ser  Gln  Thr  Phe  Pro  Pro  Pro  Ser  Leu
               245                      250                     255

Pro  Ser  Lys  Ser  Val  Ala  Met  Gln  Gln  Lys  Pro  Thr  Ala  Tyr  Val  Arg
               260                      265                     270

Pro  Met  Asp  Gly  Gln  Asp  Gln  Ala  Pro  Ser  Glu  Ser  Pro  Glu  Leu  Lys
               275                      280                     285

Pro  Leu  Pro  Glu  Asp  Tyr  Arg  Gln  Gln  Thr  Phe  Glu  Lys  Thr  Asp  Leu
     290                      295                     300

Lys  Val  Pro  Ala  Lys  Ala  Lys  Leu  Thr  Lys  Leu  Lys  Met  Pro  Ser  Gln
305                      310                      315                          320

Ser  Val  Glu  Gln  Thr  Tyr  Ser  Asn  Glu  Val  His  Cys  Val  Glu  Glu  Ile
               325                      330                     335

Leu  Lys  Glu  Met  Thr  His  Ser  Trp  Pro  Pro  Pro  Leu  Thr  Ala  Ile  His
               340                      345                     350

Thr  Pro  Ser  Thr  Ala  Glu  Pro  Ser  Lys  Phe  Pro  Phe  Pro  Thr  Lys  Asp
          355                      360                     365

Ser  Gln  His  Val  Ser  Ser  Val  Thr  Gln  Asn  Gln  Lys  Gln  Tyr  Asp  Thr
     370                      375                     380

Ser  Ser  Lys  Thr  His  Ser  Asn  Ser  Gln  Gln  Gly  Thr  Ser  Ser  Met  Leu
385                      390                      395                          400

Glu  Asp  Asp  Leu  Gln  Leu  Ser  Asp  Ser  Glu  Asp  Ser  Asp  Ser  Glu  Gln
                    405                      410                     415

Thr  Pro  Glu  Lys  Pro  Pro  Ser  Ser  Ser  Ala  Pro  Pro  Ser  Ala  Pro  Gln
               420                      425                     430

Ser  Leu  Pro  Glu  Pro  Val  Ala  Ser  Ala  His  Ser  Ser  Ala  Glu  Ser
               435                      440                     445

Glu  Ser  Thr  Ser  Asp  Ser  Asp  Ser  Ser  Asp  Ser  Glu  Ser  Glu  Ser
          450                      455                     460
```

| | | | | | | | | | | | | | | |
|---|---|---|---|---|---|---|---|---|---|---|---|---|---|---|
| Ser 465 | Ser | Ser | Asp | Ser 470 | Glu | Glu | Asn | Glu | Pro 475 | Leu | Glu | Thr | Pro | Ala Pro 480 |
| Glu | Pro | Glu | Pro | Pro 485 | Thr | Thr | Asn | Lys | Trp 490 | Gln | Leu | Asp | Asn | Trp Leu 495 |
| Thr | Lys | Val | Ser 500 | Gln | Pro | Ala | Ala | Pro 505 | Pro | Glu | Gly | Pro | Arg 510 | Ser Thr |
| Glu | Pro | Pro 515 | Arg | Arg | His | Pro | Glu 520 | Ser | Lys | Gly | Ser | Ser 525 | Asp | Ser Ala |
| Thr | Ser 530 | Gln | Glu | His | Ser | Glu 535 | Ser | Lys | Asp | Pro | Pro 540 | Pro | Lys | Ser Ser |
| Ser 545 | Lys | Ala | Pro | Arg | Ala 550 | Pro | Pro | Glu | Ala | Pro 555 | His | Pro | Gly | Lys Arg 560 |
| Ser | Cys | Gln | Lys | Ser 565 | Pro | Ala | Gln | Gln | Glu 570 | Pro | Pro | Gln | Arg 575 | Gln Thr |
| Val | Gly | Thr | Lys 580 | Gln | Pro | Lys | Lys | Pro 585 | Val | Lys | Ala | Ser | Ala 590 | Arg Ala |
| Gly | Ser | Arg 595 | Thr | Ser | Leu | Gln | Gly 600 | Glu | Arg | Glu | Pro | Gly 605 | Leu | Leu Pro |
| Tyr | Gly 610 | Ser | Arg | Asp | Gln | Thr 615 | Ser | Lys | Asp | Lys | Pro 620 | Lys | Val | Lys Thr |
| Lys 625 | Gly | Arg | Pro | Arg | Ala 630 | Ala | Ala | Ser | Asn | Glu 635 | Pro | Lys | Pro | Ala Val 640 |
| Pro | Pro | Ser | Ser | Glu 645 | Lys | Lys | Lys | His | Lys 650 | Ser | Ser | Leu | Pro | Ala Pro 655 |
| Ser | Lys | Ala | Leu 660 | Ser | Gly | Pro | Glu | Pro 665 | Ala | Lys | Asp | Asn | Val 670 | Glu Asp |
| Arg | Thr | Pro 675 | Glu | His | Phe | Ala | Leu 680 | Val | Pro | Leu | Thr | Glu 685 | Ser | Gln Gly |
| Pro | Pro | His 690 | Ser | Gly | Ser | Gly | Ser 695 | Arg | Thr | Ser | Gly | Cys 700 | Arg | Gln Ala |
| Val 705 | Val | Val | Gln | Glu | Asp 710 | Ser | Arg | Lys | Asp | Arg 715 | Leu | Pro | Leu | Pro Leu 720 |
| Arg | Asp | Thr | Lys | Leu 725 | Leu | Ser | Pro | Leu | Arg 730 | Asp | Thr | Pro | Pro 735 | Pro Gln |
| Ser | Leu | Met | Val 740 | Lys | Ile | Thr | Leu | Asp 745 | Leu | Leu | Ser | Arg | Ile 750 | Pro Gln |
| Pro | Pro | Gly 755 | Lys | Gly | Ser | Arg | Gln 760 | Arg | Lys | Ala | Glu | Asp 765 | Lys | Gln Pro |
| Pro | Ala 770 | Gly | Lys | Lys | His | Ser 775 | Ser | Glu | Lys | Arg | Ser 780 | Ser | Asp | Ser Ser |
| Ser 785 | Lys | Leu | Ala | Lys | Lys 790 | Arg | Lys | Gly | Glu | Ala 795 | Glu | Arg | Asp | Cys Asp 800 |
| Asn | Lys | Lys | Ile | Arg 805 | Leu | Glu | Lys | Glu | Ile 810 | Lys | Ser | Gln | Ser | Ser Ser 815 |
| Ser | Ser | Ser | Ser 820 | His | Lys | Glu | Ser | Ser 825 | Lys | Thr | Lys | Pro | Ser 830 | Arg Pro |
| Ser | Ser | Gln 835 | Ser | Ser | Lys | Lys | Glu 840 | Met | Leu | Pro | Pro | Pro 845 | Pro | Val Ser |
| Ser | Ser 850 | Ser | Gln | Lys | Pro | Ala 855 | Lys | Pro | Ala | Leu | Lys 860 | Arg | Ser | Arg Arg |
| Glu 865 | Ala | Asp | Thr | Cys | Gly 870 | Gln | Asp | Pro | Pro | Lys 875 | Ser | Ala | Ser | Ser Thr 880 |
| Lys | Ser | Asn | His | Lys | Asp | Ser | Ser | Ile | Pro | Lys | Gln | Arg | Arg | Val Glu |

|   |   |   |   |   | 885 |   |   |   |   | 890 |   |   |   |   | 895 |
|---|---|---|---|---|---|---|---|---|---|---|---|---|---|---|---|

Gly Lys Gly Ser Arg Ser Ser Ser Glu His Lys Gly Ser Ser Gly Asp
            900                     905                 910

Thr Ala Asn Pro Phe Pro Val Pro Ser Leu Pro Asn Gly Asn Ser Lys
            915                     920                 925

Pro Gly Lys Pro Gln Val Lys Phe Asp Lys Gln Gln Ala Asp Leu His
930                     935                     940

Met Arg Glu Ala Lys Lys Met Lys Gln Lys Ala Glu Leu Met Thr Asp
945                     950                     955                 960

Arg Val Gly Lys Ala Phe Lys Tyr Leu Glu Ala Val Leu Ser Phe Ile
            965                     970                 975

Glu Cys Gly Ile Ala Thr Glu Ser Glu Ser Gln Ser Ser Lys Ser Ala
            980                     985                 990

Tyr Ser Val Tyr Ser Glu Thr Val Asp Leu Ile Lys Phe Ile Met Ser
            995                     1000                1005

Leu Lys Ser Phe Ser Asp Ala Thr Ala Pro Thr Gln Glu Lys Ile Phe
    1010                    1015                1020

Ala Val Leu Cys Met Arg Cys Gln Ser Ile Leu Asn Met Ala Met Phe
1025                    1030                    1035                1040

Arg Cys Lys Lys Asp Ile Ala Ile Lys Tyr Ser Arg Thr Leu Asn Lys
            1045                    1050                1055

His Phe Glu Ser Ser Ser Lys Val Ala Gln Ala Pro Ser Pro Cys Ile
            1060                    1065                1070

Ala Ser Thr Gly Thr Pro Ser Pro Leu Ser Pro Met Pro Ser Pro Ala
            1075                    1080                1085

Ser Ser Val Gly Ser Gln Ser Ser Ala Gly Ser Val Gly Ser Ser Gly
    1090                    1095                1100

Val Ala Ala Thr Ile Ser Thr Pro Val Thr Ile Gln Asn Met Thr Ser
1105                    1110                    1115                1120

Ser Tyr Val Thr Ile Thr Ser His Val Leu Thr Ala Phe Asp Leu Trp
            1125                    1130                1135

Glu Gln Ala Glu Ala Leu Thr Arg Lys Asn Lys Glu Phe Phe Ala Arg
            1140                    1145                1150

Leu Ser Thr Asn Val Cys Thr Leu Ala Leu Asn Ser Ser Leu Val Asp
            1155                    1160                1165

Leu Val His Tyr Thr Arg Gln Gly Phe Gln Gln Leu Gln Glu Leu Thr
    1170                    1175                1180

Lys Thr Pro
1185

( 2 ) INFORMATION FOR SEQ ID NO:29:

( i ) SEQUENCE CHARACTERISTICS:
        ( A ) LENGTH: 3376 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 196..1902

( x i ) SEQUENCE DESCRIPTION: SEQ ID NO:29:

TTTGGGGCTG AGTTTAATAA GCGAGCGAGC GAGCAAGCGA GCGCGGGGGG AAAAAGGCAG    60

AGAATGTCCG CCATCTACCC TCCGCTCCTG GGCGCGCTCT CATTCATAGC AGCCTCTTCA   120

```
TGAATTACAG CTGAGGGGGG GCGGAGGAGG GGGGGGTACC ACACAACACC CCAGCAAACC                    180

TCCGGGCCCC CAGGC ATG GCT AGC TCG TGT TCC GTG CAG GTG AAG CTG GAG                     231
                Met Ala Ser Ser Cys Ser Val Gln Val Lys Leu Glu
                 1               5                    10

CTG GGG CAC CGC GCC CAG GTG AGG AAA AAA CCC ACC GTG GAG GGC TTC                       279
Leu Gly His Arg Ala Gln Val Arg Lys Lys Pro Thr Val Glu Gly Phe
         15                  20                  25

ACC CAC GAC TGG ATG GTG TTC GTA CGC GGT CCG GAG CAC AGT AAC ATA                       327
Thr His Asp Trp Met Val Phe Val Arg Gly Pro Glu His Ser Asn Ile
         30                  35                  40

CAG CAC TTT GTG GAG AAA GTC GTC TTC CAC TTG CAC GAA AGC TTT CCT                       375
Gln His Phe Val Glu Lys Val Val Phe His Leu His Glu Ser Phe Pro
 45                  50                  55                  60

AGG CCA AAA AGA GTG TGC AAA GAT CCA CCT TAC AAA GTA GAA GAA TCT                       423
Arg Pro Lys Arg Val Cys Lys Asp Pro Pro Tyr Lys Val Glu Glu Ser
                 65                  70                  75

GGG TAT GCT GGT TTC ATT TTG CCA ATT GAA GTT TAT TTT AAA AAC AAG                       471
Gly Tyr Ala Gly Phe Ile Leu Pro Ile Glu Val Tyr Phe Lys Asn Lys
             80                  85                  90

GAA GAA CCT AGG AAA GTC CGC TTT GAT TAT GAC TTA TTC CTG CAT CTT                       519
Glu Glu Pro Arg Lys Val Arg Phe Asp Tyr Asp Leu Phe Leu His Leu
         95                 100                 105

GAA GGC CAT CCA CCA GTG AAT CAC CTC CGC TGT GAA AAG CTA ACT TTC                       567
Glu Gly His Pro Pro Val Asn His Leu Arg Cys Glu Lys Leu Thr Phe
    110                 115                 120

AAC AAC CCC ACA GAG GAC TTT AGG AGA AAG TTG CTG AAG GCA GGA GGG                       615
Asn Asn Pro Thr Glu Asp Phe Arg Arg Lys Leu Leu Lys Ala Gly Gly
125                 130                 135                 140

GAC CCT AAT AGG AGT ATT CAT ACC AGC AGC AGC AGC AGC AGC AGC AGT                       663
Asp Pro Asn Arg Ser Ile His Thr Ser Ser Ser Ser Ser Ser Ser Ser
                145                 150                 155

AGC AGC AGC AGC AGC AGC AGC AGC AGC AGT AGC AGC AGC AGC AGC                           711
Ser Ser Ser Ser Ser Ser Ser Ser Ser Ser Ser Ser Ser Ser Ser
            160                 165                 170

AGC AGC AGC AGC AGC AGT AGC AGC AGC AGT AGC AGC AGC AGC AGC                           759
Ser Ser Ser Ser Ser Ser Ser Ser Ser Ser Ser Ser Ser Ser Ser
        175                 180                 185

AGT AGT ACC AGT TTT TCA AAG CCT CAC AAA TTA ATG AAG GAG CAC AAG                       807
Ser Ser Thr Ser Phe Ser Lys Pro His Lys Leu Met Lys Glu His Lys
    190                 195                 200

GAA AAA CCT TCT AAA GAC TCC AGA GAA CAT AAA AGT GCC TTC AAA GAA                       855
Glu Lys Pro Ser Lys Asp Ser Arg Glu His Lys Ser Ala Phe Lys Glu
205                 210                 215                 220

CCT TCC AGG GAT CAC AAC AAA TCT TCC AAA GAA TCC TCT AAG AAA CCC                       903
Pro Ser Arg Asp His Asn Lys Ser Ser Lys Glu Ser Ser Lys Lys Pro
                225                 230                 235

AAA GAA AAT AAA CCA CTG AAA GAA GAG AAA ATA GTT CCT AAG ATG GCC                       951
Lys Glu Asn Lys Pro Leu Lys Glu Glu Lys Ile Val Pro Lys Met Ala
            240                 245                 250

TTC AAG GAA CCT AAA CCC ATG TCA AAA GAG CCA AAA CCA GAT AGT AAC                       999
Phe Lys Glu Pro Lys Pro Met Ser Lys Glu Pro Lys Pro Asp Ser Asn
        255                 260                 265

TTA CTC ACC ATC ACC AGT GGA CAA GAT AAG AAG GCT CCT AGT AAA AGG                      1047
Leu Leu Thr Ile Thr Ser Gly Gln Asp Lys Lys Ala Pro Ser Lys Arg
    270                 275                 280

CCG CCC ATT TCA GAT TCT GAA GAA CTC TCA GCC AAA AAA AGG AAA AAG                      1095
Pro Pro Ile Ser Asp Ser Glu Glu Leu Ser Ala Lys Lys Arg Lys Lys
285                 290                 295                 300

AGT AGC TCA GAG GCT TTA TTT AAA AGT TTT TCT AGC GCA CCA CCA CTG                      1143
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ser | Ser | Ser | Glu | Ala | Leu | Phe | Lys | Ser | Phe | Ser | Ser | Ala | Pro | Pro | Leu |      |
|     |     |     |     | 305 |     |     |     | 310 |     |     |     |     | 315 |     |     |      |
| ATA | CTC | ACT | TGT | TCT | GCT | GAC | AAA | AAA | CAG | ATA | AAA | GAT | AAA | TCT | CAT | 1191 |
| Ile | Leu | Thr | Cys | Ser | Ala | Asp | Lys | Lys | Gln | Ile | Lys | Asp | Lys | Ser | His |      |
|     |     |     | 320 |     |     |     |     | 325 |     |     |     |     | 330 |     |     |      |
| GTC | AAG | ATG | GGA | AAG | GTC | AAA | ATT | GAA | AGT | GAG | ACA | TCA | GAG | AAG | AAG | 1239 |
| Val | Lys | Met | Gly | Lys | Val | Lys | Ile | Glu | Ser | Glu | Thr | Ser | Glu | Lys | Lys |      |
|     |     | 335 |     |     |     |     | 340 |     |     |     |     | 345 |     |     |     |      |
| AAA | TCA | ACG | TTA | CCG | CCA | TTT | GAT | GAT | ATT | GTG | GAT | CCC | AAT | GAT | TCA | 1287 |
| Lys | Ser | Thr | Leu | Pro | Pro | Phe | Asp | Asp | Ile | Val | Asp | Pro | Asn | Asp | Ser |      |
|     | 350 |     |     |     | 355 |     |     |     |     | 360 |     |     |     |     |     |      |
| GAT | GTG | GAG | GAG | AAT | ATA | TCC | TCT | AAA | TCT | GAT | TCT | GAA | CAA | CCC | AGT | 1335 |
| Asp | Val | Glu | Glu | Asn | Ile | Ser | Ser | Lys | Ser | Asp | Ser | Glu | Gln | Pro | Ser |      |
| 365 |     |     |     |     | 370 |     |     |     |     | 375 |     |     |     |     | 380 |      |
| CCT | GCC | AGC | TCC | AGC | TCC | AGC | TCC | AGC | TCC | AGC | TTC | ACA | CCA | TCC | CAG | 1383 |
| Pro | Ala | Ser | Ser | Ser | Ser | Ser | Ser | Ser | Ser | Ser | Phe | Thr | Pro | Ser | Gln |      |
|     |     |     |     | 385 |     |     |     |     | 390 |     |     |     |     | 395 |     |      |
| ACC | AGG | CAA | CAA | GGT | CCT | TTG | AGG | TCT | ATA | ATG | AAA | GAT | CTG | CAT | TCT | 1431 |
| Thr | Arg | Gln | Gln | Gly | Pro | Leu | Arg | Ser | Ile | Met | Lys | Asp | Leu | His | Ser |      |
|     |     | 400 |     |     |     |     | 405 |     |     |     |     | 410 |     |     |     |      |
| GAT | GAC | AAT | GAG | GAG | GAA | TCA | GAT | GAA | GTG | GAG | GAT | AAC | GAC | AAT | GAC | 1479 |
| Asp | Asp | Asn | Glu | Glu | Glu | Ser | Asp | Glu | Val | Glu | Asp | Asn | Asp | Asn | Asp |      |
|     |     | 415 |     |     |     |     | 420 |     |     |     |     | 425 |     |     |     |      |
| TCT | GAA | ATG | GAG | AGG | CCT | GTA | AAT | AGA | GGA | GGC | AGC | CGA | AGT | CGC | AGA | 1527 |
| Ser | Glu | Met | Glu | Arg | Pro | Val | Asn | Arg | Gly | Gly | Ser | Arg | Ser | Arg | Arg |      |
|     | 430 |     |     |     |     | 435 |     |     |     |     | 440 |     |     |     |     |      |
| GTT | AGC | TTA | AGT | GAT | GGC | AGC | GAT | AGT | GAA | AGC | AGT | TCT | GCT | TCT | TCA | 1575 |
| Val | Ser | Leu | Ser | Asp | Gly | Ser | Asp | Ser | Glu | Ser | Ser | Ser | Ala | Ser | Ser |      |
| 445 |     |     |     |     | 450 |     |     |     |     | 455 |     |     |     |     | 460 |      |
| CCC | CTA | CAT | CAC | GAA | CCT | CCA | CCA | CCC | TTA | CTA | AAA | ACC | AAC | AAC | AAC | 1623 |
| Pro | Leu | His | His | Glu | Pro | Pro | Pro | Pro | Leu | Leu | Lys | Thr | Asn | Asn | Asn |      |
|     |     |     |     | 465 |     |     |     |     | 470 |     |     |     |     | 475 |     |      |
| CAG | ATT | CTT | GAA | GTG | AAA | AGT | CCA | ATA | AAG | CAA | AGC | AAA | TCA | GAT | AAG | 1671 |
| Gln | Ile | Leu | Glu | Val | Lys | Ser | Pro | Ile | Lys | Gln | Ser | Lys | Ser | Asp | Lys |      |
|     |     |     | 480 |     |     |     |     | 485 |     |     |     |     | 490 |     |     |      |
| CAA | ATA | AAG | AAT | GGT | GAA | TGT | GAC | AAG | GCA | TAC | CTA | GAT | GAA | CTG | GTA | 1719 |
| Gln | Ile | Lys | Asn | Gly | Glu | Cys | Asp | Lys | Ala | Tyr | Leu | Asp | Glu | Leu | Val |      |
|     |     | 495 |     |     |     |     | 500 |     |     |     |     | 505 |     |     |     |      |
| GAG | CTT | CAC | AGA | AGG | TTA | ATG | ACA | TTG | AGA | GAA | AGA | CAC | ATT | CTG | CAG | 1767 |
| Glu | Leu | His | Arg | Arg | Leu | Met | Thr | Leu | Arg | Glu | Arg | His | Ile | Leu | Gln |      |
|     | 510 |     |     |     |     | 515 |     |     |     |     | 520 |     |     |     |     |      |
| CAG | ATC | GTG | AAC | CTT | ATA | GAA | GAA | ACT | GGA | CAC | TTT | CAT | ATC | ACA | AAC | 1815 |
| Gln | Ile | Val | Asn | Leu | Ile | Glu | Glu | Thr | Gly | His | Phe | His | Ile | Thr | Asn |      |
| 525 |     |     |     |     | 530 |     |     |     |     | 535 |     |     |     |     | 540 |      |
| ACA | ACA | TTT | GAT | TTT | GAT | CTT | TGC | TCG | CTG | GAC | AAA | ACC | ACA | GTC | CGT | 1863 |
| Thr | Thr | Phe | Asp | Phe | Asp | Leu | Cys | Ser | Leu | Asp | Lys | Thr | Thr | Val | Arg |      |
|     |     |     |     | 545 |     |     |     |     | 550 |     |     |     |     | 555 |     |      |
| AAA | CTA | CAG | AGT | TAC | CTG | GAA | ACA | TCT | GGA | ACA | TCC | TGAGGATATA |   |     |     | 1909 |
| Lys | Leu | Gln | Ser | Tyr | Leu | Glu | Thr | Ser | Gly | Thr | Ser |     |     |     |     |      |
|     |     |     | 560 |     |     |     |     | 565 |     |     |     |     |     |     |     |      |

| | | | | |
|---|---|---|---|---|
| ACAACTGGAT | GCATCAAGAA | CTATTGTGTT | TTTTTTTTT | GGTTTTTTTT | TTTTTGGTT | 1969 |
| GTGATTTTTT | GTTCTTGTTG | TTTATATGAA | AACACTCAAA | ATGATGCAAC | CAAAAGGGAA | 2029 |
| AAAATAAAAA | TCAAACAACC | TTCAGCTTTA | TTTTTCTTTA | AAGCCAGTCA | TCATCTCTTG | 2089 |
| ATAAAGGAGA | GGTTAAAGCA | AACCAGCCTC | AGCGGACCAC | TCTTCTCTCC | AAGGAAATCC | 2149 |
| CCGGGAAGAG | TTAGCCTGGA | TAGCCTTGAA | AACAAACAAA | TCAAACACAA | CACAAGAAAA | 2209 |
| CTCAAAGAAT | GTGTATGGTA | TCATGTATCT | CTCTGTGGTG | GTTCATTCCA | CAGGACGAAT | 2269 |
| GCATATTCAA | CACACTGCCT | TATTACATAA | CTGATCTATT | TATTATCGCA | TACAGATATT | 2329 |

```
CTAAGTCGTT GAGGGAATGA CACCATCAGA CATTATAAGT ACTTGGTCCC GTGGATGCTC      2389

TTTCAATGCA GCACCCTTGC CATCCCAAGC CCAGTGACCT TACTCGTATA CCGTGCCACT      2449

TTCCACCAAC TTTTTCCAAG TCCTTTAACT CGTTGCAGTC TGTATTTTCC ACCTTTGTT       2509

TTTCCAGTTC CAGGACACAG ATTATCAACT GGGGGGACCA AATAGCCACC TTGATTTTCT      2569

TCTTTGTGGT CTTTTTCCTG AAAGTTGGGG CCCAGTCCTT GGCTGTATCC ATGTAATGAT      2629

CTTGGACCAT GGTAGAAAAT GCACCAAATA GGATCATATG AATTGCTGTC TAGCCTTAGT      2689

CAATAAACTT GTAGGACTTT TAAACAAAAG TGTACCTGTA AATGTCCTGA ATCCAGCATT      2749

GTTGAGCTGT CATCAACATT CTTGTGTCTG TTTTACTGTT ACAATATTAG GTGAATATGG      2809

AAGTAAAGGC ATTCCACAGG ATCATCATTT AAAAAAAAG  AATTCTGGTC CTGTTTTCTA      2869

AAAAAAAAAA ACTGTTGTAG AAATTCTTAA TTTGGATCTA TTTATTAGTC AGAGTTTCAG      2929

CTTTCTTCAG CTGCCAGTGT GTTACTCATC TTTATCCTAA AAATCTGGAA TCAGAGATTT      2989

TTGTTTGTTC ACATATGATT CTCTTAGACA CTTTTATATT TGAAAAAATT AAAATCTTTC      3049

TTTGGGGAAA AATTCTTGGT TATTCTGCCA TAACAGATTA TGTATTAACT TGTAGATTCA      3109

GTGGTTCAAT ACCTGTTTAG TTGCTTGCTA ATATTTCCAG AAGGATTTCT TGTATTGGTG      3169

AAAGACGGTT GGGGATGGGG GGATTTTTTT GTTCTTGTTG TACCCTTGTT TTGAAACTAG      3229

AAATCTGTCC TGTGGCATGC AAAAGAAAGC AAATTATTTT TAAAAGAAAA AAACCAAAGT      3289

ACTTTTGGTG TCATTATTCC ATCTTCTCCA TAAGTGGAGA AATGAAAAGT AAGAACAGCT      3349

CATCTTCAAA GTTTTACTA  GAAATTC                                         3376
```

( 2 ) INFORMATION FOR SEQ ID NO:30:

( i ) SEQUENCE CHARACTERISTICS:
        ( A ) LENGTH: 568 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Met Ala Ser Ser Cys Ser Val Gln Val Lys Leu Glu Leu Gly His Arg
 1               5                  10                  15

Ala Gln Val Arg Lys Lys Pro Thr Val Glu Gly Phe Thr His Asp Trp
                20                  25                  30

Met Val Phe Val Arg Gly Pro Glu His Ser Asn Ile Gln His Phe Val
                35                  40                  45

Glu Lys Val Val Phe His Leu His Glu Ser Phe Pro Arg Pro Lys Arg
        50                  55                  60

Val Cys Lys Asp Pro Pro Tyr Lys Val Glu Glu Ser Gly Tyr Ala Gly
65                  70                  75                  80

Phe Ile Leu Pro Ile Glu Val Tyr Phe Lys Asn Lys Glu Glu Pro Arg
                    85                  90                  95

Lys Val Arg Phe Asp Tyr Asp Leu Phe Leu His Leu Glu Gly His Pro
                100                 105                 110

Pro Val Asn His Leu Arg Cys Glu Lys Leu Thr Phe Asn Asn Pro Thr
            115                 120                 125

Glu Asp Phe Arg Arg Lys Leu Leu Lys Ala Gly Gly Asp Pro Asn Arg
        130                 135                 140

Ser Ile His Thr Ser Ser Ser Ser Ser Ser Ser Ser Ser Ser Ser Ser
145                 150                 155                 160

Ser Ser Ser Ser Ser Ser Ser Ser Ser Ser Ser Ser Ser Ser
```

|   |   |   | 165 |   |   |   |   | 170 |   |   |   |   | 175 |   |
|---|---|---|---|---|---|---|---|---|---|---|---|---|---|---|
| Ser | Ser | Ser | Ser | Ser | Ser | Ser | Ser | Ser | Ser | Ser | Ser | Ser | Thr | Ser |
|   |   |   | 180 |   |   |   |   | 185 |   |   |   |   | 190 |   |
| Phe | Ser | Lys | Pro | His | Lys | Leu | Met | Lys | Glu | His | Lys | Glu | Lys | Pro | Ser |
|   |   |   | 195 |   |   |   | 200 |   |   |   | 205 |   |   |   |
| Lys | Asp | Ser | Arg | Glu | His | Lys | Ser | Ala | Phe | Lys | Glu | Pro | Ser | Arg | Asp |
|   |   |   | 210 |   |   | 215 |   |   |   | 220 |   |   |   |   |
| His | Asn | Lys | Ser | Ser | Lys | Glu | Ser | Ser | Lys | Lys | Pro | Lys | Glu | Asn | Lys |
| 225 |   |   |   |   | 230 |   |   |   | 235 |   |   |   |   | 240 |
| Pro | Leu | Lys | Glu | Glu | Lys | Ile | Val | Pro | Lys | Met | Ala | Phe | Lys | Glu | Pro |
|   |   |   |   | 245 |   |   |   | 250 |   |   |   | 255 |   |   |
| Lys | Pro | Met | Ser | Lys | Glu | Pro | Lys | Pro | Asp | Ser | Asn | Leu | Leu | Thr | Ile |
|   |   |   | 260 |   |   |   |   | 265 |   |   |   | 270 |   |   |
| Thr | Ser | Gly | Gln | Asp | Lys | Lys | Ala | Pro | Ser | Lys | Arg | Pro | Pro | Ile | Ser |
|   |   |   | 275 |   |   |   |   | 280 |   |   |   | 285 |   |   |
| Asp | Ser | Glu | Glu | Leu | Ser | Ala | Lys | Lys | Arg | Lys | Lys | Ser | Ser | Ser | Glu |
|   |   | 290 |   |   |   |   | 295 |   |   |   | 300 |   |   |   |
| Ala | Leu | Phe | Lys | Ser | Phe | Ser | Ser | Ala | Pro | Pro | Leu | Ile | Leu | Thr | Cys |
| 305 |   |   |   |   | 310 |   |   |   | 315 |   |   |   |   | 320 |
| Ser | Ala | Asp | Lys | Lys | Gln | Ile | Lys | Asp | Lys | Ser | His | Val | Lys | Met | Gly |
|   |   |   |   | 325 |   |   |   | 330 |   |   |   |   | 335 |   |
| Lys | Val | Lys | Ile | Glu | Ser | Glu | Thr | Ser | Glu | Lys | Lys | Lys | Ser | Thr | Leu |
|   |   |   |   | 340 |   |   |   | 345 |   |   |   | 350 |   |   |
| Pro | Pro | Phe | Asp | Asp | Ile | Val | Asp | Pro | Asn | Asp | Ser | Asp | Val | Glu | Glu |
|   |   |   | 355 |   |   |   |   | 360 |   |   |   | 365 |   |   |
| Asn | Ile | Ser | Ser | Lys | Ser | Asp | Ser | Glu | Gln | Pro | Ser | Pro | Ala | Ser | Ser |
|   |   | 370 |   |   |   |   | 375 |   |   |   |   | 380 |   |   |
| Ser | Ser | Ser | Ser | Ser | Ser | Ser | Phe | Thr | Pro | Ser | Gln | Thr | Arg | Gln | Gln |
| 385 |   |   |   |   |   | 390 |   |   |   | 395 |   |   |   | 400 |
| Gly | Pro | Leu | Arg | Ser | Ile | Met | Lys | Asp | Leu | His | Ser | Asp | Asp | Asn | Glu |
|   |   |   |   | 405 |   |   |   | 410 |   |   |   | 415 |   |   |
| Glu | Glu | Ser | Asp | Glu | Val | Glu | Asp | Asn | Asp | Asn | Asp | Ser | Glu | Met | Glu |
|   |   |   | 420 |   |   |   | 425 |   |   |   |   | 430 |   |   |
| Arg | Pro | Val | Asn | Arg | Gly | Gly | Ser | Arg | Ser | Arg | Arg | Val | Ser | Leu | Ser |
|   |   |   | 435 |   |   |   | 440 |   |   |   | 445 |   |   |   |
| Asp | Gly | Ser | Asp | Ser | Glu | Ser | Ser | Ser | Ala | Ser | Ser | Pro | Leu | His | His |
|   | 450 |   |   |   |   | 455 |   |   |   | 460 |   |   |   |   |
| Glu | Pro | Pro | Pro | Pro | Leu | Leu | Lys | Thr | Asn | Asn | Asn | Gln | Ile | Leu | Glu |
| 465 |   |   |   |   | 470 |   |   |   | 475 |   |   |   |   | 480 |
| Val | Lys | Ser | Pro | Ile | Lys | Gln | Ser | Lys | Ser | Asp | Lys | Gln | Ile | Lys | Asn |
|   |   |   |   | 485 |   |   |   | 490 |   |   |   | 495 |   |   |
| Gly | Glu | Cys | Asp | Lys | Ala | Tyr | Leu | Asp | Glu | Leu | Val | Glu | Leu | His | Arg |
|   |   |   | 500 |   |   |   | 505 |   |   |   | 510 |   |   |   |
| Arg | Leu | Met | Thr | Leu | Arg | Glu | Arg | His | Ile | Leu | Gln | Gln | Ile | Val | Asn |
|   |   |   | 515 |   |   |   | 520 |   |   |   | 525 |   |   |   |
| Leu | Ile | Glu | Glu | Thr | Gly | His | Phe | His | Ile | Thr | Asn | Thr | Thr | Phe | Asp |
|   |   | 530 |   |   |   |   | 535 |   |   |   | 540 |   |   |   |
| Phe | Asp | Leu | Cys | Ser | Leu | Asp | Lys | Thr | Thr | Val | Arg | Lys | Leu | Gln | Ser |
| 545 |   |   |   |   | 550 |   |   |   | 555 |   |   |   |   | 560 |
| Tyr | Leu | Glu | Thr | Ser | Gly | Thr | Ser |
|   |   |   |   | 565 |

( 2 ) INFORMATION FOR SEQ ID NO:31:

( i ) SEQUENCE CHARACTERISTICS:
   ( A ) LENGTH: 559 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:31:

```
Met Asp Asn Gln Cys Thr Val Gln Val Arg Leu Glu Leu Gly His Arg
 1               5                  10                  15
Ala Gln Leu Arg Lys Lys Pro Thr Thr Glu Gly Phe Thr His Asp Trp
            20                  25                  30
Met Val Phe Val Arg Gly Pro Glu Gln Cys Asp Ile Gln His Phe Val
            35                  40                  45
Glu Lys Val Val Phe Trp Leu His Asp Ser Phe Pro Lys Pro Arg Arg
        50                  55                  60
Val Cys Lys Glu Pro Pro Tyr Lys Val Glu Glu Ser Gly Tyr Ala Gly
65                  70                  75                  80
Phe Ile Met Pro Ile Glu Val His Phe Lys Asn Lys Glu Glu Pro Arg
                    85                  90                  95
Lys Val Cys Phe Thr Tyr Asp Leu Phe Leu Asn Leu Glu Gly Asn Pro
                100                 105                 110
Pro Val Asn His Leu Arg Cys Glu Lys Leu Thr Phe Asn Asn Pro Thr
            115                 120                 125
Thr Glu Phe Arg Tyr Lys Leu Leu Arg Ala Gly Gly Val Met Val Met
        130                 135                 140
Pro Glu Gly Ala Asp Thr Val Ser Arg Pro Ser Pro Asp Tyr Pro Met
145                 150                 155                 160
Leu Pro Thr Ile Pro Leu Ser Ala Phe Ser Asp Pro Lys Lys Thr Lys
                    165                 170                 175
Pro Ser His Gly Ser Lys Asp Ala Asn Lys Glu Ser Ser Lys Thr Ser
                180                 185                 190
Lys Pro His Lys Val Thr Lys Glu His Arg Glu Arg Pro Arg Lys Asp
            195                 200                 205
Ser Glu Ser Lys Ser Ser Ser Lys Glu Leu Glu Arg Glu Gln Ala Lys
        210                 215                 220
Ser Ser Lys Asp Thr Ser Arg Lys Leu Gly Glu Gly Arg Leu Pro Lys
225                 230                 235                 240
Glu Glu Lys Ala Pro Pro Lys Ala Ala Phe Lys Glu Pro Lys Met
                    245                 250                 255
Ala Leu Lys Glu Thr Lys Leu Glu Ser Thr Ser Pro Asn Pro Gly Pro
                260                 265                 270
Pro Pro Pro Pro Pro Pro Pro Arg Ala Ser Ser Lys Arg Pro Ala
            275                 280                 285
Thr Ala Asp Ser Pro Lys Pro Ser Ala Lys Lys Gln Lys Lys Ser Ser
        290                 295                 300
Ser Lys Gly Ser Arg Ser Ala Pro Gly Thr Ser Pro Arg Thr Ser Ser
305                 310                 315                 320
Ser Ser Ser Phe Ser Asp Lys Lys Pro Ala Lys Asp Lys Ser Ser Thr
                    325                 330                 335
Arg Gly Glu Lys Val Lys Ala Glu Ser Glu Pro Arg Glu Ala Lys Lys
                340                 345                 350
Ala Leu Glu Val Glu Glu Ser Asn Ser Glu Asp Glu Ala Ser Phe Lys
            355                 360                 365
Ser Glu Ser Ala Gln Ser Ser Pro Ser Asn Ser Ser Ser Ser Asp
```

```
            370                         375                         380
Ser Ser Ser Asp Ser Asp Phe Glu Pro Ser Gln Asn His Ser Gln Gly
385                     390                 395                     400

Pro Leu Arg Ser Met Val Glu Asp Leu Gln Ser Glu Glu Ser Asp Glu
                405                     410                415

Asp Asp Ser Ser Ser Gly Glu Glu Ala Ala Gly Lys Thr Asn Pro Gly
            420                 425                 430

Arg Asp Ser Arg Leu Ser Phe Ser Asp Ser Glu Ser Asp Asn Ser Ala
            435                 440                 445

Asp Ser Ser Leu Pro Ser Arg Glu Pro Pro Pro Gln Lys Pro Pro
    450                 455                 460

Pro Pro Asn Ser Lys Val Ser Gly Arg Arg Ser Pro Glu Ser Cys Ser
465                 470                 475                     480

Lys Pro Glu Lys Ile Leu Lys Lys Gly Thr Tyr Asp Lys Ala Tyr Thr
                485                 490                 495

Asp Glu Leu Val Glu Leu His Arg Arg Leu Met Ala Leu Arg Glu Arg
            500                 505                 510

Asn Val Leu Gln Gln Ile Val Asn Leu Ile Glu Glu Thr Gly His Phe
        515                 520                 525

Asn Val Thr Asn Thr Thr Phe Asp Phe Asp Leu Phe Ser Leu Asp Glu
    530                 535                 540

Thr Thr Val Arg Lys Leu Gln Ser Cys Leu Glu Ala Val Ala Thr
545                 550                 555
```

( 2 ) INFORMATION FOR SEQ ID NO:32:

( i ) SEQUENCE CHARACTERISTICS:
        ( A ) LENGTH: 262 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..260

( x i ) SEQUENCE DESCRIPTION: SEQ ID NO:32:

```
CA GAT GAA GTG GAG GAT AAC GAC AAT GAC TCT GAA ATG GAG AGG CCT                47
   Asp Glu Val Glu Asp Asn Asp Asn Asp Ser Glu Met Glu Arg Pro
   1               5                   10                  15

GTA AAT AGA GGA GGC AGC CGA AGT CGC AGA GTT AGC TTA AGT GAT GGC                95
Val Asn Arg Gly Gly Ser Arg Ser Arg Arg Val Ser Leu Ser Asp Gly
            20                  25                  30

AGC GAT AGT GAA AGC AGT TCT GCT TCT TCA CCC CTA CAT CAC GAA CCT                143
Ser Asp Ser Glu Ser Ser Ser Ala Ser Ser Pro Leu His His Glu Pro
            35                  40                  45

CCA CCA CCC TTA CTA AAA ACC AAC AAC AAC CAG ATT CTT GAA GTA AAA                191
Pro Pro Pro Leu Leu Lys Thr Asn Asn Asn Gln Ile Leu Glu Val Lys
        50                  55                  60

ATT CCA GCA GAT GGA GTC CAC AGG ATC AGA GTG GAC TTT AAG TTT GTG                239
Ile Pro Ala Asp Gly Val His Arg Ile Arg Val Asp Phe Lys Phe Val
        65                  70                  75

TAT TGC CAA GTC TGT TGT GAG CC                                                 262
Tyr Cys Gln Val Cys Cys Glu
80                  85
```

( 2 ) INFORMATION FOR SEQ ID NO:33:

( i ) SEQUENCE CHARACTERISTICS:
  ( A ) LENGTH: 86 amino acids
  ( B ) TYPE: amino acid
  ( D ) TOPOLOGY: linear ( i i ) MOLECULE TYPE: protein ( x i ) SEQUENCE DESCRIPTION: SEQ ID NO:33:

```
Asp Glu Val Glu Asp Asn Asp Asn Asp Ser Glu Met Glu Arg Pro Val
  1               5                  10                  15

Asn Arg Gly Gly Ser Arg Ser Arg Arg Val Ser Leu Ser Asp Gly Ser
                20                  25                  30

Asp Ser Glu Ser Ser Ser Ala Ser Ser Pro Leu His His Glu Pro Pro
            35                  40                  45

Pro Pro Leu Leu Lys Thr Asn Asn Asn Gln Ile Leu Glu Val Lys Ile
        50                  55                  60

Pro Ala Asp Gly Val His Arg Ile Arg Val Asp Phe Lys Phe Val Tyr
 65                  70                  75                  80

Cys Gln Val Cys Cys Glu
                85
```

( 2 ) INFORMATION FOR SEQ ID NO:34:

( i ) SEQUENCE CHARACTERISTICS:
    ( A ) LENGTH: 439 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 2..436

( x i ) SEQUENCE DESCRIPTION: SEQ ID NO:34:

```
A CCT ACT ACA GGA CCG CCA AGA AAA GAA GTT CCC AAA ACC ACT CCT           46
  Pro Thr Thr Gly Pro Pro Arg Lys Glu Val Pro Lys Thr Thr Pro
   1               5                  10                  15

AGT GAG CCC AAG AAA AAG CAG CCT CCA CCA CCA GAA TCA GGT CCA GAG         94
Ser Glu Pro Lys Lys Lys Gln Pro Pro Pro Pro Glu Ser Gly Pro Glu
                20                  25                  30

CAG AGC AAA CAG AAA AAA GTG GCT CCC CGC CCA AGT ATC CCT GTA AAA        142
Gln Ser Lys Gln Lys Lys Val Ala Pro Arg Pro Ser Ile Pro Val Lys
            35                  40                  45

CAA AAA CCA AAA GAA AAG ATT CTT GAA GTG AAA AGT CCA ATA AAG CAA        190
Gln Lys Pro Lys Glu Lys Ile Leu Glu Val Lys Ser Pro Ile Lys Gln
        50                  55                  60

AGC AAA TCA GAT AAG CAA ATA AAG AAT GGT GAA TGT GAC AAG GCA TAC        238
Ser Lys Ser Asp Lys Gln Ile Lys Asn Gly Glu Cys Asp Lys Ala Tyr
 65                  70                  75

CTA GAT GAA CTG GTA GAG CTT CAC AGA AGG TTA ATG ACA TTG AGA GAA        286
Leu Asp Glu Leu Val Glu Leu His Arg Arg Leu Met Thr Leu Arg Glu
 80                  85                  90                  95

AGA CAC ATT CTG CAG CAG ATC GTG AAC CTT ATA GAA GAA ACT GGA CAC        334
Arg His Ile Leu Gln Gln Ile Val Asn Leu Ile Glu Glu Thr Gly His
                100                 105                 110

TTT CAT ATC ACA AAC ACA ACA CTT GAT TTT GAT CTT TGC TCG CTG GAC        382
Phe His Ile Thr Asn Thr Thr Leu Asp Phe Asp Leu Cys Ser Leu Asp
            115                 120                 125

AAA ACC ACA GTC CGT AAA CTA CAG AGT TAC CTG GAA ACA TCT GGA ACA        430
Lys Thr Thr Val Arg Lys Leu Gln Ser Tyr Leu Glu Thr Ser Gly Thr
        130                 135                 140
```

```
TCC TGAGGA                                                                                      439
Ser

145
```

(2) INFORMATION FOR SEQ ID NO:35:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:35:

```
Pro  Thr  Thr  Gly  Pro  Pro  Arg  Lys  Glu  Val  Pro  Lys  Thr  Thr  Pro  Ser
  1              5                        10                      15

Glu  Pro  Lys  Lys  Lys  Gln  Pro  Pro  Pro  Glu  Ser  Gly  Pro  Glu  Gln
            20                      25                  30

Ser  Lys  Gln  Lys  Lys  Val  Ala  Pro  Arg  Pro  Ser  Ile  Pro  Val  Lys  Gln
            35                      40                      45

Lys  Pro  Lys  Glu  Lys  Ile  Leu  Glu  Val  Lys  Ser  Pro  Ile  Lys  Gln  Ser
       50                      55                  60

Lys  Ser  Asp  Lys  Gln  Ile  Lys  Asn  Gly  Glu  Cys  Asp  Lys  Ala  Tyr  Leu
 65                       70                  75                      80

Asp  Glu  Leu  Val  Glu  Leu  His  Arg  Arg  Leu  Met  Thr  Leu  Arg  Glu  Arg
                 85                      90                      95

His  Ile  Leu  Gln  Gln  Ile  Val  Asn  Leu  Ile  Glu  Glu  Thr  Gly  His  Phe
                100                     105                     110

His  Ile  Thr  Asn  Thr  Thr  Leu  Asp  Phe  Asp  Leu  Cys  Ser  Leu  Asp  Lys
            115                     120                     125

Thr  Thr  Val  Arg  Lys  Leu  Gln  Ser  Tyr  Leu  Glu  Thr  Ser  Gly  Thr  Ser
       130                     135                     140
```

(2) INFORMATION FOR SEQ ID NO:36:

(i) SEQUENCE CHARACTERISTICS:
        (A) LENGTH: 343 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..341

(xi) SEQUENCE DESCRIPTION: SEQ ID NO:36:

```
CA ACG TTA CCG CCA TTT GAT GAT ATT GTG GAT CCC AAT GAT TCA GAT                47
   Thr Leu Pro Pro Phe Asp Asp Ile Val Asp Pro Asn Asp Ser Asp
    1           5               10              15

GTG GAG GAG AAT ATA TCC TCT AAA TCT GAT TTT GTG TAT TGC CAA GTC              95
Val Glu Glu Asn Ile Ser Ser Lys Ser Asp Phe Val Tyr Cys Gln Val
                20              25                  30

TGT TGT GAG CCC TTC CAC AAG TTT TGT TTA GAG GAG AAC GAG CGC CCT             143
Cys Cys Glu Pro Phe His Lys Phe Cys Leu Glu Glu Asn Glu Arg Pro
            35              40                  45

CTG GAG GAC CAG CTG GAA AAT TGG TGT TGT CGT CGT TGC AAA TTC TGT             191
Leu Glu Asp Gln Leu Glu Asn Trp Cys Cys Arg Arg Cys Lys Phe Cys
         50              55                  60

CAC GTT TGT GGA AGG CAA CAT CAG GCT ACA AAG CAG CTG CTG GAG TGT             239
```

```
His Val Cys Gly Arg Gln His Gln Ala Thr Lys Gln Leu Leu Glu Cys
     65                  70                  75

AAT AAG TGC CGA AAC AGC TAT CAC CCT GAG TGC CTG GGA CCA AAC TAC        287
Asn Lys Cys Arg Asn Ser Tyr His Pro Glu Cys Leu Gly Pro Asn Tyr
 80              85                  90                      95

CCC ACC AAA CCC ACA AAG AAG AAG AAA GTC TGG ATC TGT ACC AAG TGT        335
Pro Thr Lys Pro Thr Lys Lys Lys Lys Val Trp Ile Cys Thr Lys Cys
                100                 105                 110

GTT CGC TG                                                              343
Val Arg
```

( 2 ) INFORMATION FOR SEQ ID NO:37:

( i ) SEQUENCE CHARACTERISTICS:
    ( A ) LENGTH: 113 amino acids
    ( B ) TYPE: amino acid
    ( D ) TOPOLOGY: linear ( i i ) MOLECULE TYPE: protein ( x i ) SEQUENCE DESCRIPTION: SEQ ID NO:37:

```
Thr Leu Pro Pro Phe Asp Asp Ile Val Asp Pro Asn Asp Ser Asp Val
 1               5                  10                  15

Glu Glu Asn Ile Ser Ser Lys Ser Asp Phe Val Tyr Cys Gln Val Cys
             20                  25                  30

Cys Glu Pro Phe His Lys Phe Cys Leu Glu Glu Asn Glu Arg Pro Leu
         35                  40                  45

Glu Asp Gln Leu Glu Asn Trp Cys Cys Arg Arg Cys Lys Phe Cys His
     50                  55                  60

Val Cys Gly Arg Gln His Gln Ala Thr Lys Gln Leu Leu Glu Cys Asn
 65                  70                  75                  80

Lys Cys Arg Asn Ser Tyr His Pro Glu Cys Leu Gly Pro Asn Tyr Pro
             85                  90                  95

Thr Lys Pro Thr Lys Lys Lys Lys Val Trp Ile Cys Thr Lys Cys Val
            100                 105                 110

Arg
```

( 2 ) INFORMATION FOR SEQ ID NO:38:

( i ) SEQUENCE CHARACTERISTICS:
    ( A ) LENGTH: 11
    ( B ) TYPE: nucleic acid
    ( C ) STRANDEDNESS: single
    ( D ) TOPOLOGY: linear ( x i ) SEQUENCE DESCRIPTION: SEQ ID NO:38:
         ATTCTTGAAG T ( 2 ) INFORMATION FOR SEQ ID NO:39:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( x i ) SEQUENCE DESCRIPTION: SEQ ID NO:39:
         TCCTCAGGAT GTTCCAGATG T ( 2 ) INFORMATION FOR SEQ ID NO:40:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( x i ) SEQUENCE DESCRIPTION: SEQ ID NO:40:
GGCTCACAAC AGACTTGGCA A ( 2 ) INFORMATION FOR SEQ ID NO:41:

( i ) SEQUENCE CHARACTERISTICS:
( A ) LENGTH: 21
( B ) TYPE: nucleic acid
( C ) STRANDEDNESS: single
( D ) TOPOLOGY: linear ( x i ) SEQUENCE DESCRIPTION: SEQ ID NO:41:
ACCTACTACA GGACCGCCAA G ( 2 ) INFORMATION FOR SEQ ID NO:42:

( i ) SEQUENCE CHARACTERISTICS:
( A ) LENGTH: 21
( B ) TYPE: nucleic acid
( C ) STRANDEDNESS: single
( D ) TOPOLOGY: linear ( x i ) SEQUENCE DESCRIPTION: SEQ ID NO:42:
CAGATGAAGT GGAGGATAAC G ( 2 ) INFORMATION FOR SEQ ID NO:43:

( i ) SEQUENCE CHARACTERISTICS:
( A ) LENGTH: 21
( B ) TYPE: nucleic acid
( C ) STRANDEDNESS: single
( D ) TOPOLOGY: linear ( x i ) SEQUENCE DESCRIPTION: SEQ ID NO:43:
CAGCGAACAC ACTTGGTACA G ( 2 ) INFORMATION FOR SEQ ID NO:44:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO:44:
CAACGTTACC GCCATTTGAT